US011192923B2

(12) United States Patent
Alvarez

(10) Patent No.: US 11,192,923 B2
(45) Date of Patent: Dec. 7, 2021

(54) POLYPEPTIDES INCLUDING A BETA-TRICALCIUM PHOSPHATE-BINDING SEQUENCE AND USES THEREOF

(71) Applicant: Theradaptive, Inc., Frederick, MD (US)

(72) Inventor: Luis Alvarez, Lexington, MA (US)

(73) Assignee: Theradaptive, Inc., Frederick, MD (US)

( * ) Notice: Subject to any disclaimer, the term of this patent is extended or adjusted under 35 U.S.C. 154(b) by 0 days.

(21) Appl. No.: 16/892,141

(22) Filed: Jun. 3, 2020

(65) Prior Publication Data

US 2020/0291068 A1  Sep. 17, 2020

Related U.S. Application Data

(63) Continuation of application No. PCT/US2019/055939, filed on Oct. 11, 2019.

(60) Provisional application No. 62/744,941, filed on Oct. 12, 2018.

(51) Int. Cl.

| C07K 7/08 | (2006.01) |
|---|---|
| C07K 14/51 | (2006.01) |
| C07K 14/00 | (2006.01) |
| A61P 19/00 | (2006.01) |
| C07K 14/475 | (2006.01) |
| A61K 38/18 | (2006.01) |
| A61K 38/04 | (2006.01) |
| A61K 38/16 | (2006.01) |

(52) U.S. Cl.
CPC .............. *C07K 7/08* (2013.01); *A61K 38/04* (2013.01); *A61K 38/16* (2013.01); *A61K 38/1875* (2013.01); *A61P 19/00* (2018.01); *C07K 14/001* (2013.01); *C07K 14/475* (2013.01); *C07K 14/51* (2013.01)

(58) Field of Classification Search
None
See application file for complete search history.

(56) References Cited

U.S. PATENT DOCUMENTS

| 5,152,791 | A | 10/1992 | Hakamatsuka et al. |
|---|---|---|---|
| 5,491,082 | A | 2/1996 | Suzuki et al. |
| 5,820,632 | A | 10/1998 | Constantz et al. |
| 5,906,828 | A | 5/1999 | Cima et al. |
| 6,455,495 | B1 | 9/2002 | Orgel et al. |
| 6,949,251 | B2 | 9/2005 | Dalal et al. |
| 7,172,629 | B2 | 2/2007 | McKay |
| 7,323,542 | B2 | 1/2008 | Balian |
| 7,572,766 | B2 | 8/2009 | Beyer, Jr. et al. |
| 7,871,978 | B2 | 1/2011 | Balian |
| 7,977,313 | B2 | 7/2011 | Gron et al. |
| 8,022,040 | B2 | 9/2011 | Bertozzi et al. |
| 8,075,562 | B2 | 12/2011 | Murphy et al. |
| 8,383,769 | B2 | 2/2013 | Peled et al. |
| 8,420,774 | B2 | 4/2013 | Murphy et al. |
| 8,778,869 | B2 | 7/2014 | Murphy et al. |
| 8,846,860 | B2 | 9/2014 | Murphy et al. |
| 9,295,755 | B2 | 3/2016 | Murphy |
| 10,329,327 | B2 | 6/2019 | Alvarez et al. |
| 2004/0197892 | A1 | 10/2004 | Moore et al. |
| 2005/0084962 | A1 | 4/2005 | Simon |
| 2005/0085623 | A1 | 4/2005 | Balian |
| 2006/0193916 | A1 | 8/2006 | Lazarova et al. |
| 2006/0292198 | A1 | 12/2006 | Dalal et al. |
| 2008/0095817 | A1 | 4/2008 | Murphy |
| 2008/0214468 | A1 | 9/2008 | Balian |
| 2008/0279908 | A1 | 11/2008 | Bertozzi et al. |
| 2009/0087472 | A1 | 4/2009 | Murphy et al. |
| 2010/0049322 | A1 | 2/2010 | McKay |
| 2011/0129611 | A1 | 6/2011 | Murphy et al. |
| 2011/0305760 | A1 | 12/2011 | Murphy et al. |
| 2012/0028913 | A1 | 2/2012 | Peled et al. |
| 2013/0149457 | A1 | 6/2013 | Murphy et al. |
| 2014/0037593 | A1 | 2/2014 | Alvarez et al. |

FOREIGN PATENT DOCUMENTS

| CN | 102532272 A | 7/2012 |
|---|---|---|
| CN | 104193803 A | 12/2014 |
| WO | WO-0202593 A2 | 1/2002 |
| WO | WO-03026590 A2 | 4/2003 |
| WO | WO-2005039616 A1 | 5/2005 |
| WO | WO-2006078464 A2 | 7/2006 |
| WO | WO-2009020550 A2 | 2/2009 |
| WO | WO-2009108934 A2 | 9/2009 |

(Continued)

OTHER PUBLICATIONS

Alvarez et al.: Tethering of epidermal growth factor (EGF) to beta tricalcium phosphate (βTCP) via fusion to a high affinity, multimeric βTCP-binding peptide: effects on human multipotent stromal cells/connective tissue progenitors. PLoS One. 10(6):e0129600:1-21 (2015).

Bradshaw et al.: SPaRC-null mice exhibit increased adiposity without significant differences in overall body weight. PNaS 100(10):6045-6050 (2003).

Bublil et al.: The EGF receptor family: spearheading a merger of signaling and therapeutics. Current Opinion in Cell Biology 19:124-134 (2007).

(Continued)

*Primary Examiner* — Kevin S Orwig
(74) *Attorney, Agent, or Firm* — Wilson Sonsini Goodrich & Rosati

(57) ABSTRACT

Provided herein are beta-TCP binding sequences and chimeric polypeptides that include one or more beta-TCP binding sequences and a mammalian growth factor, compositions comprising any of these chimeric polypeptides (and optionally, beta-TCP), and methods of promoting bone or cartilage formulation, methods of replacing and/or repairing bone or cartilage, and methods of treating a bone fraction or bone loss that include administration of any of these compositions.

20 Claims, 12 Drawing Sheets

Specification includes a Sequence Listing.

(56) References Cited

FOREIGN PATENT DOCUMENTS

| WO | WO-2009126648 A1 | 10/2009 |
|----|------------------|---------|
| WO | WO-2010051032 A1 | 5/2010 |
| WO | WO-2010052715 A2 | 5/2010 |
| WO | WO-2012078671 A2 | 6/2012 |
| WO | WO-2020077265 A1 | 4/2020 |

OTHER PUBLICATIONS

Cao et al.: Phage display peptide probes for imaging early response to bevacizumab treatment. Amino Acids. 41(5):1103-1112 (2011).
Carrodeguas et al.: Alpha-tricalcium phosphate: synthesis, properties and biomedical applications. Acta Biomaterialia 7:3536-3546 (2011).
Cheng et al.: A new protocol for high-yield purification of recombinant human CXCL8(3-72)K11R/G31P expressed in *Escherichia coli*. Protein Expression and Purification 61:65-72 (2008).
Cho et al.: The effects of synthetic peptide derived from hBMP-2 on bone formation in rabbit calvarial defect. Tissue Engineering and Regenerative Medicine 5(3):488-497 (2008).
Citri et al.: EGF-ERBB signalling: towards the systems level. Molecular Cell Biology 7:505-516 (2006).
Dickens et al.: Crystallographic studies of the role of Mg as a stabilizing impurity in beta-Ca3(PO4)2. I. The crystal structure of pure beta-Ca3(PO4)2. Journal of Solid State Chemistry 10(3):232-248 (1974).
Dickerson et al.: Identification and design of peptides for the rapid, high-yield formation of nanoparticulate TiO2 from aqueous solutions at room temperature. Chemistry of Materials 20(4):1578-1584 (2008).
Erbe et al.: Potential of an ultraporous beta-tricalcium phosphate synthetic cancellous bone void filler and bone marrow aspirate composite graft. Eur. Spine J. 10:S141-S146 (2001).
Fan et al.: Tethered epidermal growth factor provides a survival advantage to mesenchymal stem cells. Stem Cells 25:1241-1251 (2007).
Fleming Jr., J.E., Intraoperative harvest and concentration of human bone marrow osteoprogenitors for enhancement of spinal fusion. In Orthopedic Tissue Engineering Basic Science and Practice, V.M. Goldberg and A.I. Caplan eds. (NY: Marcel Dekker, inc.), pp. 51-65 (2004).
Friedlaender et al.: Osteogenic protein-1 (bone morphogenetic protein-7) in the treatment of tibial nonunions. J. Bone Joint Surg. Am., 83(A Suppl 1, Pt 2):S151-S158 (2001).
Gao et al.: Molecular cloning, structure, expression, and chomosomal localization of the human osterix (SP7) gene. Gene 2341:101-110 (2004).
Gibbs et al.: Epidermal growth factor and keratinocyte growth factor differentially regulate epidermal migration, growth, and differentiation. Wound Repair and Regeneration 8(3):192-203 (2000).
Glick et al.: Ligand recognition by influenza virus. The Journal of Biological Chemistry 266(35):23660-23669 (1991).
Griffith L.G., Emerging design principles in biomaterials and scaffolds for tissue engineering. Ann. N.Y. Acad. Sci. 961:83-95 (2002).
Gronthos et al.: The growth factor requirements of STRO-1-positive human bone marrow stromal precursosrs under serum-deprived conditions in vitro. Blood 85(4):929-940 (1995).
Gungormus et al.: Regulation of in vitro calcium phosphate mineralization by combinatorially selected hydroxyapatite-binding peptides. Biomacromolecules 9(3):966-973 (2008).
Hamilton et al.: Improved bone morphogenetic protein-2 retention in an injectable collagen matrix Using Bifunctional Peptides. PLoS One 8(8):e70715 [1-10] (2013).
Handl et al.: Hitting multiple targets with multimeric ligands. Expert Opin. 8(6):565-586 (2004).
Hoang et al.: Bone recognition mechanism of porcine osteocalcin from crystal structure. Nature 425:977-980 (2003).
Huang et al.: MimoDB 2.0: a mimotope database and beyond. Nucleic Acids Research 40(Database issue):D271-D277 (2012).
Jay et al.: Engineered bivalent ligands to bias ErbB receptor-mediated signaling and phenotypes. J. Biol. Chem. 286:27729-27740 (2011).
Kenan et al.: Peptide-PEG amphiphiles as brief communication cytophobic coatings for mammalian and bacterial cells. Chemistry & Biology 13:695-700 (2006).
Kim et al.: Extracellular calcium-binding peptide-modified ceramics stimulate regeneration of calvarial bone defects. Tissue Engineering and Regenerative Medicine 13:57-65 (2016).
Kimura et al.: Effects of platelet derived growth factor, epidermal growth factor and transforming growth factor-beta on the growth of human marrow fibroblasts. British Journal of Haematology 69(1):9-12 (1988).
Kitov et al.: Optimization of tether length in nonglycosidically linked bivalent ligands that target sites 2 and 1 of a shiga-like toxin. J. Am. Chem. Soc. 125:3284-3294 (2003).
Kratchmarova et al.: Mechanism of divergent growth factor effects in mesenchymal stem cell differentiation. Science 308:1472-1477 (2005).
Krueger et al.: Tailoring chimeric ligands for studying and biasing ErbB receptor family interactions. Angew. Chem. Int. Ed. 53:2662-2666 (2014).
Kuhl et al.: Tethered epidermal growth factor as a paradigm for growth factor-induced stimulation from the solid phase. Nature Medicine 2(9):1022-1027 (1996).
Maheshwari et al.: Biophysical integration of effects of epidermal growth factor and fibronectin on fibroblast migration. Biophysical Journal 76:2814-2823 (1999).
Marcantonio et al.: The influence of tethered epidermal growth factor on connective tissue progenitor colony formation. Biomaterials 30(27):4629-4638 (2009).
Martino et al.: Extracellular matrix-inspired growth factor delivery systems for bone regeneration. Advanced Drug Delivery Reviews 94:41-52 (2015).
Martino et al.: Growth factors engineered for super-affinity to the extracellular matrix enhance tissue healing. Science 343(6173):885-888 (2014).
Martyre et al.: Increased intraplatelet levels of platelet-derived growth factor and transforming growth factor-β in patients with myelofibrosis with myeloid metaplasia. British Journal of Haematology. 77:80-86 (1991).
Matsubara et al.: BMP2 regulates osterix through Msx2 and Runx2 during osteoblast differentiation. Journal of Biological Chemistry 283:29119-29125 (2008).
Mehta et al.: Synergistic effects of tethered growth factors and adhesion ligands on DNA synthesis and function of primary hepatocytes cultured on soft synthetic hydrogels. Biomaterials 31(17):4657-4671 (2010).
Miettinen et al.: Epidermal growth factor receptor function is necessary for normal craniofacial development and palate closure. Nature Genetics 22:69-73 (1999).
Mikami et al.: Inductive effects of dexamethasone on the mineralization and the osteoblastic gene expressions in mature osteoblast-like ROS17/2.8 cells. Biochem Biophys Res Comm 362(2):368-372 (2007).
Muschler et al.: Engineering principles of clinical cell-based tissue engineering. Journal of Bone Joint Surg. 86-A(7):1541-1558 (2004).
NCBI. GenBank Accession No. NP_001191.1: Bone morphogenetic protein 2 preproprotein [*Homo sapiens*], entire document (2018).
Nuschke et al.: Epidermal growth factor tethered to beta-tricalcium phosphate bone scaffolds via a high-affinity binding peptide enhances survival of human mesenchymal stem cells/multipotent stromal cells in an immune-competent parafascial implantation assay in mice. Stem Cells Translation Medicine 5:1580-1586 (2016).
Ogose et al.: Comparison of hydroxyapatite and beta tricalcium phosphate as bone substitutes after exclusion of bone tumors. Biomedical Materials Research Part B: Applied Biomaterials 72B:94-101 (2005).
Orii et al.: Beta-tricalcium phosphate (beta-TCP) graft combined with bone marrow stromal cells (MSCs) for posterolateral spine fusion. J Med Dent Sci 52:51-57 (2005).
Owen et al.: Clonal analysis in vitro of osteogenic differentiation of marrow DFU-F. J Cell Science 87:731-738 (1987).

(56) References Cited

OTHER PUBLICATIONS

PCT/US2011/063592 international Preliminary Report on Patentability dated Jun. 20, 2013.
PCT/US2011/063592 International Search Report and Written Opinion dated Feb. 14, 2013.
PCT/US2019/055939 International Search Report and Written Opinion dated Feb. 5, 2020.
Pickens et al.: Nonspanning bivalent ligands as improved surface receptor binding inhibitors of the cholera toxin B pentamer. Chemistry & Biology 11:1205-1215 (2004).
Pinkas-Kramarski et al.: Diversification of neu differentiation factor and epidermal growth factor signaling by combinatorial receptor interactions. The EMBO Journal 15(10):2452-2467 (1996).
Platt et al.: Sustained epidermal growth factor receptor levels and activation by tethered ligand binding enhances osteogenic differentiation of multi-potent marrow stromal cells. J. Cell Physiol. 221(2):306-317 (2009).
Qin et al.: Amphiregulin is a novel growth factor involved in normal bone development and in the cellular response to parathyroid hormone stimulation. Journal of Biological Chemistry 280:3974-3981 (2005).
Rieker et al.: Molecular applications of fusions to leucine zippers. Methods in Enzymology 328:282-296 (2000).
Sanghvi et al.: Biomaterials functionalization using a novel peptide that selectively binds to a conducting polymer. Nature Materials 4:496-502 (2005).
Satomura et al.: Receptor tyrosine kinase expression in human bone marrow stromal cells. Journal of Cellular Physiology 177(3):426-438 (1998).
Segvich, S.J. Design of peptides with targeted apatite and human bone marrow stromal cell adhesion for bone tissue engineering. (Doctoral Dissertation), Proquest UMI Publication No. 3343205 (2009).
Seker et al.: Quantitative affinity of genetically engineered repeating polypeptides to inorganic surfaces. Biomacromolecules 10:250-257 (2009).
Shen et al.: Tuning the erosion rate of artificial protein hydrogels through control of network topology. Nature Materials 5:153-158 (2006).
Sibilia et al.: Mice humanized for the EGF receptor display hypomorphic phenotypes in skin, bone and heart. Development 130(19):4515-4525 (2003).
Stemcell Technologies product description for human bone marrow stromal cells, frozen, Cat No. 70022 (2014; made of record).
Su et al.: Conformational Selectivity of Peptides for Single-Walled Carbon Nanotubes. J. Phys. Chem. B 110(47):23623-23627 (2006).
Tamama et al.: Epidermal growth factor as a candidate for ex vivo expansion of bone marrow-derived mesenchymal stem cells. Stem Cells 24:686-695 (2006).
U.S. Appl. No. 13/991,842 Notice of Allowance dated Feb. 6, 2019.
U.S. Appl. No. 13/991,842 Office Action dated Jul. 1, 2015.
U.S. Appl. No. 13/991,842 Office Action dated Jul. 13, 2017.
U.S. Appl. No. 13/991,842 Office Action dated Nov. 18, 2016.
U.S. Appl. No. 13/991,842 Office Action dated Nov. 21, 2014.
U.S. Appl. No. 13/991,842 Supplemental Notice of Allowability dated Mar. 28, 2019.
Wang et al.: Epidermal growth factor receptor-deficient mice have delayed primary encochondral ossification because of defective osteoclast recruitment. Journal of Biological Chemistry 279(51):53848-53856 (2004).
Whaley et al.: Selection of peptides with semiconductor binding specificity for directed nanocrystal assembly. Nature 405:665-668 (2000).
Yashima et al.: Crystal structure analysis of beta-tricalcium phosphate Ca3(PO4)2 by neutron powder diffraction. Journal of Solid State Chemistry 175(2):272-277 (2003).
Yazici et al.: Bi-functional chimeric peptide coatings for improved osteointegration of titanium implants. Minerals, Metals and Materials Society / AIME 2011 Meeting (2011).
Yuca et al.: In vitro labeling of hydroxyapatite minerals by an engineered protein. Biotechnology and Bioengineering 108:1021-1030 (2011).
Zeltinger et al.: Effect of pore size and void fraction on cellular adhesion, proliferation, and matrix deposition. Tissue Engineering 7(5):557-572 (2001).
Zhang et al.: Artificial polypeptide scaffold for protein immobilization. J Am Chem Soc. 127:10136-10137 (2005).
Zhang et al.: New Ouabain-Conjugated Peptide Found From Phage Displayed Peptide Library. American Journal of Hypertension, Ltd. 17:619-623.
Ziros et al.: The bone-specific transcriptional regulator Cbfal is a target of mechanical signals in osteoblastic cells, Journal of Biological Chemistry 277(26):23934-23941 (2002).
Dudak et al., Enhancing the affinity of SEB-binding peptides by repeating their sequence. Biopolymers 98(2):145-154 (2011).
Bateman et al., Platelet-derived growth factor enhancement of two alloplastic bone matrices. J. Periodontology 76(11):1833-1841 (2005).
Chan et al., Expression of epidermal growth factor in transgenic mice causes growth retardation. Journal of Biological Chemistry 275(49):38693-38698 (2000).
Freeman M., Reiterative use of the EGF receptor triggers differentiation of all cell types in the *Drosophila* eye. Cell 87:651-660 (1996).
Kuznetsov et al., Factors required for bone marrow stromal fibroblast colony formation in vitro. British Journal of Haematology 97:561-570 (1997).
Moll et al., Designed heterodimerizing leucine zippers with a range of pls and stabilities up to 10exp(−15) M. Protein Science 10:649-655 (2001).
Termine et al., Osteonetin, a bone-specific protein linking mineral to collagen. Cell 26:99-105 (1981).
Tokumaru et al., Ectodomain shedding of epidermal growth factor receptor ligands is required for keratinocyte migration in cutaneous wound healing. Journal of Cell Biology 151(2):209-219 (2000).
Traverse et al., EGF triggers neuronal differentiation of PC12 cells that overexpress the EGF receptor. Curr Biol., 4(8):694-701 (1994).
Tzahar et al., A hierarchical network of interreceptor interactions determines signal transduction by neu differentiation factor/ neuregulin and epidermal growth factor. Molecular and Cellular Biology 16(10):5276-5287 (1996).

Group C β-TCP Putty

Rat # 52 BL    Wk 2    Wk 4    Wk 6    Wk 8

Rat # 56 BL    Wk 2    Wk 4    Wk 6    Wk 8

1

2

3

4

```
                          SEQUENCE LISTING

<160> NUMBER OF SEQ ID NOS: 100

<210> SEQ ID NO 1
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 1

Leu Leu Ala Asp Thr Thr His His Arg Pro Trp Thr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 2

Val Ile Gly Glu Ser Thr His His Arg Pro Trp Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 3

Leu Ile Ala Asp Ser Thr His His Ser Pro Trp Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 4

Ile Leu Ala Glu Ser Thr His His Lys Pro Trp Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 5

Ile Leu Ala Glu Thr Thr His His Arg Pro Trp Ser
1               5                   10

<210> SEQ ID NO 6
<211> LENGTH: 12
<212> TYPE: PRT
<213> ORGANISM: Artificial Sequence
```

```
<220> FEATURE:
<223> OTHER INFORMATION: Synthetic Sequence

<400> SEQUENCE: 6

Ile Ile Gly Glu Ser Ser His His Lys Pro Phe Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 7

Gly Leu Gly Asp Thr Thr His His Arg Pro Trp Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 8

Val Leu Gly Asp Thr Thr His His Lys Pro Trp Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 9

Ile Val Ala Asp Ser Thr His His Arg Pro Trp Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 10

Ser Thr Ala Asp Thr Ser His His Arg Pro Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 11

Thr Ser Gly Gly Glu Ser Thr His His Arg Pro Ser
1               5                   10

<210> SEQ ID NO 12
<211> LENGTH: 12
<212> TYPE: PRT
<213> ORGANISM: Artificial Sequence
<220> FEATURE:
```

<223> OTHER INFORMATION: Synthetic Sequence

<400> SEQUENCE: 12

Thr Ser Gly Gly Glu Ser Ser His His Lys Pro Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 13

Thr Gly Ser Gly Asp Ser Ser His His Arg Pro Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 14

Gly Ser Ser Gly Glu Ser Thr His His Lys Pro Ser Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 15

Val Gly Ala Asp Ser Thr His His Arg Pro Val Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 16

Gly Ala Ala Asp Thr Thr His His Arg Pro Val Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 17

Ala Gly Ala Asp Thr Thr His His Arg Pro Val Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Sequence

```
<400> SEQUENCE: 18

Gly Gly Ala Asp Thr Thr His His Arg Pro Ala Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 19

Gly Gly Ala Asp Thr Thr His His Arg Pro Gly Thr
1               5                   10

<210> SEQ ID NO 20
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 20

Leu Leu Ala Asp Thr Thr His His Arg Pro Trp Thr Val Ile Gly Glu
1               5                   10                  15

Ser Thr His His Arg Pro Trp Ser
            20

<210> SEQ ID NO 21
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 21

Leu Leu Ala Asp Thr Thr His His Arg Pro Trp Thr Val Ile Gly Glu
1               5                   10                  15

Ser Thr His His Arg Pro Trp Ser Ile Ile Gly Glu Ser Ser His His
            20                  25                  30

Lys Pro Phe Thr
        35

<210> SEQ ID NO 22
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 22

Leu Leu Ala Asp Thr Thr His His Arg Pro Trp Thr Val Ile Gly Glu
1               5                   10                  15

Ser Thr His His Arg Pro Trp Ser Ile Ile Gly Glu Ser Ser His His
            20                  25                  30

Lys Pro Phe Thr Gly Leu Gly Asp Thr Thr His His Arg Pro Trp Gly
        35                  40                  45

Ile Leu Ala Glu Ser Thr His His Lys Pro Trp Thr
    50                  55                  60

<210> SEQ ID NO 23
<211> LENGTH: 24
```

```
<212> TYPE: PRT
<213> ORGANISM: Artificial Sequence
<220> FEATURE:
<223> OTHER INFORMATION: Synthetic Sequence

<400> SEQUENCE: 23

Leu Leu Ala Asp Thr Thr His His Arg Pro Trp Thr Ile Leu Ala Glu
1               5                   10                  15

Ser Thr His His Lys Pro Trp Thr
            20

<210> SEQ ID NO 24
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 24

Leu Leu Ala Asp Thr Thr His His Arg Pro Trp Thr Ile Leu Ala Glu
1               5                   10                  15

Ser Thr His His Lys Pro Trp Thr Leu Leu Ala Asp Thr Thr His His
            20                  25                  30

Arg Pro Trp Thr Ile Leu Ala Glu Ser Thr His His Lys Pro Trp Thr
        35                  40                  45

Leu Leu Ala Asp Thr Thr His His Arg Pro Trp Thr
    50                  55                  60

<210> SEQ ID NO 25
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 25

Leu Leu Ala Asp Thr Thr His His Arg Pro Trp Thr Gly Leu Gly Asp
1               5                   10                  15

Thr Thr His His Arg Pro Trp Gly
            20

<210> SEQ ID NO 26
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 26

Leu Leu Ala Asp Thr Thr His His Arg Pro Trp Thr Gly Leu Gly Asp
1               5                   10                  15

Thr Thr His His Arg Pro Trp Gly Leu Leu Ala Asp Thr Thr His His
            20                  25                  30

Arg Pro Trp Thr
        35

<210> SEQ ID NO 27
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 27
```

Leu Leu Ala Asp Thr Thr His His Arg Pro Trp Thr Gly Leu Gly Asp
1               5                   10                  15

Thr Thr His His Arg Pro Trp Gly Leu Leu Ala Asp Thr Thr His His
                20                  25                  30

Arg Pro Trp Thr Gly Leu Gly Asp Thr Thr His Arg Pro Trp Gly
            35                  40                  45

Leu Leu Ala Asp Thr Thr His His Arg Pro Trp Thr
        50                  55                  60

<210> SEQ ID NO 28
<211> LENGTH: 84
<212> TYPE: PRT
<213> ORGANISM: Artificial Sequence
<220> FEATURE:
<223> OTHER INFORMATION: Synthetic Sequence

<400> SEQUENCE: 28

Leu Leu Ala Asp Thr Thr His His Arg Pro Trp Thr Gly Leu Gly Asp
1               5                   10                  15

Thr Thr His His Arg Pro Trp Gly Leu Leu Ala Asp Thr Thr His His
                20                  25                  30

Arg Pro Trp Thr Gly Leu Gly Asp Thr Thr His Arg Pro Trp Gly
            35                  40                  45

Leu Leu Ala Asp Thr Thr His His Arg Pro Trp Thr Gly Leu Gly Asp
        50                  55                  60

Thr Thr His His Arg Pro Trp Gly Leu Leu Ala Asp Thr Thr His His
65                  70                  75                  80

Arg Pro Trp Thr

<210> SEQ ID NO 29
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 29

Ser Thr Ala Asp Thr Ser His His Arg Pro Ser Thr Ser Gly Gly Glu
1               5                   10                  15

Ser Thr His His Arg Pro Ser Thr Ser Gly Gly Glu Ser Ser His His
                20                  25                  30

Lys Pro Ser Thr Gly Ser Gly Asp Ser Ser His His Arg Pro Ser Gly
            35                  40                  45

Ser Ser Gly Glu Ser Thr His His Lys Pro Ser Thr
        50                  55                  60

<210> SEQ ID NO 30
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 30

Val Gly Ala Asp Ser Thr His His Arg Pro Val Thr Gly Ala Ala Asp
1               5                   10                  15

Thr Thr His His Arg Pro Val Thr Ala Gly Ala Asp Thr Thr His His
                20                  25                  30

Arg Pro Val Thr Gly Gly Ala Asp Thr Thr His His Arg Pro Ala Thr

-continued

```
                35                  40                  45

Gly Gly Ala Asp Thr Thr His His Arg Pro Gly Thr
    50                  55                  60

<210> SEQ ID NO 31
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 31

Ser Thr Ala Asp Thr Ser His His Arg Pro Ser Leu Leu Ala Asp Thr
1               5                   10                  15

Thr His His Arg Pro Trp Thr Thr Ser Gly Gly Glu Ser Thr His His
            20                  25                  30

Arg Pro Ser Val Gly Ala Asp Ser Thr His His Arg Pro Val Thr Thr
        35                  40                  45

Ser Gly Gly Glu Ser Ser His His Lys Pro Ser Gly Ala Ala Asp Thr
    50                  55                  60

Thr His His Arg Pro Val Thr Thr Gly Ser Gly Asp Ser Ser His His
65                  70                  75                  80

Arg Pro Ser Gly Ser Ser Gly Glu Ser Thr His His Lys Pro Ser Thr
                85                  90                  95

Gly Gly Ala Asp Thr Thr His His Arg Pro Ala Thr
            100                 105

<210> SEQ ID NO 32
<211> LENGTH: 396
<212> TYPE: PRT
<213> ORGANISM: Homo sapiens

<400> SEQUENCE: 32

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190
```

Asp Thr Arg Leu Val Asn Gln Asn Ala Ser Arg Trp Glu Ser Phe Asp
         195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 33
<211> LENGTH: 37
<212> TYPE: PRT
<213> ORGANISM: Artificial Sequence
<220> FEATURE:
<223> OTHER INFORMATION: Linker sequence

<400> SEQUENCE: 33

Thr Gly Gly Ser Gly Glu Gly Gly Thr Gly Ala Ser Thr Gly Gly Ser
1               5                   10                  15

Ala Gly Thr Gly Gly Ser Gly Gly Thr Thr Ser Gly Glu Ala Gly Gly
            20                  25                  30

Ser Ser Gly Ala Gly
        35

<210> SEQ ID NO 34
<211> LENGTH: 5
<212> TYPE: PRT
<213> ORGANISM: Artificial Sequence
<220> FEATURE:
<223> OTHER INFORMATION: Linker sequence

<400> SEQUENCE: 34

Gly Ala Gly Thr Gly
1               5

<210> SEQ ID NO 35
<211> LENGTH: 12
<212> TYPE: PRT
<213> ORGANISM: Artificial Sequence
<220> FEATURE:
<223> OTHER INFORMATION: Consensus sequence

```
<220> FEATURE:
<221> NAME/KEY: X
<222> LOCATION: (1)..(1)
<223> OTHER INFORMATION: Xaa=V, L, I, G, S, T or A
<220> FEATURE:
<221> NAME/KEY: X
<222> LOCATION: (2)..(2)
<223> OTHER INFORMATION: Xaa=I, L, V, Q, T, S, G or A
<220> FEATURE:
<221> NAME/KEY: X
<222> LOCATION: (3)..(3)
<223> OTHER INFORMATION: Xaa=G, A, V or S
<220> FEATURE:
<221> NAME/KEY: X
<222> LOCATION: (4)..(4)
<223> OTHER INFORMATION: Xaa=E, D, L or G
<220> FEATURE:
<221> NAME/KEY: X
<222> LOCATION: (5)..(5)
<223> OTHER INFORMATION: Xaa=S, T, P T, E or D
<220> FEATURE:
<221> NAME/KEY: X
<222> LOCATION: (6)..(6)
<223> OTHER INFORMATION: Xaa=T or S
<220> FEATURE:
<221> NAME/KEY: X
<222> LOCATION: (7)..(7)
<223> OTHER INFORMATION: Xaa=H, T or S
<220> FEATURE:
<221> NAME/KEY: X
<222> LOCATION: (8)..(8)
<223> OTHER INFORMATION: Xaa=H or T
<220> FEATURE:
<221> NAME/KEY: X
<222> LOCATION: (9)..(9)
<223> OTHER INFORMATION: Xaa=R, S, K, P or H
<220> FEATURE:
<221> NAME/KEY: X
<222> LOCATION: (10)..(10)
<223> OTHER INFORMATION: Xaa=P, S, R or K
<220> FEATURE:
<221> NAME/KEY: X
<222> LOCATION: (11)..(11)
<223> OTHER INFORMATION: Xaa=W, F, S, P, V, A or G
<220> FEATURE:
<221> NAME/KEY: X
<222> LOCATION: (12)..(12)
<223> OTHER INFORMATION: Xaa=S, T G or A
<220> FEATURE:
<221> NAME/KEY: X
<222> LOCATION: (12)..(12)
<223> OTHER INFORMATION: Xaa=is absent or is S, T G, or A

<400> SEQUENCE: 35

Xaa Xaa Xaa Xaa Xaa Xaa Xaa Xaa Xaa Xaa Xaa Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 36

Ala Ala Ala Asp Thr Thr His His Arg Pro Trp Thr
1               5                   10

<210> SEQ ID NO 37
<211> LENGTH: 60
<212> TYPE: PRT
<213> ORGANISM: Artificial Sequence
<220> FEATURE:
<223> OTHER INFORMATION: Synthetic Sequence
```

```
<400> SEQUENCE: 37

Ala Ala Ala Asp Thr Thr His His Arg Pro Trp Thr Ala Ala Ala Asp
1               5                   10                  15

Thr Thr His His Arg Pro Trp Thr Ala Ala Ala Asp Thr Thr His His
            20                  25                  30

Arg Pro Trp Thr Ala Ala Ala Asp Thr Thr His His Arg Pro Trp Thr
        35                  40                  45

Ala Ala Ala Asp Thr Thr His His Arg Pro Trp Thr
    50                  55                  60

<210> SEQ ID NO 38
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 38

Leu Leu Ala Asp Ala Ala His His Arg Pro Trp Thr Leu Leu Ala Asp
1               5                   10                  15

Ala Ala His His Arg Pro Trp Thr Leu Leu Ala Asp Ala Ala His His
            20                  25                  30

Arg Pro Trp Thr Leu Leu Ala Asp Ala Ala His His Arg Pro Trp Thr
        35                  40                  45

Leu Leu Ala Asp Ala Ala His His Arg Pro Trp Thr
    50                  55                  60

<210> SEQ ID NO 39
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 39

Leu Leu Ala Asp Thr Thr Ala Ala Arg Pro Trp Thr Leu Leu Ala Asp
1               5                   10                  15

Thr Thr Ala Ala Arg Pro Trp Thr Leu Leu Ala Asp Thr Thr Ala Ala
            20                  25                  30

Arg Pro Trp Thr Leu Leu Ala Asp Thr Thr Ala Ala Arg Pro Trp Thr
        35                  40                  45

Leu Leu Ala Asp Thr Thr Ala Ala Arg Pro Trp Thr
    50                  55                  60

<210> SEQ ID NO 40
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 40

Leu Leu Ala Asp Thr Thr His His Arg Pro Trp Thr Leu Leu Ala Asp
1               5                   10                  15

Thr Thr His His Arg Pro Trp Thr
            20

<210> SEQ ID NO 41
<211> LENGTH: 36
<212> TYPE: PRT
<213> ORGANISM: Artificial Sequence
```

<220> FEATURE:
<223> OTHER INFORMATION: Synthetic Sequence

<400> SEQUENCE: 41

Leu Leu Ala Asp Thr Thr His His Arg Pro Trp Thr Leu Leu Ala Asp
1               5                   10                  15

Thr Thr His His Arg Pro Trp Thr Leu Leu Ala Asp Thr Thr His His
            20                  25                  30

Arg Pro Trp Thr
            35

<210> SEQ ID NO 42
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 42

Leu Leu Ala Asp Thr Thr His His Arg Pro Trp Thr Leu Leu Ala Asp
1               5                   10                  15

Thr Thr His His Arg Pro Trp Thr Leu Leu Ala Asp Thr Thr His His
            20                  25                  30

Arg Pro Trp Thr Leu Leu Ala Asp Thr Thr His His Arg Pro Trp Thr
            35                  40                  45

Leu Leu Ala Asp Thr Thr His His Arg Pro Trp Thr
        50                  55                  60

<210> SEQ ID NO 43
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 43

Ser Thr Ser Gly Ser Thr Val Ile Gly Glu Ser Thr His His Arg Pro
1               5                   10                  15

Trp Ser Leu Ile Ala Asp Ser Thr His His Ser Pro Thr Ile Leu
            20                  25                  30

Ala Glu Ser Thr His His Lys Pro Trp Thr Ile Leu Ala Glu Thr Thr
            35                  40                  45

His His Arg Pro Trp Ser Ile Ile Gly Glu Ser Ser His His Lys Pro
        50                  55                  60

Phe Thr Gly Leu Gly Asp Thr Thr His Arg Pro Trp Gly Val Leu
65                  70                  75                  80

Gly Asp Thr Thr His His Lys Pro Trp Thr Ile Val Ala Asp Ser Thr
            85                  90                  95

His His Arg Pro Trp Thr Gly Gln Val Leu Pro Thr Thr Thr Pro Ser
            100                 105                 110

Ser Pro Ser Thr Thr Ser Gly Ser
            115                 120

<210> SEQ ID NO 44
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 44

```
Leu Leu Ala Asp Thr Thr His His Arg Pro Trp Thr Val Ile Gly Glu
1               5                   10                  15

Ser Thr His His Arg Pro Trp Ser Ile Ile Gly Glu Ser Ser His His
                20                  25                  30

Lys Pro Phe Thr Gly Leu Gly Asp Thr Thr His His Arg Pro Trp Gly
            35                  40                  45

Ile Leu Ala Glu Ser Thr His His Lys Pro Trp Thr Ala Thr Gly Gly
50                  55                  60

Ser Gly Glu Gly Gly Thr Gly Ala Ser Thr Gly Gly Ser Ala Gly Thr
65                  70                  75                  80

Gly Gly Ser Gly Gly Thr Thr Ser Gly Glu Ala Gly Gly Ser Ser Gly
                85                  90                  95

Ala Gly
```

<210> SEQ ID NO 45
<211> LENGTH: 97
<212> TYPE: PRT
<213> ORGANISM: Artificial Sequence
<220> FEATURE:
<223> OTHER INFORMATION: Synthetic Sequence

<400> SEQUENCE: 45

```
Leu Leu Ala Asp Thr Thr His His Arg Pro Trp Thr Gly Leu Gly Asp
1               5                   10                  15

Thr Thr His His Arg Pro Trp Gly Leu Leu Ala Asp Thr Thr His His
                20                  25                  30

Arg Pro Trp Thr Gly Leu Gly Asp Thr Thr His His Arg Pro Trp Gly
            35                  40                  45

Leu Leu Ala Asp Thr Thr His His Arg Pro Trp Thr Thr Gly Gly Ser
50                  55                  60

Gly Glu Gly Gly Thr Gly Ala Ser Thr Gly Gly Ser Ala Gly Thr Gly
65                  70                  75                  80

Gly Ser Gly Gly Thr Thr Ser Gly Glu Ala Gly Gly Ser Ser Gly Ala
                85                  90                  95

Gly
```

<210> SEQ ID NO 46
<211> LENGTH: 1207
<212> TYPE: PRT
<213> ORGANISM: Homo sapiens

<400> SEQUENCE: 46

```
Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
                20                  25                  30

Leu Ala Gly Asn Gly Asn Ser Thr Cys Val Gly Pro Ala Pro Phe Leu
            35                  40                  45

Ile Phe Ser His Gly Asn Ser Ile Phe Arg Ile Asp Thr Glu Gly Thr
50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
                100                 105                 110
```

```
Asn Ile Glu Lys Asn Val Ser Gly Met Ala Ile Asn Trp Ile Asn Glu
            115                 120                 125

Glu Val Ile Trp Ser Asn Gln Gln Glu Gly Ile Ile Thr Val Thr Asp
    130                 135                 140

Met Lys Gly Asn Asn Ser His Ile Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
                180                 185                 190

Lys Ala Leu Leu Glu Thr Ser Glu Lys Ile Thr Ala Val Ser Leu Asp
                195                 200                 205

Val Leu Asp Lys Arg Leu Phe Trp Ile Gln Tyr Asn Arg Glu Gly Ser
            210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
            275                 280                 285

Phe Val Pro Leu Gly Glu Leu Lys Val Val His Pro Leu Ala Gln Pro
            290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
            355                 360                 365

Leu Gly Cys Lys Asn Thr Pro Gly Ser Tyr Tyr Cys Thr Cys Pro Val
            370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
            435                 440                 445

Gln Leu Cys Val Pro Leu Ser Pro Val Ser Trp Glu Cys Asp Cys Phe
450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
            515                 520                 525
```

Ala His Thr Ala Leu Lys Trp Ile Glu Arg Ala Asn Met Asp Gly Ser
            530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                    565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
            595                 600                 605

Ala Lys Arg Leu Phe Trp Thr Asp Thr Gly Ile Asn Pro Arg Ile Glu
610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                    645                 650                 655

Tyr Trp Cys Asp Ala Lys Gln Ser Val Ile Glu Met Ala Asn Leu Asp
                660                 665                 670

Gly Ser Lys Arg Arg Arg Leu Thr Gln Asn Asp Val Gly His Pro Phe
            675                 680                 685

Ala Val Ala Val Phe Glu Asp Tyr Val Trp Phe Ser Asp Trp Ala Met
690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                    725                 730                 735

Leu Ala Lys Pro Gly Ala Asp Pro Cys Leu Tyr Gln Asn Gly Gly Cys
                740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                    805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                    885                 890                 895

Cys Arg Cys Ser Glu Gly Tyr Gln Gly Asp Gly Ile His Cys Leu Asp
                900                 905                 910

Ile Asp Glu Cys Gln Leu Gly Glu His Ser Cys Gly Glu Asn Ala Ser
            915                 920                 925

Cys Thr Asn Thr Glu Gly Gly Tyr Thr Cys Met Cys Ala Gly Arg Leu
930                 935                 940

Ser Glu Pro Gly Leu Ile Cys Pro Asp Ser Thr Pro Pro Pro His Leu

```
                  945            950            955            960
Arg Glu Asp Asp His His Tyr Ser Val Arg Asn Ser Asp Ser Glu Cys
                      965                970                975
Pro Leu Ser His Asp Gly Tyr Cys Leu His Asp Gly Val Cys Met Tyr
                      980                985                990
Ile Glu Ala Leu Asp Lys Tyr Ala Cys Asn Cys Val Val Gly Tyr Ile
                      995               1000               1005
Gly Glu Arg Cys Gln Tyr Arg Asp Leu Lys Trp Trp Glu Leu Arg
             1010               1015               1020
His Ala Gly His Gly Gln Gln Gln Lys Val Ile Val Val Ala Val
             1025               1030               1035
Cys Val Val Val Leu Val Met Leu Leu Leu Leu Ser Leu Trp Gly
             1040               1045               1050
Ala His Tyr Tyr Arg Thr Gln Lys Leu Leu Ser Lys Asn Pro Lys
             1055               1060               1065
Asn Pro Tyr Glu Glu Ser Ser Arg Asp Val Arg Ser Arg Arg Pro
             1070               1075               1080
Ala Asp Thr Glu Asp Gly Met Ser Ser Cys Pro Gln Pro Trp Phe
             1085               1090               1095
Val Val Ile Lys Glu His Gln Asp Leu Lys Asn Gly Gly Gln Pro
             1100               1105               1110
Val Ala Gly Glu Asp Gly Gln Ala Ala Asp Gly Ser Met Gln Pro
             1115               1120               1125
Thr Ser Trp Arg Gln Glu Pro Gln Leu Cys Gly Met Gly Thr Glu
             1130               1135               1140
Gln Gly Cys Trp Ile Pro Val Ser Ser Asp Lys Gly Ser Cys Pro
             1145               1150               1155
Gln Val Met Glu Arg Ser Phe His Met Pro Ser Tyr Gly Thr Gln
             1160               1165               1170
Thr Leu Glu Gly Gly Val Glu Lys Pro His Ser Leu Leu Ser Ala
             1175               1180               1185
Asn Pro Leu Trp Gln Gln Arg Ala Leu Asp Pro Pro His Gln Met
             1190               1195               1200
Glu Leu Thr Gln
             1205

<210> SEQ ID NO 47
<211> LENGTH: 211
<212> TYPE: PRT
<213> ORGANISM: Homo sapiens

<400> SEQUENCE: 47

Met Arg Thr Leu Ala Cys Leu Leu Leu Gly Cys Gly Tyr Leu Ala
1               5                  10                 15
His Val Leu Ala Glu Glu Ala Glu Ile Pro Arg Glu Val Ile Glu Arg
                    20                 25                 30
Leu Ala Arg Ser Gln Ile His Ser Ile Arg Asp Leu Gln Arg Leu Leu
                    35                 40                 45
Glu Ile Asp Ser Val Gly Ser Glu Asp Ser Leu Asp Thr Ser Leu Arg
       50                 55                 60
Ala His Gly Val His Ala Thr Lys His Val Pro Glu Lys Arg Pro Leu
    65                     70                 75                 80
Pro Ile Arg Arg Lys Arg Ser Ile Glu Glu Ala Val Pro Ala Val Cys
                    85                 90                 95
```

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
        180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 48
<211> LENGTH: 158
<212> TYPE: PRT
<213> ORGANISM: Homo sapiens

<400> SEQUENCE: 48

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155

<210> SEQ ID NO 49
<211> LENGTH: 155
<212> TYPE: PRT
<213> ORGANISM: Homo sapiens

<400> SEQUENCE: 49

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

```
Thr Arg Asp Arg Ser Asp Gln His Ile Gln Leu Gln Leu Ser Ala Glu
         50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 50
<211> LENGTH: 288
<212> TYPE: PRT
<213> ORGANISM: Homo sapiens

<400> SEQUENCE: 50

Met Val Gly Val Gly Gly Gly Asp Val Glu Asp Val Thr Pro Arg Pro
 1               5                  10                  15

Gly Gly Cys Gln Ile Ser Gly Arg Gly Ala Arg Gly Cys Asn Gly Ile
                 20                  25                  30

Pro Gly Ala Ala Ala Trp Glu Ala Ala Leu Pro Arg Arg Arg Pro Arg
             35                  40                  45

Arg His Pro Ser Val Asn Pro Arg Ser Arg Ala Ala Gly Ser Pro Arg
 50                  55                  60

Thr Arg Gly Arg Arg Thr Glu Glu Arg Pro Ser Gly Ser Arg Leu Gly
 65                  70                  75                  80

Asp Arg Gly Arg Gly Arg Ala Leu Pro Gly Gly Arg Leu Gly Gly Arg
                 85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270
```

-continued

```
Gly Pro Gly Gln Lys Ala Ile Leu Phe Leu Pro Met Ser Ala Lys Ser
            275                 280                 285

<210> SEQ ID NO 51
<211> LENGTH: 207
<212> TYPE: PRT
<213> ORGANISM: Homo sapiens

<400> SEQUENCE: 51

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 52
<211> LENGTH: 159
<212> TYPE: PRT
<213> ORGANISM: Homo sapiens

<400> SEQUENCE: 52

Val Pro Ser Ala Gly Gln Leu Ala Leu Phe Ala Leu Gly Ile Val Leu
1               5                   10                  15

Ala Ala Cys Gln Ala Leu Glu Asn Ser Thr Ser Pro Leu Ser Ala Asp
            20                  25                  30

Pro Pro Val Ala Ala Val Val Ser His Phe Asn Asp Cys Pro Asp
        35                  40                  45

Ser His Thr Gln Phe Cys Phe His Gly Thr Cys Arg Phe Leu Val Gln
    50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
            100                 105                 110
```

```
Leu Ile Ile Thr Cys Val Leu Ile His Cys Cys Gln Val Arg Lys His
        115                 120                 125

Cys Glu Trp Cys Arg Ala Leu Ile Cys Arg His Glu Lys Pro Ser Ala
    130                 135                 140

Leu Leu Lys Gly Arg Thr Ala Cys Cys His Ser Glu Thr Val Val
145                 150                 155

<210> SEQ ID NO 53
<211> LENGTH: 390
<212> TYPE: PRT
<213> ORGANISM: Homo sapiens

<400> SEQUENCE: 53

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
```

```
            325                 330                 335
Ser Lys Val Leu Ala Leu Tyr Asn Gln His Asn Pro Gly Ala Ser Ala
                340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
        370                 375                 380

Arg Ser Cys Lys Cys Ser
385                 390

<210> SEQ ID NO 54
<211> LENGTH: 412
<212> TYPE: PRT
<213> ORGANISM: Homo sapiens

<400> SEQUENCE: 54

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300
```

-continued

```
Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
            325                 330                 335

Lys Gly Tyr Tyr Ala Asn Phe Cys Ser Gly Pro Cys Pro Tyr Leu Arg
        340                 345                 350

Ser Ala Asp Thr Thr His Ser Thr Val Leu Gly Leu Tyr Asn Thr Leu
    355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 55
<211> LENGTH: 402
<212> TYPE: PRT
<213> ORGANISM: Homo sapiens

<400> SEQUENCE: 55

Met Thr Ala Leu Pro Gly Pro Leu Trp Leu Leu Gly Leu Ala Leu Cys
1               5                   10                  15

Ala Leu Gly Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
        35                  40                  45

Leu Ala Val Leu Gly Leu Pro Gly Arg Pro Arg Pro Arg Ala Pro Pro
50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
    130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270
```

```
Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
                340                 345                 350

Leu Val His Leu Met Met Pro Asp Ala Val Pro Lys Ala Cys Cys Ala
                355                 360                 365

Pro Thr Lys Leu Ser Ala Thr Ser Val Leu Tyr Tyr Asp Ser Ser Asn
370                 375                 380

Asn Val Ile Leu Arg Lys His Arg Asn Met Val Val Lys Ala Cys Gly
385                 390                 395                 400

Cys His

<210> SEQ ID NO 56
<211> LENGTH: 399
<212> TYPE: PRT
<213> ORGANISM: Homo sapiens

<400> SEQUENCE: 56

Met Ala Ala Arg Pro Gly Leu Leu Trp Leu Leu Gly Leu Ala Leu Cys
1               5                   10                  15

Val Leu Gly Gly Gly His Leu Ser His Pro Pro His Val Phe Pro Gln
                20                  25                  30

Arg Arg Leu Gly Val Arg Glu Pro Arg Asp Met Gln Arg Glu Ile Arg
            35                  40                  45

Glu Val Leu Gly Leu Pro Gly Arg Pro Arg Ser Arg Ala Pro Val Gly
50                  55                  60

Ala Ala Gln Gln Pro Ala Ser Ala Pro Leu Phe Met Leu Asp Leu Tyr
65                  70                  75                  80

Arg Ala Met Thr Asp Asp Ser Gly Gly Thr Pro Gln Pro His Leu
                85                  90                  95

Asp Arg Ala Asp Leu Ile Met Ser Phe Val Asn Ile Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
                180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Glu Asp Gly His Ser
210                 215                 220

Ile Asp Pro Gly Leu Ala Gly Leu Leu Gly Arg Gln Ala Pro Arg Ser
225                 230                 235                 240
```

Arg Gln Pro Phe Met Val Gly Phe Phe Arg Ala Asn Gln Ser Pro Val
                245                 250                 255

Arg Ala Pro Arg Thr Ala Arg Pro Leu Lys Lys Gln Leu Asn Gln
            260                 265                 270

Ile Asn Gln Leu Pro His Ser Asn Lys His Leu Gly Ile Leu Asp Asp
        275                 280                 285

Gly His Gly Ser His Gly Arg Glu Val Cys Arg Arg His Glu Leu Tyr
290                 295                 300

Val Ser Phe Arg Asp Leu Gly Trp Leu Asp Ser Val Ile Ala Pro Gln
305                 310                 315                 320

Gly Tyr Ser Ala Tyr Tyr Cys Ala Gly Glu Cys Ile Tyr Pro Leu Asn
                325                 330                 335

Ser Cys Met Asn Ser Thr Asn His Ala Thr Met Gln Ala Leu Val His
            340                 345                 350

Leu Met Lys Pro Asp Ile Ile Pro Lys Val Cys Cys Val Pro Thr Glu
        355                 360                 365

Leu Ser Ala Ile Ser Leu Leu Tyr Tyr Asp Arg Asn Asn Val Ile
370                 375                 380

Leu Arg Arg Glu Arg Asn Met Val Val Gln Ala Cys Gly Cys His
385                 390                 395

<210> SEQ ID NO 57
<211> LENGTH: 396
<212> TYPE: PRT
<213> ORGANISM: Homo sapiens

<400> SEQUENCE: 57

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His

```
                210                 215                 220
Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 58
<211> LENGTH: 408
<212> TYPE: PRT
<213> ORGANISM: Homo sapiens

<400> SEQUENCE: 58

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190
```

-continued

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
            245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
            275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
            325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
            370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
            405

<210> SEQ ID NO 59
<211> LENGTH: 454
<212> TYPE: PRT
<213> ORGANISM: Homo sapiens

<400> SEQUENCE: 59

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
            85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
            115                 120                 125

Leu Ser Arg Thr Thr Pro Leu Thr Thr Gln Ser Pro Pro Leu Ala Ser
            130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
            165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
            195                 200                 205

Phe Glu Asn Glu Thr Ile Lys Ile Ser Ile Tyr Gln Ile Ile Lys Glu
210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
            245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
            275                 280                 285

Val Gly Arg Gln Gly Pro Gln Ser Lys Gln Pro Phe Met Val Ala Phe
            290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser His Gln Asp Ser Ser
            325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
            355                 360                 365

Asp Trp Ile Ile Ala Pro Glu Gly Tyr Ala Ala Phe Tyr Cys Asp Gly
            370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
            405                 410                 415

Pro Cys Cys Ala Pro Thr Lys Leu Asn Ala Ile Ser Val Leu Tyr Phe
            420                 425                 430

Asp Asp Ser Ser Asn Val Ile Leu Lys Lys Tyr Arg Asn Met Val Val
            435                 440                 445

Arg Ser Cys Gly Cys His
450

<210> SEQ ID NO 60
<211> LENGTH: 513
<212> TYPE: PRT
<213> ORGANISM: Homo sapiens

<400> SEQUENCE: 60

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln

```
                65                  70                  75                  80
Lys Glu Ile Leu Ser Val Leu Gly Leu Pro His Arg Pro Arg Pro Leu
                    85                  90                  95
His Gly Leu Gln Gln Pro Gln Pro Ala Leu Arg Gln Gln Glu Glu
                100                 105                 110
Gln Gln Gln Gln Gln Leu Pro Arg Gly Glu Pro Pro Pro Gly Arg
                115                 120                 125
Leu Lys Ser Ala Pro Leu Phe Met Leu Asp Leu Tyr Asn Ala Leu Ser
130                 135                 140
Ala Asp Asn Asp Glu Asp Gly Ala Ser Glu Gly Glu Arg Gln Gln Ser
145                 150                 155                 160
Trp Pro His Glu Ala Ala Ser Ser Ser Gln Arg Arg Gln Pro Pro Pro
                165                 170                 175
Gly Ala Ala His Pro Leu Asn Arg Lys Ser Leu Leu Ala Pro Gly Ser
                180                 185                 190
Gly Ser Gly Gly Ala Ser Pro Leu Thr Ser Ala Gln Asp Ser Ala Phe
                195                 200                 205
Leu Asn Asp Ala Asp Met Val Met Ser Phe Val Asn Leu Val Glu Tyr
210                 215                 220
Asp Lys Glu Phe Ser Pro Arg Gln Arg His His Lys Glu Phe Lys Phe
225                 230                 235                 240
Asn Leu Ser Gln Ile Pro Glu Gly Glu Val Val Thr Ala Ala Glu Phe
                245                 250                 255
Arg Ile Tyr Lys Asp Cys Val Met Gly Ser Phe Lys Asn Gln Thr Phe
                260                 265                 270
Leu Ile Ser Ile Tyr Gln Val Leu Gln Glu His Gln His Arg Asp Ser
                275                 280                 285
Asp Leu Phe Leu Leu Asp Thr Arg Val Val Trp Ala Ser Glu Glu Gly
                290                 295                 300
Trp Leu Glu Phe Asp Ile Thr Ala Thr Ser Asn Leu Trp Val Val Thr
305                 310                 315                 320
Pro Gln His Asn Met Gly Leu Gln Leu Ser Val Val Thr Arg Asp Gly
                325                 330                 335
Val His Val His Pro Arg Ala Ala Gly Leu Val Gly Arg Asp Gly Pro
                340                 345                 350
Tyr Asp Lys Gln Pro Phe Met Val Ala Phe Phe Lys Val Ser Glu Val
                355                 360                 365
His Val Arg Thr Thr Arg Ser Ala Ser Ser Arg Arg Arg Gln Gln Ser
                370                 375                 380
Arg Asn Arg Ser Thr Gln Ser Gln Asp Val Ala Arg Val Ser Ser Ala
385                 390                 395                 400
Ser Asp Tyr Asn Ser Ser Glu Leu Lys Thr Ala Cys Arg Lys His Glu
                405                 410                 415
Leu Tyr Val Ser Phe Gln Asp Leu Gly Trp Gln Asp Trp Ile Ile Ala
                420                 425                 430
Pro Lys Gly Tyr Ala Ala Asn Tyr Cys Asp Gly Glu Cys Ser Phe Pro
                435                 440                 445
Leu Asn Ala His Met Asn Ala Thr Asn His Ala Ile Val Gln Thr Leu
                450                 455                 460
Val His Leu Met Asn Pro Glu Tyr Val Pro Lys Pro Cys Cys Ala Pro
465                 470                 475                 480
Thr Lys Leu Asn Ala Ile Ser Val Leu Tyr Phe Asp Asp Asn Ser Asn
                485                 490                 495
```

Val Ile Leu Lys Lys Tyr Arg Asn Met Val Arg Ala Cys Gly Cys
            500                 505                 510

His

<210> SEQ ID NO 61
<211> LENGTH: 431
<212> TYPE: PRT
<213> ORGANISM: Homo sapiens

<400> SEQUENCE: 61

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

```
Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 62
<211> LENGTH: 429
<212> TYPE: PRT
<213> ORGANISM: Homo sapiens

<400> SEQUENCE: 62

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
```

```
                   290                 295                 300
Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
                340                 345                 350

Ala Tyr Glu Cys Lys Gly Gly Cys Phe Phe Pro Leu Ala Asp Asp Val
                355                 360                 365

Thr Pro Thr Lys His Ala Ile Val Gln Thr Leu Val His Leu Lys Phe
                370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
                420                 425

<210> SEQ ID NO 63
<211> LENGTH: 424
<212> TYPE: PRT
<213> ORGANISM: Homo sapiens

<400> SEQUENCE: 63

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
                20                  25                  30

Glu Glu Asp Met Ser Leu Phe Gly Asp Val Phe Ser Glu Gln Asp Gly
            35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
                100                 105                 110

Leu Phe Ser Gln Pro Val Ser Phe Asn Gly Leu Arg Lys Tyr Pro Leu
            115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
                180                 185                 190

Gly Thr Asn Ser Glu Trp Glu Thr Phe Asp Val Thr Asp Ala Ile Arg
            195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240
```

-continued

```
Ile Asp Thr Ser Ala Gln Asn Lys His Asn Pro Leu Leu Ile Val Phe
            245                 250                 255

Ser Asp Asp Gln Ser Ser Asp Lys Glu Arg Lys Glu Glu Leu Asn Glu
        260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
        290                 295                 300

Asn Ile Ile Tyr Asp Ser Thr Ala Arg Ile Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
                340                 345                 350

Arg Gly Val Cys Asn Tyr Pro Leu Ala Glu His Leu Thr Pro Thr Lys
                355                 360                 365

His Ala Ile Ile Gln Ala Leu Val His Leu Lys Asn Ser Gln Lys Ala
            370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 64
<211> LENGTH: 407
<212> TYPE: PRT
<213> ORGANISM: Homo sapiens

<400> SEQUENCE: 64

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
        50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
                100                 105                 110

Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190
```

```
Val Tyr Leu Gln Ile Leu Arg Leu Lys Pro Leu Thr Gly Glu Gly Thr
            195                 200                 205

Ala Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
            245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                    325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
            370                 375                 380

Phe Asn Asp Lys Gln Gln Ile Ile Tyr Gly Lys Ile Pro Gly Met Val
385                 390                 395                 400

Val Asp Arg Cys Gly Cys Ser
            405

<210> SEQ ID NO 65
<211> LENGTH: 450
<212> TYPE: PRT
<213> ORGANISM: Homo sapiens

<400> SEQUENCE: 65

Met Asp Leu Ser Ala Ala Ala Ala Leu Cys Leu Trp Leu Leu Ser Ala
1               5                   10                  15

Cys Arg Pro Arg Asp Gly Leu Glu Ala Ala Ala Val Leu Arg Ala Ala
            20                  25                  30

Gly Ala Gly Pro Val Arg Ser Pro Gly Gly Gly Gly Gly Gly Gly Gly
            35                  40                  45

Gly Gly Arg Thr Leu Ala Gln Ala Ala Gly Ala Ala Ala Val Pro Ala
        50                  55                  60

Ala Ala Val Pro Arg Ala Arg Ala Ala Arg Arg Ala Ala Gly Ser Gly
65                  70                  75                  80

Phe Arg Asn Gly Ser Val Val Pro His His Phe Met Met Ser Leu Tyr
                85                  90                  95

Arg Ser Leu Ala Gly Arg Ala Pro Ala Gly Ala Ala Ala Val Ser Ala
            100                 105                 110

Ser Gly His Gly Arg Ala Asp Thr Ile Thr Gly Phe Thr Asp Gln Ala
            115                 120                 125

Thr Gln Asp Glu Ser Ala Ala Glu Thr Gly Gln Ser Phe Leu Phe Asp
            130                 135                 140

Val Ser Ser Leu Asn Asp Ala Asp Glu Val Val Gly Ala Glu Leu Arg
```

```
            145                 150                 155                 160
        Val Leu Arg Arg Gly Ser Pro Glu Ser Gly Pro Gly Ser Trp Thr Ser
                        165                 170                 175

Pro Pro Leu Leu Leu Leu Ser Thr Cys Pro Gly Ala Ala Arg Ala Pro
                        180                 185                 190

Arg Leu Leu Tyr Ser Arg Ala Ala Glu Pro Leu Val Gly Gln Arg Trp
                        195                 200                 205

Glu Ala Phe Asp Val Ala Asp Ala Met Arg Arg His Arg Arg Glu Pro
                        210                 215                 220

Arg Pro Pro Arg Ala Phe Cys Leu Leu Leu Arg Ala Val Ala Gly Pro
        225                 230                 235                 240

Val Pro Ser Pro Leu Ala Leu Arg Arg Leu Gly Phe Gly Trp Pro Gly
                        245                 250                 255

Gly Gly Gly Ser Ala Ala Glu Glu Arg Ala Val Leu Val Val Ser Ser
                        260                 265                 270

Arg Thr Gln Arg Lys Glu Ser Leu Phe Arg Glu Ile Arg Ala Gln Ala
                        275                 280                 285

Arg Ala Leu Gly Ala Ala Leu Ala Ser Glu Pro Leu Pro Asp Pro Gly
                        290                 295                 300

Thr Gly Thr Ala Ser Pro Arg Ala Val Ile Gly Gly Arg Arg Arg Arg
        305                 310                 315                 320

Arg Thr Ala Leu Ala Gly Thr Arg Thr Ala Gln Gly Ser Gly Gly Gly
                        325                 330                 335

Ala Gly Arg Gly His Gly Arg Arg Gly Arg Ser Arg Cys Ser Arg Lys
                        340                 345                 350

Pro Leu His Val Asp Phe Lys Glu Leu Gly Trp Asp Trp Ile Ile
                        355                 360                 365

Ala Pro Leu Asp Tyr Glu Ala Tyr His Cys Glu Gly Leu Cys Asp Phe
                        370                 375                 380

Pro Leu Arg Ser His Leu Glu Pro Thr Asn His Ala Ile Ile Gln Thr
        385                 390                 395                 400

Leu Leu Asn Ser Met Ala Pro Asp Ala Ala Pro Ala Ser Cys Cys Val
                        405                 410                 415

Pro Ala Arg Leu Ser Pro Ile Ser Ile Leu Tyr Ile Asp Ala Ala Asn
                        420                 425                 430

Asn Val Val Tyr Lys Gln Tyr Glu Asp Met Val Val Glu Ala Cys Gly
                        435                 440                 445

Cys Arg
            450

<210> SEQ ID NO 66
<211> LENGTH: 455
<212> TYPE: PRT
<213> ORGANISM: Homo sapiens

<400> SEQUENCE: 66

Met Asp Thr Pro Arg Val Leu Leu Ser Ala Val Phe Leu Ile Ser Phe
1               5                   10                  15

Leu Trp Asp Leu Pro Gly Phe Gln Gln Ala Ser Ile Ser Ser Ser Ser
                20                  25                  30

Ser Ser Ala Glu Leu Gly Ser Thr Lys Gly Met Arg Ser Arg Lys Glu
                35                  40                  45

Gly Lys Met Gln Arg Ala Pro Arg Asp Ser Asp Ala Gly Arg Glu Gly
            50                  55                  60
```

-continued

```
Gln Glu Pro Gln Pro Arg Pro Gln Asp Glu Pro Arg Ala Gln Gln Pro
 65                  70                  75                  80

Arg Ala Gln Glu Pro Pro Gly Arg Gly Pro Arg Val Val Pro His Glu
                 85                  90                  95

Tyr Met Leu Ser Ile Tyr Arg Thr Tyr Ser Ile Ala Glu Lys Leu Gly
            100                 105                 110

Ile Asn Ala Ser Phe Phe Gln Ser Ser Lys Ser Ala Asn Thr Ile Thr
        115                 120                 125

Ser Phe Val Asp Arg Gly Leu Asp Leu Ser His Thr Pro Leu Arg
    130                 135                 140

Arg Gln Lys Tyr Leu Phe Asp Val Ser Met Leu Ser Asp Lys Glu Glu
145                 150                 155                 160

Leu Val Gly Ala Glu Leu Arg Leu Phe Arg Gln Ala Pro Ser Ala Pro
                165                 170                 175

Trp Gly Pro Pro Ala Gly Pro Leu His Val Gln Leu Phe Pro Cys Leu
            180                 185                 190

Ser Pro Leu Leu Leu Asp Ala Arg Thr Leu Asp Pro Gln Gly Ala Pro
        195                 200                 205

Pro Ala Gly Trp Glu Val Phe Asp Val Trp Gln Gly Leu Arg His Gln
210                 215                 220

Pro Trp Lys Gln Leu Cys Leu Glu Leu Arg Ala Ala Trp Gly Glu Leu
225                 230                 235                 240

Asp Ala Gly Glu Ala Glu Arg Ala Arg Gly Pro Gln Pro Pro
                245                 250                 255

Pro Pro Asp Leu Arg Ser Leu Gly Phe Gly Arg Arg Val Arg Pro Pro
            260                 265                 270

Gln Glu Arg Ala Leu Leu Val Val Phe Thr Arg Ser Gln Arg Lys Asn
        275                 280                 285

Leu Phe Ala Glu Met Arg Glu Gln Leu Gly Ser Ala Glu Ala Gly
    290                 295                 300

Pro Gly Ala Gly Ala Glu Gly Ser Trp Pro Pro Ser Gly Ala Pro
305                 310                 315                 320

Asp Ala Arg Pro Trp Leu Pro Ser Pro Gly Arg Arg Arg Arg Thr
                325                 330                 335

Ala Phe Ala Ser Arg His Gly Lys Arg His Gly Lys Lys Ser Arg Leu
            340                 345                 350

Arg Cys Ser Lys Lys Pro Leu His Val Asn Phe Lys Glu Leu Gly Trp
        355                 360                 365

Asp Asp Trp Ile Ile Ala Pro Leu Glu Tyr Glu Ala Tyr His Cys Glu
    370                 375                 380

Gly Val Cys Asp Phe Pro Leu Arg Ser His Leu Glu Pro Thr Asn His
385                 390                 395                 400

Ala Ile Ile Gln Thr Leu Met Asn Ser Met Asp Pro Gly Ser Thr Pro
                405                 410                 415

Pro Ser Cys Cys Val Pro Thr Lys Leu Thr Pro Ile Ser Ile Leu Tyr
            420                 425                 430

Ile Asp Ala Gly Asn Asn Val Val Tyr Lys Gln Tyr Glu Asp Met Val
        435                 440                 445

Val Glu Ser Cys Gly Cys Arg
    450                 455
```

<210> SEQ ID NO 67
<211> LENGTH: 392
<212> TYPE: PRT

<213> ORGANISM: Homo sapiens

<400> SEQUENCE: 67

```
Met Val Leu Leu Ser Ile Leu Arg Ile Leu Phe Leu Cys Glu Leu Val
1               5                   10                  15
Leu Phe Met Glu His Arg Ala Gln Met Ala Glu Gly Gly Gln Ser Ser
            20                  25                  30
Ile Ala Leu Leu Ala Glu Ala Pro Thr Leu Pro Leu Ile Glu Glu Leu
        35                  40                  45
Leu Glu Glu Ser Pro Gly Glu Gln Pro Arg Lys Pro Arg Leu Leu Gly
    50                  55                  60
His Ser Leu Arg Tyr Met Leu Glu Leu Tyr Arg Arg Ser Ala Asp Ser
65                  70                  75                  80
His Gly His Pro Arg Glu Asn Arg Thr Ile Gly Ala Thr Met Val Arg
                85                  90                  95
Leu Val Lys Pro Leu Thr Asn Val Ala Arg Pro His Arg Gly Thr Trp
            100                 105                 110
His Ile Gln Ile Leu Gly Phe Pro Leu Arg Pro Asn Arg Gly Leu Tyr
        115                 120                 125
Gln Leu Val Arg Ala Thr Val Val Tyr Arg His Leu Gln Leu Thr
    130                 135                 140
Arg Phe Asn Leu Ser Cys His Val Glu Pro Trp Val Gln Lys Asn Pro
145                 150                 155                 160
Thr Asn His Phe Pro Ser Ser Glu Gly Asp Ser Ser Lys Pro Ser Leu
                165                 170                 175
Met Ser Asn Ala Trp Lys Glu Met Asp Ile Thr Gln Leu Val Gln Gln
            180                 185                 190
Arg Phe Trp Asn Asn Lys Gly His Arg Ile Leu Arg Leu Arg Phe Met
        195                 200                 205
Cys Gln Gln Gln Lys Asp Ser Gly Gly Leu Glu Leu Trp His Gly Thr
    210                 215                 220
Ser Ser Leu Asp Ile Ala Phe Leu Leu Leu Tyr Phe Asn Asp Thr His
225                 230                 235                 240
Lys Ser Ile Arg Lys Ala Lys Phe Leu Pro Arg Gly Met Glu Glu Phe
                245                 250                 255
Met Glu Arg Glu Ser Leu Leu Arg Arg Thr Arg Gln Ala Asp Gly Ile
            260                 265                 270
Ser Ala Glu Val Thr Ala Ser Ser Lys His Ser Gly Pro Glu Asn
    275                 280                 285
Asn Gln Cys Ser Leu His Pro Phe Gln Ile Ser Phe Arg Gln Leu Gly
    290                 295                 300
Trp Asp His Trp Ile Ile Ala Pro Pro Phe Tyr Thr Pro Asn Tyr Cys
305                 310                 315                 320
Lys Gly Thr Cys Leu Arg Val Leu Arg Asp Gly Leu Asn Ser Pro Asn
                325                 330                 335
His Ala Ile Ile Gln Asn Leu Ile Asn Gln Leu Val Asp Gln Ser Val
            340                 345                 350
Pro Arg Pro Ser Cys Val Pro Tyr Lys Tyr Val Pro Ile Ser Val Leu
        355                 360                 365
Met Ile Glu Ala Asn Gly Ser Ile Leu Tyr Lys Glu Tyr Glu Gly Met
    370                 375                 380
Ile Ala Glu Ser Cys Thr Cys Arg
385                 390
```

-continued

```
<210> SEQ ID NO 68
<211> LENGTH: 1301
<212> TYPE: PRT
<213> ORGANISM: Homo sapiens

<400> SEQUENCE: 68
```

Met Lys Ile Ile Thr Tyr Phe Cys Ile Trp Ala Val Ala Trp Ala Ile
1               5                   10                  15

Pro Val Pro Gln Ser Lys Pro Leu Glu Arg His Val Glu Lys Ser Met
            20                  25                  30

Asn Leu His Leu Leu Ala Arg Ser Asn Val Ser Val Gln Asp Glu Leu
        35                  40                  45

Asn Ala Ser Gly Thr Ile Lys Glu Ser Gly Val Leu Val His Glu Gly
50                  55                  60

Asp Arg Gly Arg Gln Glu Asn Thr Gln Asp Gly His Lys Gly Glu Gly
65                  70                  75                  80

Asn Gly Ser Lys Trp Ala Glu Val Gly Gly Lys Ser Phe Ser Thr Tyr
                85                  90                  95

Ser Thr Leu Ala Asn Glu Glu Gly Asn Ile Glu Gly Trp Asn Gly Asp
            100                 105                 110

Thr Gly Lys Ala Glu Thr Tyr Gly His Asp Gly Ile His Gly Lys Glu
        115                 120                 125

Glu Asn Ile Thr Ala Asn Gly Ile Gln Gly Gln Val Ser Ile Ile Asp
    130                 135                 140

Asn Ala Gly Ala Thr Asn Arg Ser Asn Thr Asn Gly Asn Thr Asp Lys
145                 150                 155                 160

Asn Thr Gln Asn Gly Asp Val Gly Asp Ala Gly His Asn Glu Asp Val
                165                 170                 175

Ala Val Val Gln Glu Asp Gly Pro Gln Val Ala Gly Ser Asn Asn Ser
            180                 185                 190

Thr Asp Asn Glu Asp Glu Ile Ile Glu Asn Ser Cys Arg Asn Glu Gly
        195                 200                 205

Asn Thr Ser Glu Ile Thr Pro Gln Ile Asn Ser Lys Arg Asn Gly Thr
    210                 215                 220

Lys Glu Ala Glu Val Thr Pro Gly Thr Gly Glu Asp Ala Gly Leu Asp
225                 230                 235                 240

Asn Ser Asp Gly Ser Pro Ser Gly Asn Gly Ala Asp Glu Asp Glu Asp
                245                 250                 255

Glu Gly Ser Gly Asp Asp Glu Asp Glu Ala Gly Asn Gly Lys Asp
            260                 265                 270

Ser Ser Asn Asn Ser Lys Gly Gln Glu Gly Gln Asp His Gly Lys Glu
        275                 280                 285

Asp Asp His Asp Ser Ser Ile Gly Gln Asn Ser Asp Ser Lys Glu Tyr
    290                 295                 300

Tyr Asp Pro Glu Gly Lys Glu Asp Pro His Asn Glu Val Asp Gly Asp
305                 310                 315                 320

Lys Thr Ser Lys Ser Glu Glu Asn Ser Ala Gly Ile Pro Glu Asp Asn
                325                 330                 335

Gly Ser Gln Arg Ile Glu Asp Thr Gln Lys Leu Asn His Arg Glu Ser
            340                 345                 350

Lys Arg Val Glu Asn Arg Ile Thr Lys Glu Ser Glu Thr His Ala Val
        355                 360                 365

Gly Lys Ser Gln Asp Lys Gly Ile Glu Ile Lys Gly Pro Ser Ser Gly
    370                 375                 380

```
Asn Arg Asn Ile Thr Lys Glu Val Gly Lys Gly Asn Glu Gly Lys Glu
385                 390                 395                 400

Asp Lys Gly Gln His Gly Met Ile Leu Gly Lys Gly Asn Val Lys Thr
            405                 410                 415

Gln Gly Glu Val Val Asn Ile Glu Gly Pro Gly Gln Lys Ser Glu Pro
        420                 425                 430

Gly Asn Lys Val Gly His Ser Asn Thr Gly Ser Asp Ser Asn Ser Asp
        435                 440                 445

Gly Tyr Asp Ser Tyr Asp Phe Asp Asp Lys Ser Met Gln Gly Asp Asp
        450                 455                 460

Pro Asn Ser Ser Asp Glu Ser Asn Gly Asn Asp Asp Ala Asn Ser Glu
465                 470                 475                 480

Ser Asp Asn Asn Ser Ser Ser Arg Gly Asp Ala Ser Tyr Asn Ser Asp
                485                 490                 495

Glu Ser Lys Asp Asn Gly Asn Gly Ser Asp Ser Lys Gly Ala Glu Asp
            500                 505                 510

Asp Asp Ser Asp Ser Thr Ser Asp Thr Asn Asn Ser Asp Ser Asn Gly
        515                 520                 525

Asn Gly Asn Asn Gly Asn Asp Asp Asn Asp Lys Ser Asp Ser Gly Lys
530                 535                 540

Gly Lys Ser Asp Ser Ser Asp Ser Asp Ser Ser Asp Ser Ser Asn Ser
545                 550                 555                 560

Ser Asp Ser Ser Asp Ser Ser Asp Ser Asp Ser Asp Ser Asp Asn Ser
                565                 570                 575

Ser Ser Asp Ser Asp Ser Ser Asp Ser Asp Ser Ser Asp Ser Ser Asp
                580                 585                 590

Ser Asp Ser Ser Asp Ser Asn Ser Ser Asp Ser Ser Asp Ser Ser
            595                 600                 605

Asp Ser Ser Asp Ser Ser Asp Ser Ser Asp Ser Ser Asp Ser Lys Ser
            610                 615                 620

Asp Ser Ser Lys Ser Glu Ser Asp Ser Ser Asp Ser Ser Lys Ser
625                 630                 635                 640

Asp Ser Ser Asp Ser Asn Ser Ser Asp Ser Ser Asp Asn Ser Asp Ser
                645                 650                 655

Ser Asp Ser Ser Asn Ser Ser Asn Ser Ser Asp Ser Ser Asp Ser Ser
            660                 665                 670

Asp Ser Ser Asp Ser Ser Ser Ser Asp Ser Ser Asn Ser Ser Asp
            675                 680                 685

Ser Ser Asp Ser Ser Asp Ser Ser Asn Ser Ser Glu Ser Ser Asp Ser
            690                 695                 700

Ser Asp Ser Ser Asp Ser Asp Ser Ser Asp Ser Ser Asp Ser Ser Asn
705                 710                 715                 720

Ser Asn Ser Ser Asp Ser Asp Ser Ser Asn Ser Ser Asp Ser Ser Asp
                725                 730                 735

Ser Ser Asn Ser Ser Asp Ser Ser Asp Ser Ser Asp Ser Ser Asn Ser
            740                 745                 750

Ser Asp Ser Ser Asp Ser Ser Asp Ser Ser Asn Ser Ser Asp Ser Ser
            755                 760                 765

Asp Ser Ser Asp Ser Ser Asp Ser Asp Ser Ser Asn Ser Ser Asp
            770                 775                 780

Ser Asn Asp Ser Ser Asn Ser Ser Asp Ser Ser Asp Ser Ser Asn Ser
            785                 790                 795                 800
```

Ser Asp Ser Ser Asn Ser Ser Asp Ser Ser Asp Ser Ser
            805                 810                 815

Asp Ser Asp Ser Ser Asn Ser Ser Asp Ser Ser Asn Ser Asp Ser
            820                 825                 830

Ser Asp Ser Ser Asn Ser Ser Asp Ser Ser Asp Ser Ser
            835                 840                 845

Asp Gly Ser Asp Ser Asp Ser Ser Asn Arg Ser Asp Ser Asn Ser
            850                 855                 860

Ser Asp Ser Ser Asp Ser Ser Asp Ser Asn Ser Ser Asp Ser Ser
865                 870                 875                 880

Asp Ser Ser Asp Ser Asn Glu Ser Ser Asn Ser Ser Asp Ser Asp
            885                 890                 895

Ser Ser Asn Ser Ser Asp Ser Asp Ser Ser Asp Ser Ser Asn Ser Ser
            900                 905                 910

Asp Ser Ser Asp Ser Ser Asn Ser Ser Asp Ser Ser Glu Ser Ser Asn
            915                 920                 925

Ser Ser Asp Asn Ser Asn Ser Ser Asp Ser Ser Asn Ser Ser Asp Ser
            930                 935                 940

Ser Asp Ser Ser Asp Ser Ser Asn Ser Ser Asp Ser Ser Asn Ser Ser
945                 950                 955                 960

Asp Ser Ser Asn Ser Ser Asp Ser Ser Asp Ser Asn Ser Ser Asp Ser
            965                 970                 975

Ser Asp Ser Ser Asn Ser Ser Asp Ser Ser Asp Ser Ser Asp Ser Ser
            980                 985                 990

Asp Ser Ser Asp Ser Ser Asp Ser Ser Asn Ser Ser Asp Ser Ser Asp
            995                 1000                1005

Ser Ser Asp Ser Ser Asp Ser Ser Asn Ser Ser Asp Ser Ser Asn
            1010                1015                1020

Ser Ser Asp Ser Ser Asn Ser Ser Asp Ser Ser Asp Ser Ser Asp
            1025                1030                1035

Ser Ser Asp Ser Ser Asp Ser Ser Asp Ser Ser Asp Ser Ser Asp
            1040                1045                1050

Ser Ser Asn Ser Ser Asp Ser Ser Asp Ser Ser Asp Ser Ser Asp
            1055                1060                1065

Ser Ser Asp Ser Ser Asp Ser Ser Asp Ser Ser Asp Ser Ser Glu
            1070                1075                1080

Ser Ser Asp Ser Ser Asp Ser Ser Asn Ser Ser Asp Ser Ser Asp
            1085                1090                1095

Ser Ser Asp Ser Ser Asp Ser Ser Asp Ser Ser Asp Ser Ser Asp
            1100                1105                1110

Ser Ser Asp Ser Ser Asp Ser Ser Asn Ser Ser Asp Ser Ser Asp
            1115                1120                1125

Ser Ser Asp Ser Ser Asp Ser Ser Asp Ser Ser Asn Ser Ser Asp
            1130                1135                1140

Ser Ser Asp Ser Ser Glu Ser Ser Asp Ser Ser Asp Ser Ser Asp
            1145                1150                1155

Ser Ser Asp Ser Ser Asp Ser Ser Asp Ser Ser Asp Ser Ser Asp
            1160                1165                1170

Ser Ser Asp Ser Ser Asn Ser Ser Asp Ser Ser Asp Ser Ser Asp
            1175                1180                1185

Ser Ser Asp Ser Ser Asp Ser Ser Asp Ser Ser Asp Ser Ser Asp
            1190                1195                1200

Ser Ser Asp Ser Ser Asp Ser Ser Asp Ser Ser Asp Ser Ser Asp

```
                 1205                1210                1215
Ser Ser Asp Ser Ser Asp Ser Asp Ser Ser Asp Ser Asn Glu
        1220                1225                1230

Ser Ser Asp Ser Ser Asp Ser Asp Ser Ser Asp Ser Ser Asn
        1235                1240                1245

Ser Ser Asp Ser Ser Asp Ser Asp Ser Ser Asp Ser Thr Ser
        1250                1255                1260

Asp Ser Asn Asp Glu Ser Asp Ser Gln Ser Lys Ser Gly Asn Gly
        1265                1270                1275

Asn Asn Asn Gly Ser Asp Ser Asp Ser Asp Ser Glu Gly Ser Asp
        1280                1285                1290

Ser Asn His Ser Thr Ser Asp Asp
        1295                1300

<210> SEQ ID NO 69
<211> LENGTH: 372
<212> TYPE: PRT
<213> ORGANISM: Homo sapiens

<400> SEQUENCE: 69

Met Pro Pro Pro Gln Gln Gly Pro Cys Gly His His Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45

Pro Gln Gly Ala Pro Arg Leu Arg Pro Val Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Ala Ser Ala Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Gly Pro Gly Gly Ala Cys Arg Ala Arg Arg Leu
            260                 265                 270
```

```
Tyr Val Ser Phe Arg Glu Val Gly Trp His Arg Trp Val Ile Ala Pro
            275                 280                 285

Arg Gly Phe Leu Ala Asn Tyr Cys Gln Gly Gln Cys Ala Leu Pro Val
    290                 295                 300

Ala Leu Ser Gly Ser Gly Pro Pro Ala Leu Asn His Ala Val Leu
305                 310                 315                 320

Arg Ala Leu Met His Ala Ala Pro Gly Ala Asp Leu Pro Cys
                325                 330                 335

Cys Val Pro Ala Arg Leu Ser Pro Ile Ser Val Leu Phe Phe Asp Asn
                340                 345                 350

Ser Asp Asn Val Val Leu Arg Gln Tyr Glu Asp Met Val Val Asp Glu
            355                 360                 365

Cys Gly Cys Arg
            370

<210> SEQ ID NO 70
<211> LENGTH: 364
<212> TYPE: PRT
<213> ORGANISM: Homo sapiens

<400> SEQUENCE: 70

Met Leu Arg Phe Leu Pro Asp Leu Ala Phe Ser Phe Leu Leu Ile Leu
1               5                   10                  15

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Gly
        115                 120                 125

Leu Asp Leu Gly Pro Asn Ser Tyr Tyr Asn Leu Gly Pro Glu Leu Glu
    130                 135                 140

Leu Ala Leu Phe Leu Val Gln Glu Pro His Val Trp Gly Gln Thr Thr
145                 150                 155                 160

Pro Lys Pro Gly Lys Met Phe Val Leu Arg Ser Val Pro Trp Pro Gln
                165                 170                 175

Gly Ala Val His Phe Asn Leu Leu Asp Val Ala Lys Asp Trp Asn Asp
            180                 185                 190

Asn Pro Arg Lys Asn Phe Gly Leu Phe Leu Glu Ile Leu Val Lys Glu
        195                 200                 205

Asp Arg Asp Ser Gly Val Asn Phe Gln Pro Glu Asp Thr Cys Ala Arg
    210                 215                 220

Leu Arg Cys Ser Leu His Ala Ser Leu Leu Val Val Thr Leu Asn Pro
225                 230                 235                 240

Asp Gln Cys His Pro Ser Arg Lys Arg Arg Ala Ala Ile Pro Val Pro
                245                 250                 255

Lys Leu Ser Cys Lys Asn Leu Cys His Arg His Gln Leu Phe Ile Asn
            260                 265                 270
```

-continued

Phe Arg Asp Leu Gly Trp His Lys Trp Ile Ile Ala Pro Lys Gly Phe
            275                 280                 285

Met Ala Asn Tyr Cys His Gly Glu Cys Pro Phe Ser Leu Thr Ile Ser
    290                 295                 300

Leu Asn Ser Ser Asn Tyr Ala Phe Met Gln Ala Leu Met His Ala Val
305                 310                 315                 320

Asp Pro Glu Ile Pro Gln Ala Val Cys Ile Pro Thr Lys Leu Ser Pro
                325                 330                 335

Ile Ser Met Leu Tyr Gln Asp Asn Asp Asn Val Ile Leu Arg His
                340                 345                 350

Tyr Glu Asp Met Val Val Asp Glu Cys Gly Cys Gly
                355                 360

<210> SEQ ID NO 71
<211> LENGTH: 501
<212> TYPE: PRT
<213> ORGANISM: Homo sapiens

<400> SEQUENCE: 71

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                     120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ala Leu Leu Asp Val Arg Ser Val Pro Gly Leu Asp Gly

```
            275                 280                 285
Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Arg Gln Val
                325                 330                 335

His Glu Lys Ala Leu Phe Leu Val Phe Gly Arg Thr Lys Lys Arg Asp
                340                 345                 350

Leu Phe Phe Asn Glu Ile Lys Ala Arg Ser Gly Gln Asp Asp Lys Thr
                355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
                420                 425                 430

Cys Glu Phe Pro Leu Arg Ser His Leu Glu Pro Thr Asn His Ala Val
                435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
                500

<210> SEQ ID NO 72
<211> LENGTH: 450
<212> TYPE: PRT
<213> ORGANISM: Homo sapiens

<400> SEQUENCE: 72

Met Asp Leu Ser Ala Ala Ala Leu Cys Leu Trp Leu Leu Ser Ala
1               5                   10                  15

Cys Arg Pro Arg Asp Gly Leu Glu Ala Ala Val Leu Arg Ala Ala
                20                  25                  30

Gly Ala Gly Pro Val Arg Ser Pro Gly Gly Gly Gly Gly Gly Gly
                35                  40                  45

Gly Gly Arg Thr Leu Ala Gln Ala Ala Gly Ala Ala Val Pro Ala
    50                  55                  60

Ala Ala Val Pro Arg Ala Arg Ala Ala Arg Ala Ala Gly Ser Gly
65                  70                  75                  80

Phe Arg Asn Gly Ser Val Val Pro His His Phe Met Met Ser Leu Tyr
                85                  90                  95

Arg Ser Leu Ala Gly Arg Ala Pro Ala Gly Ala Ala Val Ser Ala
                100                 105                 110

Ser Gly His Gly Arg Ala Asp Thr Ile Thr Gly Phe Thr Asp Gln Ala
                115                 120                 125

Thr Gln Asp Glu Ser Ala Ala Glu Thr Gly Gln Ser Phe Leu Phe Asp
    130                 135                 140
```

```
Val Ser Ser Leu Asn Asp Ala Asp Glu Val Gly Ala Glu Leu Arg
145                 150                 155                 160

Val Leu Arg Arg Gly Ser Pro Glu Ser Gly Pro Gly Ser Trp Thr Ser
            165                 170                 175

Pro Pro Leu Leu Leu Leu Ser Thr Cys Pro Gly Ala Ala Arg Ala Pro
            180                 185                 190

Arg Leu Leu Tyr Ser Arg Ala Ala Glu Pro Leu Val Gly Gln Arg Trp
            195                 200                 205

Glu Ala Phe Asp Val Ala Asp Ala Met Arg Arg His Arg Arg Glu Pro
210                 215                 220

Arg Pro Pro Arg Ala Phe Cys Leu Leu Leu Arg Ala Val Ala Gly Pro
225                 230                 235                 240

Val Pro Ser Pro Leu Ala Leu Arg Arg Leu Gly Phe Gly Trp Pro Gly
            245                 250                 255

Gly Gly Gly Ser Ala Ala Glu Glu Arg Ala Val Leu Val Val Ser Ser
            260                 265                 270

Arg Thr Gln Arg Lys Glu Ser Leu Phe Arg Glu Ile Arg Ala Gln Ala
            275                 280                 285

Arg Ala Leu Gly Ala Ala Leu Ala Ser Glu Pro Leu Pro Asp Pro Gly
            290                 295                 300

Thr Gly Thr Ala Ser Pro Arg Ala Val Ile Gly Gly Arg Arg Arg Arg
305                 310                 315                 320

Arg Thr Ala Leu Ala Gly Thr Arg Thr Ala Gln Gly Ser Gly Gly Gly
            325                 330                 335

Ala Gly Arg Gly His Gly Arg Arg Gly Arg Ser Arg Cys Ser Arg Lys
            340                 345                 350

Pro Leu His Val Asp Phe Lys Glu Leu Gly Trp Asp Asp Trp Ile Ile
            355                 360                 365

Ala Pro Leu Asp Tyr Glu Ala Tyr His Cys Glu Gly Leu Cys Asp Phe
            370                 375                 380

Pro Leu Arg Ser His Leu Glu Pro Thr Asn His Ala Ile Ile Gln Thr
385                 390                 395                 400

Leu Leu Asn Ser Met Ala Pro Asp Ala Ala Pro Ala Ser Cys Cys Val
            405                 410                 415

Pro Ala Arg Leu Ser Pro Ile Ser Ile Leu Tyr Ile Asp Ala Ala Asn
            420                 425                 430

Asn Val Val Tyr Lys Gln Tyr Glu Asp Met Val Val Glu Ala Cys Gly
            435                 440                 445

Cys Arg
450

<210> SEQ ID NO 73
<211> LENGTH: 375
<212> TYPE: PRT
<213> ORGANISM: Homo sapiens

<400> SEQUENCE: 73

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60
```

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

<210> SEQ ID NO 74
<211> LENGTH: 308
<212> TYPE: PRT
<213> ORGANISM: Homo sapiens

<400> SEQUENCE: 74

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu

```
            50                  55                  60
Thr Arg Leu Arg Ala Asn Gln Ser Trp Glu Asp Ser Asn Thr Asp Leu
 65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 75
<211> LENGTH: 412
<212> TYPE: PRT
<213> ORGANISM: Homo sapiens

<400> SEQUENCE: 75

Met Thr Asp Arg Gln Thr Asp Thr Ala Pro Ser Pro Ser Tyr His Leu
  1               5                  10                  15

Leu Pro Gly Arg Arg Thr Val Asp Ala Ala Ala Ser Arg Gly Gln
                 20                  25                  30

Gly Pro Glu Pro Ala Pro Gly Gly Val Glu Gly Val Gly Ala Arg
             35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Arg Gly Pro Gln Trp Arg Leu Gly
            100                 105                 110
```

```
Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 76
<211> LENGTH: 560
<212> TYPE: PRT
<213> ORGANISM: Homo sapiens

<400> SEQUENCE: 76

Met Phe Ala Arg Met Ser Asp Leu His Val Leu Leu Met Ala Leu
1               5                   10                  15

Val Gly Lys Thr Ala Cys Gly Phe Ser Leu Met Ser Leu Leu Glu Ser
            20                  25                  30

Leu Asp Pro Asp Trp Thr Pro Asp Gln Tyr Asp Tyr Tyr Glu Asp
        35                  40                  45

Tyr Asn Gln Glu Glu Asn Thr Ser Ser Thr His Ala Glu Asn
    50                  55                  60

Pro Asp Trp Tyr Tyr Thr Glu Asp Gln Ala Asp Pro Cys Gln Pro Asn
65                  70                  75                  80
```

```
Pro Cys Glu His Gly Gly Asp Cys Leu Val His Gly Ser Thr Phe Thr
             85                  90                  95
Cys Ser Cys Leu Ala Pro Phe Ser Gly Asn Lys Cys Gln Lys Val Gln
            100                 105                 110
Asn Thr Cys Lys Asp Asn Pro Cys Gly Arg Gly Gln Cys Leu Ile Thr
            115                 120                 125
Gln Ser Pro Pro Tyr Tyr Arg Cys Val Cys Lys His Pro Tyr Thr Gly
        130                 135                 140
Pro Ser Cys Ser Gln Val Val Pro Val Cys Arg Pro Asn Pro Cys Gln
145                 150                 155                 160
Asn Gly Ala Thr Cys Ser Arg His Lys Arg Arg Ser Lys Phe Thr Cys
                165                 170                 175
Ala Cys Pro Asp Gln Phe Lys Gly Lys Phe Cys Glu Ile Gly Ser Asp
            180                 185                 190
Asp Cys Tyr Val Gly Asp Gly Tyr Ser Tyr Arg Gly Lys Met Asn Arg
        195                 200                 205
Thr Val Asn Gln His Ala Cys Leu Tyr Trp Asn Ser His Leu Leu Leu
        210                 215                 220
Gln Glu Asn Tyr Asn Met Phe Met Glu Asp Ala Glu Thr His Gly Ile
225                 230                 235                 240
Gly Glu His Asn Phe Cys Arg Asn Pro Asp Ala Asp Glu Lys Pro Trp
                245                 250                 255
Cys Phe Ile Lys Val Thr Asn Asp Lys Val Lys Trp Glu Tyr Cys Asp
            260                 265                 270
Val Ser Ala Cys Ser Ala Gln Asp Val Ala Tyr Pro Glu Glu Ser Pro
        275                 280                 285
Thr Glu Pro Ser Thr Lys Leu Pro Gly Phe Asp Ser Cys Gly Lys Thr
        290                 295                 300
Glu Ile Ala Glu Arg Lys Ile Lys Arg Ile Tyr Gly Gly Phe Lys Ser
305                 310                 315                 320
Thr Ala Gly Lys His Pro Trp Gln Ala Ser Leu Gln Ser Ser Leu Pro
                325                 330                 335
Leu Thr Ile Ser Met Pro Gln Gly His Phe Cys Gly Gly Ala Leu Ile
            340                 345                 350
His Pro Cys Trp Val Leu Thr Ala Ala His Cys Thr Asp Ile Lys Thr
        355                 360                 365
Arg His Leu Lys Val Val Leu Gly Asp Gln Asp Leu Lys Lys Glu Glu
        370                 375                 380
Phe His Glu Gln Ser Phe Arg Val Glu Lys Ile Phe Lys Tyr Ser His
385                 390                 395                 400
Tyr Asn Glu Arg Asp Glu Ile Pro His Asn Asp Ile Ala Leu Leu Lys
                405                 410                 415
Leu Lys Pro Val Asp Gly His Cys Ala Leu Glu Ser Lys Tyr Val Lys
            420                 425                 430
Thr Val Cys Leu Pro Asp Gly Ser Phe Pro Ser Gly Ser Glu Cys His
        435                 440                 445
Ile Ser Gly Trp Gly Val Thr Glu Thr Gly Lys Gly Ser Arg Gln Leu
        450                 455                 460
Leu Asp Ala Lys Val Lys Leu Ile Ala Asn Thr Leu Cys Asn Ser Arg
465                 470                 475                 480
Gln Leu Tyr Asp His Met Ile Asp Asp Ser Met Ile Cys Ala Gly Asn
                485                 490                 495
```

Leu Gln Lys Pro Gly Gln Asp Thr Cys Gln Asp Ser Gly Gly Pro
                500                 505                 510

Leu Thr Cys Glu Lys Asp Gly Thr Tyr Tyr Val Tyr Gly Ile Val Ser
            515                 520                 525

Trp Gly Leu Glu Cys Gly Lys Arg Pro Gly Val Tyr Thr Gln Val Thr
530                 535                 540

Lys Phe Leu Asn Trp Ile Lys Ala Thr Ile Lys Ser Glu Ser Gly Phe
545                 550                 555                 560

<210> SEQ ID NO 77
<211> LENGTH: 418
<212> TYPE: PRT
<213> ORGANISM: Homo sapiens

<400> SEQUENCE: 77

Met Arg Ser Leu Leu Leu Ser Ala Phe Cys Leu Leu Glu Ala Ala
1               5                   10                  15

Leu Ala Ala Glu Val Lys Lys Pro Ala Ala Ala Ala Pro Gly Thr
                20                  25                  30

Ala Glu Lys Leu Ser Pro Lys Ala Ala Thr Leu Ala Glu Arg Ser Ala
            35                  40                  45

Gly Leu Ala Phe Ser Leu Tyr Gln Ala Met Ala Lys Asp Gln Ala Val
50                  55                  60

Glu Asn Ile Leu Val Ser Pro Val Val Ala Ser Ser Leu Gly Leu
65                  70                  75                  80

Val Ser Leu Gly Gly Lys Ala Thr Thr Ala Ser Gln Ala Lys Ala Val
                85                  90                  95

Leu Ser Ala Glu Gln Leu Arg Asp Glu Glu Val His Ala Gly Leu Gly
            100                 105                 110

Glu Leu Leu Arg Ser Leu Ser Asn Ser Thr Ala Arg Asn Val Thr Trp
            115                 120                 125

Lys Leu Gly Ser Arg Leu Tyr Gly Pro Ser Ser Val Ser Phe Ala Asp
130                 135                 140

Asp Phe Val Arg Ser Ser Lys Gln His Tyr Asn Cys Glu His Ser Lys
145                 150                 155                 160

Ile Asn Phe Arg Asp Lys Arg Ser Ala Leu Gln Ser Ile Asn Glu Trp
                165                 170                 175

Ala Ala Gln Thr Thr Asp Gly Lys Leu Pro Glu Val Thr Lys Asp Val
            180                 185                 190

Glu Arg Thr Asp Gly Ala Leu Leu Val Asn Ala Met Phe Phe Lys Pro
            195                 200                 205

His Trp Asp Glu Lys Phe His His Lys Met Val Asp Asn Arg Gly Phe
210                 215                 220

Met Val Thr Arg Ser Tyr Thr Val Gly Val Met Met Met His Arg Thr
225                 230                 235                 240

Gly Leu Tyr Asn Tyr Tyr Asp Asp Glu Lys Glu Lys Leu Gln Ile Val
                245                 250                 255

Glu Met Pro Leu Ala His Lys Leu Ser Ser Leu Ile Ile Leu Met Pro
            260                 265                 270

His His Val Glu Pro Leu Glu Arg Leu Glu Lys Leu Leu Thr Lys Glu
            275                 280                 285

Gln Leu Lys Ile Trp Met Gly Lys Met Gln Lys Ala Val Ala Ile
            290                 295                 300

Ser Leu Pro Lys Gly Val Val Glu Val Thr His Asp Leu Gln Lys His
305                 310                 315                 320

```
Leu Ala Gly Leu Gly Leu Thr Glu Ala Ile Asp Lys Asn Lys Ala Asp
            325                 330                 335

Leu Ser Arg Met Ser Gly Lys Lys Asp Leu Tyr Leu Ala Ser Val Phe
            340                 345                 350

His Ala Thr Ala Phe Glu Leu Asp Thr Asp Gly Asn Pro Phe Asp Gln
            355                 360                 365

Asp Ile Tyr Gly Arg Glu Glu Leu Arg Ser Pro Lys Leu Phe Tyr Ala
        370                 375                 380

Asp His Pro Phe Ile Phe Leu Val Arg Asp Thr Gln Ser Gly Ser Leu
385                 390                 395                 400

Leu Phe Ile Gly Arg Leu Val Arg Pro Lys Gly Asp Lys Met Arg Asp
                405                 410                 415

Glu Leu

<210> SEQ ID NO 78
<211> LENGTH: 207
<212> TYPE: PRT
<213> ORGANISM: Homo sapiens

<400> SEQUENCE: 78

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 79
<211> LENGTH: 194
<212> TYPE: PRT
<213> ORGANISM: Homo sapiens

<400> SEQUENCE: 79

Met His Lys Trp Ile Leu Thr Trp Ile Leu Pro Thr Leu Leu Tyr Arg
1               5                   10                  15
```

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 80
<211> LENGTH: 233
<212> TYPE: PRT
<213> ORGANISM: Homo sapiens

<400> SEQUENCE: 80

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

```
Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 81
<211> LENGTH: 281
<212> TYPE: PRT
<213> ORGANISM: Homo sapiens

<400> SEQUENCE: 81

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 82
<211> LENGTH: 370
<212> TYPE: PRT
<213> ORGANISM: Homo sapiens

<400> SEQUENCE: 82
```

```
Met Gly Leu Trp Ala Leu Leu Pro Gly Trp Val Ser Ala Thr Leu Leu
 1               5                  10                  15

Leu Ala Leu Ala Ala Leu Pro Ala Ala Leu Ala Ala Asn Ser Ser Gly
             20                  25                  30

Arg Trp Trp Gly Ile Val Asn Val Ala Ser Ser Thr Asn Leu Leu Thr
         35                  40                  45

Asp Ser Lys Ser Leu Gln Leu Val Leu Glu Pro Ser Leu Gln Leu Leu
 50                  55                  60

Ser Arg Lys Gln Arg Arg Leu Ile Arg Gln Asn Pro Gly Ile Leu His
 65                  70                  75                  80

Ser Val Ser Gly Gly Leu Gln Ser Ala Val Arg Glu Cys Lys Trp Gln
                 85                  90                  95

Phe Arg Asn Arg Arg Trp Asn Cys Pro Thr Ala Pro Gly Pro His Leu
             100                 105                 110

Phe Gly Lys Ile Val Asn Arg Gly Cys Arg Glu Thr Ala Phe Ile Phe
             115                 120                 125

Ala Ile Thr Ser Ala Gly Val Thr His Ser Val Ala Arg Ser Cys Ser
         130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
             165                 170                 175

Gly Arg Leu Phe Gly Arg Glu Phe Val Asp Ser Gly Glu Lys Gly Arg
             180                 185                 190

Asp Leu Arg Phe Leu Met Asn Leu His Asn Asn Glu Ala Gly Arg Thr
             195                 200                 205

Thr Val Phe Ser Glu Met Arg Gln Glu Cys Lys Cys His Gly Met Ser
210                 215                 220

Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
             245                 250                 255

Leu Tyr Gly Asn Arg Gly Ser Asn Arg Ala Ser Arg Ala Glu Leu Leu
             260                 265                 270

Arg Leu Glu Pro Glu Asp Pro Ala His Lys Pro Pro Ser Pro His Asp
             275                 280                 285

Leu Val Tyr Phe Glu Lys Ser Pro Asn Phe Cys Thr Tyr Ser Gly Arg
             290                 295                 300

Leu Gly Thr Ala Gly Thr Ala Gly Arg Ala Cys Asn Ser Ser Ser Pro
305                 310                 315                 320

Ala Leu Asp Gly Cys Glu Leu Leu Cys Cys Gly Arg Gly His Arg Thr
                 325                 330                 335

Arg Thr Gln Arg Val Thr Glu Arg Cys Asn Cys Thr Phe His Trp Cys
             340                 345                 350

Cys His Val Ser Cys Arg Asn Cys Thr His Thr Arg Val Leu His Glu
             355                 360                 365

Cys Leu
    370

<210> SEQ ID NO 83
<211> LENGTH: 360
<212> TYPE: PRT
<213> ORGANISM: Homo sapiens

<400> SEQUENCE: 83
```

Met Asn Ala Pro Leu Gly Gly Ile Trp Leu Trp Pro Leu Leu Leu
1               5                   10                  15

Thr Trp Leu Thr Pro Glu Val Asn Ser Ser Trp Trp Tyr Met Arg Ala
            20                  25                  30

Thr Gly Gly Ser Ser Arg Val Met Cys Asp Asn Val Pro Gly Leu Val
        35                  40                  45

Ser Ser Gln Arg Gln Leu Cys His Arg His Pro Asp Val Met Arg Ala
    50                  55                  60

Ile Ser Gln Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95

Phe Gly Arg Val Leu Leu Arg Ser Ser Arg Glu Ser Ala Phe Val Tyr
            100                 105                 110

Ala Ile Ser Ser Ala Gly Val Val Phe Ala Ile Thr Arg Ala Cys Ser
        115                 120                 125

Gln Gly Glu Val Lys Ser Cys Ser Cys Asp Pro Lys Lys Met Gly Ser
    130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175

Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
        195                 200                 205

His Gly Val Ser Gly Ser Cys Thr Leu Arg Thr Cys Trp Leu Ala Met
    210                 215                 220

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
                245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
        275                 280                 285

Thr Ala Gly Arg Val Cys Asn Leu Thr Ser Arg Gly Met Asp Ser Cys
    290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
                325                 330                 335

Gln Asp Cys Leu Glu Ala Leu Asp Val His Thr Cys Lys Ala Pro Lys
            340                 345                 350

Asn Ala Asp Trp Thr Thr Ala Thr
        355                 360

<210> SEQ ID NO 84
<211> LENGTH: 391
<212> TYPE: PRT
<213> ORGANISM: Homo sapiens

<400> SEQUENCE: 84

Met Leu Arg Pro Gly Gly Ala Glu Glu Ala Ala Gln Leu Pro Leu Arg

```
          1               5                   10                  15
Arg Ala Ser Ala Pro Val Pro Val Pro Ser Pro Ala Ala Pro Asp Gly
                    20                  25                  30

Ser Arg Ala Ser Ala Arg Leu Gly Leu Ala Cys Leu Leu Leu Leu Leu
            35                  40                  45

Leu Leu Thr Leu Pro Ala Arg Val Asp Thr Ser Trp Trp Tyr Ile Gly
        50                  55                  60

Ala Leu Gly Ala Arg Val Ile Cys Asp Asn Ile Pro Gly Leu Val Ser
65                  70                  75                  80

Arg Gln Arg Gln Leu Cys Gln Arg Tyr Pro Asp Ile Met Arg Ser Val
                85                  90                  95

Gly Glu Gly Ala Arg Glu Trp Ile Arg Glu Cys Gln His Gln Phe Arg
            100                 105                 110

His His Arg Trp Asn Cys Thr Thr Leu Asp Arg Asp His Thr Val Phe
        115                 120                 125

Gly Arg Val Met Leu Arg Ser Ser Arg Glu Ala Ala Phe Val Tyr Ala
        130                 135                 140

Ile Ser Ser Ala Gly Val Val His Ala Ile Thr Arg Ala Cys Ser Gln
145                 150                 155                 160

Gly Glu Leu Ser Val Cys Ser Cys Asp Pro Tyr Thr Arg Gly Arg His
                165                 170                 175

His Asp Gln Arg Gly Asp Phe Asp Trp Gly Gly Cys Ser Asp Asn Ile
            180                 185                 190

His Tyr Gly Val Arg Phe Ala Lys Ala Phe Val Asp Ala Lys Glu Lys
        195                 200                 205

Arg Leu Lys Asp Ala Arg Ala Leu Met Asn Leu His Asn Asn Arg Cys
210                 215                 220

Gly Arg Thr Ala Val Arg Arg Phe Leu Lys Leu Glu Cys Lys Cys His
225                 230                 235                 240

Gly Val Ser Gly Ser Cys Thr Leu Arg Thr Cys Trp Arg Ala Leu Ser
                245                 250                 255

Asp Phe Arg Arg Thr Gly Asp Tyr Leu Arg Arg Tyr Asp Gly Ala
            260                 265                 270

Val Gln Val Met Ala Thr Gln Asp Gly Ala Asn Phe Thr Ala Ala Arg
        275                 280                 285

Gln Gly Tyr Arg Arg Ala Thr Arg Thr Asp Leu Val Tyr Phe Asp Asn
        290                 295                 300

Ser Pro Asp Tyr Cys Val Leu Asp Lys Ala Ala Gly Ser Leu Gly Thr
305                 310                 315                 320

Ala Gly Arg Val Cys Ser Lys Thr Ser Lys Gly Thr Asp Gly Cys Glu
                325                 330                 335

Ile Met Cys Cys Gly Arg Gly Tyr Asp Thr Thr Arg Val Thr Arg Val
            340                 345                 350

Thr Gln Cys Glu Cys Lys Phe His Trp Cys Cys Ala Val Arg Cys Lys
        355                 360                 365

Glu Cys Arg Asn Thr Val Asp Val His Thr Cys Lys Ala Pro Lys Lys
        370                 375                 380

Ala Glu Trp Leu Asp Gln Thr
385                 390

<210> SEQ ID NO 85
<211> LENGTH: 355
<212> TYPE: PRT
<213> ORGANISM: Homo sapiens
```

<400> SEQUENCE: 85

```
Met Glu Pro His Leu Leu Gly Leu Leu Gly Leu Leu Gly Gly
1               5                   10                  15

Thr Arg Val Leu Ala Gly Tyr Pro Ile Trp Trp Ser Leu Ala Leu Gly
                20                  25                  30

Gln Gln Tyr Thr Ser Leu Gly Ser Gln Pro Leu Leu Cys Gly Ser Ile
                35                  40                  45

Pro Gly Leu Val Pro Lys Gln Leu Arg Phe Cys Arg Asn Tyr Ile Glu
    50                  55                  60

Ile Met Pro Ser Val Ala Glu Gly Val Lys Leu Gly Ile Gln Glu Cys
65                  70                  75                  80

Gln His Gln Phe Arg Gly Arg Arg Trp Asn Cys Thr Thr Ile Asp Asp
                85                  90                  95

Ser Leu Ala Ile Phe Gly Pro Val Leu Asp Lys Ala Thr Arg Glu Ser
                100                 105                 110

Ala Phe Val His Ala Ile Ala Ser Ala Gly Val Ala Phe Ala Val Thr
                115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
                180                 185                 190

Ala Gly Arg Thr Thr Ile Leu Asp His Met His Leu Lys Cys Lys Cys
                195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
                260                 265                 270

Asp Leu Val Tyr Tyr Glu Asn Ser Pro Asn Phe Cys Glu Pro Asn Pro
                275                 280                 285

Glu Thr Gly Ser Phe Gly Thr Arg Asp Arg Thr Cys Asn Val Thr Ser
                290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
                340                 345                 350

Thr Cys Lys
        355
```

<210> SEQ ID NO 86
<211> LENGTH: 352
<212> TYPE: PRT
<213> ORGANISM: Homo sapiens

<400> SEQUENCE: 86

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 87
<211> LENGTH: 351
<212> TYPE: PRT
<213> ORGANISM: Homo sapiens

<400> SEQUENCE: 87

Met Ser Pro Arg Ser Cys Leu Arg Ser Leu Arg Leu Leu Val Phe Ala
1               5                   10                  15

Val Phe Ser Ala Ala Ala Ser Asn Trp Leu Tyr Leu Ala Lys Leu Ser
```

```
              20                  25                  30
Ser Val Gly Ser Ile Ser Glu Glu Thr Cys Glu Lys Leu Lys Gly
             35                  40                  45
Leu Ile Gln Arg Gln Val Gln Met Cys Lys Arg Asn Leu Glu Val Met
 50                  55                  60
Asp Ser Val Arg Arg Gly Ala Gln Leu Ala Ile Glu Glu Cys Gln Tyr
 65                  70                  75                  80
Gln Phe Arg Asn Arg Arg Trp Asn Cys Ser Thr Leu Asp Ser Leu Pro
                 85                  90                  95
Val Phe Gly Lys Val Val Thr Gln Gly Thr Arg Glu Ala Ala Phe Val
            100                 105                 110
Tyr Ala Ile Ser Ser Ala Gly Val Ala Phe Ala Val Thr Arg Ala Cys
            115                 120                 125
Ser Ser Gly Glu Leu Glu Lys Cys Gly Cys Asp Arg Thr Val His Gly
            130                 135                 140
Val Ser Pro Gln Gly Phe Gln Trp Ser Gly Cys Ser Asp Asn Ile Ala
145                 150                 155                 160
Tyr Gly Val Ala Phe Ser Gln Ser Phe Val Asp Val Arg Glu Arg Ser
                165                 170                 175
Lys Gly Ala Ser Ser Arg Ala Leu Met Asn Leu His Asn Asn Glu
            180                 185                 190
Ala Gly Arg Lys Ala Ile Leu Thr His Met Arg Val Glu Cys Lys Cys
            195                 200                 205
His Gly Val Ser Gly Ser Cys Glu Val Lys Thr Cys Trp Arg Ala Val
            210                 215                 220
Pro Pro Phe Arg Gln Val Gly His Ala Leu Lys Glu Lys Phe Asp Gly
225                 230                 235                 240
Ala Thr Glu Val Glu Pro Arg Arg Val Gly Ser Ser Arg Ala Leu Val
                245                 250                 255
Pro Arg Asn Ala Gln Phe Lys Pro His Thr Asp Glu Asp Leu Val Tyr
            260                 265                 270
Leu Glu Pro Ser Pro Asp Phe Cys Glu Gln Asp Met Arg Ser Gly Val
            275                 280                 285
Leu Gly Thr Arg Gly Arg Thr Cys Asn Lys Thr Ser Lys Ala Ile Asp
            290                 295                 300
Gly Cys Glu Leu Leu Cys Cys Gly Arg Gly Phe His Thr Ala Gln Val
305                 310                 315                 320
Glu Leu Ala Glu Arg Cys Ser Cys Lys Phe His Trp Cys Cys Phe Val
                325                 330                 335
Lys Cys Arg Gln Cys Gln Arg Leu Val Glu Leu His Thr Cys Arg
            340                 345                 350

<210> SEQ ID NO 88
<211> LENGTH: 380
<212> TYPE: PRT
<213> ORGANISM: Homo sapiens

<400> SEQUENCE: 88

Met Lys Lys Ser Ile Gly Ile Leu Ser Pro Gly Val Ala Leu Gly Met
 1               5                  10                  15
Ala Gly Ser Ala Met Ser Ser Lys Phe Phe Leu Val Ala Leu Ala Ile
             20                  25                  30
Phe Phe Ser Phe Ala Gln Val Val Ile Glu Ala Asn Ser Trp Trp Ser
             35                  40                  45
```

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
            115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
            195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
            275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
            355                 360                 365

Lys Cys Thr Glu Ile Val Asp Gln Phe Val Cys Lys
    370                 375                 380

<210> SEQ ID NO 89
<211> LENGTH: 359
<212> TYPE: PRT
<213> ORGANISM: Homo sapiens

<400> SEQUENCE: 89

Met Pro Ser Leu Leu Leu Phe Thr Ala Ala Leu Leu Ser Ser Trp
1               5                   10                  15

Ala Gln Leu Leu Thr Asp Ala Asn Ser Trp Trp Ser Leu Ala Leu Asn
            20                  25                  30

Pro Val Gln Arg Pro Glu Met Phe Ile Ile Gly Ala Gln Pro Val Cys
        35                  40                  45

```
Ser Gln Leu Pro Gly Leu Ser Pro Gly Gln Arg Lys Leu Cys Gln Leu
    50                  55                  60

Tyr Gln Glu His Met Ala Tyr Ile Gly Glu Gly Ala Lys Thr Gly Ile
65                  70                  75                  80

Lys Glu Cys Gln His Gln Phe Arg Gln Arg Trp Asn Cys Ser Thr
                85                  90                  95

Ala Asp Asn Ala Ser Val Phe Gly Arg Val Met Gln Ile Gly Ser Arg
                100                 105                 110

Glu Thr Ala Phe Thr His Ala Val Ser Ala Ala Gly Val Val Asn Ala
                115                 120                 125

Ile Ser Arg Ala Cys Arg Glu Gly Glu Leu Ser Thr Cys Gly Cys Ser
    130                 135                 140

Arg Thr Ala Arg Pro Lys Asp Leu Pro Arg Asp Trp Leu Trp Gly Gly
145                 150                 155                 160

Cys Gly Asp Asn Val Glu Tyr Gly Tyr Arg Phe Ala Lys Glu Phe Val
                165                 170                 175

Asp Ala Arg Glu Arg Glu Lys Asn Phe Ala Lys Gly Ser Glu Glu Gln
                180                 185                 190

Gly Arg Val Leu Met Asn Leu Gln Asn Asn Glu Ala Gly Arg Arg Ala
                195                 200                 205

Val Tyr Lys Met Ala Asp Val Ala Cys Lys Cys His Gly Val Ser Gly
    210                 215                 220

Ser Cys Ser Leu Lys Thr Cys Trp Leu Gln Leu Ala Glu Phe Arg Lys
225                 230                 235                 240

Val Gly Asp Arg Leu Lys Glu Lys Tyr Asp Ser Ala Ala Ala Met Arg
                245                 250                 255

Val Thr Arg Lys Gly Arg Leu Glu Leu Val Asn Ser Arg Phe Thr Gln
                260                 265                 270

Pro Thr Pro Glu Asp Leu Val Tyr Val Asp Pro Ser Pro Asp Tyr Cys
                275                 280                 285

Leu Arg Asn Glu Ser Thr Gly Ser Leu Gly Thr Gln Gly Arg Leu Cys
    290                 295                 300

Asn Lys Thr Ser Glu Gly Met Asp Gly Cys Glu Leu Met Cys Cys Gly
305                 310                 315                 320

Arg Gly Tyr Asn Gln Phe Lys Ser Val Gln Val Glu Arg Cys His Cys
                325                 330                 335

Lys Phe His Trp Cys Cys Phe Val Arg Cys Lys Lys Cys Thr Glu Ile
                340                 345                 350

Val Asp Gln Tyr Ile Cys Lys
    355

<210> SEQ ID NO 90
<211> LENGTH: 365
<212> TYPE: PRT
<213> ORGANISM: Homo sapiens

<400> SEQUENCE: 90

Met Leu Pro Pro Leu Pro Ser Arg Leu Gly Leu Leu Leu Leu Leu
1               5                   10                  15

Leu Cys Pro Ala His Val Gly Gly Leu Trp Trp Ala Val Gly Ser Pro
                20                  25                  30

Leu Val Met Asp Pro Thr Ser Ile Cys Arg Lys Ala Arg Arg Leu Ala
                35                  40                  45

Gly Arg Gln Ala Glu Leu Cys Gln Ala Glu Pro Glu Val Val Ala Glu
```

```
            50                  55                  60
Leu Ala Arg Gly Ala Arg Leu Gly Val Arg Glu Cys Gln Phe Gln Phe
 65                  70                  75                  80

Arg Phe Arg Arg Trp Asn Cys Ser Ser His Ser Lys Ala Phe Gly Arg
                 85                  90                  95

Ile Leu Gln Gln Asp Ile Arg Glu Thr Ala Phe Val Phe Ala Ile Thr
                100                 105                 110

Ala Ala Gly Ala Ser His Ala Val Thr Gln Ala Cys Ser Met Gly Glu
            115                 120                 125

Leu Leu Gln Cys Gly Cys Gln Ala Pro Arg Gly Arg Ala Pro Pro Arg
        130                 135                 140

Pro Ser Gly Leu Pro Gly Thr Pro Gly Pro Pro Gly Pro Ala Gly Ser
145                 150                 155                 160

Pro Glu Gly Ser Ala Ala Trp Glu Trp Gly Cys Gly Asp Asp Val
                165                 170                 175

Asp Phe Gly Asp Glu Lys Ser Arg Leu Phe Met Asp Ala Arg His Lys
                180                 185                 190

Arg Gly Arg Gly Asp Ile Arg Ala Leu Val Gln Leu His Asn Asn Glu
            195                 200                 205

Ala Gly Arg Leu Ala Val Arg Ser His Thr Arg Thr Glu Cys Lys Cys
        210                 215                 220

His Gly Leu Ser Gly Ser Cys Ala Leu Arg Thr Cys Trp Gln Lys Leu
225                 230                 235                 240

Pro Pro Phe Arg Glu Val Gly Ala Arg Leu Leu Glu Arg Phe His Gly
                245                 250                 255

Ala Ser Arg Val Met Gly Thr Asn Asp Gly Lys Ala Leu Leu Pro Ala
            260                 265                 270

Val Arg Thr Leu Lys Pro Pro Gly Arg Ala Asp Leu Leu Tyr Ala Ala
        275                 280                 285

Asp Ser Pro Asp Phe Cys Ala Pro Asn Arg Arg Thr Gly Ser Pro Gly
290                 295                 300

Thr Arg Gly Arg Ala Cys Asn Ser Ser Ala Pro Asp Leu Ser Gly Cys
305                 310                 315                 320

Asp Leu Leu Cys Cys Gly Arg Gly His Arg Gln Glu Ser Val Gln Leu
                325                 330                 335

Glu Glu Asn Cys Leu Cys Arg Phe His Trp Cys Cys Val Val Gln Cys
            340                 345                 350

His Arg Cys Arg Val Arg Lys Glu Leu Ser Leu Cys Leu
        355                 360                 365

<210> SEQ ID NO 91
<211> LENGTH: 349
<212> TYPE: PRT
<213> ORGANISM: Homo sapiens

<400> SEQUENCE: 91

Met Asn Arg Lys Ala Arg Arg Cys Leu Gly His Leu Phe Leu Ser Leu
 1               5                  10                  15

Gly Met Val Tyr Leu Arg Ile Gly Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60
```

```
Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 92
<211> LENGTH: 349
<212> TYPE: PRT
<213> ORGANISM: Homo sapiens

<400> SEQUENCE: 92

Met His Arg Asn Phe Arg Lys Trp Ile Phe Tyr Val Phe Leu Cys Phe
1               5                   10                  15

Gly Val Leu Tyr Val Lys Leu Gly Ala Leu Ser Ser Val Val Ala Leu
            20                  25                  30

Gly Ala Asn Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95
```

-continued

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345

<210> SEQ ID NO 93
<211> LENGTH: 386
<212> TYPE: PRT
<213> ORGANISM: Homo sapiens

<400> SEQUENCE: 93

Met Leu Cys Cys Ile Gln Cys Leu Cys Leu Val Ser Pro Phe Pro Thr
1               5                   10                  15

Leu Thr Pro Cys Gln Gly Gly Pro His Cys Leu Ile Pro Ile His Leu
            20                  25                  30

Cys Leu Thr Phe Ser Leu Phe Gly Arg Ser Val Asn Asn Phe Leu Ile
        35                  40                  45

Thr Gly Pro Lys Ala Tyr Leu Thr Tyr Thr Thr Ser Val Ala Leu Gly
    50                  55                  60

Ala Gln Ser Gly Ile Glu Glu Cys Lys Phe Gln Phe Ala Trp Glu Arg
65                  70                  75                  80

Trp Asn Cys Pro Glu Asn Ala Leu Gln Leu Ser Thr His Asn Arg Leu
                85                  90                  95

Arg Ser Ala Thr Arg Glu Thr Ser Phe Ile His Ala Ile Ser Ser Ala
            100                 105                 110

Gly Val Met Tyr Ile Ile Thr Lys Asn Cys Ser Met Gly Asp Phe Glu

-continued

```
            115                 120                 125
Asn Cys Gly Cys Asp Gly Ser Asn Asn Gly Lys Thr Gly Gly His Gly
    130                 135                 140
Trp Ile Trp Gly Gly Cys Ser Asp Asn Val Glu Phe Gly Glu Arg Ile
145                 150                 155                 160
Ser Lys Leu Phe Val Asp Ser Leu Glu Lys Gly Lys Asp Ala Arg Ala
                165                 170                 175
Leu Met Asn Leu His Asn Asn Arg Ala Gly Arg Leu Ala Val Arg Ala
            180                 185                 190
Thr Met Lys Arg Thr Cys Lys Cys His Gly Ile Ser Gly Ser Cys Ser
        195                 200                 205
Ile Gln Thr Cys Trp Leu Gln Leu Ala Glu Phe Arg Glu Met Gly Asp
    210                 215                 220
Tyr Leu Lys Ala Lys Tyr Asp Gln Ala Leu Lys Ile Glu Met Asp Lys
225                 230                 235                 240
Arg Gln Leu Arg Ala Gly Asn Ser Ala Glu Gly His Trp Val Pro Ala
                245                 250                 255
Glu Ala Phe Leu Pro Ser Ala Glu Ala Glu Leu Ile Phe Leu Glu Glu
            260                 265                 270
Ser Pro Asp Tyr Cys Thr Cys Asn Ser Ser Leu Gly Ile Tyr Gly Thr
        275                 280                 285
Glu Gly Arg Glu Cys Leu Gln Asn Ser His Asn Thr Ser Arg Trp Glu
    290                 295                 300
Arg Arg Ser Cys Gly Arg Leu Cys Thr Glu Cys Gly Leu Gln Val Glu
305                 310                 315                 320
Glu Arg Lys Thr Glu Val Ile Ser Ser Cys Asn Cys Lys Phe Gln Trp
                325                 330                 335
Cys Cys Thr Val Lys Cys Asp Gln Cys Arg His Val Thr Met Ser Asn
            340                 345                 350
Pro Ala Val Leu Leu Gly Ile Arg Arg Ile Glu Ala Lys Asn Glu Arg
        355                 360                 365
Val Leu Phe Arg Leu Leu Lys Ser Ser Leu Trp Leu Gln Ile Tyr Ala
    370                 375                 380
Asp Lys
385

<210> SEQ ID NO 94
<211> LENGTH: 351
<212> TYPE: PRT
<213> ORGANISM: Homo sapiens

<400> SEQUENCE: 94

Met Phe Leu Ser Lys Pro Ser Val Tyr Ile Cys Leu Phe Thr Cys Val
1               5                   10                  15
Leu Gln Leu Ser His Ser Trp Ser Val Asn Asn Phe Leu Met Thr Gly
            20                  25                  30
Pro Lys Ala Tyr Leu Ile Tyr Ser Ser Ser Val Ala Ala Gly Ala Gln
        35                  40                  45
Ser Gly Ile Glu Glu Cys Lys Tyr Gln Phe Ala Trp Asp Arg Trp Asn
    50                  55                  60
Cys Pro Glu Arg Ala Leu Gln Leu Ser Ser His Gly Gly Leu Arg Ser
65                  70                  75                  80
Ala Asn Arg Glu Thr Ala Phe Val His Ala Ile Ser Ser Ala Gly Val
                85                  90                  95
```

Met Tyr Thr Leu Thr Arg Asn Cys Ser Leu Gly Asp Phe Asp Asn Cys
            100                 105                 110

Gly Cys Asp Asp Ser Arg Asn Gly Gln Leu Gly Gly Gln Gly Trp Leu
            115                 120                 125

Trp Gly Gly Cys Ser Asp Asn Val Gly Phe Gly Glu Ala Ile Ser Lys
        130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
            165                 170                 175

Lys Arg Thr Cys Lys Cys His Gly Val Ser Gly Ser Cys Thr Thr Gln
            180                 185                 190

Thr Cys Trp Leu Gln Leu Pro Glu Phe Arg Glu Val Gly Ala His Leu
        195                 200                 205

Lys Glu Lys Tyr His Ala Ala Leu Lys Val Asp Leu Leu Gln Gly Ala
        210                 215                 220

Gly Asn Ser Ala Ala Gly Arg Gly Ala Ile Ala Asp Thr Phe Arg Ser
225                 230                 235                 240

Ile Ser Thr Arg Glu Leu Val His Leu Glu Asp Ser Pro Asp Tyr Cys
            245                 250                 255

Leu Glu Asn Lys Thr Leu Gly Leu Leu Gly Thr Glu Gly Arg Glu Cys
            260                 265                 270

Leu Arg Arg Gly Arg Ala Leu Gly Arg Trp Glu Arg Ser Cys Arg
            275                 280                 285

Arg Leu Cys Gly Asp Cys Gly Leu Ala Val Glu Glu Arg Arg Ala Glu
        290                 295                 300

Thr Val Ser Ser Cys Asn Cys Lys Phe His Trp Cys Cys Ala Val Arg
305                 310                 315                 320

Cys Glu Gln Cys Arg Arg Val Thr Lys Tyr Phe Cys Ser Arg Ala
            325                 330                 335

Glu Arg Pro Arg Gly Gly Ala Ala His Lys Pro Gly Arg Lys Pro
            340                 345                 350

<210> SEQ ID NO 95
<211> LENGTH: 365
<212> TYPE: PRT
<213> ORGANISM: Homo sapiens

<400> SEQUENCE: 95

Met Leu Asp Gly Ser Pro Leu Ala Arg Trp Leu Ala Ala Ala Phe Gly
1               5                   10                  15

Leu Thr Leu Leu Leu Ala Ala Leu Arg Pro Ser Ala Ala Tyr Phe Gly
            20                  25                  30

Leu Thr Gly Ser Glu Pro Leu Thr Ile Leu Pro Leu Thr Leu Glu Pro
        35                  40                  45

Glu Ala Ala Ala Gln Ala His Tyr Lys Ala Cys Asp Arg Leu Lys Leu
    50                  55                  60

Glu Arg Lys Gln Arg Arg Met Cys Arg Arg Asp Pro Gly Val Ala Glu
65                  70                  75                  80

Thr Leu Val Glu Ala Val Ser Met Ser Ala Leu Glu Cys Gln Phe Gln
            85                  90                  95

Phe Arg Phe Glu Arg Trp Asn Cys Thr Leu Glu Gly Arg Tyr Arg Ala
            100                 105                 110

Ser Leu Leu Lys Arg Gly Phe Lys Glu Thr Ala Phe Leu Tyr Ala Ile
        115                 120                 125

```
Ser Ser Ala Gly Leu Thr His Ala Leu Ala Lys Ala Cys Ser Ala Gly
    130                 135                 140

Arg Met Glu Arg Cys Thr Cys Asp Glu Ala Pro Asp Leu Glu Asn Arg
145                 150                 155                 160

Glu Ala Trp Gln Trp Gly Gly Cys Gly Asp Asn Leu Lys Tyr Ser Ser
                165                 170                 175

Lys Phe Val Lys Glu Phe Leu Gly Arg Arg Ser Ser Lys Asp Leu Arg
            180                 185                 190

Ala Arg Val Asp Phe His Asn Asn Leu Val Gly Val Lys Val Ile Lys
        195                 200                 205

Ala Gly Val Glu Thr Thr Cys Lys Cys His Gly Val Ser Gly Ser Cys
    210                 215                 220

Thr Val Arg Thr Cys Trp Arg Gln Leu Ala Pro Phe His Glu Val Gly
225                 230                 235                 240

Lys His Leu Lys His Lys Tyr Glu Thr Ala Leu Lys Val Gly Ser Thr
                245                 250                 255

Thr Asn Glu Ala Ala Gly Glu Ala Gly Ala Ile Ser Pro Pro Arg Gly
            260                 265                 270

Arg Ala Ser Gly Ala Gly Gly Ser Asp Pro Leu Pro Arg Thr Pro Glu
        275                 280                 285

Leu Val His Leu Asp Asp Ser Pro Ser Phe Cys Leu Ala Gly Arg Phe
    290                 295                 300

Ser Pro Gly Thr Ala Gly Arg Arg Cys His Arg Glu Lys Asn Cys Glu
305                 310                 315                 320

Ser Ile Cys Cys Gly Arg Gly His Asn Thr Gln Ser Arg Val Val Thr
                325                 330                 335

Arg Pro Cys Gln Cys Gln Val Arg Trp Cys Cys Tyr Val Glu Cys Arg
            340                 345                 350

Gln Cys Thr Gln Arg Glu Glu Val Tyr Thr Cys Lys Gly
        355                 360                 365

<210> SEQ ID NO 96
<211> LENGTH: 357
<212> TYPE: PRT
<213> ORGANISM: Homo sapiens

<400> SEQUENCE: 96

Met Arg Pro Pro Pro Ala Leu Ala Leu Ala Gly Leu Cys Leu Leu Ala
1               5                   10                  15

Leu Pro Ala Ala Ala Ser Tyr Phe Gly Leu Thr Gly Arg Glu Val
            20                  25                  30

Leu Thr Pro Phe Pro Gly Leu Gly Thr Ala Ala Pro Ala Gln Gly
        35                  40                  45

Gly Ala His Leu Lys Gln Cys Asp Leu Leu Lys Leu Ser Arg Arg Gln
    50                  55                  60

Lys Gln Leu Cys Arg Arg Glu Pro Gly Leu Ala Glu Thr Leu Arg Asp
65                  70                  75                  80

Ala Ala His Leu Gly Leu Leu Glu Cys Gln Phe Gln Phe Arg His Glu
                85                  90                  95

Arg Trp Asn Cys Ser Leu Glu Gly Arg Met Gly Leu Leu Lys Arg Gly
            100                 105                 110

Phe Lys Glu Thr Ala Phe Leu Tyr Ala Val Ser Ser Ala Ala Leu Thr
        115                 120                 125

His Thr Leu Ala Arg Ala Cys Ser Ala Gly Arg Met Glu Arg Cys Thr
```

```
        130                 135                 140
Cys Asp Asp Ser Pro Gly Leu Glu Ser Arg Gln Ala Trp Gln Trp Gly
145                 150                 155                 160

Val Cys Gly Asp Asn Leu Lys Tyr Ser Thr Lys Phe Leu Ser Asn Phe
                165                 170                 175

Leu Gly Ser Lys Arg Gly Asn Lys Asp Leu Arg Ala Arg Ala Asp Ala
            180                 185                 190

His Asn Thr His Val Gly Ile Lys Ala Val Lys Ser Gly Leu Arg Thr
        195                 200                 205

Thr Cys Lys Cys His Gly Val Ser Gly Ser Cys Ala Val Arg Thr Cys
210                 215                 220

Trp Lys Gln Leu Ser Pro Phe Arg Glu Thr Gly Gln Val Leu Lys Leu
225                 230                 235                 240

Arg Tyr Asp Ser Ala Val Lys Val Ser Ser Ala Thr Asn Glu Ala Leu
                245                 250                 255

Gly Arg Leu Glu Leu Trp Ala Pro Ala Arg Gln Gly Ser Leu Thr Lys
            260                 265                 270

Gly Leu Ala Pro Arg Ser Gly Asp Leu Val Tyr Met Glu Asp Ser Pro
        275                 280                 285

Ser Phe Cys Arg Pro Ser Lys Tyr Ser Pro Gly Thr Ala Gly Arg Val
    290                 295                 300

Cys Ser Arg Glu Ala Ser Cys Ser Ser Leu Cys Cys Gly Arg Gly Tyr
305                 310                 315                 320

Asp Thr Gln Ser Arg Leu Val Ala Phe Ser Cys His Cys Gln Val Gln
                325                 330                 335

Trp Cys Cys Tyr Val Glu Cys Gln Gln Cys Val Gln Glu Glu Leu Val
            340                 345                 350

Tyr Thr Cys Lys His
        355

<210> SEQ ID NO 97
<211> LENGTH: 417
<212> TYPE: PRT
<213> ORGANISM: Homo sapiens

<400> SEQUENCE: 97

Met Gly Ser Ala His Pro Arg Pro Trp Leu Arg Leu Arg Pro Gln Pro
1               5                   10                  15

Gln Pro Arg Pro Ala Leu Trp Val Leu Leu Phe Phe Leu Leu Leu Leu
                20                  25                  30

Ala Ala Ala Met Pro Arg Ser Ala Pro Asn Asp Ile Leu Asp Leu Arg
            35                  40                  45

Leu Pro Pro Glu Pro Val Leu Asn Ala Asn Thr Val Cys Leu Thr Leu
        50                  55                  60

Pro Gly Leu Ser Arg Arg Gln Met Glu Val Cys Val Arg His Pro Asp
65                  70                  75                  80

Val Ala Ala Ser Ala Ile Gln Gly Ile Gln Ile Ala Ile His Glu Cys
                85                  90                  95

Gln His Gln Phe Arg Asp Gln Arg Trp Asn Cys Ser Ser Leu Glu Thr
            100                 105                 110

Arg Asn Lys Ile Pro Tyr Glu Ser Pro Ile Phe Ser Arg Gly Phe Arg
        115                 120                 125

Glu Ser Ala Phe Ala Tyr Ala Ile Ala Ala Ala Gly Val Val His Ala
    130                 135                 140
```

```
Val Ser Asn Ala Cys Ala Leu Gly Lys Leu Lys Ala Cys Gly Cys Asp
145                 150                 155                 160

Ala Ser Arg Arg Gly Asp Glu Glu Ala Phe Arg Arg Lys Leu His Arg
                165                 170                 175

Leu Gln Leu Asp Ala Leu Gln Arg Gly Lys Gly Leu Ser His Gly Val
            180                 185                 190

Pro Glu His Pro Ala Leu Pro Thr Ala Ser Pro Gly Leu Gln Asp Ser
        195                 200                 205

Trp Glu Trp Gly Gly Cys Ser Pro Asp Met Gly Phe Gly Glu Arg Phe
    210                 215                 220

Ser Lys Asp Phe Leu Asp Ser Arg Glu Pro His Arg Asp Ile His Ala
225                 230                 235                 240

Arg Met Arg Leu His Asn Asn Arg Val Gly Arg Gln Ala Val Met Glu
                245                 250                 255

Asn Met Arg Arg Lys Cys Lys Cys His Gly Thr Ser Gly Ser Cys Gln
                260                 265                 270

Leu Lys Thr Cys Trp Gln Val Thr Pro Glu Phe Arg Thr Val Gly Ala
            275                 280                 285

Leu Leu Arg Ser Arg Phe His Arg Ala Thr Leu Ile Arg Pro His Asn
        290                 295                 300

Arg Asn Gly Gly Gln Leu Glu Pro Gly Pro Ala Gly Ala Pro Ser Pro
305                 310                 315                 320

Ala Pro Gly Ala Pro Gly Pro Arg Arg Ala Ser Pro Ala Asp Leu
                325                 330                 335

Val Tyr Phe Glu Lys Ser Pro Asp Phe Cys Glu Arg Glu Pro Arg Leu
                340                 345                 350

Asp Ser Ala Gly Thr Val Gly Arg Leu Cys Asn Lys Ser Ser Ala Gly
            355                 360                 365

Ser Asp Gly Cys Gly Ser Met Cys Cys Gly Arg Gly His Asn Ile Leu
        370                 375                 380

Arg Gln Thr Arg Ser Glu Arg Cys His Cys Arg Phe His Trp Cys Cys
385                 390                 395                 400

Phe Val Val Cys Glu Glu Cys Arg Ile Thr Glu Trp Val Ser Val Cys
                405                 410                 415

Lys

<210> SEQ ID NO 98
<211> LENGTH: 389
<212> TYPE: PRT
<213> ORGANISM: Homo sapiens

<400> SEQUENCE: 98

Met Leu Glu Glu Pro Arg Pro Arg Pro Pro Ser Gly Leu Ala Gly
1               5                   10                  15

Leu Leu Phe Leu Ala Leu Cys Ser Arg Ala Leu Ser Asn Glu Ile Leu
                20                  25                  30

Gly Leu Lys Leu Pro Gly Glu Pro Leu Thr Ala Asn Thr Val Cys
            35                  40                  45

Leu Thr Leu Ser Gly Leu Ser Lys Arg Gln Leu Gly Leu Cys Leu Arg
        50                  55                  60

Asn Pro Asp Val Thr Ala Ser Ala Leu Gln Gly Leu His Ile Ala Val
65                  70                  75                  80

His Glu Cys Gln His Gln Leu Arg Asp Gln Arg Trp Asn Cys Ser Ala
                85                  90                  95
```

-continued

```
Leu Glu Gly Gly Gly Arg Leu Pro His His Ser Ala Ile Leu Lys Arg
            100                 105                 110

Gly Phe Arg Glu Ser Ala Phe Ser Phe Ser Met Leu Ala Ala Gly Val
        115                 120                 125

Met His Ala Val Ala Thr Ala Cys Ser Leu Gly Lys Leu Val Ser Cys
    130                 135                 140

Gly Cys Gly Trp Lys Gly Ser Gly Glu Gln Asp Arg Leu Arg Ala Lys
145                 150                 155                 160

Leu Leu Gln Leu Gln Ala Leu Ser Arg Gly Lys Ser Phe Pro His Ser
                165                 170                 175

Leu Pro Ser Pro Gly Pro Gly Ser Ser Pro Ser Pro Gly Pro Gln Asp
            180                 185                 190

Thr Trp Glu Trp Gly Gly Cys Asn His Asp Met Asp Phe Gly Glu Lys
        195                 200                 205

Phe Ser Arg Asp Phe Leu Asp Ser Arg Glu Ala Pro Arg Asp Ile Gln
    210                 215                 220

Ala Arg Met Arg Ile His Asn Asn Arg Val Gly Arg Gln Val Val Thr
225                 230                 235                 240

Glu Asn Leu Lys Arg Lys Cys Lys Cys His Gly Thr Ser Gly Ser Cys
                245                 250                 255

Gln Phe Lys Thr Cys Trp Arg Ala Ala Pro Glu Phe Arg Ala Val Gly
            260                 265                 270

Ala Ala Leu Arg Glu Arg Leu Gly Arg Ala Ile Phe Ile Asp Thr His
        275                 280                 285

Asn Arg Asn Ser Gly Ala Phe Gln Pro Arg Leu Arg Pro Arg Arg Leu
    290                 295                 300

Ser Gly Glu Leu Val Tyr Phe Glu Lys Ser Pro Asp Phe Cys Glu Arg
305                 310                 315                 320

Asp Pro Thr Met Gly Ser Pro Gly Thr Arg Gly Arg Ala Cys Asn Lys
                325                 330                 335

Thr Ser Arg Leu Leu Asp Gly Cys Gly Ser Leu Cys Cys Gly Arg Gly
            340                 345                 350

His Asn Val Leu Arg Gln Thr Arg Val Glu Arg Cys His Cys Arg Phe
        355                 360                 365

His Trp Cys Cys Tyr Val Leu Cys Asp Glu Cys Lys Val Thr Glu Trp
    370                 375                 380

Val Asn Val Cys Lys
385

<210> SEQ ID NO 99
<211> LENGTH: 354
<212> TYPE: PRT
<213> ORGANISM: Homo sapiens

<400> SEQUENCE: 99

Met Arg Ala Arg Pro Gln Val Cys Glu Ala Leu Leu Phe Ala Leu Ala
1               5                   10                  15

Leu Gln Thr Gly Val Cys Tyr Gly Ile Lys Trp Leu Ala Leu Ser Lys
            20                  25                  30

Thr Pro Ser Ala Leu Ala Leu Asn Gln Thr Gln His Cys Lys Gln Leu
        35                  40                  45

Glu Gly Leu Val Ser Ala Gln Val Gln Leu Cys Arg Ser Asn Leu Glu
    50                  55                  60

Leu Met His Thr Val Val His Ala Ala Arg Glu Val Met Lys Ala Cys
65                  70                  75                  80
```

```
Arg Arg Ala Phe Ala Asp Met Arg Trp Asn Cys Ser Ser Ile Glu Leu
                85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ile Ser His Ala Ile Ala Arg
        115                 120                 125

Ala Cys Thr Ser Gly Asp Leu Pro Gly Cys Ser Cys Gly Pro Val Pro
130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300

Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
                325                 330                 335

Cys Tyr Val Thr Cys Arg Arg Cys Glu Arg Thr Val Glu Arg Tyr Val
            340                 345                 350

Cys Lys

<210> SEQ ID NO 100
<211> LENGTH: 364
<212> TYPE: PRT
<213> ORGANISM: Homo sapiens

<400> SEQUENCE: 100

Met Asp Arg Ala Ala Leu Leu Gly Leu Ala Arg Leu Cys Ala Leu Trp
1               5                   10                  15

Ala Ala Leu Leu Val Leu Phe Pro Tyr Gly Ala Gln Gly Asn Trp Met
            20                  25                  30

Trp Leu Gly Ile Ala Ser Phe Gly Val Pro Glu Lys Leu Gly Cys Ala
        35                  40                  45

Asn Leu Pro Leu Asn Ser Arg Gln Lys Glu Leu Cys Arg Lys Pro
50                  55                  60

Tyr Leu Leu Pro Ser Ile Arg Glu Gly Ala Arg Leu Gly Ile Gln Glu
65                  70                  75                  80

Cys Gly Ser Gln Phe Arg His Glu Arg Trp Asn Cys Met Ile Thr Ala
                85                  90                  95
```

-continued

```
Ala Ala Thr Thr Ala Pro Met Gly Ala Ser Pro Leu Phe Gly Tyr Glu
            100                 105                 110

Leu Ser Ser Gly Thr Lys Glu Thr Ala Phe Ile Tyr Ala Val Met Ala
            115                 120                 125

Ala Gly Leu Val His Ser Val Thr Arg Ser Cys Ser Ala Gly Asn Met
            130                 135                 140

Thr Glu Cys Ser Cys Asp Thr Thr Leu Gln Asn Gly Gly Ser Ala Ser
145                 150                 155                 160

Glu Gly Trp His Trp Gly Gly Cys Ser Asp Asp Val Gln Tyr Gly Met
                165                 170                 175

Trp Phe Ser Arg Lys Phe Leu Asp Phe Pro Ile Gly Asn Thr Thr Gly
            180                 185                 190

Lys Glu Asn Lys Val Leu Leu Ala Met Asn Leu His Asn Asn Glu Ala
            195                 200                 205

Gly Arg Gln Ala Val Ala Lys Leu Met Ser Val Asp Cys Arg Cys His
            210                 215                 220

Gly Val Ser Gly Ser Cys Ala Val Lys Thr Cys Trp Lys Thr Met Ser
225                 230                 235                 240

Ser Phe Glu Lys Ile Gly His Leu Leu Lys Asp Lys Tyr Glu Asn Ser
                245                 250                 255

Ile Gln Ile Ser Asp Lys Thr Lys Arg Lys Met Arg Arg Glu Lys
            260                 265                 270

Asp Gln Arg Lys Ile Pro Ile His Lys Asp Asp Leu Leu Tyr Val Asn
            275                 280                 285

Lys Ser Pro Asn Tyr Cys Val Glu Asp Lys Lys Leu Gly Ile Pro Gly
            290                 295                 300

Thr Gln Gly Arg Glu Cys Asn Arg Thr Ser Glu Gly Ala Asp Gly Cys
305                 310                 315                 320

Asn Leu Leu Cys Cys Gly Arg Gly Tyr Asn Thr His Val Val Arg His
                325                 330                 335

Val Glu Arg Cys Glu Cys Lys Phe Ile Trp Cys Cys Tyr Val Arg Cys
            340                 345                 350

Arg Arg Cys Glu Ser Met Thr Asp Val His Thr Cys
            355                 360
```

POLYPEPTIDES INCLUDING A BETA-TRICALCIUM PHOSPHATE-BINDING SEQUENCE AND USES THEREOF

CROSS-REFERENCE TO RELATED APPLICATIONS

This application is a Continuation of PCT International Application No. PCT/US2019/055939, filed Oct. 11, 2019, which claims the benefit of U.S. Provisional Patent Application Ser. No. 62/744,941, filed Oct. 12, 2018; both of which are incorporated herein by reference in their entirety.

STATEMENT AS TO FEDERALLY SPONSORED RESEARCH

This invention was made with government support under grant numbers W81XWH-18-C-0182 and W81XWH-18-C-0325 awarded by the United States Army Medical Research and Materiel Command. The government has certain rights in the invention.

SEQUENCE LISTING

The instant application contains a Sequence Listing which has been submitted electronically in ASCII format and is hereby incorporated by reference in its entirety. Said ASCII copy, created on Jul. 30, 2021, is named 50222-702_301_SL.txt and is 215,917 bytes in size.

TECHNICAL FIELD

The present disclosure relates generally to the field of molecular biology, and more specifically, to methods of treating bone and cartilage loss of defects in a mammal.

BACKGROUND

In the U.S., an average of six million people break a bone annually. Of these bone defects, the majority heal without problems. However, 5-10% will heal poorly or not at all (American Academy of Orthopaedic Surgeons). Large defects, also known as critical-sized bone defects, may not heal spontaneously and can lead to non-unions. A non-union occurs when there is no indication of healing for at least three months and no expectation of further healing (American Academy of Orthopaedic Surgeons). Currently, bone grafting is regarded as the "gold standard" for treating large or segmental bone defects. However, there are limitations with this treatment such as donor site pain, risk of rejection, limited donor supply and risk of transmission of infectious disease.

The repair of critical and complex bone and cartilage defects is also limited by poor tissue regrowth on implanted orthopedic substrates. Reasons for poor tissue regrowth include the loss of implanted progenitor cells within 48 hours post-implantation and the scarcity of progenitor cells. Another contributing factor is that current orthopedic substrates fail to facilitate sufficient tissue regeneration.

SUMMARY

The present invention is based on the discovery that the use of composition including β-tricalcium phosphate (β-TCP) and a chimeric polypeptide including at least one β-TCP binding sequence and a mammalian growth factor (e.g., bone morphogenetic protein 2 (BMP-2) can vastly improve bone healing and accelerate tissue regrowth. Thus, provided herein are chimeric polypeptides that include one or more β-TCP binding sequences, and a mammalian growth factor, compositions comprising any of these chimeric polypeptides (and optionally, β-TCP), and methods of promoting bone or cartilage formulation, methods of replacing and/or repairing bone or cartilage, and methods of treating a bone fraction or bone loss that include administration of any of these compositions. The compositions and methods provided herein can increase and sustain the number of progenitor cells at sites of bone and/or cartilage injury through stem cell capture. The compositions and methods provided herein can also be applied to soft tissue repair or localized delivery of a therapeutic.

Provided herein are chimeric polypeptides that include: (i) one or more β-tricalcium phosphate (βTCP)-binding sequence(s), wherein at least one of the one or more β-TCP-binding sequence(s) is selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor.

In some embodiments, the chimeric polypeptide includes two or more β-TCP-binding sequences.

In some embodiments, each neighboring pair of the two or more β-TCP binding sequences directly abut each other.

In some embodiments, each neighboring pair of the two or more β-TCP binding sequences are separated by a linker sequence.

In some embodiments, the chimeric polypeptide includes at least two different β-TCP-binding sequences.

In some embodiments, the chimeric polypeptide includes two or more copies of the same β-TCP-binding sequence.

In some embodiments, at least one of the two or more β-TCP-binding sequences is LLADTTHHRPWT (SEQ ID NO: 1) or GQVLPTTTPSSP (SEQ ID NO: 103).

In some embodiments, the at least two different β-TCP-binding sequences include LLADTTHHRPWT (SEQ ID NO: 1) and VIGESTHHRPWS (SEQ ID NO: 2).

In some embodiments, the chimeric polypeptide includes the sequence of LLADTTHHRPWTVIGESTHHRPWS (SEQ ID NO: 20).

In some embodiments, the at least two different β-TCP-binding sequences include LLADTTHHRPWT (SEQ ID NO: 1), VIGESTHHRPWS (SEQ ID NO: 2), and IIGESSHHKPFT (SEQ ID NO: 6).

In some embodiments, the chimeric polypeptide includes the sequence of LLADTTHHRPWTVIGESTHHRPWSIIGESSHHKPFT (SEQ ID NO: 21).

In some embodiments, the at least two different β-TCP-binding sequences include LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4).

In some embodiments, the chimeric polypeptide includes the sequence of LLADTTHHRPWTVIGESTHHRPWSIIGESSHHKPFTGLGDTTHHRPWGILAESTHHKPWT (SEQ ID NO: 22).

In some embodiments, the at least two β-TCP-binding sequences include LLADTTHHRPWT (SEQ ID NO: 1) and ILAESTHHKPWT (SEQ ID NO: 4).

In some embodiments, the chimeric polypeptide includes at least one copy of the sequence LLADTTHHRPWTILAESTHHKPWT (SEQ ID NO: 23).

In some embodiments, the chimeric polypeptide includes the sequence of LLADTTHHRPWTILAESTHHKPWTLLADTTHHRPWTILAESTHHKPWTLLADTTHHRP WT (SEQ ID NO: 24).

In some embodiments, the at least two β-TCP-binding sequences include LLADTTHHRPWT (SEQ ID NO: 1) and GLGDTTHHRPWG (SEQ ID NO: 7).

In some embodiments, the chimeric polypeptide includes at least one copy of the sequence LLADTTHHRPWTGLGDTTHHRPWG (SEQ ID NO: 25).

In some embodiments, the chimeric polypeptide includes the sequence of LLADTTHHRPWTGLGDTTHHRPWGLLADTTHHRPWT (SEQ ID NO: 26).

In some embodiments, the chimeric polypeptide includes the sequence of LLADTTHHRPWTGLGDTTHHRPWGLLADTTHHRPWTGLGDTTHHRPWGLLADTTHHRPWT (SEQ ID NO: 27).

In some embodiments, the chimeric polypeptide includes the sequence of LLADTTHHRPWTGLGDTTHHRPWGLLADTTHHRPWTGLGDTTHHRPWGLLADTTHHRPWTGLGDTTHHRPWGLLADTTHHRPWT (SEQ ID NO: 28).

In some embodiments, the at least two β-TCP-binding sequences include STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), and GSSGESTHHKPST (SEQ ID NO: 14).

In some embodiments, the chimeric polypeptide includes the sequence of STADTSHHRPSTSGGESTHHRPSTSGGESSHHKPSTGSGDSSHHRPSGSSGESTHHKPST (SEQ ID NO: 29).

In some embodiments, the at least two β-TCP-binding sequences include VGADSTHHRPVT (SEQ ID NO: 15), GAADTTHHRPVT SEQ ID NO: 16), AGADTTHHRPVT (SEQ ID NO: 17), GGADTTHHRPAT (SEQ ID NO: 18) and GGADTTHHRPGT (SEQ ID NO: 19).

In some embodiments, the chimeric polypeptide includes the sequence of VGADSTHHRPVTGAADTTHHRPVTAGADTTHHRPVTGGADTTHHRPATGGADTTHHR PGT (SEQ ID NO: 30).

In some embodiments, the at least two different β-TCP-binding sequences include STADTSHHRPS (SEQ ID NO: 10), LLADTTHHRPWT (SEQ ID NO: 1), TSGGESTHHRPS (SEQ ID NO: 11), VGADSTHHRPVT (SEQ ID NO: 15), TSGGESSHHKPS (SEQ ID NO: 12), GAADTTHHRPVT (SEQ ID NO: 16), TGSGDSSHHRPS (SEQ ID NO: 13), GSSGESTHHKPS (SEQ ID NO: 101), and TGGADTTHHRPAT (SEQ ID NO: 102).

In some embodiments, the chimeric polypeptide includes the sequence of STADTSHHRPSLLADTTHHRPWTTSGGESTHHRPSVGADSTHHRPVTTSGGESSHHKPSGAADTTHHRPVTTGSGDSSHHRPSGSSGESTHHKPSTGGADTTHHRPAT (SEQ ID NO: 31).

In some embodiments of any the chimeric polypeptides described herein, the mammalian growth factor is selected from the group consisting of: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12) bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15 (GDF15), vascular endothelial growth factor (VEGF), hyaluronic acid binding protein (HABP), collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), and wnt family member 16 (WNT16).

In some embodiments, the mammalian growth factor is BMP-2.

In some embodiments, the BMP-2 includes an amino acid sequence of MVAGTRCLLALLLPQVLLGGAAGLVPELGRRKFAAASSGRPSSQPSDEVLSEFELRLLS MFGLKQRPTPSRDAVVPPYMLDLYRRHSGQPGSPAPDHRLERAASRANTVRSFHHEESL EELPETSGKTTRRFFFNLSSIPTEEFITSAELQVFREQMQDALGNNSSFHHRINIYEIIKPAT ANSKFPVTRLLDTRLVNQNASRWESFDVTPAVMRWTAQGHANHGFVVEVAHLEEKQG VSKRHVRISRSLHQDEHSWSQIRPLLVTFGHDGKGHPLHKREKRQAKHKQRKRLKSSC KRHPLYVDFSDVGWNDWIVAPPGYHAFYCHGECPFPLADHLNSTNHAIVQTLVNSVNS KIPKACCVPTELSAISMLYLDENEKVVLKNYQDMVVEGCGCR (SEQ ID NO: 32).

In some embodiments, the BMP-2 consists of the amino acid of SEQ ID NO: 32.

In some embodiments of any of the chimeric polypeptides described herein, the chimeric polypeptide further comprises a linker sequence between a neighboring pair of a β-TCP-binding sequence and the growth factor.

In some embodiments, the linker sequence includes TGGSGEGGTGASTGGSAGTGGSGGTTSGEAGGSSGAG (SEQ ID NO: 33).

In some embodiments, the linker sequence consists of SEQ ID NO: 33.

In some embodiments, the linker sequence includes GAGTG (SEQ ID NO: 104).

In some embodiments, the linker sequence consists of SEQ ID NO: 34.

In some embodiments of any of the chimeric polypeptides described herein, chimeric polypeptide binds to β-TCP with a $K_D$ of about 1 picomolar to about 100 micromolar.

Also provided herein are compositions includes any of one of the chimeric polypeptides described herein.

In some embodiments, the composition further includes β-TCP. In some embodiments, the β-TCP is formulated as a powder, a putty, or a paste. In some embodiments, the β-TCP is disposed on or in a scaffold, a mesh, or a sponge.

In some embodiments of any of the compositions described herein, the composition is a pharmaceutical composition.

Also provided herein are kits that include any of the compositions described herein.

Provided herein are chimeric polypeptides that include: (i) one or more β-TCP-binding sequence(s) comprising an amino acid sequence of Formula I: $A_0B_0C_0D_0E_0F_0G_0H_0I_0J_0K_0L_0$ (Formula I) (SEQ ID NO: 35), wherein: $A_0$ is V, L, I, G, S, T or A; $B_0$ is I, L, V, Q, T, S, G or A; $C_0$ is G, A, V or S; $D_0$ is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A); and (ii) a mammalian growth factor, wherein Formula I does not include LLADTTHHRPWT (SEQ ID NO: 1).

In some embodiments, the chimeric polypeptide includes two or more β-TCP-binding sequences of Formula I.

In some embodiments, each neighboring pair of the two or more β-TCP binding sequences of Formula I directly abut each other.

In some embodiments, each neighboring pair of the two or more β-TCP binding sequences of Formula I are separated by a linker sequence.

In some embodiments, the chimeric polypeptide includes at least two different β-TCP-binding sequences of Formula I.

In some embodiments, the chimeric polypeptide includes two or more copies of the same β-TCP-binding sequence of Formula I.

In some embodiments, the chimeric polypeptide further includes a β-TCP-binding sequence that does not includes a sequence of Formula I.

In some embodiments of any of the chimeric polypeptides described herein, the mammalian growth factor is selected from the group consisting of: EGF, PDGF, IGF-1, FGF, FGF2, FGF18, TGF-α, TGF-β, TGF-β1, TGF-β3, OP-1, OP-2, OP-3, BMP-2, BMP-3, BMP-4, BMP-5, BMP-6, BMP-7, BMP-9, BMP-10, BMP-12, BMP-11, BMP-13, BMP-15, DPP, Vgr, GDF-1, GDF-3, GDF-5, GDF-6, GDF-7, GDF8, GDF11, GDF15, VEGF, HABP, CBP, FGF-18, KGF, TNFα, TRAIL, WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the mammalian growth factor is BMP-2. In some embodiments, the BMP-2 includes an amino acid sequence of MVAGTRCLLALLLPQVLLG-GAAGLVPELGRRKFAAASSGRPSSQPSDEVLSEF-ELRLLS MFGLKQRPTPSRDAVVPPYMLDYRRHSG-QPGSPAPDHRLERAASRANTVRSFHHEESL EEL-PETSGKTTRRFFFNLSSIPTEEFITSAELQVFREQMQ-DALGNNSSFHHRINIYEIIKPAT ANSKFPVTRLL-DTRLVNQNASRWESFDVTPAVMRWTAQGHANH-GFVVEVAHLEEKQG VSKRHVRISRSLHQDEHSWSQ-IRPLLVTFGHDGKGHPLHKREKRQAKHKQRKR-LKSSC KRHPLYVDFSDVGWNDWIVAPPGYHAFYCH-GECPFPLADHLNSTNHAIVQTLVNSVNS KIPKACCV-PTELSAISMLYLDENEKVVLKNYQDMVVEGCGCR (SEQ ID NO: 32).

In some embodiments, the BMP-2 consists of the amino acid of SEQ ID NO: 32.

In some embodiments of any of the chimeric polypeptides described herein, the chimeric polypeptide further includes a linker sequence between a neighboring pair of a β-TCP-binding sequence and the growth factor.

In some embodiments, the linker sequence includes TGGSGEGGT-GASTGGSAGTGGSGGTTSGEAGGSSGAG (SEQ ID NO: 33).

In some embodiments, the linker sequence consists of SEQ ID NO: 33.

In some embodiments, the linker sequence includes GSGATG (SEQ ID NO: 34).

In some embodiments, the linker sequence consists of SEQ ID NO: 34.

In some embodiments of any of the chimeric polypeptides described herein, the chimeric polypeptide binds to β-TCP with a $K_D$ of about 1 picomolar to about 100 micromolar.

Also provided herein are compositions including any of one of the chimeric polypeptides described herein.

In some embodiments, the composition further includes β-TCP. In some embodiments, the β-TCP is formulated as a powder, a putty, or a paste. In some embodiments, the β-TCP is disposed on or in a scaffold, a mesh, or a sponge.

In some embodiments of any of the compostions described herein, the composition is a pharmaceutical composition.

Also provided herein are kits includes any of the compositions described herein.

Provided herein are methods of promoting bone or cartilage formation in a subject in need thereof that include: administering to the subject a therapeutically effective amount of any of the compositions described herein.

Also provided herein are methods of replacing and/or repairing bone or cartilage in a subject in need thereof that include: administering to the subject a therapeutically effective amount of any of the compositions described herein.

Also provided herein are methods of treating a bone fracture or bone loss in a subject in need thereof, that include: administering to the subject a therapeutically effective amount of any of the compositions described herein.

In some embodiments of any of the methods described herein, the subject has a bone fracture. In some embodiments of any of the methods described herein, the subject has a bone defect. In some embodiments of any of the methods described herein, the subject has a cartilage tear or cartilage defect. In some embodiments of any of the methods described herein, the subject has cartilage loss.

Also provided herein are β-tricalcium phosphate-binding polypeptides including at least one sequence selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGA-DTTHHRPGT (SEQ ID NO: 19).

Also provided herein are β-tricalcium phosphate-binding polypeptides including an amino acid sequence of Formula I: $A_0B_0C_0D_0E_0F_0G_0H_0I_0J_0K_0L_0$ (Formula I) (SEQ ID NO: 35), wherein: $A_0$ is V, L, I, G, S, T or A; $B_0$ is I, L, V, Q, T, S, G or A; $C_0$ is G, A, V or S; $D_0$ is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A); wherein Formula I does not include LLADTTHHRPWT (SEQ ID NO: 1).

The term "subject" as used herein refers to any mammal. A subject therefore refers to, for example, mice, rats, dogs, cats, horses, cows, pigs, guinea pigs, rats, humans, monkeys, and the like. When the subject is a human, the subject may be referred to herein as a patient. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon), a human, or a rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine, or primate animals) may be employed.

The term "bone defect" refers to the absence or loss (e.g., partial loss) of bone at an anatomical location in a subject where it would otherwise be present in a control healthy subject. A bone defect may be the result of, e.g., an infection (e.g., osteomyelitis), a tumor, a trauma, or an adverse event of a treatment. A bone defect may also affect the muscles, soft tissue, tendons, or joints surrounding the bone defect and cause injury. In some embodiments, a bone defect includes damage to a soft tissue.

The term "cartilage defect" refers to the absence or loss (e.g., partial loss) of cartilage at an anatomical location in a subject where it would otherwise be present in a control healthy subject. A cartilage defect may be the result of, e.g., disease, osteochondritis, osteonecrosis, or trauma. For example, a cartilage defect may affect the knee joint.

"Affinity" refers to the strength of the sum total of non-covalent interactions between a β-TCP binding sequence (or a chimeric polypeptide or polypeptide comprising a β-TCP binding sequence) and its binding partner (e.g., β-TCP). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining affinity are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
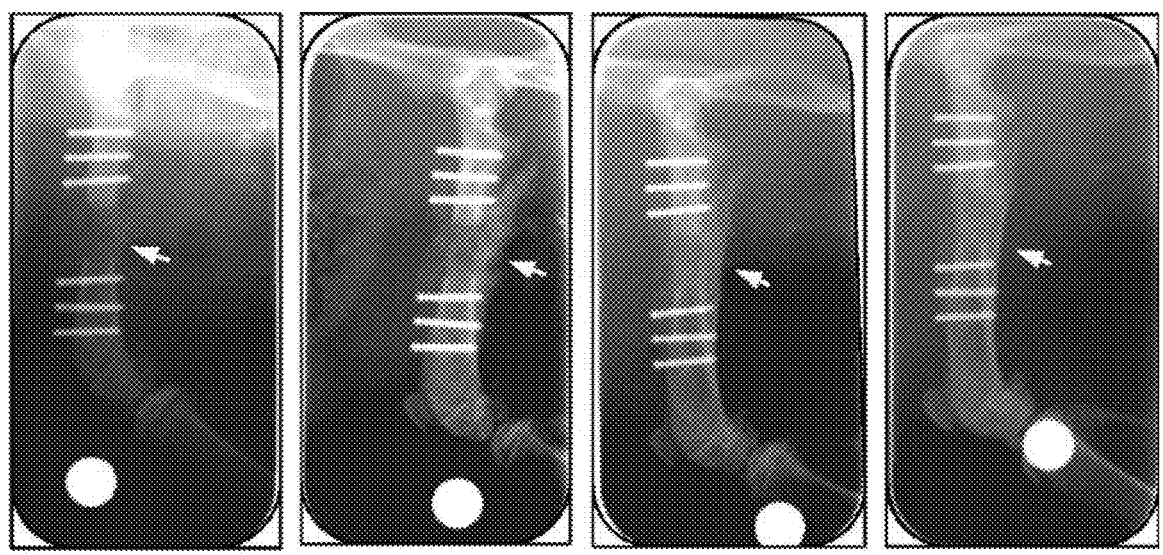
FIG. 1A are representative in vivo radiographs (lateromedial orientation) of animals from experimental Group A.

Provided herein are chimeric polypeptides that include: (i) one or more (e.g., two, three, four, five, six, seven, eight, nine, or ten) β-tricalcium phosphate (βTCP)-binding sequence(s), where at least one of the one or more β-TCP-binding sequence(s) is selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor (e.g., any of the exemplary mammalian growth factors described herein or known in the art).

Also provided herein are chimeric polypeptides that include (i) one or more β-TCP-binding sequence(s) including an amino acid sequence of Formula I:

$A_0B_0C_0D_0E_0F_0G_0H_0I_0J_0K_0L_0$(Formula I) (SEQ ID NO: 35), where:

$A_0$ is V, L, I, G, S, T or A;
$B_0$ is I, L, V, Q, T, S, G or A;
$C_0$ is G, A, V or S;
$D_0$ is E, D, L or G;
$E_0$ is S, T, P T, E or D;
$F_0$ is T or S;
$G_0$ is H, T or S;
$H_0$ is H or T;
$I_0$ is R, S, K, P or H;
$J_0$ is P, S, R or K;
$K_0$ is W, F, S, P, V, A or G; and
$L_0$ is absent or is S, T G, (or A); and
(ii) a mammalian growth factor (e.g., any of the exemplary mammalian growth factors described herein or known in the art),
where Formula I does not include LLADTTHHRPWT (SEQ ID NO: 1).

Also provided herein are β-tricalcium phosphate-binding polypeptides that include at least one (e.g., two, three, four, five, six, seven, eight, nine, or ten) sequence selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19). Some embodiments of these polypeptides can further include a mammalian growth factor (e.g., any of the exemplary mammalian growth factors described herein or known in the art).

Also provided herein are β-tricalcium phosphate-binding polypeptides that include an amino acid sequence of Formula I:

$A_0B_0C_0D_0E_0F_0G_0H_0I_0J_0K_0L_0$(Formula I) (SEQ ID NO: 35), where:

$A_0$ is V, L, I, G, S, T or A;
$B_0$ is I, L, V, Q, T, S, G or A;
$C_0$ is G, A, V or S;
$D_0$ is E, D, L or G;
$E_0$ is S, T, P T, E or D;
$F_0$ is T or S;
$G_0$ is H, T or S;
$H_0$ is H or T;
$I_0$ is R, S, K, P or H;
$J_0$ is P, S, R or K;
$K_0$ is W, F, S, P, V, A or G; and
$L_0$ is absent or is S, T G, (or A);
where Formula I does not include LLADTTHHRPWT (SEQ ID NO: 1). Some embodiments of these polypeptides can further include a mammalian growth factor (e.g., any of the exemplary mammalian growth factors described herein or known in the art). In some embodiments, any of the chimeric polypeptides described herein can bind to one or more substrates comprising ζTCP (e.g., a Mastergraft strip, Vitoss Foam Pack, chronOS Strip, Vitoss Micromorsels, LifeInk500, Hyperelastic Bone, bioactive glass, ζTCP powder, ζTCP spray dried powder, hydroxyapaptite powder, hydroxyapatite-coated bone screw, ζTCP granules, hydroxyapatite granules, and ReBOSSIS). In some embodiments, any of the chimeric polypeptides described herein can bind to silicon nitride or a substrate comprising silicon nitride.

Also provided herein are compositions that include any of the chimeric polypeptides or β-tricalcium phosphate-binding polypeptides described herein. In some embodiments, the compositions can further include a substrate including ζTCP (e.g., (e.g., a Mastergraft strip, Vitoss Foam Pack, chronOS Strip, Vitoss Micromorsels, LifeInk500, Hyperelastic Bone, bioactive glass, ζTCP powder, ζTCP spray dried powder, hydroxyapaptite powder, hydroxyapatite-coated bone screw, ζTCP granules, hydroxyapatite granules, and ReBOSSIS). In some embodiments, the compositions can further include a substrate comprising silicon nitride.

Also provided herein are kits that include any of these compositions. Also provided are methods of promoting bone or cartilage formation in a subject in need thereof, methods of replacing and/or repairing bone or cartilage in a subject in need thereof, and methods of treating a bone fraction or bone loss in a subject in need thereof that include administering to the subject any of the compositions described herein.

Non-limiting aspects of these polypeptides, compositions, kits, and methods are described below, and can be used in any combination without limitation. Additional aspects of these polypeptides, compositions, kits, and methods are known in the art.

Chimeric Polypeptides

The chimeric polypeptides described herein include a β-TCP binding sequence and can bind β-TCP (e.g., any of the exemplary types of β-TCP described herein or known in the art). In some examples, the chimeric polypeptides can include: (i) one or more (e.g., two, three, four, five, six, seven, eight, nine, or ten) β-tricalcium phosphate (βTCP)-binding sequence(s), where at least one of the one or more β-TCP-binding sequence(s) is selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor (e.g., any of the exemplary mammalian growth factors described herein or known in the art).

In some examples, the chimeric polypeptides can include: (i) one or more β-TCP-binding sequence(s) including an amino acid sequence of Formula I: $A_0B_0C_0D_0E_0F_0G_0H_0I_0J_0K_0L_0$ (Formula I) (SEQ ID NO: 35), wherein:
$A_0$ is V, L, I, G, S, T, or A;
$B_0$ is I, L, V, Q, T, S, G, or A;
$C_0$ is G, A, V, or S;
$D_0$ is E, D, L, or G;
$E_0$ is S, T, P T, E, or D;
$F_0$ is T or S;
$G_0$ is H, T, or S;
$H_0$ is H or T;
$I_0$ is R, S, K, P, or H;
$J_0$ is P, S, R, or K;
$K_0$ is W, F, S, P, V, A, or G; and
$L_0$ is absent or is S, T, G, or A; and (ii) a mammalian growth factor (e.g., any of the exemplary mammalian growth factors described herein or known in the art), where Formula I does not include LLADTTHHRPWT (SEQ ID NO: 1).

Non-limiting examples of β-TCP binding sequences that may be present in any of the chimeric polypeptides described herein are listed in Table A below.

TABLE A

Exemplary β-TCP binding sequences

| β-TCP binding sequence | SEQ ID NO: |
|---|---|
| LLADTTHHRPWT | 1 |
| VIGESTHHRPWS | 2 |
| LIADSTHHSPWT | 3 |
| ILAESTHHKPWT | 4 |
| ILAETTHHRPWS | 5 |
| IIGESSHHKPFT | 6 |
| GLGDTTHHRPWG | 7 |
| VLGDTTHHKPWT | 8 |
| IVADSTHHRPWT | 9 |
| STADTSHHRPS | 10 |
| TSGGESTHHRPS | 11 |
| TSGGESSHHKPS | 12 |
| TGSGDSSHHRPS | 13 |
| GSSGESTHHKPST | 14 |
| VGADSTHHRPVT | 15 |
| GAADTTHHRPVT | 16 |
| AGADTTHHRPVT | 17 |
| GGADTTHHRPAT | 18 |
| GGADTTHHRPGT | 19 |
| LLADTTHHRPWTVIGESTHHRPWS | 20 |
| LLADTTHHRPWTVIGESTHHRPWSIIGESSHHKPFT | 21 |
| LLADTTHHRPWTVIGESTHHRPWSIIGESSHHKPFTGLGDTTHHRPWGILAESTHHKPWT | 22 |
| LLADTTHHRPWTILAESTHHKPWT | 23 |
| LLADTTHHRPWTILAESTHHKPWTLLADTTHHRPWTILAESTHHKPWTLLADTTHHRPWT | 24 |
| LLADTTHHRPWTGLGDTTHHRPWG | 25 |
| LLADTTHHRPWTGLGDTTHHRPWGLLADTTHHRPWT | 26 |
| LLADTTHHRPWTGLGDTTHHRPWGLLADTTHHRPWTGLGDTTHHRPWGLLADTTHHRPWT | 27 |
| LLADTTHHRPWTGLGDTTHHRPWGLLADTTHHRPWTGLGDTTHHRPWGLLADTTHHRPWTGLGDTTHHRPWGLLADTTHHRPWT | 28 |
| STADTSHHRPSTSGGESTHHRPSTSGGESSHHKPSTGSGDSSHHRPSGSSGESTHHKPST | 29 |
| VGADSTHHRPVTGAADTTHHRPVTAGADTTHHRPVTGGADTTHHRPATGGADTTHHRPGT | 30 |
| STADTSHHRPSLLADTTHHRPWTTSGGESTHHRPSVGADSTHHRPVTTSGGESSHHKPSGAADTTHHRPVTTGSGDSSHHRPSGSSGESTHHKPSTGGADTTHHRPAT | 31 |
| AAADTTHHRPWT | 36 |
| AAADTTHHRPWTAAADTTHHRPWTAAADTTHHRPWTAAADTTHHRPWTAAADTTHHRPWT | 37 |
| LLADAAHHRPWTLLADAAHHRPWTLLADAAHHRPWTLLADAAHHRPWTLLADAAHHRPWT | 38 |
| LLADTTAARPWTLLADTTAARPWTLLADTTAARPWTLLADTTAARPWTLLADTTAARPWT | 39 |
| LLADTTHHRPWTLLADTTHHRPWT | 40 |

TABLE A-continued

Exemplary β-TCP binding sequences

| β-TCP binding sequence | SEQ ID NO: |
|---|---|
| LLADTTHHRPWTLLADTTHHRPWTLLADTTHHRPWT | 41 |
| LLADTTHHRPWTLLADTTHHRPWTLLADTTHHRPWT LLADTTHHRPWTLLADTTHHRPWT | 42 |
| STSGSTVIGESTHHRPWSLIADSTHHSPWTILAESTHHKPWT ILAETTHHRPWSIIGESSHHKPFTGLGDTTHHRPWGVLGDTT HHKPWTIVADSTHHRPWTGQVLPTTTPSSPSTTSGS | 43 |

In some embodiments, any of the chimeric polypeptides described herein can includes two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, 20, 21, or 22) β-TCP-binding sequences (e.g., any of the exemplary β-TCP-binding sequences described herein). In some embodiments, each neighboring pair of the two or more β-TCP binding sequences directly abut each other. In some embodiments, each neighboring pair of the two or more β-TCP binding sequences (e.g., any of the exemplary β-TCP-binding sequences described herein) are separated by a linker sequence.

In some embodiments, the chimeric polypeptides can include at least two (e.g., at least three, at least four, at least five, at least six, at least seven, at least eight, at least nine, or at least ten; or 2, 3, 4, 5, 6, 7, 8, 9, or 10) different β-TCP-binding sequences (e.g., any of the exemplary β-TCP-binding sequences described herein).

In some embodiments, at least one of the two or more different β-TCP-binding sequences is LLADTTHHRPWT (SEQ ID NO: 1) or GQVLPTTTPSSP (SEQ ID NO: 103). In some embodiments, the at least two different β-TCP-binding sequences include LLADTTHHRPWT (SEQ ID NO: 1) and VIGESTHHRPWS (SEQ ID NO: 2). In some embodiments, the chimeric polypeptide includes the sequence of LLADTTHHRPWTVIGESTHHRPWS (SEQ ID NO: 20).

In some embodiments, the at least two different β-TCP-binding sequences include LLADTTHHRPWT (SEQ ID NO: 1), VIGESTHHRPWS (SEQ ID NO: 2), and IIGESSHHKPFT (SEQ ID NO: 6). In some embodiments, the chimeric polypeptide includes the sequence of LLADTTHHRPWTVIGESTHHRPWSIIGESSHHKPFT (SEQ ID NO: 21).

In some embodiments, the at least two different β-TCP-binding sequences include LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4). In some embodiments, the chimeric polypeptide includes the sequence of:

(SEQ ID NO: 22)
LLADTTHHRPWTVIGESTHHRPWSIIGESSHHKPFTGLGDTTHHRPWGIL
AESTHHKPWT.

In some embodiments, the at least two β-TCP-binding sequences include LLADTTHHRPWT (SEQ ID NO: 1) and ILAESTHHKPWT (SEQ ID NO: 4). In some embodiments, the chimeric polypeptide includes at least one copy of the sequence LLADTTHHRPWTILAESTHHKPWT (SEQ ID NO: 23). In some embodiments, the chimeric polypeptide includes the sequence of LLADTTHHRPWTILAES-THHKPWTLLADTTHHRPWTILAESTHHKPWTL-LADTTHHRP WT (SEQ ID NO: 24).

In some embodiments, the at least two β-TCP-binding sequences include LLADTTHHRPWT (SEQ ID NO: 1) and GLGDTTHHRPWG (SEQ ID NO: 7). In some embodiments, the chimeric polypeptide includes at least one copy of the sequence of LLADTTHHRPWTGLGDTTHHRPWG (SEQ ID NO: 25). In some embodiments, the chimeric polypeptide includes the sequence of LLADTTHHRPWTGLGDTTHHRPWGLLADTTHHR-PWT (SEQ ID NO: 26). In some embodiments, the chimeric polypeptide includes the sequence of LLADTTHHRPW-TGLGDTTHHRPWGLLADTTHHRPWTGLGDTTHHR-PWGLLADTTHHR PWT (SEQ ID NO: 27). In some embodiments, the chimeric polypeptide includes the sequence of LLADTTHHRPWTGLGDTTHHRPWGL-LADTTHHRPWTGLGDTTHHRPWGLLADTTHHR PWTGLGDTTHHRPWGLLADTTHHRPWT (SEQ ID NO: 28).

In some embodiments, the at least two different β-TCP-binding sequences include STADTSHHRPS (SEQ ID NO: 10), TSGGESTHHRPS (SEQ ID NO: 11), TSG-GESSHHKPS (SEQ ID NO: 12), TGSGDSSHHRPS (SEQ ID NO: 13), and GSSGESTHHKPST (SEQ ID NO: 14). In some embodiments, the chimeric polypeptide includes the sequence of STADTSHHRPSTSGGESTHHRPSTSG-GESSHHKPSTGSGDSSHHRPSGSSGESTHHKPST (SEQ ID NO: 29).

In some embodiments, the at least two different β-TCP-binding sequences include VGADSTHHRPVT (SEQ ID NO: 15), GAADTTHHRPVT SEQ ID NO: 16), AGA-DTTHHRPVT (SEQ ID NO: 17), GGADTTHHRPAT (SEQ ID NO: 18) and GGADTTHHRPGT (SEQ ID NO: 19). In some embodiments, the chimeric polypeptide includes the sequence of VGADSTHHRPVTGAADTTHHRPVTAGA-DTTHHRPVTGGADTTHHRPATGGADTTHHR PGT (SEQ ID NO: 30).

In some embodiments, the at least two different β-TCP-binding sequences include STADTSHHRPS (SEQ ID NO: 10), LLADTTHHRPWT (SEQ ID NO: 1), TSG-GESTHHRPS (SEQ ID NO: 11), VGADSTHHRPVT (SEQ ID NO: 15), TSGGESSHHKPS (SEQ ID NO: 12), GAADTTHHRPVT (SEQ ID NO: 16), TGSGDSSHHRPS (SEQ ID NO: 13), GSSGESTHHKPS (SEQ ID NO: 101), and TGGADTTHHRPAT (SEQ ID NO: 102). In some embodiments, the chimeric polypeptide includes the sequence of:

(SEQ ID NO: 31)
STADTSHHRPSLLADTTHHRPWTTSGGESTHHRPSVGADSTHHRPVTTSG
GESSHHKPSGAADTTHHRPVTTGSGDSSHHRPSGSSGESTHHKPSTGGAD
TTHHRPAT.

In some embodiments, the chimeric polypeptides can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, or 20) copies of the same β-TCP-binding sequence (e.g., any of the exemplary β-TCP-binding sequences described herein).

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 1.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 2.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 3.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 4.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 5.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 6.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 7.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 8.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 9.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 10.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 11.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 12.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 13.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 14.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 15.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 16.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 17.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 18.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 19.

In some embodiments, the chimeric polypeptide further comprises a linker sequence (e.g., any of the exemplary linker sequences described herein or known in the art) between a neighboring pair of a β-TCP-binding sequence (e.g., any of the exemplary β-TCP binding sequences described herein) and the mammalian growth factor (e.g., any of the exemplary mammalian growth factor described herein). In some embodiments, the linker sequence can include the sequence of TGGSGEGGT-GASTGGSAGTGGSGGTTSGEAGGSSGAG (SEQ ID NO: 33). In some embodiments, the linker sequence consists of TGGSGEGGTGASTGGSAGTGGSGGTTSGEAGG-SSGAG (SEQ ID NO: 33). In some embodiments, the linker sequence includes the sequence of GSGATG (SEQ ID NO: 34). In some embodiments, the linker sequence consists of GSGATG (SEQ ID NO: 34).

In some embodiments, where the chimeric polypeptide comprises two or more β-TCP-binding sequences, a linker sequence (e.g., any of the exemplary linker sequences described herein or known in the art) can be between any of the pairs (e.g., all of the pairs) of neighboring β-TCP-binding sequences.

In some embodiments, the chimeric polypeptide can include a signal sequence at its N-terminus. In some embodiments, the chimeric polypeptide can further include a tag sequence (e.g., a poly-His tag, chitin-binding protein (CBP), maltose-binding protein (MBP), strep-tag, glutathione-S-transferase (GST), thioredoxin, or Fc region). Additional examples of tags are known in the art.

The chimeric polypeptide described herein can bind to β-TCP (e.g., any of the types of β-TCP described herein) with a dissociation equilibrium constant ($K_d$) of about 1 pM to about 100 μM (e.g., about 1 pM to about 95 μM, about 1 pM to about 90 μM, about 1 pM to about 85 μM, about 1 pM to about 80 pM, about 1 pM to about 75 μM, about 1 pM to about 70 μM, about 1 pM to about 65 pM, about 1 pM to about 60 pM, about 1 pM to about 55 μM, about 1 pM to about 50 μM, about 1 pM to about 45 μM, about 1 pM to about 40 μM, about 1 pM to about 45 μM, about 1 pM to about 40 μM, about 1 pM to about 35 pM, about 1 pM to about 30 μM, about 1 pM to about 25 μM, about 1 pM to about 20 μM, about 1 pM to about 15 pM, about 1 pM to about 10 μM, about 1 pM to about 5 μM, about 1 pM to about 2 μM, about 1 pM to about 1 μM, about 1 pM to about 950 nM, about 1 pM to about 900 nM, about 1 pM to about 850 nM, about 1 pM to about 800 nM, about 1 pM to about 750 nM, about 1 pM to about 700 nM, about 1 pM to about 650 nM, about 1 pM to about 600 nM, about 1 pM to about 550 nM, about 1 pM to about 500 nM, about 1 pM to about 450 nM, about 1 pM to about 400 nM, about 1 pM to about 350 nM, about 1 pM to about 300 nM, about 1 pM to about 250 nM, about 1 pM to about 200 nM, about 1 pM to about 150 nM, about 1 pM to about 100 nM, about 1 pM to about 95 nM, about 1 pM to about 90 nM, about 1 pM to about 85 nM, about 1 pM to about 80 nM, about 1 pM to about 75 nM, about 1 pM to about 70 nM, about 1 pM to about 75 nM, about 1 pM to about 70 nM, about 1 pM to about 65 nM, about 1 pM to about 60 nM, about 1 pM to about 55 nM, about 1 pM to about 50 nM, about 1 pM to about 45 nM, about 1 pM to about 40 nM, about 1 pM to about 35 nM, about 1 pM to about 30 nM, about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 95 pM, about 1 pM to about 90 pM, about 1 pM to about 85 pM, about 1 pM to about 80 pM, about 1 pM to about 75 pM, about 1 pM to about 70 pM, about 1 pM to about 75 pM, about 1 pM to about 70 pM, about 1 pM to about 65 pM, about 1 pM to about 60 pM, about 1 pM to about 55 pM, about 1 pM to about 50 pM, about 1 pM to about 45 pM, about 1 pM to about 40 pM, about 1 pM to about 35 pM, about 1 pM to about 30 pM, about 1 pM to about 25 pM, about 1 pM to about 20 pM, about 1 pM to about 15 pM, about 1 pM to about 10 pM, about 1 pM to about 5 pM, about 1 pM to about 2 pM, about 2 pM to about 100 μM, about 2 pM to about 95 μM, about 2 pM to about 90 μM, about 2 pM to about 85 μM, about 2 pM to about 80 μM, about 2 pM to about 75 μM, about 2 pM to about 70 μM, about 2 pM to about 65 μM, about 2 pM to about 60 μM, about 2 pM to about 55 μM, about 2 pM to about 50 μM, about 2 pM to about 45 μM, about 2 pM to about 40 μM, about 2 pM to about 45 μM, about 2 pM to about 40 μM, about 2 pM to about 35 μM, about 2 pM to about 30 μM, about 2 pM to about 25 μM, about 2 pM to about 20 μM, about 2 pM to about 15 μM, about 2 pM to about 10 μM, about 2 pM to about 5 μM, about 2 pM to about 2 μM, about 2 pM to about 1 μM, about 2 pM to about 950 nM, about 2 pM to about 900 nM, about 2 pM to about 850 nM, about 2 pM to about 800 nM, about 2 pM to about 750 nM, about 2 pM to about 700 nM, about 2 pM to about 650 nM, about 2 pM to about 600 nM, about 2 pM to about 550 nM, about 2 pM to about 500 nM, about 2 pM to about 450 nM, about 2 pM to about 400 nM, about 2 pM to about 350 nM, about 2 pM to about 300 nM, about 2 pM to about 250 nM, about 2 pM to about 200 nM, about 2 pM to about 150 nM, about 2 pM to about 100 nM, about 2 pM to about 95 nM, about 2 pM to about 90 nM, about 2 pM to about 85 nM, about 2 pM to about 80 nM, about 2 pM to about 75 nM, about 2 pM to about 70 nM, about 2 pM to about 75 nM, about 2 pM to about 70 nM, about 2 pM to about 65 nM, about 2 pM to about 60 nM, about 2 pM to about 55 nM, about 2 pM to about 50 nM, about 2 pM to about 45 nM, about 2 pM to about 40 nM, about 2 pM to about 35 nM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 95 pM, about 2 pM to about 90 pM, about 2 pM to about 85 pM, about 2 pM to about 80 pM, about 2 pM to about 75 pM, about 2 pM to about 70 pM, about 2 pM to about 75 pM, about 2 pM to about 70 pM, about 2 pM to about 65 pM, about 2 pM to about 60 pM, about 2 pM to about 55 pM, about 2 pM to about 50 pM, about 2 pM to about 45 pM, about 2 pM to about 40 pM, about 2 pM to about 35 pM, about 2 pM to about 30 pM, about 2 pM to about 25 pM, about 2 pM to about 20 pM, about 2 pM to about 15 pM, about 2 pM to about 10 pM, about 2 pM to about 5 pM, about 5 pM to about 100 μM, about 5 pM to about 95 μM, about 5 pM to about 90 μM, about 5 pM to about 85 μM, about 5 pM to about 80 μM, about 5 pM to about 75 μM, about 5 pM to about 70 μM, about 5 pM to about 65 μM, about 5 pM to about 60 μM, about 5 pM to about 55 μM, about 5 pM to about 50 μM, about 5 pM to about 45 μM, about 5 pM to about 40 μM, about 5 pM to about 45 μM, about 5 pM to about 40 μM, about 5 pM to about 35 μM, about 5 pM to about 30 μM, about 5 pM to about 25 μM, about 5 pM to about 20 μM, about 5 pM to about 15 μM, about 5 pM to about 10 μM, about 5 pM to about 5 μM, about 5 pM to about 2 μM, about 5 pM to about 1 μM, about 5 pM to about 950 nM, about 5 pM to about 900 nM, about 5 pM to about 850 nM, about 5 pM to about 800 nM, about 5 pM to about 750 nM, about 5 pM to about 700 nM, about 5 pM to about 650 nM, about 5 pM to about 600 nM, about 5 pM to about 550 nM, about 5 pM to about 500 nM, about 5 pM to about 450 nM, about 5 pM to about 400 nM, about 5 pM to about 350 nM, about 5 pM to about 300 nM, about 5 pM to about 250 nM, about 5 pM to about 200 nM, about 5 pM to about 150 nM, about 5 pM to about 100 nM, about 5 pM to about 95 nM, about 5 pM to about 90 nM, about 5 pM to about 85 nM, about 5 pM to about 80 nM, about 5 pM to about 75 nM, about 5 pM to about 70 nM, about 5 pM to about 75 nM, about 5 pM to about 70 nM, about 5 pM to about 65 nM, about 5 pM to about 60 nM, about 5 pM to about 55 nM, about 5 pM to about 50 nM, about 5 pM to about 45 nM, about 5 pM to about 40 nM, about 5 pM to about 35 nM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 95 pM, about 5 pM to about 90 pM, about 5 pM to about 85 pM, about 5 pM to about 80 pM, about 5 pM to about 75 pM, about 5 pM to about 70 pM, about 5 pM to about 75 pM, about 5 pM to about 70 pM, about 5 pM to about 65 pM, about 5 pM to about 60 pM, about 5 pM to about 55 pM, about 5 pM to about 50 pM, about 5 pM to about 45 pM, about 5 pM to about 40 pM, about 5 pM to about 35 pM, about 5 pM to about 30 pM, about 5 pM to about 25 pM, about 5 pM to about 20 pM, about 5 pM to about 15 pM, about 5 pM to about 10 pM, about 10 pM to about 100 µM, about 10 pM to about 95 µM, about 10 pM to about 90 µM, about 10 pM to about 85 µM, about 10 pM to about 80 µM, about 10 pM to about 75 µM, about 10 pM to about 70 µM, about 10 pM to about 65 µM, about 10 pM to about 60 µM, about 10 pM to about 55 µM, about 10 pM to about 50 µM, about 10 pM to about 45 µM, about 10 pM to about 40 µM, about 10 pM to about 45 µM, about 10 pM to about 40 µM, about 10 pM to about 35 µM, about 10 pM to about 30 µM, about 10 pM to about 25 µM, about 10 pM to about 20 µM, about 10 pM to about 15 µM, about 10 pM to about 10 µM, about 10 pM to about 5 µM, about 10 pM to about 2 µM, about 10 pM to about 1 µM, about 10 pM to about 950 nM, about 10 pM to about 900 nM, about 10 pM to about 850 nM, about 10 pM to about 800 nM, about 10 pM to about 750 nM, about 10 pM to about 700 nM, about 10 pM to about 650 nM, about 10 pM to about 600 nM, about 10 pM to about 550 nM, about 10 pM to about 500 nM, about 10 pM to about 450 nM, about 10 pM to about 400 nM, about 10 pM to about 350 nM, about 10 pM to about 300 nM, about 10 pM to about 250 nM, about 10 pM to about 200 nM, about 10 pM to about 150 nM, about 10 pM to about 100 nM, about 10 pM to about 95 nM, about 10 pM to about 90 nM, about 10 pM to about 85 nM, about 10 pM to about 80 nM, about 10 pM to about 75 nM, about 10 pM to about 70 nM, about 10 pM to about 75 nM, about 10 pM to about 70 nM, about 10 pM to about 65 nM, about 10 pM to about 60 nM, about 10 pM to about 55 nM, about 10 pM to about 50 nM, about 10 pM to about 45 nM, about 10 pM to about 40 nM, about 10 pM to about 35 nM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 95 pM, about 10 pM to about 90 pM, about 10 pM to about 85 pM, about 10 pM to about 80 pM, about 10 pM to about 75 pM, about 10 pM to about 70 pM, about 10 pM to about 75 pM, about 10 pM to about 70 pM, about 10 pM to about 65 pM, about 10 pM to about 60 pM, about 10 pM to about 55 pM, about 10 pM to about 50 pM, about 10 pM to about 45 pM, about 10 pM to about 40 pM, about 10 pM to about 35 pM, about 10 pM to about 30 pM, about 10 pM to about 25 pM, about 10 pM to about 20 pM, about 10 pM to about 15 pM, about 20 pM to about 100 µM, about 20 pM to about 95 µM, about 20 pM to about 90 µM, about 20 pM to about 85 µM, about 20 pM to about 80 µM, about 20 pM to about 75 µM, about 20 pM to about 70 µM, about 20 pM to about 65 µM, about 20 pM to about 60 µM, about 20 pM to about 55 µM, about 20 pM to about 50 µM, about 20 pM to about 45 µM, about 20 pM to about 40 µM, about 20 pM to about 45 µM, about 20 pM to about 40 µM, about 20 pM to about 35 µM, about 20 pM to about 30 µM, about 20 pM to about 25 µM, about 20 pM to about 20 µM, about 20 pM to about 15 µM, about 20 pM to about 10 µM, about 20 pM to about 5 µM, about 20 pM to about 2 µM, about 20 pM to about 1 µM, about 20 pM to about 950 nM, about 20 pM to about 900 nM, about 20 pM to about 850 nM, about 20 pM to about 800 nM, about 20 pM to about 750 nM, about 20 pM to about 700 nM, about 20 pM to about 650 nM, about 20 pM to about 600 nM, about 20 pM to about 550 nM, about 20 pM to about 500 nM, about 20 pM to about 450 nM, about 20 pM to about 400 nM, about 20 pM to about 350 nM, about 20 pM to about 300 nM, about 20 pM to about 250 nM, about 20 pM to about 200 nM, about 20 pM to about 150 nM, about 20 pM to about 100 nM, about 20 pM to about 95 nM, about 20 pM to about 90 nM, about 20 pM to about 85 nM, about 20 pM to about 80 nM, about 20 pM to about 75 nM, about 20 pM to about 70 nM, about 20 pM to about 75 nM, about 20 pM to about 70 nM, about 20 pM to about 65 nM, about 20 pM to about 60 nM, about 20 pM to about 55 nM, about 20 pM to about 50 nM, about 20 pM to about 45 nM, about 20 pM to about 40 nM, about 20 pM to about 35 nM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 200 pM, about 20 pM to about 150 pM, about 20 pM to about 100 pM, about 20 pM to about 95 pM, about 20 pM to about 90 pM, about 20 pM to about 85 pM, about 20 pM to about 80 pM, about 20 pM to about 75 pM, about 20 pM to about 70 pM, about 20 pM to about 75 pM, about 20 pM to about 70 pM, about 20 pM to about 65 pM, about 20 pM to about 60 pM, about 20 pM to about 55 pM, about 20 pM to about 50 pM, about 20 pM to about 45 pM, about 20 pM to about 40 pM, about 20 pM to about 35 pM, about 20 pM to about 30 pM, about 20 pM to about 25 pM, about 50 pM to about 100 µM, about 50 pM to about 95 µM, about 50 pM to about 90 µM, about 50 pM to about 85 µM, about 50 pM to about 80 µM, about 50 pM to about 75 µM, about 50 pM to about 70 µM, about 50 pM to about 65 µM, about 50 pM to about 60 µM, about 50 pM to about 55 µM, about 50 pM to about 50 µM, about 50 pM to about 45 µM, about 50 pM to about 40 µM, about 50 pM to about 45 µM, about 50 pM to about 40 µM, about 50 pM to about 35 µM, about 50 pM to about 30 µM, about 50 pM to about 25 µM, about 50 pM to about 20 µM, about 50 pM to about 15 µM, about 50 pM to about 10 µM, about 50 pM to about 5 µM, about 50 pM to about 2 µM, about 50 pM to about 1 µM, about 50 pM to about 950 nM, about 50 pM to about 900 nM, about 50 pM to about 850 nM, about 50 pM to about 800 nM, about 50 pM to about 750 nM, about 50 pM to about 700 nM, about 50 pM to about 650 nM, about 50 pM to about 600 nM, about 50 pM to about 550 nM, about 50 pM to about 500 nM, about 50 pM to about 450 nM, about 50 pM to about 400 nM, about 50 pM to about 350 nM, about 50 pM to about 300 nM, about 50 pM to about 250 nM, about 50 pM to about 200 nM, about 50 pM to about 150 nM, about 50 pM to about 100 nM, about 50 pM to about 95 nM, about 50 pM to about 90 nM, about 50 pM to about 85 nM, about 50 pM to about 80 nM, about 50 pM to about 75 nM, about 50 pM to about 70 nM, about 50 pM to about 75 nM, about 50 pM to about 70 nM, about 50 pM to about 65 nM, about 50 pM to about 60 nM, about 50 pM to about 55 nM, about 50 pM to about 50 nM, about 50 pM to about 45 nM, about 50 pM to about 40 nM, about 50 pM to about 35 nM, about 50 pM to about 30 nM, about 50 pM to about 25 nM, about 50 pM to about 20 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 95 pM, about 50 pM to about 90 pM, about 50 pM to about 85 pM, about 50 pM to about 80 pM, about 50 pM to about 75 pM, about 50 pM to about 70 pM, about 50 pM to about 75 pM, about 50 pM to about 70 pM, about 50 pM to about 65 pM, about 50 pM to about 60 pM, about 50 pM to about 55 pM, about 100 pM to about 100 µM, about 100 pM to about 95 µM, about 100 pM to about 90 µM, about 100 pM to about 85 µM, about 100 pM to about 80 µM, about 100 pM to about 75 µM, about 100 pM to about 70 µM, about 100 pM to about 65 µM, about 100 pM to about 60 µM, about 100 pM to about 55 µM, about 100 pM to about 50 µM, about 100 pM to about 45 µM, about 100 pM to about 40 µM, about 100 pM to about 45 µM, about 100 pM to about 40 µM, about 100 pM to about 35 µM, about 100 pM to about 30 µM, about 100 pM to about 25 µM, about 100 pM to about 20 µM, about 100 pM to about 15 µM, about 100 pM to about 10 µM, about 100 pM to about 5 µM, about 100 pM to about 2 µM, about 100 pM to about 1 µM, about 100 pM to about 950 nM, about 100 pM to about 900 nM, about 100 pM to about 850 nM, about 100 pM to about 800 nM, about 100 pM to about 750 nM, about 100 pM to about 700 nM, about 100 pM to about 650 nM, about 100 pM to about 600 nM, about 100 pM to about 550 nM, about 100 pM to about 500 nM, about 100 pM to about 450 nM, about 100 pM to about 400 nM, about 100 pM to about 350 nM, about 100 pM to about 300 nM, about 100 pM to about 250 nM, about 100 pM to about 200 nM, about 100 pM to about 150 nM, about 100 pM to about 100 nM, about 100 pM to about 95 nM, about 100 pM to about 90 nM, about 100 pM to about 85 nM, about 100 pM to about 80 nM, about 100 pM to about 75 nM, about 100 pM to about 70 nM, about 100 pM to about 75 nM, about 100 pM to about 70 nM, about 100 pM to about 65 nM, about 100 pM to about 60 nM, about 100 pM to about 55 nM, about 100 pM to about 50 nM, about 100 pM to about 45 nM, about 100 pM to about 40 nM, about 100 pM to about 35 nM, about 100 pM to about 30 nM, about 100 pM to about 25 nM, about 100 pM to about 20 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 200 pM to about 100 µM, about 200 pM to about 95 µM, about 200 pM to about 90 µM, about 200 pM to about 85 µM, about 200 pM to about 80 µM, about 200 pM to about 75 µM, about 200 pM to about 70 µM, about 200 pM to about 65 µM, about 200 pM to about 60 µM, about 200 pM to about 55 µM, about 200 pM to about 50 µM, about 200 pM to about 45 µM, about 200 pM to about 40 µM, about 200 pM to about 45 µM, about 200 pM to about 40 µM, about 200 pM to about 35 µM, about 200 pM to about 30 µM, about 200 pM to about 25 µM, about 200 pM to about 20 µM, about 200 pM to about 15 µM, about 200 pM to about 10 µM, about 200 pM to about 5 µM, about 200 pM to about 2 µM, about 200 pM to about 1 µM, about 200 pM to about 950 nM, about 200 pM to about 900 nM, about 200 pM to about 850 nM, about 200 pM to about 800 nM, about 200 pM to about 750 nM, about 200 pM to about 700 nM, about 200 pM to about 650 nM, about 200 pM to about 600 nM, about 200 pM to about 550 nM, about 200 pM to about 500 nM, about 200 pM to about 450 nM, about 200 pM to about 400 nM, about 200 pM to about 350 nM, about 200 pM to about 300 nM, about 200 pM to about 250 nM, about 200 pM to about 200 nM, about 200 pM to about 150 nM, about 200 pM to about 100 nM, about 200 pM to about 95 nM, about 200 pM to about 90 nM, about 200 pM to about 85 nM, about 200 pM to about 80 nM, about 200 pM to about 75 nM, about 200 pM to about 70 nM, about 200 pM to about 75 nM, about 200 pM to about 70 nM, about 200 pM to about 65 nM, about 200 pM to about 60 nM, about 200 pM to about 55 nM, about 200 pM to about 50 nM, about 200 pM to about 45 nM, about 200 pM to about 40 nM, about 200 pM to about 35 nM, about 200 pM to about 30 nM, about 200 pM to about 25 nM, about 200 pM to about 20 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 100 µM, about 300 pM to about 95 µM, about 300 pM to about 90 µM, about 300 pM to about 85 µM, about 300 pM to about 80 µM, about 300 pM to about 75 µM, about 300 pM to about 70 µM, about 300 pM to about 65 µM, about 300 pM to about 60 µM, about 300 pM to about 55 µM, about 300 pM to about 50 µM, about 300 pM to about 45 µM, about 300 pM to about 40 µM, about 300 pM to about 45 µM, about 300 pM to about 40 µM, about 300 pM to about 35 µM, about 300 pM to about 30 µM, about 300 pM to about 25 µM, about 300 pM to about 20 µM, about 300 pM to about 15 µM, about 300 pM to about 10 µM, about 300 pM to about 5 µM, about 300 pM to about 2 µM, about 300 pM to about 1 µM, about 300 pM to about 950 nM, about 300 pM to about 900 nM, about 300 pM to about 850 nM, about 300 pM to about 800 nM, about 300 pM to about 750 nM, about 300 pM to about 700 nM, about 300 pM to about 650 nM, about 300 pM to about 600 nM, about 300 pM to about 550 nM, about 300 pM to about 500 nM, about 300 pM to about 450 nM, about 300 pM to about 400 nM, about 300 pM to about 350 nM, about 300 pM to about 300 nM, about 300 pM to about 250 nM, about 300 pM to about 200 nM, about 300 pM to about 150 nM, about 300 pM to about 100 nM, about 300 pM to about 95 nM, about 300 pM to about 90 nM, about 300 pM to about 85 nM, about 300 pM to about 80 nM, about 300 pM to about 75 nM, about 300 pM to about 70 nM, about 300 pM to about 75 nM, about 300 pM to about 70 nM, about 300 pM to about 65 nM, about 300 pM to about 60 nM, about 300 pM to about 55 nM, about 300 pM to about 50 nM, about 300 pM to about 45 nM, about 300 pM to about 40 nM, about 300 pM to about 35 nM, about 300 pM to about 30 nM, about 300 pM to about 25 nM, about 300 pM to about 20 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 100 µM, about 400 pM to about 95 µM, about 400 pM to about 90 µM, about 400 pM to about 85 µM, about 400 pM to about 80 µM, about 400 pM to about 75 µM, about 400 pM to about 70 µM, about 400 pM to about 65 µM, about 400 pM to about 60 µM, about 400 pM to about 55 µM, about 400 pM to about 50 µM, about 400 pM to about 45 µM, about 400 pM to about 40 µM, about 400 pM to about 45 µM, about 400 pM to about 40 µM, about 400 pM to about 35 µM, about 400 pM to about 30 µM, about 400 pM to about 25 µM, about 400 pM to about 20 µM, about 400 pM to about 15 µM, about 400 pM to about 10 µM, about 400 pM to about 5 µM, about 400 pM to about 2 µM, about 400 pM to about 1 µM, about 400 pM to about 950 nM, about 400 pM to about 900 nM, about 400 pM to about 850 nM, about 400 pM to about 800 nM, about 400 pM to about 750 nM, about 400 pM to about 700 nM, about 400 pM to about 650 nM, about 400 pM to about 600 nM, about 400 pM to about 550 nM, about 400 pM to about 500 nM, about 400 pM to about 450 nM, about 400 pM to about 400 nM, about 400 pM to about 350 nM, about 400 pM to about 300 nM, about 400 pM to about 250 nM, about 400 pM to about 200 nM, about 400 pM to about 150 nM, about 400 pM to about 100 nM, about 400 pM to about 95 nM, about 400 pM to about 90 nM, about 400 pM to about 85 nM, about 400 pM to about 80 nM, about 400 pM to about 75 nM, about 400 pM to about 70 nM, about 400 pM to about 75 nM, about 400 pM to about 70 nM, about 400 pM to about 65 nM, about 400 pM to about 60 nM, about 400 pM to about 55 nM, about 400 pM to about 50 nM, about 400 pM to about 45 nM, about 400 pM to about 40 nM, about 400 pM to about 35 nM, about 400 pM to about 30 nM, about 400 pM to about 25 nM, about 400 pM to about 20 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 400 pM to about 450 pM, about 500 pM to about 100 µM, about 500 pM to about 95 µM, about 500 pM to about 90 µM, about 500 pM to about 85 pM, about 500 pM to about 80 µM, about 500 pM to about 75 µM, about 500 pM to about 70 µM, about 500 pM to about 65 µM, about 500 pM to about 60 µM, about 500 pM to about 55 µM, about 500 pM to about 50 µM, about 500 pM to about 45 µM, about 500 pM to about 40 µM, about 500 pM to about 45 µM, about 500 pM to about 40 µM, about 500 pM to about 35 µM, about 500 pM to about 30 µM, about 500 pM to about 25 µM, about 500 pM to about 20 µM, about 500 pM to about 15 µM, about 500 pM to about 10 µM, about 500 pM to about 5 µM, about 500 pM to about 2 µM, about 500 pM to about 1 µM, about 500 pM to about 950 nM, about 500 pM to about 900 nM, about 500 pM to about 850 nM, about 500 pM to about 800 nM, about 500 pM to about 750 nM, about 500 pM to about 700 nM, about 500 pM to about 650 nM, about 500 pM to about 600 nM, about 500 pM to about 550 nM, about 500 pM to about 500 nM, about 500 pM to about 450 nM, about 500 pM to about 400 nM, about 500 pM to about 350 nM, about 500 pM to about 300 nM, about 500 pM to about 250 nM, about 500 pM to about 200 nM, about 500 pM to about 150 nM, about 500 pM to about 100 nM, about 500 pM to about 95 nM, about 500 pM to about 90 nM, about 500 pM to about 85 nM, about 500 pM to about 80 nM, about 500 pM to about 75 nM, about 500 pM to about 70 nM, about 500 pM to about 75 nM, about 500 pM to about 70 nM, about 500 pM to about 65 nM, about 500 pM to about 60 nM, about 500 pM to about 55 nM, about 500 pM to about 50 nM, about 500 pM to about 45 nM, about 500 pM to about 40 nM, about 500 pM to about 35 nM, about 500 pM to about 30 nM, about 500 pM to about 25 nM, about 500 pM to about 20 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 100 µM, about 600 pM to about 95 µM, about 600 pM to about 90 µM, about 600 pM to about 85 µM, about 600 pM to about 80 µM, about 600 pM to about 75 µM, about 600 pM to about 70 µM, about 600 pM to about 65 µM, about 600 pM to about 60 µM, about 600 pM to about 55 µM, about 600 pM to about 50 µM, about 600 pM to about 45 µM, about 600 pM to about 40 µM, about 600 pM to about 45 µM, about 600 pM to about 40 µM, about 600 pM to about 35 µM, about 600 pM to about 30 µM, about 600 pM to about 25 µM, about 600 pM to about 20 µM, about 600 pM to about 15 µM, about 600 pM to about 10 µM, about 600 pM to about 5 µM, about 600 pM to about 2 µM, about 600 pM to about 1 µM, about 600 pM to about 950 nM, about 600 pM to about 900 nM, about 600 pM to about 850 nM, about 600 pM to about 800 nM, about 600 pM to about 750 nM, about 600 pM to about 700 nM, about 600 pM to about 650 nM, about 600 pM to about 600 nM, about 600 pM to about 550 nM, about 600 pM to about 500 nM, about 600 pM to about 450 nM, about 600 pM to about 400 nM, about 600 pM to about 350 nM, about 600 pM to about 300 nM, about 600 pM to about 250 nM, about 600 pM to about 200 nM, about 600 pM to about 150 nM, about 600 pM to about 100 nM, about 600 pM to about 95 nM, about 600 pM to about 90 nM, about 600 pM to about 85 nM, about 600 pM to about 80 nM, about 600 pM to about 75 nM, about 600 pM to about 70 nM, about 600 pM to about 75 nM, about 600 pM to about 70 nM, about 600 pM to about 65 nM, about 600 pM to about 60 nM, about 600 pM to about 55 nM, about 600 pM to about 50 nM, about 600 pM to about 45 nM, about 600 pM to about 40 nM, about 600 pM to about 35 nM, about 600 pM to about 30 nM, about 600 pM to about 25 nM, about 600 pM to about 20 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 100 µM, about 700 pM to about 95 µM, about 700 pM to about 90 µM, about 700 pM to about 85 µM, about 700 pM to about 80 µM, about 700 pM to about 75 µM, about 700 pM to about 70 µM, about 700 pM to about 65 µM, about 700 pM to about 60 µM, about 700 pM to about 55 µM, about 700 pM to about 50 µM, about 700 pM to about 45 µM, about 700 pM to about 40 µM, about 700 pM to about 45 µM, about 700 pM to about 40 µM, about 700 pM to about 35 µM, about 700 pM to about 30 µM, about 700 pM to about 25 µM, about 700 pM to about 20 µM, about 700 pM to about 15 µM, about 700 pM to about 10 µM, about 700 pM to about 5 µM, about 700 pM to about 2 µM, about 700 pM to about 1 µM, about 700 pM to about 950 nM, about 700 pM to about 900 nM, about 700 pM to about 850 nM, about 700 pM to about 800 nM, about 700 pM to about 750 nM, about 700 pM to about 700 nM, about 700 pM to about 650 nM, about 700 pM to about 600 nM, about 700 pM to about 550 nM, about 700 pM to about 500 nM, about 700 pM to about 450 nM, about 700 pM to about 400 nM, about 700 pM to about 350 nM, about 700 pM to about 300 nM, about 700 pM to about 250 nM, about 700 pM to about 200 nM, about 700 pM to about 150 nM, about 700 pM to about 100 nM, about 700 pM to about 95 nM, about 700 pM to about 90 nM, about 700 pM to about 85 nM, about 700 pM to about 80 nM, about 700 pM to about 75 nM, about 700 pM to about 70 nM, about 700 pM to about 75 nM, about 700 pM to about 70 nM, about 700 pM to about 65 nM, about 700 pM to about 60 nM, about 700 pM to about 55 nM, about 700 pM to about 50 nM, about 700 pM to about 45 nM, about 700 pM to about 40 nM, about 700 pM to about 35 nM, about 700 pM to about 30 nM, about 700 pM to about 25 nM, about 700 pM to about 20 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 100 µM, about 800 pM to about 95 µM, about 800 pM to about 90 µM, about 800 pM to about 85 µM, about 800 pM to about 80 µM, about 800 pM to about 75 µM, about 800 pM to about 70 µM, about 800 pM to about 65 µM, about 800 pM to about 60 µM, about 800 pM to about 55 µM, about 800 pM to about 50 µM, about 800 pM to about 45 µM, about 800 pM to about 40 µM, about 800 pM to about 45 µM, about 800 pM to about 40 µM, about 800 pM to about 35 µM, about 800 pM to about 30 µM, about 800 pM to about 25 µM, about 800 pM to about 20 µM, about 800 pM to about 15 µM, about 800 pM to about 10 µM, about 800 pM to about 5 µM, about 800 pM to about 2 µM, about 800 pM to about 1 µM, about 800 pM to about 950 nM, about 800 pM to about 900 nM, about 800 pM to about 850 nM, about 800 pM to about 800 nM, about 800 pM to about 750 nM, about 800 pM to about 700 nM, about 800 pM to about 650 nM, about 800 pM to about 600 nM, about 800 pM to about 550 nM, about 800 pM to about 500 nM, about 800 pM to about 450 nM, about 800 pM to about 400 nM, about 800 pM to about 350 nM, about 800 pM to about 300 nM, about 800 pM to about 250 nM, about 800 pM to about 200 nM, about 800 pM to about 150 nM, about 800 pM to about 100 nM, about 800 pM to about 95 nM, about 800 pM to about 90 nM, about 800 pM to about 85 nM, about 800 pM to about 80 nM, about 800 pM to about 75 nM, about 800 pM to about 70 nM, about 800 pM to about 75 nM, about 800 pM to about 70 nM, about 800 pM to about 65 nM, about 800 pM to about 60 nM, about 800 pM to about 55 nM, about 800 pM to about 50 nM, about 800 pM to about 45 nM, about 800 pM to about 40 nM, about 800 pM to about 35 nM, about 800 pM to about 30 nM, about 800 pM to about 25 nM, about 800 pM to about 20 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 100 µM, about 900 pM to about 95 µM, about 900 pM to about 90 µM, about 900 pM to about 85 µM, about 900 pM to about 80 µM, about 900 pM to about 75 µM, about 900 pM to about 70 µM, about 900 pM to about 65 µM, about 900 pM to about 60 µM, about 900 pM to about 55 µM, about 900 pM to about 50 µM, about 900 pM to about 45 µM, about 900 pM to about 40 µM, about 900 pM to about 45 µM, about 900 pM to about 40 µM, about 900 pM to about 35 µM, about 900 pM to about 30 µM, about 900 pM to about 25 µM, about 900 pM to about 20 µM, about 900 pM to about 15 µM, about 900 pM to about 10 µM, about 900 pM to about 5 µM, about 900 pM to about 2 µM, about 900 pM to about 1 µM, about 900 pM to about 950 nM, about 900 pM to about 900 nM, about 900 pM to about 850 nM, about 900 pM to about 800 nM, about 900 pM to about 750 nM, about 900 pM to about 700 nM, about 900 pM to about 650 nM, about 900 pM to about 600 nM, about 900 pM to about 550 nM, about 900 pM to about 500 nM, about 900 pM to about 450 nM, about 900 pM to about 400 nM, about 900 pM to about 350 nM, about 900 pM to about 300 nM, about 900 pM to about 250 nM, about 900 pM to about 200 nM, about 900 pM to about 150 nM, about 900 pM to about 100 nM, about 900 pM to about 95 nM, about 900 pM to about 90 nM, about 900 pM to about 85 nM, about 900 pM to about 80 nM, about 900 pM to about 75 nM, about 900 pM to about 70 nM, about 900 pM to about 75 nM, about 900 pM to about 70 nM, about 900 pM to about 65 nM, about 900 pM to about 60 nM, about 900 pM to about 55 nM, about 900 pM to about 50 nM, about 900 pM to about 45 nM, about 900 pM to about 40 nM, about 900 pM to about 35 nM, about 900 pM to about 30 nM, about 900 pM to about 25 nM, about 900 pM to about 20 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 100 μM, about 1 nM to about 95 μM, about 1 nM to about 90 μM, about 1 nM to about 85 μM, about 1 nM to about 80 μM, about 1 nM to about 75 μM, about 1 nM to about 70 μM, about 1 nM to about 65 μM, about 1 nM to about 60 μM, about 1 nM to about 55 μM, about 1 nM to about 50 μM, about 1 nM to about 45 μM, about 1 nM to about 40 μM, about 1 nM to about 45 μM, about 1 nM to about 40 μM, about 1 nM to about 35 μM, about 1 nM to about 30 μM, about 1 nM to about 25 μM, about 1 nM to about 20 μM, about 1 nM to about 15 μM, about 1 nM to about 10 μM, about 1 nM to about 5 μM, about 1 nM to about 2 μM, about 1 nM to about 1 μM, about 1 nM to about 950 nM, about 1 nM to about 900 nM, about 1 nM to about 850 nM, about 1 nM to about 800 nM, about 1 nM to about 750 nM, about 1 nM to about 700 nM, about 1 nM to about 650 nM, about 1 nM to about 600 nM, about 1 nM to about 550 nM, about 1 nM to about 500 nM, about 1 nM to about 450 nM, about 1 nM to about 400 nM, about 1 nM to about 350 nM, about 1 nM to about 300 nM, about 1 nM to about 250 nM, about 1 nM to about 200 nM, about 1 nM to about 150 nM, about 1 nM to about 100 nM, about 1 nM to about 95 nM, about 1 nM to about 90 nM, about 1 nM to about 85 nM, about 1 nM to about 80 nM, about 1 nM to about 75 nM, about 1 nM to about 70 nM, about 1 nM to about 75 nM, about 1 nM to about 70 nM, about 1 nM to about 65 nM, about 1 nM to about 60 nM, about 1 nM to about 55 nM, about 1 nM to about 50 nM, about 1 nM to about 45 nM, about 1 nM to about 40 nM, about 1 nM to about 35 nM, about 1 nM to about 30 nM, about 1 nM to about 25 nM, about 1 nM to about 20 nM, about 1 nM to about 15 nM, about 1 nM to about 10 nM, about 1 nM to about 5 nM, about 1 nM to about 2 nM, about 2 nM to about 100 μM, about 2 nM to about 95 μM, about 2 nM to about 90 μM, about 2 nM to about 85 μM, about 2 nM to about 80 μM, about 2 nM to about 75 μM, about 2 nM to about 70 μM, about 2 nM to about 65 μM, about 2 nM to about 60 μM, about 2 nM to about 55 μM, about 2 nM to about 50 μM, about 2 nM to about 45 μM, about 2 nM to about 40 μM, about 2 nM to about 45 μM, about 2 nM to about 40 μM, about 2 nM to about 35 μM, about 2 nM to about 30 μM, about 2 nM to about 25 μM, about 2 nM to about 20 μM, about 2 nM to about 15 μM, about 2 nM to about 10 μM, about 2 nM to about 5 μM, about 2 nM to about 2 μM, about 2 nM to about 1 μM, about 2 nM to about 950 nM, about 2 nM to about 900 nM, about 2 nM to about 850 nM, about 2 nM to about 800 nM, about 2 nM to about 750 nM, about 2 nM to about 700 nM, about 2 nM to about 650 nM, about 2 nM to about 600 nM, about 2 nM to about 550 nM, about 2 nM to about 500 nM, about 2 nM to about 450 nM, about 2 nM to about 400 nM, about 2 nM to about 350 nM, about 2 nM to about 300 nM, about 2 nM to about 250 nM, about 2 nM to about 200 nM, about 2 nM to about 150 nM, about 2 nM to about 100 nM, about 2 nM to about 95 nM, about 2 nM to about 90 nM, about 2 nM to about 85 nM, about 2 nM to about 80 nM, about 2 nM to about 75 nM, about 2 nM to about 70 nM, about 2 nM to about 75 nM, about 2 nM to about 70 nM, about 2 nM to about 65 nM, about 2 nM to about 60 nM, about 2 nM to about 55 nM, about 2 nM to about 50 nM, about 2 nM to about 45 nM, about 2 nM to about 40 nM, about 2 nM to about 35 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 5 nM to about 100 μM, about 5 nM to about 95 μM, about 5 nM to about 90 μM, about 5 nM to about 85 μM, about 5 nM to about 80 μM, about 5 nM to about 75 μM, about 5 nM to about 70 μM, about 5 nM to about 65 μM, about 5 nM to about 60 μM, about 5 nM to about 55 μM, about 5 nM to about 50 μM, about 5 nM to about 45 μM, about 5 nM to about 40 μM, about 5 nM to about 45 μM, about 5 nM to about 40 μM, about 5 nM to about 35 μM, about 5 nM to about 30 μM, about 5 nM to about 25 μM, about 5 nM to about 20 μM, about 5 nM to about 15 μM, about 5 nM to about 10 μM, about 5 nM to about 5 μM, about 5 nM to about 2 μM, about 5 nM to about 1 μM, about 5 nM to about 950 nM, about 5 nM to about 900 nM, about 5 nM to about 850 nM, about 5 nM to about 800 nM, about 5 nM to about 750 nM, about 5 nM to about 700 nM, about 5 nM to about 650 nM, about 5 nM to about 600 nM, about 5 nM to about 550 nM, about 5 nM to about 500 nM, about 5 nM to about 450 nM, about 5 nM to about 400 nM, about 5 nM to about 350 nM, about 5 nM to about 300 nM, about 5 nM to about 250 nM, about 5 nM to about 200 nM, about 5 nM to about 150 nM, about 5 nM to about 100 nM, about 5 nM to about 95 nM, about 5 nM to about 90 nM, about 5 nM to about 85 nM, about 5 nM to about 80 nM, about 5 nM to about 75 nM, about 5 nM to about 70 nM, about 5 nM to about 75 nM, about 5 nM to about 70 nM, about 5 nM to about 65 nM, about 5 nM to about 60 nM, about 5 nM to about 55 nM, about 5 nM to about 50 nM, about 5 nM to about 45 nM, about 5 nM to about 40 nM, about 5 nM to about 35 nM, about 5 nM to about 30 nM, about 5 nM to about 25 nM, about 5 nM to about 20 nM, about 5 nM to about 15 nM, about 5 nM to about 10 nM, about 10 nM to about 100 μM, about 10 nM to about 95 μM, about 10 nM to about 90 μM, about 10 nM to about 85 μM, about 10 nM to about 80 μM, about 10 nM to about 75 μM, about 10 nM to about 70 μM, about 10 nM to about 65 μM, about 10 nM to about 60 μM, about 10 nM to about 55 μM, about 10 nM to about 50 μM, about 10 nM to about 45 μM, about 10 nM to about 40 μM, about 10 nM to about 45 μM, about 10 nM to about 40 μM, about 10 nM to about 35 μM, about 10 nM to about 30 μM, about 10 nM to about 25 μM, about 10 nM to about 20 μM, about 10 nM to about 15 μM, about 10 nM to about 10 μM, about 10 nM to about 5 μM, about 10 nM to about 2 μM, about 10 nM to about 1 μM, about 10 nM to about 950 nM, about 10 nM to about 900 nM, about 10 nM to about 850 nM, about 10 nM to about 800 nM, about 10 nM to about 750 nM, about 10 nM to about 700 nM, about 10 nM to about 650 nM, about 10 nM to about 600 nM, about 10 nM to about 550 nM, about 10 nM to about 500 nM, about 10 nM to about 450 nM, about 10 nM to about 400 nM, about 10 nM to about 350 nM, about 10 nM to about 300 nM, about 10 nM to about 250 nM, about 10 nM to about 200 nM, about 10 nM to about 150 nM, about 10 nM to about 100 nM, about 10 nM to about 95 nM, about 10 nM to about 90 nM, about 10 nM to about 85 nM, about 10 nM to about 80 nM, about 10 nM to about 75 nM, about 10 nM to about 70 nM, about 10 nM to about 75 nM, about 10 nM to about 70 nM, about 10 nM to about 65 nM, about 10 nM to about 60 nM, about 10 nM to about 55 nM, about 10 nM to about 50 nM, about 10 nM to about 45 nM, about 10 nM to about 40 nM, about 10 nM to about 35 nM, about 10 nM to about 30 nM, about 10 nM to about 25 nM, about 10 nM to about 20 nM, about 10 nM to about 15 nM, about 20 nM to about 100 µM, about 20 nM to about 95 µM, about 20 nM to about 90 µM, about 20 nM to about 85 µM, about 20 nM to about 80 µM, about 20 nM to about 75 µM, about 20 nM to about 70 µM, about 20 nM to about 65 µM, about 20 nM to about 60 µM, about 20 nM to about 55 µM, about 20 nM to about 50 µM, about 20 nM to about 45 µM, about 20 nM to about 40 µM, about 20 nM to about 45 µM, about 20 nM to about 40 µM, about 20 nM to about 35 µM, about 20 nM to about 30 µM, about 20 nM to about 25 µM, about 20 nM to about 20 µM, about 20 nM to about 15 µM, about 20 nM to about 10 µM, about 20 nM to about 5 µM, about 20 nM to about 2 µM, about 20 nM to about 1 µM, about 20 nM to about 950 nM, about 20 nM to about 900 nM, about 20 nM to about 850 nM, about 20 nM to about 800 nM, about 20 nM to about 750 nM, about 20 nM to about 700 nM, about 20 nM to about 650 nM, about 20 nM to about 600 nM, about 20 nM to about 550 nM, about 20 nM to about 500 nM, about 20 nM to about 450 nM, about 20 nM to about 400 nM, about 20 nM to about 350 nM, about 20 nM to about 300 nM, about 20 nM to about 250 nM, about 20 nM to about 200 nM, about 20 nM to about 150 nM, about 20 nM to about 100 nM, about 20 nM to about 95 nM, about 20 nM to about 90 nM, about 20 nM to about 85 nM, about 20 nM to about 80 nM, about 20 nM to about 75 nM, about 20 nM to about 75 nM, about 20 nM to about 70 nM, about 20 nM to about 65 nM, about 20 nM to about 60 nM, about 20 nM to about 55 nM, about 20 nM to about 50 nM, about 20 nM to about 45 nM, about 20 nM to about 40 nM, about 20 nM to about 35 nM, about 20 nM to about 30 nM, about 20 nM to about 25 nM, about 50 nM to about 100 µM, about 50 nM to about 95 µM, about 50 nM to about 90 µM, about 50 nM to about 85 µM, about 50 nM to about 80 µM, about 50 nM to about 75 µM, about 50 nM to about 70 µM, about 50 nM to about 65 µM, about 50 nM to about 60 µM, about 50 nM to about 55 µM, about 50 nM to about 50 µM, about 50 nM to about 45 µM, about 50 nM to about 40 µM, about 50 nM to about 45 µM, about 50 nM to about 40 µM, about 50 nM to about 35 µM, about 50 nM to about 30 µM, about 50 nM to about 25 µM, about 50 nM to about 20 µM, about 50 nM to about 15 µM, about 50 nM to about 10 µM, about 50 nM to about 5 µM, about 50 nM to about 2 µM, about 50 nM to about 1 µM, about 50 nM to about 950 nM, about 50 nM to about 900 nM, about 50 nM to about 850 nM, about 50 nM to about 800 nM, about 50 nM to about 750 nM, about 50 nM to about 700 nM, about 50 nM to about 650 nM, about 50 nM to about 600 nM, about 50 nM to about 550 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 150 nM, about 50 nM to about 100 nM, about 50 nM to about 95 nM, about 50 nM to about 90 nM, about 50 nM to about 85 nM, about 50 nM to about 80 nM, about 50 nM to about 75 nM, about 50 nM to about 75 nM, about 50 nM to about 70 nM, about 50 nM to about 70 nM, about 50 nM to about 65 nM, about 50 nM to about 60 nM, about 50 nM to about 55 nM, about 100 nM to about 100 µM, about 100 nM to about 95 µM, about 100 nM to about 90 µM, about 100 nM to about 85 µM, about 100 nM to about 80 µM, about 100 nM to about 75 µM, about 100 nM to about 70 µM, about 100 nM to about 65 µM, about 100 nM to about 60 µM, about 100 nM to about 55 µM, about 100 nM to about 50 µM, about 100 nM to about 45 µM, about 100 nM to about 40 µM, about 100 nM to about 45 µM, about 100 nM to about 40 µM, about 100 nM to about 35 µM, about 100 nM to about 30 µM, about 100 nM to about 25 µM, about 100 nM to about 20 µM, about 100 nM to about 15 µM, about 100 nM to about 10 µM, about 100 nM to about 5 µM, about 100 nM to about 2 µM, about 100 nM to about 1 µM, about 100 nM to about 950 nM, about 100 nM to about 900 nM, about 100 nM to about 850 nM, about 100 nM to about 800 nM, about 100 nM to about 750 nM, about 100 nM to about 700 nM, about 100 nM to about 650 nM, about 100 nM to about 600 nM, about 100 nM to about 550 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 150 nM, about 200 nM to about 100 µM, about 200 nM to about 95 µM, about 200 nM to about 90 µM, about 200 nM to about 85 µM, about 200 nM to about 80 µM, about 200 nM to about 75 µM, about 200 nM to about 70 µM, about 200 nM to about 65 µM, about 200 nM to about 60 µM, about 200 nM to about 55 µM, about 200 nM to about 50 µM, about 200 nM to about 45 µM, about 200 nM to about 40 µM, about 200 nM to about 45 µM, about 200 nM to about 40 µM, about 200 nM to about 35 µM, about 200 nM to about 30 µM, about 200 nM to about 25 µM, about 200 nM to about 20 µM, about 200 nM to about 15 µM, about 200 nM to about 10 µM, about 200 nM to about 5 µM, about 200 nM to about 2 µM, about 200 nM to about 1 pM, about 200 nM to about 950 nM, about 200 nM to about 900 nM, about 200 nM to about 850 nM, about 200 nM to about 800 nM, about 200 nM to about 750 nM, about 200 nM to about 700 nM, about 200 nM to about 650 nM, about 200 nM to about 600 nM, about 200 nM to about 550 nM, about 200 nM to about 500 nM, about 200 nM to about 450 nM, about 200 nM to about 400 nM, about 200 nM to about 350 nM, about 200 nM to about 300 nM, about 200 nM to about 250 nM, about 300 nM to about 100 µM, about 300 nM to about 95 µM, about 300 nM to about 90 µM, about 300 nM to about 85 µM, about 300 nM to about 80 µM, about 300 nM to about 75 µM, about 300 nM to about 70 µM, about 300 nM to about 65 µM, about 300 nM to about 60 µM, about 300 nM to about 55 µM, about 300 nM to about 50 µM, about 300 nM to about 45 µM, about 300 nM to about 40 µM, about 300 nM to about 45 µM, about 300 nM to about 40 µM, about 300 nM to about 35 µM, about 300 nM to about 30 µM, about 300 nM to about 25 µM, about 300 nM to about 20 µM, about 300 nM to about 15 µM, about 300 nM to about 10 µM, about 300 nM to about 5 µM, about 300 nM to about 2 µM, about 300 nM to about 1 µM, about 300 nM to about 950 nM, about 300 nM to about 900 nM, about 300 nM to about 850 nM, about 300 nM to about 800 nM, about 300 nM to about 750 nM, about 300 nM to about 700 nM, about 300 nM to about 650 nM, about 300 nM to about 600 nM, about 300 nM to about 550 nM, about 300 nM to about 500 nM, about 300 nM to about 450 nM, about 300 nM to about 400 nM, about 300 nM to about 350 nM, about 400 nM to about 100 µM, about 400 nM to about 95 µM, about 400 nM to about 90 µM, about 400 nM to about 85 µM, about 400 nM to about 80 µM, about 400 nM to about 75 µM, about 400 nM to about 70 µM, about 400 nM to about 65 µM, about 400 nM to about 60 µM, about 400 nM to about 55 µM, about 400 nM to about 50 µM, about 400 nM to about 45 µM, about 400 nM to about 40 µM, about 400 nM to about 45 µM, about 400 nM to about 40 µM, about 400 nM to about 35 µM, about 400 nM to about 30 µM, about 400 nM to about 25 µM, about 400 nM to about 20 µM, about 400 nM to about 15 µM, about 400 nM to about 10 µM, about 400 nM to about 5 µM, about 400 nM to about 2 µM, about 400 nM to about 1 µM, about 400 nM to about 950 nM, about 400 nM to about 900 nM, about 400 nM to about 850 nM, about 400 nM to about 800 nM, about 400 nM to about 750 nM, about 400 nM to about 700 nM, about 400 nM to about 650 nM, about 400 nM to about 600 nM, about 400 nM to about 550 nM, about 400 nM to about 500 nM, about 400 nM to about 450 nM, about 500 nM to about 100 μM, about 500 nM to about 95 μM, about 500 nM to about 90 μM, about 500 nM to about 85 μM, about 500 nM to about 80 μM, about 500 nM to about 75 μM, about 500 nM to about 70 μM, about 500 nM to about 65 μM, about 500 nM to about 60 μM, about 500 nM to about 55 μM, about 500 nM to about 50 μM, about 500 nM to about 45 μM, about 500 nM to about 40 μM, about 500 nM to about 45 μM, about 500 nM to about 40 μM, about 500 nM to about 35 μM, about 500 nM to about 30 μM, about 500 nM to about 25 μM, about 500 nM to about 20 μM, about 500 nM to about 15 μM, about 500 nM to about 10 μM, about 500 nM to about 5 μM, about 500 nM to about 2 μM, about 500 nM to about 1 μM, about 500 nM to about 950 nM, about 500 nM to about 900 nM, about 500 nM to about 850 nM, about 500 nM to about 800 nM, about 500 nM to about 750 nM, about 500 nM to about 700 nM, about 500 nM to about 650 nM, about 500 nM to about 600 nM, about 500 nM to about 550 nM, about 600 nM to about 100 μM, about 600 nM to about 95 μM, about 600 nM to about 90 μM, about 600 nM to about 85 μM, about 600 nM to about 80 μM, about 600 nM to about 75 μM, about 600 nM to about 70 μM, about 600 nM to about 65 μM, about 600 nM to about 60 μM, about 600 nM to about 55 μM, about 600 nM to about 50 μM, about 600 nM to about 45 μM, about 600 nM to about 40 μM, about 600 nM to about 45 μM, about 600 nM to about 40 μM, about 600 nM to about 35 μM, about 600 nM to about 30 μM, about 600 nM to about 25 μM, about 600 nM to about 20 μM, about 600 nM to about 15 μM, about 600 nM to about 10 μM, about 600 nM to about 5 μM, about 600 nM to about 2 μM, about 600 nM to about 1 μM, about 600 nM to about 950 nM, about 600 nM to about 900 nM, about 600 nM to about 850 nM, about 600 nM to about 800 nM, about 600 nM to about 750 nM, about 600 nM to about 700 nM, about 600 nM to about 650 nM, about 700 nM to about 100 μM, about 700 nM to about 95 μM, about 700 nM to about 90 μM, about 700 nM to about 85 μM, about 700 nM to about 80 μM, about 700 nM to about 75 μM, about 700 nM to about 70 μM, about 700 nM to about 65 μM, about 700 nM to about 60 μM, about 700 nM to about 55 μM, about 700 nM to about 50 μM, about 700 nM to about 45 μM, about 700 nM to about 40 μM, about 700 nM to about 45 μM, about 700 nM to about 40 μM, about 700 nM to about 35 μM, about 700 nM to about 30 μM, about 700 nM to about 25 μM, about 700 nM to about 20 μM, about 700 nM to about 15 μM, about 700 nM to about 10 μM, about 700 nM to about 5 μM, about 700 nM to about 2 μM, about 700 nM to about 1 μM, about 700 nM to about 950 nM, about 700 nM to about 900 nM, about 700 nM to about 850 nM, about 700 nM to about 800 nM, about 700 nM to about 750 nM, about 800 nM to about 100 μM, about 800 nM to about 95 μM, about 800 nM to about 90 μM, about 800 nM to about 85 μM, about 800 nM to about 80 μM, about 800 nM to about 75 μM, about 800 nM to about 70 μM, about 800 nM to about 65 μM, about 800 nM to about 60 μM, about 800 nM to about 55 μM, about 800 nM to about 50 μM, about 800 nM to about 45 μM, about 800 nM to about 40 μM, about 800 nM to about 45 μM, about 800 nM to about 40 μM, about 800 nM to about 35 μM, about 800 nM to about 30 μM, about 800 nM to about 25 μM, about 800 nM to about 20 μM, about 800 nM to about 15 μM, about 800 nM to about 10 μM, about 800 nM to about 5 μM, about 800 nM to about 2 μM, about 800 nM to about 1 μM, about 800 nM to about 950 nM, about 800 nM to about 900 nM, about 800 nM to about 850 nM, about 900 nM to about 100 μM, about 900 nM to about 95 μM, about 900 nM to about 90 μM, about 900 nM to about 85 μM, about 900 nM to about 80 μM, about 900 nM to about 75 μM, about 900 nM to about 70 μM, about 900 nM to about 65 μM, about 900 nM to about 60 μM, about 900 nM to about 55 μM, about 900 nM to about 50 μM, about 900 nM to about 45 μM, about 900 nM to about 40 μM, about 900 nM to about 45 μM, about 900 nM to about 40 μM, about 900 nM to about 35 μM, about 900 nM to about 30 μM, about 900 nM to about 25 μM, about 900 nM to about 20 μM, about 900 nM to about 15 μM, about 900 nM to about 10 μM, about 900 nM to about 5 μM, about 900 nM to about 2 μM, about 900 nM to about 1 μM, about 900 nM to about 950 nM, about 1 μM to about 100 μM, about 1 μM to about 95 μM, about 1 μM to about 90 μM, about 1 μM to about 85 μM, about 1 μM to about 80 μM, about 1 μM to about 75 pM, about 1 μM to about 70 μM, about 1 μM to about 65 μM, about 1 μM to about 60 μM, about 1 μM to about 55 μM, about 1 μM to about 50 μM, about 1 μM to about 45 μM, about 1 μM to about 40 μM, about 1 μM to about 45 μM, about 1 μM to about 40 μM, about 1 μM to about 35 μM, about 1 μM to about 30 μM, about 1 μM to about 25 μM, about 1 μM to about 20 μM, about 1 μM to about 15 μM, about 1 μM to about 10 μM, about 1 μM to about 5 μM, about 1 μM to about 2 μM, about 2 μM to about 100 μM, about 2 μM to about 95 μM, about 2 μM to about 90 μM, about 2 μM to about 85 μM, about 2 μM to about 80 μM, about 2 μM to about 75 μM, about 2 μM to about 70 μM, about 2 μM to about 65 μM, about 2 μM to about 60 μM, about 2 μM to about 55 μM, about 2 μM to about 50 μM, about 2 μM to about 45 μM, about 2 μM to about 40 μM, about 2 μM to about 45 μM, about 2 μM to about 40 μM, about 2 μM to about 35 μM, about 2 μM to about 30 μM, about 2 μM to about 25 μM, about 2 μM to about 20 μM, about 2 μM to about 15 μM, about 2 μM to about 10 μM, about 2 μM to about 5 μM, about 5 μM to about 100 μM, about 5 μM to about 95 μM, about 5 LM to about 90 μM, about 5 μM to about 85 μM, about 5 μM to about 80 μM, about 5 μM to about 75 μM, about 5 μM to about 70 μM, about 5 μM to about 65 μM, about 5 μM to about 60 μM, about 5 μM to about 55 μM, about 5 μM to about 50 μM, about 5 μM to about 45 μM, about 5 μM to about 40 μM, about 5 μM to about 45 pM, about 5 μM to about 40 μM, about 5 μM to about 35 μM, about 5 μM to about 30 μM, about 5 μM to about 25 μM, about 5 μM to about 20 μM, about 5 μM to about 15 μM, about 5 μM to about 10 μM, about 10 μM to about 100 μM, about 10 μM to about 95 μM, about 10 μM to about 90 μM, about 10 μM to about 85 μM, about 10 μM to about 80 μM, about 10 μM to about 75 μM, about 10 μM to about 70 μM, about 10 μM to about 65 μM, about 10 μM to about 60 μM, about 10 μM to about 55 μM, about μM to about 50 μM, about 10 μM to about 45 pM, about 10 μM to about 40 μM, about 10 μM to about 45 μM, about 10 μM to about 40 μM, about 10 μM to about 35 μM, about 10 μM to about 30 μM, about 10 μM to about 25 μM, about 10 μM to about 20 μM, about 10 μM to about 15 μM, about 20 μM to about 100 μM, about 20 μM to about 95 μM, about 20 μM to about 90 μM, about 20 μM to about 85 μM, about 20 μM to about 80 μM, about 20 μM to about 75 μM, about 20 μM to about 70 μM, about 20 μM to about 65 μM, about 20 μM to about 60 μM, about 20 μM to about 55 μM, about 20 μM to about 50 μM, about 20 μM to about 45 μM, about 20 μM to about 40 μM, about 20 μM to about 45 μM, about 20 μM to about 40 μM, about 20 μM to about 35 μM, about 20 µM to about 30 µM, about 20 µM to about 25 µM, about 30 µM to about 100 µM, about 30 µM to about 95 µM, about 30 µM to about 90 µM, about 30 µM to about 85 µM, about 30 µM to about 80 µM, about 30 µM to about 75 µM, about 30 µM to about 70 µM, about 30 µM to about 65 µM, about 30 µM to about 60 µM, about 30 µM to about 55 µM, about 30 µM to about 50 µM, about 30 µM to about 45 µM, about 30 µM to about 40 µM, about 30 µM to about 45 µM, about 30 µM to about 40 µM, about 30 µM to about 35 µM, about 40 µM to about 100 µM, about 40 µM to about 95 µM, about 40 µM to about 90 µM, about 40 µM to about 85 µM, about 40 µM to about 80 µM, about 40 µM to about 75 µM, about 40 µM to about 70 µM, about 40 µM to about 65 µM, about 40 µM to about 60 µM, about 40 µM to about 55 µM, about 40 µM to about 50 µM, about 40 µM to about 45 µM, about 50 µM to about 100 µM, about 50 µM to about 95 µM, about 50 µM to about 90 µM, about 50 µM to about 85 µM, about 50 µM to about 80 µM, about 50 µM to about 75 µM, about 50 µM to about 70 µM, about 50 µM to about 65 µM, about 50 µM to about 60 µM, about 50 µM to about 55 µM, about 60 µM to about 100 µM, about 60 µM to about 95 µM, about 60 µM to about 90 µM, about 60 µM to about 85 µM, about 60 µM to about 80 µM, about 60 µM to about 75 µM, about 60 µM to about 70 µM, about 60 µM to about 65 µM, about 70 µM to about 100 µM, about 70 µM to about 95 µM, about 70 µM to about 90 µM, about 70 µM to about 85 µM, about 70 µM to about 80 µM, about 70 µM to about 75 µM, about 80 µM to about 100 µM, about 80 µM to about 95 µM, about 80 µM to about 90 µM, about 80 µM to about 85 µM, about 90 µM to about 100 pM, or about 90 µM to about 95 µM) (e.g., as measured using SPR in phosphate buffered saline).

In some embodiments, the chimeric polypeptides described herein can have a total length of about 20 amino acids to about 1400 amino acids, about 20 amino acids to about 1350 amino acids, about 20 amino acids to about 1300 amino acids, about 20 amino acids to about 1250 amino acids, about 20 amino acids to about 1200 amino acids, about 20 amino acids to about 1150 amino acids, about 20 amino acids to about 1100 amino acids, about 20 amino acid to about 1050 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 250 amino acids, about 20 amino acids to about 200 amino acids, about 20 amino acids to about 150 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1400 amino acids, about 25 amino acids to about 1350 amino acids, about 25 amino acids to about 1300 amino acids, about 25 amino acids to about 1250 amino acids, about 25 amino acids to about 1200 amino acids, about 25 amino acids to about 1150 amino acids, about 25 amino acids to about 1100 amino acids, about 25 amino acid to about 1050 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 250 amino acids, about 25 amino acids to about 200 amino acids, about 25 amino acids to about 150 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1400 amino acids, about 30 amino acids to about 1350 amino acids, about 30 amino acids to about 1300 amino acids, about 30 amino acids to about 1250 amino acids, about 30 amino acids to about 1200 amino acids, about 30 amino acids to about 1150 amino acids, about 30 amino acids to about 1100 amino acids, about 30 amino acid to about 1050 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 250 amino acids, about 30 amino acids to about 200 amino acids, about 30 amino acids to about 150 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1400 amino acids, about 35 amino acids to about 1350 amino acids, about 35 amino acids to about 1300 amino acids, about 35 amino acids to about 1250 amino acids, about 35 amino acids to about 1200 amino acids, about 35 amino acids to about 1150 amino acids, about 35 amino acids to about 1100 amino acids, about 35 amino acid to about 1050 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 250 amino acids, about 35 amino acids to about 200 amino acids, about 35 amino acids to about 150 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 1400 amino acids, about 40 amino acids to about 1350 amino acids, about 40 amino acids to about 1300 amino acids, about 40 amino acids to about 1250 amino acids, about 40 amino acids to about 1200 amino acids, about 40 amino acids to about 1150 amino acids, about 40 amino acids to about 1100 amino acids, about 40 amino acid to about 1050 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 150 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 1400 amino acids, about 45 amino acids to about 1350 amino acids, about 45 amino acids to about 1300 amino acids, about 45 amino acids to about 1250 amino acids, about 45 amino acids to about 1200 amino acids, about 45 amino acids to about 1150 amino acids, about 45 amino acids to about 1100 amino acids, about 45 amino acid to about 1050 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 250 amino acids, about 45 amino acids to about 200 amino acids, about 45 amino acids to about 150 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 1400 amino acids, about 50 amino acids to about 1350 amino acids, about 50 amino acids to about 1300 amino acids, about 50 amino acids to about 1250 amino acids, about 50 amino acids to about 1200 amino acids, about 50 amino acids to about 1150 amino acids, about 50 amino acids to about 1100 amino acids, about 50 amino acid to about 1050 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 1400 amino acids, about 60 amino acids to about 1350 amino acids, about 60 amino acids to about 1300 amino acids, about 60 amino acids to about 1250 amino acids, about 60 amino acids to about 1200 amino acids, about 60 amino acids to about 1150 amino acids, about 60 amino acids to about 1100 amino acids, about 60 amino acid to about 1050 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 150 amino acids, about 60 amino acids to about 100 amino acids, about 60 amino acids to about 90 amino acids, about 60 amino acids to about 80 amino acids, about 60 amino acids to about 70 amino acids, about 70 amino acids to about 1400 amino acids, about 70 amino acids to about 1350 amino acids, about 70 amino acids to about 1300 amino acids, about 70 amino acids to about 1250 amino acids, about 70 amino acids to about 1200 amino acids, about 70 amino acids to about 1150 amino acids, about 70 amino acids to about 1100 amino acids, about 70 amino acid to about 1050 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 250 amino acids, about 70 amino acids to about 200 amino acids, about 70 amino acids to about 150 amino acids, about 70 amino acids to about 100 amino acids, about 70 amino acids to about 90 amino acids, about 70 amino acids to about 80 amino acids, about 80 amino acids to about 1400 amino acids, about 80 amino acids to about 1350 amino acids, about 80 amino acids to about 1300 amino acids, about 80 amino acids to about 1250 amino acids, about 80 amino acids to about 1200 amino acids, about 80 amino acids to about 1150 amino acids, about 80 amino acids to about 1100 amino acids, about 80 amino acid to about 1050 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 150 amino acids, about 80 amino acids to about 100 amino acids, about 80 amino acids to about 90 amino acids, about 90 amino acids to about 1400 amino acids, about 90 amino acids to about 1350 amino acids, about 90 amino acids to about 1300 amino acids, about 90 amino acids to about 1250 amino acids, about 90 amino acids to about 1200 amino acids, about 90 amino acids to about 1150 amino acids, about 90 amino acids to about 1100 amino acids, about 90 amino acid to about 1050 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 250 amino acids, about 90 amino acids to about 200 amino acids, about 90 amino acids to about 150 amino acids, about 90 amino acids to about 100 amino acids, about 100 amino acids to about 1400 amino acids, about 100 amino acids to about 1350 amino acids, about 100 amino acids to about 1300 amino acids, about 100 amino acids to about 1250 amino acids, about 100 amino acids to about 1200 amino acids, about 100 amino acids to about 1150 amino acids, about 100 amino acids to about 1100 amino acids, about 100 amino acid to about 1050 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 1400 amino acids, about 150 amino acids to about 1350 amino acids, about 150 amino acids to about 1300 amino acids, about 150 amino acids to about 1250 amino acids, about 150 amino acids to about 1200 amino acids, about 150 amino acids to about 1150 amino acids, about 150 amino acids to about 1100 amino acids, about 150 amino acid to about 1050 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 1400 amino acids, about 200 amino acids to about 1350 amino acids, about 200 amino acids to about 1300 amino acids, about 200 amino acids to about 1250 amino acids, about 200 amino acids to about 1200 amino acids, about 200 amino acids to about 1150 amino acids, about 200 amino acids to about 1100 amino acids, about 200 amino acid to about 1050 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 1400 amino acids, about 250 amino acids to about 1350 amino acids, about 250 amino acids to about 1300 amino acids, about 250 amino acids to about 1250 amino acids, about 250 amino acids to about 1200 amino acids, about 250 amino acids to about 1150 amino acids, about 250 amino acids to about 1100 amino acids, about 250 amino acid to about 1050 amino acids, about 250 amino acids to about 1000 amino acids, about 250 amino acids to about 950 amino acids, about 250 amino acids to about 900 amino acids, about 250 amino acids to about 850 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 1400 amino acids, about 300 amino acids to about 1350 amino acids, about 300 amino acids to about 1300 amino acids, about 300 amino acids to about 1250 amino acids, about 300 amino acids to about 1200 amino acids, about 300 amino acids to about 1150 amino acids, about 300 amino acids to about 1100 amino acids, about 300 amino acid to about 1050 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1400 amino acids, about 350 amino acids to about 1350 amino acids, about 350 amino acids to about 1300 amino acids, about 350 amino acids to about 1250 amino acids, about 350 amino acids to about 1200 amino acids, about 350 amino acids to about 1150 amino acids, about 350 amino acids to about 1100 amino acids, about 350 amino acid to about 1050 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1400 amino acids, about 400 amino acids to about 1350 amino acids, about 400 amino acids to about 1300 amino acids, about 400 amino acids to about 1250 amino acids, about 400 amino acids to about 1200 amino acids, about 400 amino acids to about 1150 amino acids, about 400 amino acids to about 1100 amino acids, about 400 amino acid to about 1050 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1400 amino acids, about 450 amino acids to about 1350 amino acids, about 450 amino acids to about 1300 amino acids, about 450 amino acids to about 1250 amino acids, about 450 amino acids to about 1200 amino acids, about 450 amino acids to about 1150 amino acids, about 450 amino acids to about 1100 amino acids, about 450 amino acid to about 1050 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1400 amino acids, about 500 amino acids to about 1350 amino acids, about 500 amino acids to about 1300 amino acids, about 500 amino acids to about 1250 amino acids, about 500 amino acids to about 1200 amino acids, about 500 amino acids to about 1150 amino acids, about 500 amino acids to about 1100 amino acids, about 500 amino acid to about 1050 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1400 amino acids, about 550 amino acids to about 1350 amino acids, about 550 amino acids to about 1300 amino acids, about 550 amino acids to about 1250 amino acids, about 550 amino acids to about 1200 amino acids, about 550 amino acids to about 1150 amino acids, about 550 amino acids to about 1100 amino acids, about 550 amino acid to about 1050 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1400 amino acids, about 600 amino acids to about 1350 amino acids, about 600 amino acids to about 1300 amino acids, about 600 amino acids to about 1250 amino acids, about 600 amino acids to about 1200 amino acids, about 600 amino acids to about 1150 amino acids, about 600 amino acids to about 1100 amino acids, about 600 amino acid to about 1050 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1400 amino acids, about 650 amino acids to about 1350 amino acids, about 650 amino acids to about 1300 amino acids, about 650 amino acids to about 1250 amino acids, about 650 amino acids to about 1200 amino acids, about 650 amino acids to about 1150 amino acids, about 650 amino acids to about 1100 amino acids, about 650 amino acid to about 1050 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1400 amino acids, about 700 amino acids to about 1350 amino acids, about 700 amino acids to about 1300 amino acids, about 700 amino acids to about 1250 amino acids, about 700 amino acids to about 1200 amino acids, about 700 amino acids to about 1150 amino acids, about 700 amino acids to about 1100 amino acids, about 700 amino acid to about 1050 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1400 amino acids, about 750 amino acids to about 1350 amino acids, about 750 amino acids to about 1300 amino acids, about 750 amino acids to about 1250 amino acids, about 750 amino acids to about 1200 amino acids, about 750 amino acids to about 1150 amino acids, about 750 amino acids to about 1100 amino acids, about 750 amino acid to about 1050 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1400 amino acids, about 800 amino acids to about 1350 amino acids, about 800 amino acids to about 1300 amino acids, about 800 amino acids to about 1250 amino acids, about 800 amino acids to about 1200 amino acids, about 800 amino acids to about 1150 amino acids, about 800 amino acids to about 1100 amino acids, about 800 amino acid to about 1050 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1400 amino acids, about 850 amino acids to about 1350 amino acids, about 850 amino acids to about 1300 amino acids, about 850 amino acids to about 1250 amino acids, about 850 amino acids to about 1200 amino acids, about 850 amino acids to about 1150 amino acids, about 850 amino acids to about 1100 amino acids, about 850 amino acid to about 1050 amino acids, about 850 amino acids to about 1000 amino acids, about 850 amino acids to about 950 amino acids, about 850 amino acids to about 900 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acid to about 1050 amino acids, about 900 amino acids to about 1000 amino acids, about 900 amino acids to about 950 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acid to about 1050 amino acids, about 950 amino acids to about 1000 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acid to about 1050 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1400 amino acids, about 1250 amino acids to about 1350 amino acids, about 1250 amino acids to about 1300 amino acids, about 1300 amino acids to about 1400 amino acids, about 1300 amino acids to about 1350 amino acids, or about 1350 amino acids to about 1400 amino acids.

For example, the chimeric polypeptide may include: LLADTTHHRPWTVIGESTHHRPWSIIGESSHHKPF-TGLGDTTHHRPWGILAESTHHKPWT A TGGSGEGGT-GASTGGSAGTGGSGGTTSGEAGGSSGAG (SEQ ID NO: 44). In some instances the chimeric polypeptide includes a β-TCP binding sequence and a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 44.

For example, the chimeric polypeptide may include: LLADTTHHRPWTGLGDTTHHRPWGLLADTTHHRP-WTGLGDTTHHRPWGLLADTTHHR PWT TGGSGEG-GTGASTGGSAGTGGSGGTTSGEAGGSSGAG (SEQ ID NO: 45. In some instances the chimeric polypeptide includes a β-TCP binding sequence and a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 45.

A variety of different methods known in the art can be used to determine the $K_D$ values of any of the chimeric polypeptides described herein for binding to β-TCP (e.g., any of the types of β-TCP described herein) (e.g., an electrophoretic mobility shift assay, a filter binding assay, surface plasmon resonance, and a biomolecular binding kinetics assay, etc.) The chimeric polypeptides provided herein are useful orthopedic materials, and can be used as bone void fillers and for bone reconstructions. The chimeric polypeptides described herein are osteo-conductive and easily resorbed.

Linkers

In some instances, a neighboring pair (or each neighboring pair) of two β-TCP binding sequences directly abut each other. In other instances, a neighboring pair (or each neighboring pair) of two β-TCP binding sequences are separated by a linker sequence. For example, a linker sequence can be 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 95 amino acids, about 2 amino acids to about 90 amino acids, about 2 amino acids to about 85 amino acids, about 2 amino acids to about 80 amino acids, about 2 amino acids to about 75 amino acids, about 2 amino acids to about 70 amino acids, about 2 amino acids to about 65 amino acids, about 2 amino acids to about 60 amino acids, about 2 amino acids to about 55 amino acids, about 2 amino acids to about 50 amino acids, about 2 amino acids to about 45 amino acids, about 2 amino acids to about 40 amino acids, about 2 amino acids to about 38 amino acids, about 2 amino acids to about 36 amino acids, about 2 amino acids to about 34 amino acids, about 2 amino acids to about 32 amino acids, about 2 amino acids to about 30 amino acids, about 2 amino acids to about 28 amino acids, about 2 amino acids to about 26 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 95 amino acids, about 4 amino acids to about 90 amino acids, about 4 amino acids to about 85 amino acids, about 4 amino acids to about 80 amino acids, about 4 amino acids to about 75 amino acids, about 4 amino acids to about 70 amino acids, about 4 amino acids to about 65 amino acids, about 4 amino acids to about 60 amino acids, about 4 amino acids to about 55 amino acids, about 4 amino acids to about 50 amino acids, about 4 amino acids to about 45 amino acids, about 4 amino acids to about 40 amino acids, about 4 amino acids to about 38 amino acids, about 4 amino acids to about 36 amino acids, about 4 amino acids to about 34 amino acids, about 4 amino acids to about 32 amino acids, about 4 amino acids to about 30 amino acids, about 4 amino acids to about 28 amino acids, about 4 amino acids to about 26 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 95 amino acids, about 6 amino acids to about 90 amino acids, about 6 amino acids to about 85 amino acids, about 6 amino acids to about 80 amino acids, about 6 amino acids to about 75 amino acids, about 6 amino acids to about 70 amino acids, about 6 amino acids to about 65 amino acids, about 6 amino acids to about 60 amino acids, about 6 amino acids to about 55 amino acids, about 6 amino acids to about 50 amino acids, about 6 amino acids to about 45 amino acids, about 6 amino acids to about 40 amino acids, about 6 amino acids to about 38 amino acids, about 6 amino acids to about 36 amino acids, about 6 amino acids to about 34 amino acids, about 6 amino acids to about 32 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 95 amino acids, about 8 amino acids to about 90 amino acids, about 8 amino acids to about 85 amino acids, about 8 amino acids to about 80 amino acids, about 8 amino acids to about 75 amino acids, about 8 amino acids to about 70 amino acids, about 8 amino acids to about 65 amino acids, about 8 amino acids to about 60 amino acids, about 8 amino acids to about 55 amino acids, about 8 amino acids to about 50 amino acids, about 8 amino acids to about 45 amino acids, about 8 amino acids to about 40 amino acids, about 8 amino acids to about 38 amino acids, about 8 amino acids to about 36 amino acids, about 8 amino acids to about 34 amino acids, about 8 amino acids to about 32 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 38 amino acids, about 10 amino acids to about 36 amino acids, about 10 amino acids to about 34 amino acids, about 10 amino acids to about 32 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 95 amino acids, about 12 amino acids to about 90 amino acids, about 12 amino acids to about 85 amino acids, about 12 amino acids to about 80 amino acids, about 12 amino acids to about 75 amino acids, about 12 amino acids to about 70 amino acids, about 12 amino acids to about 65 amino acids, about 12 amino acids to about 60 amino acids, about 12 amino acids to about 55 amino acids, about 12 amino acids to about 50 amino acids, about 12 amino acids to about 45 amino acids, about 12 amino acids to about 40 amino acids, about 12 amino acids to about 38 amino acids, about 12 amino acids to about 36 amino acids, about 12 amino acids to about 34 amino acids, about 12 amino acids to about 32 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 95 amino acids, about 14 amino acids to about 90 amino acids, about 14 amino acids to about 85 amino acids, about 14 amino acids to about 80 amino acids, about 14 amino acids to about 75 amino acids, about 14 amino acids to about 70 amino acids, about 14 amino acids to about 65 amino acids, about 14 amino acids to about 60 amino acids, about 14 amino acids to about 55 amino acids, about 14 amino acids to about 50 amino acids, about 14 amino acids to about 45 amino acids, about 14 amino acids to about 40 amino acids, about 14 amino acids to about 38 amino acids, about 14 amino acids to about 36 amino acids, about 14 amino acids to about 34 amino acids, about 14 amino acids to about 32 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 95 amino acids, about 16 amino acids to about 90 amino acids, about 16 amino acids to about 85 amino acids, about 16 amino acids to about 80 amino acids, about 16 amino acids to about 75 amino acids, about 16 amino acids to about 70 amino acids, about 16 amino acids to about 65 amino acids, about 16 amino acids to about 60 amino acids, about 16 amino acids to about 55 amino acids, about 16 amino acids to about 50 amino acids, about 16 amino acids to about 45 amino acids, about 16 amino acids to about 40 amino acids, about 16 amino acids to about 38 amino acids, about 16 amino acids to about 36 amino acids, about 16 amino acids to about 34 amino acids, about 16 amino acids to about 32 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 95 amino acids, about 18 amino acids to about 90 amino acids, about 18 amino acids to about 85 amino acids, about 18 amino acids to about 80 amino acids, about 18 amino acids to about 75 amino acids, about 18 amino acids to about 70 amino acids, about 18 amino acids to about 65 amino acids, about 18 amino acids to about 60 amino acids, about 18 amino acids to about 55 amino acids, about 18 amino acids to about 50 amino acids, about 18 amino acids to about 45 amino acids, about 18 amino acids to about 40 amino acids, about 18 amino acids to about 38 amino acids, about 18 amino acids to about 36 amino acids, about 18 amino acids to about 34 amino acids, about 18 amino acids to about 32 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 38 amino acids, about 20 amino acids to about 36 amino acids, about 20 amino acids to about 34 amino acids, about 20 amino acids to about 32 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 100 amino acids, about 22 amino acids to about 95 amino acids, about 22 amino acids to about 90 amino acids, about 22 amino acids to about 85 amino acids, about 22 amino acids to about 80 amino acids, about 22 amino acids to about 75 amino acids, about 22 amino acids to about 70 amino acids, about 22 amino acids to about 65 amino acids, about 22 amino acids to about 60 amino acids, about 22 amino acids to about 55 amino acids, about 22 amino acids to about 50 amino acids, about 22 amino acids to about 45 amino acids, about 22 amino acids to about 40 amino acids, about 22 amino acids to about 38 amino acids, about 22 amino acids to about 36 amino acids, about 22 amino acids to about 34 amino acids, about 22 amino acids to about 32 amino acids, about 22 amino acids to about 30 amino acids, about 22 amino acids to about 28 amino acids, about 22 amino acids to about 26 amino acids, about 22 amino acids to about 24 amino acids, about 24 amino acids to about 100 amino acids, about 24 amino acids to about 95 amino acids, about 24 amino acids to about 90 amino acids, about 24 amino acids to about 85 amino acids, about 24 amino acids to about 80 amino acids, about 24 amino acids to about 75 amino acids, about 24 amino acids to about 70 amino acids, about 24 amino acids to about 65 amino acids, about 24 amino acids to about 60 amino acids, about 24 amino acids to about 55 amino acids, about 24 amino acids to about 50 amino acids, about 24 amino acids to about 45 amino acids, about 24 amino acids to about 40 amino acids, about 24 amino acids to about 38 amino acids, about 24 amino acids to about 36 amino acids, about 24 amino acids to about 34 amino acids, about 24 amino acids to about 32 amino acids, about 24 amino acids to about 30 amino acids, about 24 amino acids to about 28 amino acids, about 24 amino acids to about 26 amino acids, about 26 amino acids to about 100 amino acids, about 26 amino acids to about 95 amino acids, about 26 amino acids to about 90 amino acids, about 26 amino acids to about 85 amino acids, about 26 amino acids to about 80 amino acids, about 26 amino acids to about 75 amino acids, about 26 amino acids to about 70 amino acids, about 26 amino acids to about 65 amino acids, about 26 amino acids to about 60 amino acids, about 26 amino acids to about 55 amino acids, about 26 amino acids to about 50 amino acids, about 26 amino acids to about 45 amino acids, about 26 amino acids to about 40 amino acids, about 26 amino acids to about 38 amino acids, about 26 amino acids to about 36 amino acids, about 26 amino acids to about 34 amino acids, about 26 amino acids to about 32 amino acids, about 26 amino acids to about 30 amino acids, about 26 amino acids to about 28 amino acids, about 28 amino acids to about 100 amino acids, about 28 amino acids to about 95 amino acids, about 28 amino acids to about 90 amino acids, about 28 amino acids to about 85 amino acids, about 28 amino acids to about 80 amino acids, about 28 amino acids to about 75 amino acids, about 28 amino acids to about 70 amino acids, about 28 amino acids to about 65 amino acids, about 28 amino acids to about 60 amino acids, about 28 amino acids to about 55 amino acids, about 28 amino acids to about 50 amino acids, about 28 amino acids to about 45 amino acids, about 28 amino acids to about 40 amino acids, about 28 amino acids to about 38 amino acids, about 28 amino acids to about 36 amino acids, about 28 amino acids to about 34 amino acids, about 28 amino acids to about 32 amino acids, about 28 amino acids to about 30 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 38 amino acids, about 30 amino acids to about 36 amino acids, about 30 amino acids to about 34 amino acids, about 30 amino acids to about 32 amino acids, about 32 amino acids to about 100 amino acids, about 32 amino acids to about 95 amino acids, about 32 amino acids to about 90 amino acids, about 32 amino acids to about 85 amino acids, about 32 amino acids to about 80 amino acids, about 32 amino acids to about 75 amino acids, about 32 amino acids to about 70 amino acids, about 32 amino acids to about 65 amino acids, about 32 amino acids to about 60 amino acids, about 32 amino acids to about 55 amino acids, about 32 amino acids to about 50 amino acids, about 32 amino acids to about 45 amino acids, about 32 amino acids to about 40 amino acids, about 32 amino acids to about 38 amino acids, about 32 amino acids to about 36 amino acids, about 32 amino acids to about 34 amino acids, about 34 amino acids to about 100 amino acids, about 34 amino acids to about 95 amino acids, about 34 amino acids to about 90 amino acids, about 34 amino acids to about 85 amino acids, about 34 amino acids to about 80 amino acids, about 34 amino acids to about 75 amino acids, about 34 amino acids to about 70 amino acids, about 34 amino acids to about 65 amino acids, about 34 amino acids to about 60 amino acids, about 34 amino acids to about 55 amino acids, about 34 amino acids to about 50 amino acids, about 34 amino acids to about 45 amino acids, about 34 amino acids to about 40 amino acids, about 34 amino acids to about 38 amino acids, about 34 amino acids to about 36 amino acids, about 36 amino acids to about 100 amino acids, about 36 amino acids to about 95 amino acids, about 36 amino acids to about 90 amino acids, about 36 amino acids to about 85 amino acids, about 36 amino acids to about 80 amino acids, about 36 amino acids to about 75 amino acids, about 36 amino acids to about 70 amino acids, about 36 amino acids to about 65 amino acids, about 36 amino acids to about 60 amino acids, about 36 amino acids to about 55 amino acids, about 36 amino acids to about 50 amino acids, about 36 amino acids to about 45 amino acids, about 36 amino acids to about 40 amino acids, about 36 amino acids to about 38 amino acids, about 38 amino acids to about 100 amino acids, about 38 amino acids to about 95 amino acids, about 38 amino acids to about 90 amino acids, about 38 amino acids to about 85 amino acids, about 38 amino acids to about 80 amino acids, about 38 amino acids to about 75 amino acids, about 38 amino acids to about 70 amino acids, about 38 amino acids to about 65 amino acids, about 38 amino acids to about 60 amino acids, about 38 amino acids to about 55 amino acids, about 38 amino acids to about 50 amino acids, about 38 amino acids to about 45 amino acids, about 38 amino acids to about 40 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 100 amino acids, about 80 amino acids to about 95 amino acids, about 80 amino acids to about 90 amino acids, about 80 amino acids to about 85 amino acids, about 85 amino acids to about 100 amino acids, about 85 amino acids to about 95 amino acids, about 85 amino acids to about 90 amino acids, about 90 amino acids to about 100 amino acids, about 90 amino acids to about 95 amino acids, or about 95 amino acids to about 100 amino acids.

For example, a linker sequence can comprise or consist of TGGSGEGGT-GASTGGSAGTGGSGGTTSGEAGGSSGAG (SEQ ID NO: 33) or GSGATG (SEQ ID NO: 34). In some instances the chimeric polypeptide includes a linker that has an amino acid sequence that is at least 70% (e.g., at least 75%, at least 80%, at least 85%, at least 90%, at least 95%, at least 96%, at least 97%, at least 98%, at least 99%) sequence identity to SEQ ID NO: 33. For example, a linker sequence can comprise or consist of the sequences of GSGS (SEQ ID NO:105), GSGSGS (SEQ ID NO:106), SGSG (SEQ ID NO:107), SGSGSG (SEQ ID NO:108), GSSG (SEQ ID NO:109), SS (SEQ ID NO:112), or GGGGS (SEQ ID NO:110).

Growth Factors

A β-TCP-binding sequence as described herein can be tethered to a mammalian growth factor. In some instances, a linker sequence (e.g., any of the linker sequences described herein or known in the art) is disposed between the β-TCP-binding sequence and the mammalian growth factor.

Mammalian growth factors can be osteoinductive molecules that are capable of initiating and enhancing the bone repair process. Bone morphogenetic proteins (BMP) represent a distinct subset of the transforming growth factor-3 family. A number of these BMP (BMP-2, BMP-7, and BMP-14) enhance the speed of bone healing in defects and non-unions.

Non-limiting examples of mammalian growth factors are described herein. In some instances, the mammalian growth factor is selected from the group of: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12), bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15 (GDF15), vascular endothelial growth factor (VEGF), hyaluronic acid binding protein (HABP), and collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), and wnt family member 16 (WNT16).

For example, the mammalian growth factor can be a human growth factor. Non-limiting examples of human growth factors are provided in Table B.

TABLE B

Exemplary human growth factors

| Name | Exemplary Human Protein Sequence | SEQ ID NO: |
|---|---|---|
| EGF | MLLTLIILLPVVSKFSFVSLSAPQHWSCPEGTLAGNGNSTCVG PAPFLIFSHGNSIFRIDTEGTNYEQLVVDAGVSVIMDFHYNEK RIYWVDLERQLLQRVFLNGSRQERVCNIEKNVSGMAINWIN EEVIWSNQQEGIITVTDMKGNNSHILLSALKYPANVAVDPVE RFIFWSSEVAGSLYRADLDGVGVKALLETSEKITAVSLDVLD KRLFWIQYNREGSNSLICSCDYDGGSVHISKHPTQHNLFAMS LFGDRIFYSTWKMKTIWIANKHTGKDMVRINLHSSFVPLGEL KVVHPLAQPKAEDDTWEPEQKLCKLRKGNCSSTVCGQDLQ SHLCMCAEGYALSRDRKYCEDVNECAFWNHGCTLGCKNTP GSYYCTCPVGFVLLPDGKRCHQLVSCPRNVSECSHDCVLTSE GPLCFCPEGSVLERDGKTCSGCSSPDNGGCSQLCVPLSPVSW ECDCFPGYDLQLDEKSCAASGPQPFLLFANSQDIRHMHFDGT DYGTLLSQQMGMVYALDHDPVENKIYFAHTALKWIERANM DGSQRERLIEEGVDVPEGLAVDWIGRRFYWTDRGKSLIGRSD LNGKRSKIITKENISQPRGIAVHPMAKRLFWTDTGINPRIESSS LQGLGRLVIASSDLIWPSGITIDFLTDKLYWCDAKQSVIEMA NLDGSKRRRLTQNDVGHPFAVAVFEDYVWFSDWAMPSVM RVNKRTGKDRVRLQGSMLKPSSLVVVHPLAKPGADPCLYQ NGGCEHICKKRLGTAWCSCREGFMKASDGKTCLALDGHQL LAGGEVDLKNQVTPLDILSKTRVSEDNITESQHMLVAEEVIVS DQDDCAPVGCSMYARCISEGEDATCQCLKGFAGDGKLCSDI DECEMGVPVCPPASSKCINTEGGYVCRCSEGYQGDGIHCLDI DECQLGEHSCGENASCTNTEGGYTCMCAGRLSEPGLICPDST | 46 |

TABLE B-continued

Exemplary human growth factors

| Name | Exemplary Human Protein Sequence | SEQ ID NO: |
|---|---|---|
| | PPPHLREDDHHYSVRNSDSECPLSHDGYCLHDGVCMYIEAL DKYACNCVVGYIGERCQYRDLKWWELRHAGHGQQQKVIV VAVCVVVLVMLLLLSLWGAHYYRTQKLLSKNPKNPYEESS RDVRSRRPADTEDGMSSCPQPWFVVIKEHQDLKNGGQPVAG EDGQAADGSMQPTSWRQEPQLCGMGTEQGCWIPVSSDKGS CPQVMERSFHMPSYGTQTLEGGVEKPHSLLSANPLWQQRAL DPPHQMELTQ | |
| PDGF | MRTLACLLLLGCYLAHVLAEEAEIPREVIERLARSQIHSIRD LQRLLEIDSVGSEDSLDTSLRAHGVHATKHVPEKRPLPIRRKR SIEEAVPAVCKTRTVIYEIPRSQVDPTSANFLIWPPCVEVKRC TGCCNTSSVKCQPSRVHHRSVKVAKVEYVRKKPKLKEVQV RLEEHLECACATTSLNPDYREEDTGRPRESGKKRKRKRLKPT | 47 |
| IGF-1 | MGKISSLPTQLFKCCFCDFLKVKMHTMSSSHLFYLALCLLTF TSSATAGPETLCGAELVDALQFVCGDRGFYFNKPTGYGSSSR RAPQTGIVDECCFRSCDLRRLEMYCAPLKPAKSARSVRAQR HTDMPKTQKYQPPSTNKNTKSQRRKGSTFEERK | 48 |
| FGF | MAEGEITTFTALTEKFNLPPGNYKKPKLLYCSNGGHFLRILPD GTVDGTRDRSDQHIQLQLSAESVGEVYIKSTETGQYLAMDT DGLLYGSQTPNEECLFLERLEENHYNTYISKKHAEKNWFVG LKKNGSCKRGPRTHYGQKAILFLPLPVSSD | 49 |
| FGF2 | MVGVGGGDVEDVTPRPGGCQISGRGARGCNGIPGAAAWEA ALPRRRPRRHPSVNPRSRAAGSPRTRGRRTEERPSGSRLGDR GRGRALPGGRLGGRGRGRAPERVGGRGRGRGTAAPRAAPA ARGSRPGPAGTMAAGSITTLPALPEDGGSGAFPPGHFKDPKR LYCKNGGFFLRIHPDGRVDGVREKSDPHIKLQLQAEERGVVS IKGVCANRYLAMKEDGRLLASKCVTDECFFFERLESNNYNT YRSRKYTSWYVALKRTGQYKLGSKTGPGQKAILFLPMSAKS | 50 |
| FGF18 | MVSAPSACTCLCLHFLLLCFQVQVLVAEENVDFRIHVENQTR ARDDVSRKQLRLYQLYSRTSGKHIQVLGRRISARGEDGDKY AQLLVETDTFGSQVRIKGKETEFYLCMNRKGKLVGKPDGTS KECVFIEKVLENNYTALMSAKYSGWYVGFTKKGRPRKGPKT RENQQDVHFMKRYPKGQPELQKPFKYTTVTKRSRRIRPTHP A | 51 |
| TGF-α | MVPSAGQLALFALGIVLAACQALENSTSPLSADPPVAAAVVS HFNDCPDSHTQFCFHGTCRFLVQEDKPACVCHSGYVGARCE HADLLAVVAASQKKQAITALVVVSIVALAVLIITCVLIHCCQ VRKHCEWCRALICRHEKPSALLKGRTACCHSETVV | 52 |
| TGF-β1 | NIPPSGLRLLPLLLPLLWLLVLTPGRPAAGLSTCKTIDMELVK RKRIEAIRGQILSKLRLASPPSQGEVPPGPLPEAVLALYNSTRD RVAGESAEPEPEPEADYYAKEVTRVLMVETHNEIYDKFKQS THSIYMFENTSELREAVPEPVLLSRAELRLLRLKLKVEQHVEL YQKYSNNSWRYLSNRLLAPSDSPEWLSFDVTGVVRQWLSR GGEIEGFRLSAHCSCDSRDNTLQVDINGFTTGRRGDLATIHG MNRPFLLLMATPLERAQHLQSSRHRRALDTNYCFSSTEKNC CVRQLYIDFRKDLGWKWIHEPKGYHANFCLGCPYIWSLDT QYSKVLALYNQHNPGASAAPCCVPQALEPLPIVYYVGRKPK VEQLSNMIVRSCKCS | 53 |
| TGF-β3 | MKMHLQRALVVLALLNFATVSLSLSTCTTLDFGHIKKKRVE AIRGQILSKLRLTSPPEPTVMTHVPYQVLALYNSTRELLEEM HGEREEGCTQENTESEYYAKEIHKEDMIQGLAEHNELAVCP KGITSKVERENVSSVEKNRTNLFRAEFRVLRVPNPSSKRNEQ RIELFQILRPDEHIAKQRYIGGKNLPTRGTAEWLSFDVTDTVR EWLLRRESNLGLEISIHCPCHTFQPNGDILENIHEVMEIKFKG VDNEDDHGRGDLGRLKKQKDHHNPHLILMMIPPHRLDNPG QGGQRKKRALDTNYCFRNLEENCCVRPLYIDFRQDLGWKW VHEPKGYYANFCSGPCYLRSADTTHSTVLGLYNTLNPEASA SPCCVPQDLEPLTILYYVGRTPKVEQLSNMVVKSCKCS | 54 |
| OP-2 (BMP-8) | MTALPGPLWLLGLALCALGGGGPGLRPPPGCPQRRLGARER RDVQREILAVLGLGPGRPRPRAPPAASRLPASAPLFMLDLYHA MAGDDDEDGAPAERRLGRADLVMSFVNMVERDRALGHQE PHWKEEREDLTQIPAGEAVTAAEFRIYKVPSIHLLNRTLHVS MEQVVQEQSNRESDLEFLDLQTLRAGDEGWLVLDVTAASD CWLLKRHKDLGLRLYVETEDGHSVDPGLAGLLGQRAPRSQ QPFVVTFERASPSPIRTPRAVRPLRRRQPKKSNELPQANRLPGI FDDVHGSHGRQVCRRHELYVSFQDLGWLDWVIAPQGYSAY | 55 |

TABLE B-continued

Exemplary human growth factors

| Name | Exemplary Human Protein Sequence | SEQ ID NO: |
|---|---|---|
| | YCEGECSFPLDSCMNATNHAILQSLVHLMMPDAVPKACCAP TKLSATSVLYYDSSNNVILRKHRNMVVKACGCH | |
| OP-3 | MAARPGLLWLLGLALCVLGGGHLSHPPHVFPQRRLGVREPR DMQREIREVLGLPGRPRSRAPVGAAQQPASAPLFMLDLYRA MTDDSGGGTPQPHLDRADLIMSFVNIVERDRTLGYQEPHWK EFHFDLTQIPAGEAVTAAEFRIYKEPSTHPLNTTLHISMFEVV QEHSNRESDLFFLDLQTLRSGDEGWLVLDITAASDRWLLNH HKDLGLRLYVETEDGHSIDPGLAGLLGRQAPRSRQPFMVGFF RANQSPVRAPRTARPLKKKQLNQINQLPHSNKHLGILDDGH GSHGREVCRRHELYVSFRDLGWLDSVIAPQGYSAYYCAGEC IYPLNSCMNSTNHATMQALVHLMKPDIIPKVCCVPTELSAISL LYYDRNNNVILRRERNMVVQACGCH | 56 |
| BMP-2 | MVAGTRCLLALLLPQVLLGGAAGLVPELGRRKFAAASSGRP SSQPSDEVLSEFELRLLSMFGLKQRPTPSRDAVVPPYMLDLY RRHSGQPGSPAPDHRLERAASRANTVRSFHHEESLEELPETS GKTTRRFFFNLSSIPTEEFITSAELQVFREQMQDALGNNSSFH HRINIYEIIKPATANSKFPVTRLLDTRLVNQASRWESEDVTP AVMRWTAQGHANHGFVVEVAHLEEKQGVSKRHVRISRSLH QDEHSWSQIRPLLVTFGHDGKGHPLHKREKRQAKHKQRKRL KSSCKRHPLYVDFSDVGWNDWIVAPPGYHAFYCHGECPFPL ADHLNSTNHAIVQTLVNSVNSKIPKACCVPTELSAISMLYLD ENEKVVLKNYQDMVVEGCGCR | 32 |
| BMP-3 | MAGASRLLFLWLGCFCVSLAQGERPKPPFPELRKAVPGDRT AGGGPDSELQPQDKVSEHMLRLYDRYSTVQAARTPGSLEGG SQPWRPRLLREGNTVRSFRAAAAETLERKGLYIFNLTSLTKS ENILSATLYFCIGELGNISLSCPVSGGCSHHAQRKHIQIDLSA WTLKFSRNQSQLLGHLSVDMAKSHRDIMSWLSKDITQFLRK AKENEEFLIGFNITSKGRQLPKRRLPFPEPYILVYANDAAISEP ESVVSSLQGHRNFPTGTVPKWDSHIRAALSIERRKKRSTGVL LPLQNNELPGAEYQYKKDEVWEERKPYKTLQAQAPEKSKN KKKQRKGPHRKSQTLQFDEQTLKKARRKQWIEPRNCARRYL KVDFADIGWSEWIISPKSFDAYYCSGACQFPMPKSLKPSNHA TIQSIVRAVGVVPGIPEPCCVPEKMSSLSILFFDENKNVVLKV YPNMTVESCACR | 57 |
| BMP-4 | MIPGNRMLMVVLLCQVLLGGASHASLIPETGKKKVAEIQGH AGGRRSGQSHELLRDFEATLLQMFGLRRRPQPSKSAVIPDYM RDLYRLQSGEEEEEQIHSTGLEYPERPASRANTVRSFHHEEHL ENIPGTSENSAFRFLFNLSSIPENEVISSAELRLFREQVDQGPD WERGEHRINIYEVMKPPAEVVPGHLITRLLDTRLVHENVTR WETFDVSPAVLRWTREKQPNYGLAIEVTHLHQTRTHQGQH VRISRSLPQGSGNWAQLRPLLVTFGHDGRGHALTRRRRAKR SPKHHSQRARKKNKNCRRHSLYVDFSDVGWNDWIVAPPGY QAFYCHGDCPFPLADHLNSTNHAIVQTLVNSVNSSIPKACCV PTELSAISMLYLDEYDKVVLKNYQEMVVEGCGCR | 58 |
| BMP-5 | MHLTVFLLKGIVGFLWSCWVLVGYAKGGLGDNHVHSSFIYR RLRNHERREIQREILSILGLPHRPRPFSPGKQASSAPLFMLDLY NAMTNEENPEESEYSVRASLAEETRGARKGYPASPNGYPRRI QLSRTTPLTTQSPPLASLHDTNFLNDADMVMSFVNLVERDK DFSHQRRHYKEFRFDLTQIPHGEAVTAAEFRIYKDRSNNRFE NETIKISIYQIIKEYTNRDADLELLDTRKAQALDVGWLVEDIT VTSNHWVINPQNNLGLQLCAETGDGRSINVKSAGLVGRQGP QSKQPFMVAFFKASEVLLRSVRAANKRKNQNRNKSSSHQDS SRMSSVGDYNTSEQKQACKKHELYVSFRDLGWQDWIIAPEG YAAFYCDGECSFPLNAHMNATNHAIVQTLVHLMFPDHVPKP CCAPTKLNAISVLYFDDSSNVILKKYRNMVVRSCGCH | 59 |
| BMP-6/VGR | MPGLGRRAQWLCWWWGLLCSCCGPPPLRPPLPAAAAAAG GQLLGDGGSPGRTEQPPPSPQSSSGFLYRRLKTQEKREMQKE ILSVLGLPHRPRPLHGLQQPQPPALRQQEEQQQQQLPRGEP PPGRLKSAPLFMLDLYNALSADNDEDGASEGERQQSWPHEA ASSSQRRQPPPGAAHPLNRKSLLAPGSGSGGASPLTSAQDSA FLNDADMVMSFVNLVEYDKEFSPRQRHHKEEKENLSQIPEG EVVTAAEFRIYKDCVMGSFKNQTFLISIYQVLQEHQHRDSDL FLLDTRVVWASEEGWLEFDITATSNLWVVTPQHNMGLQLSV VTRDGVHVHPRAAGLVGRDGPYDKQPFMVAFFKVSEVHVR TTRSASSRRRQQSRNRSTQSQDVARVSSASDYNSSELKTACR KHELYVSFQDLGWQDWIIAPKGYAANYCDGECSFPLNAHM NATNHAIVQTLVHLMNPEYVPKPCCAPTKLNAISVLYFDDNS NVILKKYRNMVVRACGCH | 60 |

TABLE B-continued

Exemplary human growth factors

| Name | Exemplary Human Protein Sequence | SEQ ID NO: |
|---|---|---|
| BMP-7/OP-1 | MHVRSLRAAAPHSFVALWAPLFLLRSALADESLDNEVHSSFI HRRLRSQERREMQREILSILGLPHRPRPHLQGKHNSAPMFML DLYNAMAVEEGGGPGGQGFSYPYKAVFSTQGPPLASLQDSH FLTDADMVMSFVNLVEHDKEFFHPRYHHREFREDLSKIPEGE AVTAAEFRIYKDYIRERFDNETFRISVYQVLQEHLGRESDLFL LDSRTLWASEEGWLVFDITATSNHWVVNPRHNLGLQLSVET LDGQSINPKLAGLIGRHGPQNKQPFMVAFFKATEVHFRSIRST GSKQRSQNRSKTPKNQEALRMANVAENSSSDQRQACKKHE LYVSERDLGWQDWIIAPEGYAAYYCEGECAFPLNSYMNATN HAIVQTLVHFINPETVPKPCCAPTQLNAISVLYFDDSSNVILK KYRNMVVRACGCH | 61 |
| BMP-9 | MCPGALWVALPLLSLLAGSLQGKPLQSWGRGSAGGNAHSP LGVPGGGLPEHTENLKMELENVKVDELRSLNLSGVPSQDKT RVEPPQYMIDLYNRYTSDKSTTPASNIVRSFSMEDAISITATE DEPEQKHILLENISIPRHEQITRAELRLYVSCQNHVDPSHDLK GSVVIYDVLDGTDAWDSATETKTFLVSQDIQDEGWETLEVS SAVKRWVRSDSTKSKNKLEVTVESHRKGCDTLDISVPPGSR NLPFFVVFSNDHSSGTKETRLELREMISHEQESVLKKLSKDGS TEAGESSHEEDTDGHVAAGSTLARRKRSAGAGSHCQKTSLR VNFEDIGWDSWIIAPKEYEAYECKGGCEEPLADDVTPTKHAI VQTLVHLKFPTKVGKACCVPTKLSPISVLYKDDMGVPTLKY HYEGMSVAECGCR | 62 |
| BMP-10 | MGSLVLTLCALFCLAAYLVSGSPIMNLEQSPLEEDMSLFGDV FSEQDGVDFNTLLQSMKDEFLKTLNLSDIPTQDSAKVDPPEY MLELYNKFATDRTSMPSANIIRSEKNEDLFSQPVSFNGLRKYP LLFNVSIPHHEEVIMAELRLYTLVQRDRMIYDGVDRKITIFEV LESKGDNEGERNMLVLVSGEIYGTNSEWETFDVTDAIRRWQ KSGSSTHQLEVHIESKHDEAEDASSGRLEIDTSAQNKHNPLLI VFSDDQSSDKERKEELNEMISHEQLPELDNLGLDSFSSGPEE ALLQMRSNIIYDSTARIRRNAKGNYCKRTPLYIDFKEIGWDS WIIAPPGYEAYECRGVCNYPLAEHLTPTKHAIIQALVHLKNS QKASKACCVPTKLEPISILYLDKGVVTYKFKYEGMAVSECG CR | 63 |
| BMP-11/GDF-11 | MVLAAPLLLGFLLLALELRPRGEAAEGPAAAAAAAAAAA AGVGGERSSRPAPSVAPEPDGCPVCVWRQHSRELRLESIKSQ ILSKLRLKEAPNISREVVKQLLPKAPPLQQILDLHDFQGDALQ PEDFLEEDEYHATTETVISMAQETDPAVQTDGSPLCCHFHFS PKVMFTKVLKAQLWVYLRPVPRPATVYLQILRLKPLTGEGT AGGGGGGRRHIRIRSLKIELHSRSGHWQSIDFKQVLHSWFRQ PQSNWGIEINAFDPSGTDLAVTSLGPGAEGLHPFMELRVLEN TKRSRRNLGLDCDEHSSESRCCRYPLTVDFEAFGWDWIIAPK RYKANYCSGQCEYMFMQKYPHTHLVQQANPRGSAGPCCTP TKMSPINMLYFNDKQQIIYGKIPGMVVDRCGCS | 64 |
| BMP-12 | MDLSAAAALCLWLLSACRPRDGLEAAAVLRAAGAGPVRSP GGGGGGGGGRTLAQAAGAAAVPAAAVPRARAARRAAGS GFRNGSVVPHHFMMSLYRSLAGRAPAGAAAVSASGHGRAD TITGETDQATQDESAAETGQSFLFDVSSLNDADEVVGAELRV LRRGSPESGPGSWTSPPLLLLSTCPGAARAPRLLYSRAAEPLV GQRWEAFDVADAMRRHRREPRPPRAFCLLLRAVAGPVPSPL ALRRLGFGWPGGGGSAAEERAVLVVSSRTQRKESLFREIRA QARALGAALASEPLPDGTGTASPRAVIGGRRRRRTALAGTR TAQGSGGGAGRGHGRRGRSRCSRKPLHVDFKELGWDDWII APLDYEAYHCEGLCDFPLRSHLEPTNHAIIQTLLNSMAPDAA PASCCVPARLSPISILYIDAANNVVYKQYEDMVVEACGCR | 65 |
| BMP-13/GDF-6 | MDTPRVLLSAVFLISFLWDLPGFQQASISSSSSSAELGSTKGM RSRKEGKMQRAPRDSDAGREGQEPQPRPQDEPRAQQPRAQE PPGRGPRVVPHEYMLSIYRTYSIAEKLGINASFFQSSKSANTIT SFVDRGLDDLSHTPLRRQKYLFDVSMLSDKEELVGAELRLFR QAPSAPWGPPAGPLHVQLFPCLSPLLLDARTLDPQGAPPAG WEVFDVWQGLRHQPWKQLCLELRAAWGELDAGEAEARAR GPQQPPPPDLRSLGFGRRVRPPQERALLVVFTRSQRKNLFAE MREQLGSAEAAGPGAGAEGSWPPPSGAPDARPWLPSPGRRR RRTAFASRHGKRHGKKSRLRCSKKPLHVNFKELGWDDWIIA PLEYEAYHCEGVCDFPLRSHLEPTNHAIIQTLMNSMDPGSTPP SCCVPTKLTPISILYIDAGNNVVYKQYEDMVVESCGCR | 66 |
| BMP-15 | MVLLSILRILFLCELVLFMEHRAQMAEGGQSSIALLAEAPTLP LIEELLEESPGEQPRKPRLLGHSLRYMLELYRRSADSHGHPRE NRTIGATMVRLVKPLTNVARPHRGTWHIQILGFPLRPNRGLY QLVRATVVYREIFILQLTRFNLSCHVEPWVQKNPTNHFPSSEG | 67 |

TABLE B-continued

Exemplary human growth factors

| Name | Exemplary Human Protein Sequence | SEQ ID NO: |
|---|---|---|
| | DSSKPSLMSNAWKEMDITQLVQQRFWNNKGHRILRLRFMC QQQKDSGGLELWHGTSSLDIAFLLLYFNDTHKSIRKAKFLPR GMEEFMERESLLRRTRQADGISAEVTASSSKHSGPENNQCSL HPFQISFRQLGWDHWIIAPPFYTPNYCKGTCLRVLRDGLNSP NHAIIQNLINQLVDQSVPRPSCVPYKVPISVLMIEANGSILY KEYEGMIAESCTCR | |
| DPP | MKIITYFCIWAVAWAIPVPQSKPLERHVEKSMNLHLLARSNV SVQDELNASGTIKESGVLVHEGDRGRQENTQDGHKGEGNGS KWAEVGGKSFSTYSTLANEEGNIEGWNGDTGKAETYGHDGI HGKEENITANGIQGQVSIIDNAGATNRSNTNGNTDKNTQNG DVGDAGHNEDVAVVQEDGPQVAGSNNSTDNEDEIIENSCRN EGNTSEITPQINSKRNGTKEAEVTPGTGEDAGLDNSDGSPSG NGADEDEDEGSGDDEDEEAGNGKDSSNNSKGQEGQDHGKE DDHDSSIGQNSDSKEYYDPEGKEDPHNEVDGDKTSKSEENS AGIPEDNGSQRIEDTQKLNHRESKRVENRITKESETHAVGKS QDKGIEIKGPSSGNRNITKEVGKGNEGKEDKGQHGMILGKG NVKTQGEVVNIEGPGQKSEPGNKVGHSNTGSDSNSDGYDSY DFDDKSMQGDDPNSSDESNGNDDANSESDNNSSSRGDASYN SDESKDNGNGSDSKGAEDDDSDSTSDTNNSDSNGNGNNGN DDNDKSDSGKGKSDSSDSDSSDSSNSSDSSDSSDSDSSDSNSS SDSDSSDSDSSDSSDSDSSDSSNSSDSSDSSDSSDSDSSDSSD SKSDSSKSESDSSDSDSKSDSSDSNSSDSSDNSDSSDSSNSSNS SDSSDSSDSSSSSDSSNSSDSSDSSNSSESSDSSDSDS DSSDSSDSSNSSDSDSSNSSDSDSDSSNSSDSSDSSDSSNSSD SSDSSDSSNSSDSSDSSDSSDSSDSSNSSDSNDSSNSSDSSDSS NSSDSSNSSDSSDSSDSSDSDSSNSSDSSNSSDSSDSSNSSDSS DSSDSSDGSDSDSSNRSDSSNSSDSSDSSDSSNSSDSSDSSDSN ESSNSSDSSDSSNSSDSSDSSNSSDSSDSSNSSDSSESSNSSD NSNSSDSSNSSDSSDSSDSSNSSDSSNSSDSSNSSDSSDSNSSD SSDSSNSSDSSDSSDSSDSSDSSNSSDSSDSSDSSDSSNSSD SSNSSDSSNSSDSSDSSDSSDSSDSSDSSNSSDSSDSSD SSDSSDSSDSSDSSESSDSSDSSDSSDSSDSSDSSDSSDSSD SSDSSDSSDSSNSSDSSDSSDSSDSSNSSDSSDSSESSDSSD SSDSSDSSDSSDSSDSSDSSNSSDSSDSSDSSDSSDSSDSSD SSDSSDSSDSSDSSDSSDSSDSSDSSDSDSNESSDSSDSSDSSD SSNSSDSSDSSDSTSDSNDESDSQSKSGNGNNNGSDSDSD SEGSDSNHSTSDD | 68 |
| GDF-1 | MPPPQQGPCGHHLLLLLALLLPSLPLTRAPVPPGPAAALLQA LGLRDEPQGAPRLRPVPPVMWRLFRRRDPQETRSGSRRTSPG VTLQPCHVEELGVAGNIVRHIPDRGAPTRASEPASAAGHCPE WTVVFDLSAVEPAERPSRARLELRFAAAAAAAPEGGWELSV AQAGQGAGADPGPVLLRQLVPALGPPVRAELLGAAWARNA SWPRSLRLALALRPRAPAACARLAEASLLLVTLDPRLCHPLA RPRRDAEPVLGGGPGGACRARRLYVSFREVGWHRWVIAPR GFLANYCQGQCALPVALSGSGGPPALNHAVLRALMHAAAP GAADLPCCVPARLSPISVLFFDNSDNVVLRQYEDMVVDECG CR | 69 |
| GDF-3 | MLRFLPDLAFSELLILALGQAVQFQEYVFLQFLGLDKAPSPQ KFQPVPYILKKIFQDREAAATTGVSRDLCYVKELGVRGNVLR FLPDQGFFLYPKKISQASSCLQKLLYFNLSAIKEREQLTLAQL GLDLGPNSYYNLGPELELALFLVQEPHVWGQTTPKPGKMFV LRSVPWPQGAVHFNLLDVAKDWNDNPRKNFGLFLEILVKED RDSGVNFQPEDTCARLRCSLHASLLVVTLNPDQCHPSRKRR AAIPVPKLSCKNLCHRHQLFINFRDLGWHKWIIAPKGFMANY CHGECPFSLTISLNSSNYAFMQALMHAVDPEIPQAVCIPTKLS PISMLYQDNNDNVILRHYEDMVVDECGCG | 70 |
| GDF-5 | MRLPKLLTFLLWYLAWLDLEFICTVLGAPDLGQRPQGTRPG LAKAEAKERPPLARNVFRPGGHSYGGGATNANARAKGGTG QTGGLTQPKKDEPKKLPPRPGGPEPKPGHPPQTRQATARTVT PKGQLPGGKAPPKAGSVPSSELLKKAREPGPPREPKEPERPPPI TPHEYMLSLYRTLSDADRKGGNSSVKLEAGLANTITSFIDKG QDDRGPVVRKQRYVFDISALEKDGLLGAELRILRKKPSDTAK PAAPGGGRAAQLKLSSCPSGRQPAALLDVRSVPGLDSGWE VEDIWKLERNEKNSAQLCLELEAWERGRAVDLRGLGEDRAA RQVHEKALFLVFGRTKKRDLFFNEIKARSGQDDKTVYEYLFS QRRKRRAPLATRQGKRPSKNLKARCSRKALHVNFKDMGWD DWIIAPLEYEAFHCEGLCEFPLRSHLEPTNHAVIQTLMNSMD PESTPPTCCVPTRLSPISILFIDSANNVVYKQYEDMVVESCGC R | 71 |

TABLE B-continued

Exemplary human growth factors

| Name | Exemplary Human Protein Sequence | SEQ ID NO: |
|---|---|---|
| GDF-7 | MDLSAAAALCLWLLSACRPRDGLEAAAVLRAAGAGPVRSP GGGGGGGGGRTLAQAAGAAAVPAAAVPRARAARRAAGS GERNGSVVPHHEMMSLYRSLAGRAPAGAAAVSASGHGRAD TITGETDQATQDESAAETGQSFLFDVSSLNDADEVVGAELRV LRRGSPESGPGSWTSPPLLLLSTCPGAARAPRLLYSRAAEPLV GQRWEAFDVADAMRRHRREPRPPRAFCLLLRAVAGPVPSPL ALRRLGFGWPGGGGSAAEERAVLVVSSRTQRKESLFREIRA QARALGAALASEPLPDPGTGTASPRAVIGGRRRRRTALAGTR TAQGSGGGAGRGHGRRGRSRCSRKPLHVDFKELGWDDWII APLDYEAYHCEGLCDFPLRSHLEPTNHAIIQTLLNSMAPDAA PASCCVPARLSPISILYIDAANNVVYKQYEDMVVEACGCR | 72 |
| GDF8 | MQKLQLCVYIYLFMLIVAGPVDLNENSEQKENVEKEGLCNA CTWRQNTKSSRIEAIKIQILSKLRLETAPNISKDVIRQLLPKAP PLRELIDQYDVQRDDSSDGSLEDDDYHATTETIITMPTESDFL MQVDGKPKCCFFKFSSKIQYNKVVKAQLWIYLRPVETPTTV FVQILRLIKPMKDGTRYTGIRSLKLDMNPGTGIWQSIDVKTV LQNWLKQPESNLGIEIKALDENGHDLAVTFPGPGEDGLNPFL EVKVTDTPKRSRRDFGLDCDEHSTESRCCRYPLTVDFEAFG WDWIIAPKRYKANYCSGECEFVFLQKYPHTHLVHQANPRGS AGPCCTPTKMSPINMLYFNGKEQIIYGKIPAMVVDRCGCS | 73 |
| GDF15 | MPGQELRTVNGSQMLLVLLVLSWLPHGGALSLAEASRASFP GPSELHSEDSRFRELRKRYEDLLTRLRANQSWEDSNTDLVPA PAVRILTPEVRLGSGGHLHLRISRAALPEGLPEASRLHRALFR LSPTASRSWDVTRPLRRQLSLARPQAPALHLRLSPPPSQSDQL LAESSSARPQLELHLRPQAARGRRRARARNGDHCPLGPGRC CRLHTVRASLEDLGWADWVLSPREVQVTMCIGACPSQFRAA NMHAQIKTSLHRLKPDTVPAPCCVPASYNPMVLIQKTDTGV SLQTYDDLLAKDCHCI | 74 |
| VEGF | MTDRQTDTAPSPSYHLLPGRRRTVDAAASRGQGPEPAPGGG VEGVGARGVALKLFVQLLGCSRFGGAVVRAGEAEPSGAARS ASSGREEPQPEEGEEEEEKEEERGPQWRLGARKPGSWTGEA AVCADSAPAARAPQALARASGRGGRVARRGAEESGPPHSPS RRGSASRAGPGRASETMNFLLSWVHWSLALLLYLHHAKWS QAAPMAEGGGQNHHEVVKFMDVYQRSYCHPIETLVDIFQEY PDEIEYIFKPSCVPLMRCGGCCNDEGLECVPTEESNITMQIMR IKPHQGQHIGEMSFLQHNKCECRPKKDRARQEKKSVRGKGK GQKRKRKKSRYKSWSVYVGARCCLMPWSLPGPHPCGPCSE RRKHLFVQDPQTCKCSCKNTDSRCKARQLELNERTCRCDKP RR | 75 |
| HABP | MFARMSDLHVLLLMALVGKTACGFSLMSLLESLDPDWTPD QYDYSYEDYNQEENTSSTLTHAENPDWYYTEDQADPCQPNP CEHGGDCLVHGSTFTCSCLAPFSGNKCQKVQNTCKDNPCGR GQCLITQSPPYYRCVCKHPYTGPSCSQVVPVCRPNPCQNGAT CSRHKRRSKETCACPDQFKGKECEIGSDDCYVGDGYSYRGK MNRTVNQHACLYWNSHLLLQENYNMEMEDAETHGIGEHNE CRNPDADEKPWCFIKVTNDKVKWEYCDVSACSAQDVAYPE ESPTEPSTKLPGFDSCGKTEIAERKIKRIYGGEKSTAGKHPWQ ASLQSSLPLTISMPQGHFCGGALIHPCWVLTAAHCTDIKTRH LKVVLGDQDLKKEEFHEQSERVEKIEKYSHYNERDEIPHNDI ALLLKLKPVDGHCALESKYVKTVCLPDGSFPSGSECHISGWG VTETGKGSRQLLDAKVKLIANTLCNSRQLYDHMIDDSMICA GNLQKPGQDTCQGDSGGPLTCEKDGTYYVYGIVSWGLECG KRPGVYTQVTKELNWIKATIKSESGE | 76 |
| CBP | MRSLLLLSAFCLLEAALAAEVKKPAAAAAPGTAEKLSPKAA TLAERSAGLAFSLYQAMAKDQAVENILVSPVVVASSLGLVS LGGKATTASQAKAVLSAEQLRDEEVHAGLGELLRSLSNSTA RNVTWKLGSRLYGPSSVSFADDFVRSSKQHYNCEHSKINFR DKRSALQSINEWAAQTTDGKLPEVTKDVERTDGALLVNAM FFKPHWDEKFHHKMVDNRGFMVTRSYTVGVMMMEIRTGLY NYYDDEKEKLQIVEMPLAHKLSSLIILMPHHVEPLERLEKLLT KEQLKIWMGKMQKKAVAISLPKGVVEVTHDLQKHLAGLGL TEAIDKNKADLSRMSGKKDLYLASVFHATAFELDTDGNPFD QDIYGREELRSPKLFYADHPFIFLVRDTQSGSLLFIGRLVRPK GDKMRDEL | 77 |
| FGF-18 | MYSAPSACTCLCLHFLLLCFQVQVLVAEENVDFRIHVENQTR ARDDVSRKQLRLYQLYSRTSGKHIQVLGRRISARGEDGDKY AQLLVETDTFGSQVRIKGKETEFYLCMNRKGKLVGKPDGTS KECVFIEKVLENNYTALMSAKYSGWYVGFTKKGRPRKGPKT | 78 |

TABLE B-continued

Exemplary human growth factors

| Name | Exemplary Human Protein Sequence | SEQ ID NO: |
|---|---|---|
| | RENQQDVHFMKRYPKGQPELQKPFKYTTVTKRSRRIRPTHP A | |
| KGF | MHKWILTWILPTLLYRSCFHIICLVGTISLACNDMTPEQMAT NVNCSSPERHTRSYDYMEGGDIRVRRLFCRTQWYLRIDKRG KVKGTQEMKNNYNIMEIRTVAVGIVAIKGVESEFYLAMNKE GKLYAKKECNEDCNFKELILENHYNTYASAKWTHNGGEMF VALNQKGIPVRGKKTKKEQKTAHFLPMAIT | 79 |
| TNFα | MSTESMIRDVELAEEALPKKTGGPQGSRRCLFLSLFSFLIVAG ATTLFCLLHFGVIGPQREEFPRDLSLISPLAQAVRSSSRTPSDK PVAHVVANPQAEGQLQWLNRRANALLANGVELRDNQLVVP SEGLYLIYSQVLFKGQGCPSTHVLLTHTISRIAVSYQTKVNLL SAIKSPCQRETPEGAEAKPWYEPIYLGGVFQLEKGDRLSAEIN RPDYLDFAESGQVYFGIIAL | 80 |
| TRAIL | MAMMEVQGGPSLGQTCVLIVIFTVLLQSLCVAVTYVYFTNE LKQMQDKYSKSGIACFLKEDDSYWDPNDEESMNSPCWQVK WQLRQLVRKMILRTSEETISTVQEKQQNISPLVRERGPQRVA AHITGTRGRSNTLSSPNSKNEKALGRKINSWESSRSGHSFLSN LHLRNGELVIHEKGFYYIYSQTYFRFQEEIKENTKNDKQMVQ YIYKYTSYPDPILLMKSARNSCWSKDAEYGLYSIYQGGIFEL KENDRIFVSVTNEHLIDMDHEASFFGAFLVG | 81 |
| WNT1 | MGLWALLPGWVSATLLLALAALPAALAANSSGRWWGIVNV ASSTNLLTDSKSLQLVLEPSLQLLSRKQRRLIRQNPGILHSVS GGLQSAVRECKWQFRNRRWNCPTAPGPHLFGKIVNRGCRET AFIFAITSAGVTHSVARSCSEGSIESCTCDYRRRGPGGPDWH WGGCSDNIDFGRLFGREFVDSGEKGRDLRFLMNLHNNEAGR TTVFSEMRQECKCHGMSGSCTVRTCWMRLPTLRAVGDVLR DRFDGASRVLYGNRGSNRASRAELLRLEPEDPAHKPPSPHDL VYFEKSPNFCTYSGRLGTAGTAGRACNSSSPALDGCELLCCG RGHRTRTQRVTERCNCTFHWCCHVSCRNCTHTRVLHECL | 82 |
| WNT2 | MNAPLGGIWLWLPLLLTWLTPEVNSSWWYMRATGGSSRV MCDNVPGLVSSQRQLCHRHPDVIVIRAISQGVAEWTAECQHQ FRQHRWNCNTLDRDHSLFGRVLLRSSRESAFVYAISSAGVVF AITRACSQGEVKSCSCDPKKMGSAKDSKGIFDWGGCSDNID YGIKFARAFVDAKERKGKDARALMNLHNNRAGRKAVKRFL KQECKCHGVSGSCTLRTCWLAMADFRKTGDYLWRKYNGAI QVVMNQDGTGFTVANERFKKPTKNDLVYFENSPDYCIRDRE AGSLGTAGRVCNLTSRGMDSCEVMCCGRGYDTSHVTRMTK CGCKFHWCCAVRCQDCLEALDVHTCKAPKNADWTTAT | 83 |
| WNT2B | MLRPGGAEEAAQLPLRRASAPVPVPSPAAPDGSRASARLGL ACLLLLLLLTLPARVDTSWWYIGALGARVICDNIPGLVSRQR QLCQRYPDIMRSVGEGAREWIRECQHQFRHHRWNCTTLDR DHTVFGRVMLRSSREAAFVYAISSAGVVHAITRACSQGELSV CSCDPYTRGRHHDQRGDFDWGGCSDNIHYGVRFAKAFVDA KEKRLKDARALMNLHNNRCGRTAVRRFLKLECKCHGVSGS CTLRTCWRALSDFRRTGDYLRRRYDGAVQVMATQDGANFT AARQGYRRATRTDLVYFDNSPDYCVLDKAAGSLGTAGRVC SKTSKGTDGCEIMCCGRGYDTTRVTRVTQCECKFHWCCAV RCKECRNTVDVHTCKAPKKAEWLDQT | 84 |
| WNT3 | MEPHLLGLLLGLLLGGTRVLAGYPIWWSLALGQQYTSLGSQ PLLCGSIPGLVPKQLRFCRNYIEIMPSVAEGVKLGIQECQHQF RGRRWNCTTIDDSLAIFGPVLDKATRESAFVHAIASAGVAFA VTRSCAEGTSTICGCDSHHKGPPGEGWKWGGCSEDADFGVL VSREFADARENRPDARSAMNKHNNEAGRTTILDHMHLKCK CHGLSGSCEVKTCWWAQPDFRAIGDFLKDKYDSASEMVVE KHRESRGWVETLRAKYSLFKPPTERDLVYYENSPNFCEPNPE TGSFGTRDRTCNVTSHGIDGCDLLCCGRGHNTRTEKRKEKC HCIFHWCCYVSCQECIRIYDVHTCK | 85 |
| WNT3 | AMAPLGYFLLLCSLKQALGSYPIWWSLAVGPQYSSLGSQPILC ASIPGLVPKQLRFCRNYVEIMPSVAEGIKIGIQECQHQFRGRR WNCTTVHDSLAIFGPVLDKATRESAFVHAIASAGVAFAVTRS CAEGTAAICGCSSRHQGSPGKGWKWGGCSEDIEFGGMVSRE FADARENRPDARSAMNRHNNEAGRQAIASHMHLKCKCHGL SGSCEVKTCWWSQPDFRAIGDFLKDKYDSASEMVVEKHRES RGWVETLRPRYTYFKVPTERDLVYYEASPNFCEPNPETGSFG TRDRTCNVSSHGIDGCDLLCCGRGHNARAERRREKCRCVFH WCCYVSCQECTRVYDVHTCK | 86 |

TABLE B-continued

Exemplary human growth factors

| Name | Exemplary Human Protein Sequence | SEQ ID NO: |
|---|---|---|
| WNT4 | MSPRSCLRSLRLLVFAVFSAAASNWLYLAKLSSVGSISEEETC EKLKGLIQRQVQMCKRNLEVMDSVRRGAQLAIEECQYQFRN RRWNCSTLDSLPVFGKVVTQGTREAAFVYAISSAGVAFAVT RACSSGELEKCGCDRTVHGVSPQGFQWSGCSDNIAYGVAFS QSFVDVRERSKGASSSRALMNLHNNEAGRKAILTHMRVECK CHGVSGSCEVKTCWRAVPPFRQVGHALKEKFDGATEVEPRR VGSSRALVPRNAQFKPHTDEDLVYLEPSPDFCEQDMRSGVL GTRGRTCNKTSKAIDGCELLCCGRGFHTAQVELAERCSCKF HWCCFVKCRQCQRLVELHTCR | 87 |
| WNT5A | MKKSIGILSPGVALGMAGSAMSSKFFLVALAIFFSFAQVVIEA NSWWSLGMNNPVQMSEVYIIGAQPLCSQLAGLSQGQKKLC HLYQDHMQYIGEGAKTGIKECQYQFRHRRWNCSTVDNTSV FGRVMQIGSRETAFTYAVSAAGVVNAMSRACREGELSTCGC SRAARPKDLPRDWLWGGCGDNIDYGYRFAKEFVDARERERI HAKGSYESARILMNLHNNEAGRRTVYNLADVACKCHGVSG SCSLKTCWLQLADFRKVGDALKEKYDSAAAMRLNSRGKLV QVNSRFNSPTTQDLVYIDPSPDYCVRNESTGSLGTQGRLCNK TSEGMDGCELMCCGRGYDQFKTVQTERCHCKFHWCCYVK CKKCTEIVDQFVCK | 88 |
| WNT5B | MPSLLLLFTAALLSSWAQLLTDANSWWSLALNPVQRPEMFII GAQPVCSQLPGLSPGQRKLCQLYQEHMAYIGEGAKTGIKEC QHQFRQRRWNCSTADNASVFGRVMQIGSRETAFTHAVSAA GVVNAISRACREGELSTCGCSRTARPKDLPRDWLWGGCGDN VEYGYRFAKEFVDAREREKNFAKGSEEQGRVLMNLQNNEA GRRAVYKMADVACKCHGVSGSCSLKTCWLQLAEFRKVGD RLKEKYDSAAAMRVTRKGRLELVNSRFTQPTPEDLVYVDPS PDYCLRNESTGSLGTQGRLCNKTSEGMDGCELMCCGRGYN QFKSVQVERCHCKFHWCCFVRCKKCTEIVDQYICK | 89 |
| WNT6 | MLPPLPSRLGLLLLLLLCPAHVGGLWWAVGSPLVMDPTSICR KARRLAGRQAELCQAEPEVVAELARGARLGVRECQFQFRFR RWNCSSHSKAFGRILQQDIRETAFVFAITAAGASHAVTQACS MGELLQCGCQAPRGRAPPRPSGLPGTPGPPGPAGSPEGSAA WEWGGCGDDVDFGDEKSRLFMDARHKRGRGDIRALVQLH NNEAGRLAVRSHTRTECKCHGLSGSCALRTCWQKLPPFREV GARLLERFHGASRVMGTNDGKALLPAVRTLKPPGRADLLYA ADSPDFCAPNRRTGSPGTRGRACNSSAPDLSGCDLLCCGRGH RQESVQLEENCLCRFHWCCVVQCHRCRVRKELSLCL | 90 |
| WNT7A | MNRKARRCLGHLFLSLGMVYLRIGGFSSVVALGASIICNKIP GLAPRQRAICQSRPDAIIVIGEGSQMGLDECQFQFRNGRWNC SALGERTVFGKELKVGSREAAFTYAIIAAGVAHAITAACTQG NLSDCGCDKEKQGQYHRDEGWKWGGCSADIRYGIGFAKVF VDAREIKQNARTLMNLHNNEAGRKILEENMKLECKCHGVS GSCTTKTCWTTLPQFRELGYVLKDKYNEAVHVEPVRASRNK RPTFLKIKKPLSYRKPMDTDLVYIEKSPNYCEEDPVTGSVGT QGRACNKTAPQASGCDLMCCGRGYNTHQYARVWQCNCKF HWCCYVKCNTCSERTEMYTCK | 91 |
| WNT7B | MHRNFRKWIFYVFLCFGVLYVKLGALSSVVALGANIICNKIP GLAPRQRAICQSRPDAIIVIGEGAQMGINECQYQFRFGRWNC SALGEKTVFGQELRVGSREAAFTYAITAAGVAHAVTAACSQ GNLSNCGCDREKQGYYNQAEGWKWGGCSADVRYGIDFSRR FVDAREIKKNARRLMNLHNNEAGRKVLEDRMQLECKCHGV SGSCTTKTCWTTLPKFREVGHLLKEKYNAAVQVEVVRASRL RQPTFLRIKQLRSYQKPMETDLVYIEKSPNYCEEDAATGSVG TQGRLCNRTSPGADGCDTMCCGRGYNTHQYTKVWQCNCK FHWCCFVKCNTCSERTEVFTCK | 92 |
| WNT8A | MLCCIQCLCLVSPFPTLTPCQGGPHCLIPIHLCLTFSLFGRSVN NFLITGPKAYLTYTTSVALGAQSGIEECKFQFAWERWNCPEN ALQLSTHNRLRSATRETSFIHAISSAGVMYIITKNCSMGDFEN CGCDGSNNGKTGGHGWIWGGCSDNVEFGERISKLFVDSLEK GKDARALMNLHNNRAGRLAVRATMKRTCKCHGISGSCSIQT CWLQLAEFREMGDYLKAKYDQALKIEMDKRQLRAGNSAEG HWVPAEAFLPSAEAELIFLEESPDYCTCNSSLGIYGTEGRECL QNSHNTSRWERRSCGRLCTECGLQVEERKTEVISSCNCKFQ WCCTVKCDQCRHVTMSNPAVLLGIRRIEAKNERVLFRLLKS SLWLQIYADK | 93 |
| WNT8B | MFLSKPSVYICLFTCVLQLSHSWSVNNFLMTGPKAYLIYSSS VAAGAQSGIEECKYQFAWDRWNCPERALQLSSHGGLRSAN RETAFVHAISSAGVMYTLTRNCSLGDFDNCGCDDSRNGQLG | 94 |

TABLE B-continued

Exemplary human growth factors

| Name | Exemplary Human Protein Sequence | SEQ ID NO: |
|------|----------------------------------|------------|
| | GQGWLWGGCSDNVGFGEAISKQFVDALETGQDARAAMNL<br>HNNEAGRKAVKGTMKRTCKCHGVSGSCTTQTCWLQLPEFR<br>EVGAHLKEKYHAALKVDLLQGAGNSAAGRGAIADTFRSIST<br>RELVHLEDSPDYCLENKTLGLLGTEGRECLRRGRALGRWER<br>RSCRRLCGDCGLAVEERRAETVSSCNCKFHWCCAVRCEQCR<br>RRVTKYFCSRAERPRGGAAHKPGRKP | |
| WNT9A | MLDGSPLARWLAAAFGLTLLLAALRPSAAYFGLTGSEPLTIL<br>PLTLEPEAAAQAHYKACDRLKLERKQRRMCRRDPGVAETL<br>VEAVSMSALECQFQFRFERWNCTLEGRYRASLLKRGFKETA<br>FLYAISSAGLTHALAKACSAGRMERCTCDEAPDLENREAWQ<br>WGGCGDNLKYSSKFVKEFLGRRSSKDLRARVDFHNNLVGV<br>KVIKAGVETTCKCHGVSGSCTVRTCWRQLAPFHEVGKHLKH<br>KYETALKVGSTTNEAAGEAGAISPPRGRASGAGGSDPLPRTP<br>ELVHLDDSPSFCLAGRFSPGTAGRRCHREKNCESICCGRGHN<br>TQSRVVTRPCQCQVRWCCYVECRQCTQREEVYTCKG | 95 |
| WNT9B | MRPPPALALAGLCLLALPAAAASYFGLTGREVLTPFPGLGTA<br>AAPAQGGAHLKQCDLLKLSRRQKQLCRREPGLAETLRDAA<br>HLGLLECQFQFRHERWNCSLEGRMGLLKRGFKETAFLYAVS<br>SAALTHTLARACSAGRMERCTCDDSPGLESRQAWQWGVCG<br>DNLKYSTKFLSNFLGSKRGNKDLRARADAHNTHVGIKAVKS<br>GLRTTCKCHGVSGSCAVRTCWKQLSPFRETGQVLKLRYDSA<br>VKVSSATNEALGRLELWAPARQGSLTKGLAPRSGDLVYME<br>DSPSFCRPSKYSPGTAGRVCSREASCSSLCCGRGYDTQSRLV<br>AFSCHCQVQWCCYVECQQCVQEELVYTCKH | 96 |
| WNT10A | MGSAHPRPWLRLRPQPQPRPALWVLLFFLLLLAAAMPRSAP<br>NDILDLRLPPEPVLNANTVCLTLPGLSRRQMEVCVRHPDVAA<br>SAIQGIQIAIHECQHQFRDQRWNCSSLETRNKIPYESPIFSRGF<br>RESAFAYAIAAAGVVHAVSNACALGKLKACGCDASRRGDE<br>EAFRRKLHRLQLDALQRGKGLSHGVPEHPALPTASPGLQDS<br>WEWGGCSPDMGFGERFSKDFLDSREPHRDIHARMRLHNNR<br>VGRQAVMENMRRKCKCHGTSGSCQLKTCWQVTPEFRTVGA<br>LLRSRFHRATLIRPHNRNGGQLEPGPAGAPSPAPGAPGPRRR<br>ASPADLVYFEKSPDFCEREPRLDSAGTVGRLCNKSSAGSDGC<br>GSMCCGRGHNILRQTRSERCHCRFHWCCFVVCEECRITEWV<br>SVCK | 97 |
| WNT10B | MLEEPRPRPPPSGLAGLLFLALCSRALSNEILGLKLPGEPPLTA<br>NTVCLTLSGLSKRQLGLCLRNPDVTASALQGLHIAVHECQH<br>QLRDQRWNCSALEGGGRLPHHSAILKRGFRESAFSFSMLAA<br>GVMHAVATACSLGKLVSCGCGWKGSGEQDRLRAKLLQLQ<br>ALSRGKSFPHSLPSPGPGSSPSPGPQDTWEWGGCNHDMDFG<br>EKESRDFLDSREAPRDIQARMRIHNNRVGRQVVTENLKRKC<br>KCHGTSGSCQFKTCWRAAPEFRAVGAALRERLGRAIFIDTHN<br>RNSGAFQPRLRPRRLSGELVYFEKSPDFCERDPTMGSPGTRG<br>RACNKTSRLLDGCGSLCCGRGHNVLRQTRVERCHCRFHWC<br>CYVLCDECKVTEWVNVCK | 98 |
| WNT11 | MRARPQVCEALLFALALQTGVCYGIKWLALSKTPSALALNQ<br>TQHCKQLEGLVSAQVQLCRSNLELMHTVVHAAREVMKACR<br>RAFADMRWNCSSIELAPNYLLDLERGTRESAFVYALSAAAIS<br>HAIARACTSGDLPGCSCGPVPGEPPGPGNRWGGCADNLSYG<br>LLMGAKFSDAPMKVKKTGSQANKLMRLHNSEVGRQALRAS<br>LEMKCKCHGVSGSCSIRTCWKGLQELQDVAADLKTRYLSAT<br>KVVHRPMGTRKHLVPKDLDIRPVKDSELVYLQSSPDFCMKN<br>EKVGSHGTQDRQCNKTSNGSDSCDLMCCGRGYNPYTDRVV<br>ERCHCKYHWCCYVTCRRCERTVERYVCK | 99 |
| WNT16 | MDRAALLGLARLCALWAALLVLFPYGAQGNWMWLGIASF<br>GVPEKLGCANLPLNSRQKELCKRKPYLLPSIREGARLGIQEC<br>GSQFRHERWNCMITAAATTAPMGASPLFGYELSSGTKETAFI<br>YAVMAAGLVHSVTRSCSAGNMTECSCDTTLQNGGSASEGW<br>HWGGCSDDVQYGMWFSRKFLDEPIGNTTGKENKVLLAMNL<br>HNNEAGRQAVAKLMSVDCRCHGVSGSCAVKTCWKTMSSFE<br>KIGHLLKDKYENSIQISDKTKRKMRRREKDQRKIPIHKDDLL<br>YVNKSPNYCVEDKKLGIPGTQGRECNRTSEGADGCNLLCCG<br>RGYNTHVVRHVERCECKFIWCCYVRCRRCESMTDVHTCK | 100 |

In some embodiments, the mammalian growth factor is a secreted human growth factor. In some embodiments, the mammalian growth factor is an active fragment (e.g., a fragment of a secreted human growth factor, e.g., any of the exemplary growth factors described herein) that has osteogenic activity). Non-limiting in vitro assays to determine whether a fragment of a secreted human growth factor, e.g., any of the exemplary growth factors described herein, has osteogenic activity are described in Kim et al., Amino Acids 42:1455-1465, 2012; Lee et al., *ACS Med. Chem. Lett.* 2(3):248-251, 2011; and Wang et al., *Genetics Mol. Res.* 13(2):4456-4465, 2014.

In some embodiments, a fragment of a secreted human growth factor having osteogenic activity can have 1 amino to about 40 amino acids (e.g., 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acid, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, or about 1 amino acid to about 3 amino acids) removed from the N-terminus of the secreted human growth factor and/or 1 amino acid to about 20 amino acids (e.g., 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, or about 1 amino acid to about 3 amino acids) removed from the C-terminus of the secreted human growth factor.

In some embodiments, the mammalian growth factor can have a sequence that is at least 70% identical (e.g., at least 75% identical, at least 80% identical, at least 85% identical, at least 90% identical, at least 95% identical, or at least 99% identical) to any of the sequences in Table B or any secreted human growth factor, and has osteogenic activity. As one skilled in the art can appreciate, the amino acids in a mammalian growth factor that are conserved between different species are likely important for osteogenic activity and should not be mutated, while amino acids in a mammalian growth factor that are not conserved between different species are not likely important for osteogenic activity and can be mutated.

β-TCP-Binding Polypeptides

Also provided herein are β-tricalcium phosphate (β-TCP)-binding polypeptides that include at least one (e.g., two, three, four, five, six, seven, eight, nine, ten, eleven, twelve, thirteen, fourteen, fifteen, sixteen, seventeen, eighteen, nineteen, or twenty) sequence selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19).

Also provided herein are β-TCP-binding polypeptides that include an amino acid sequence of Formula I:

$A_0B_0C_0D_0E_0F_0G_0H_0I_0J_0K_0L_0$ (Formula I) (SEQ ID NO: 35), where:

$A_0$ is V, L, I, G, S, T, or A;
$B_0$ is I, L, V, Q, T, S, G, or A;
$C_0$ is G, A, V, or S;
$D_0$ is E, D, L, or G;
$E_0$ is S, T, P T, E, or D;
$F_0$ is T or S;
$G_0$ is H, T, or S;
$H_0$ is H or T;
$I_0$ is R, S, K, P, or H;
$J_0$ is P, S, R, or K;
$K_0$ is W, F, S, P, V, A, or G; and
$L_0$ is absent or is S, T, G, (or A);
wherein Formula I does not include LLADTTHHRPWT (SEQ ID NO: 1).

In some embodiments, any of the β-TCP-binding polypeptides described herein can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, 20, 21, or 22) of any of SEQ ID NOs: 2-19 and a sequence of Formula I (not including SEQ ID NO: 1). In some embodiments, each neighboring pair of SEQ ID NOs: 2-19 and a sequence of Formula I (not including SEQ ID NO: 1) directly abut each other. In some embodiments, each neighboring pair of any of SEQ ID NOs: 2-19 and a sequence of Formula I (not including SEQ ID NO: 1) are separated by a linker sequence.

In some embodiments, the chimeric polypeptides can include at least two (e.g., at least three, at least four, at least five, at least six, at least seven, at least eight, at least nine, or at least ten; or 2, 3, 4, 5, 6, 7, 8, 9, or 10) different sequences selected from SEQ ID NOs: 2-19 and a sequence of Formula I (not including SEQ ID NO: 1).

In some embodiments, the β-TCP-binding polypeptide includes LLADTTHHRPWT (SEQ ID NO: 1) or GQVLPTTTPSSP (SEQ ID NO: 103). In some embodiments, the β-TCP-binding polypeptide includes LLADTTHHRPWT (SEQ ID NO: 1) and VIGESTHHRPWS (SEQ ID NO: 2). In some embodiments, the β-TCP-binding polypeptide includes the sequence of LLADTTHHRPWTVIGESTHHRPWS (SEQ ID NO: 20).

In some embodiments, the β-TCP-binding polypeptide includes LLADTTHHRPWT (SEQ ID NO: 1), VIGESTHHRPWS (SEQ ID NO: 2), and IIGESSHHKPFT (SEQ ID NO: 6). In some embodiments, the β-TCP-binding polypeptide includes the sequence of LLADTTHHRPWT-VIGESTHHRPWSIIGESSHHKPFT (SEQ ID NO: 21).

In some embodiments, the β-TCP-binding polypeptide includes LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4). In some embodiments, the β-TCP-binding polypeptide includes the sequence of:

(SEQ ID NO: 22)
LLADTTHHRPWTVIGESTHHRPWSIIGESSHHKPFTGLGDTTHHRPWGI
LAESTHHKPWT.

In some embodiments, the β-TCP-binding polypeptide includes LLADTTHHRPWT (SEQ ID NO: 1) and ILAESTHHKPWT (SEQ ID NO: 4). In some embodiments, the β-TCP-binding polypeptide includes at least one copy of the sequence LLADTTHHRPWTILAESTHHKPWT (SEQ ID NO: 23). In some embodiments, the β-TCP-binding polypeptide includes the sequence of LLADTTHHRPWTI-

LAESTHHKPWTLLADTTHHRPWTILAESTHHKPW-TLLADTTHHRP WT (SEQ ID NO: 24).

In some embodiments, the β-TCP-binding polypeptide includes LLADTTHHRPWT (SEQ ID NO: 1) and GLGDTTHHRPWG (SEQ ID NO: 7). In some embodiments, the β-TCP-binding polypeptide includes at least one copy of the sequence of LLADTTHHRPWTGLGD-TTHHRPWG (SEQ ID NO: 25). In some embodiments, the β-TCP-binding polypeptide includes the sequence of LLADTTHHRPWTGLGDTTHHRPWGLLADTTHHR-PWT (SEQ ID NO: 26). In some embodiments, the β-TCP-binding polypeptide includes the sequence of LLADTTHHRPWTGLGDTTHHRPWGLLADTTHH-RPWTGLGDTTHHRPWGLLADTTHHR PWT (SEQ ID NO: 27). In some embodiments, the β-TCP-binding polypeptide includes the sequence of LLADTTHHRPWTGL-GDTTHHRPWGLLADTTHHRPWTGLGDTTHHRPWG-LLADTTHHR PWTGLGDTTHHRPWGLLADTTHH-RPWT (SEQ ID NO: 28).

In some embodiments, the β-TCP-binding polypeptide includes STADTSHHRPS (SEQ ID NO: 10), TSG-GESTHHRPS (SEQ ID NO: 11), TSGGESSHHKPS (SEQ ID NO: 12), TSGGDSSHHRPS (SEQ ID NO: 13), and GSSGESTHHKPST (SEQ ID NO: 14). In some embodiments, the β-TCP-binding polypeptide includes the sequence of STADTSHHRPSTSGGESTHHRPSTSG-GESSHHKPSTGSGDSSHHRPSGSSGESTHHKPST (SEQ ID NO: 29).

In some embodiments, the β-TCP-binding polypeptide includes VGADSTHHRPVT (SEQ ID NO: 15), GAADTTHHRPVT SEQ ID NO: 16), AGADTTHHRPVT (SEQ ID NO: 17), GGADTTHHRPAT (SEQ ID NO: 18) and GGADTTHHRPGT (SEQ ID NO: 19). In some embodiments, the β-TCP-binding polypeptide includes the sequence of VGADSTHHRPVTGAADTTHHRPVTAGA-DTTHHRPVTGGADTTHHRPATGGADTTHHR PGT (SEQ ID NO: 30).

In some embodiments, the β-TCP-binding polypeptide includes STADTSHHRPS (SEQ ID NO: 10), LLADTTHHRPWT (SEQ ID NO: 1), TSGGESTHHRPS (SEQ ID NO: 11), VGADSTHHRPVT (SEQ ID NO: 15), TSGGESSHHKPS (SEQ ID NO: 12), GAADTTHHRPVT (SEQ ID NO: 16), TSGGDSSHHRPS (SEQ ID NO: 13), GSSGESTHHKPS (SEQ ID NO: 101), and TGGA-DTTHHRPAT (SEQ ID NO: 102). In some embodiments, the β-TCP-binding polypeptide includes the sequence of:

```
                                       (SEQ ID NO: 31)
STADTSHHRPSLLADTTHHRPWTTSGGESTHHRPSVGADSTHHRPVTTS
GGESSHHKPSGAADTTHHRPVTTGSGDSSHHRPSGSSGESTHHKPSTGG
ADTTHHRPAT.
```

In some embodiments, the β-TCP-binding polypeptides can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, or 20) copies of any one of SEQ ID NOs: 2-19 or a sequence of Formula I (excluding SEQ ID NO: 1).

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 1 (but excluding SEQ ID NO: 1).

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 2.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 3.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 4.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 5.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 6.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 7.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 8.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 9.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 10.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 11.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 12.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 13.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 14.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 15.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 16.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 17.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 18.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 19.

In some embodiments, the β-TCP-binding polypeptide further comprises a linker sequence (e.g., any of the exemplary linker sequences described herein or known in the art) between a neighboring pair of any of SEQ ID NOs. 2-19 and a sequence of Formula I (excluding SEQ ID NO: 1). In some embodiments, the linker sequence can include the sequence of TGGSGEGGTGASTGGSAGTGGSGGTTSGEAG-GSSGAG (SEQ ID NO: 33). In some embodiments, the linker sequence consists of TGGSGEGGT-GASTGGSAGTGGSGGTTSGEAGGSSGAG (SEQ ID NO: 33). In some embodiments, the linker sequence includes the sequence of GSGATG (SEQ ID NO: 34). In some embodiments, the linker sequence consists of GSGATG (SEQ ID NO: 34).

In some embodiments, where the β-TCP-binding polypeptide comprises two or more or any of SEQ ID Nos. 2-19 and a sequence of Formula I (excluding SEQ ID NO: 1), a linker sequence (e.g., any of the exemplary linker sequences described herein or known in the art) can be between any of the pairs (e.g., all of the pairs) of neighboring sequences selected from the group of SEQ ID NOs: 2-19 and a sequence of Formula I (excluding SEQ ID NO: 1).

In some embodiments, the β-TCP-binding polypeptide can include a signal sequence at its N-terminus. In some embodiments, the β-TCP-binding polypeptide can further include a tag sequence (e.g., a poly-His tag, chitin-binding protein (CBP), maltose-binding protein (MBP), strep-tag, glutathione-S-transferase (GST), thioredoxin, or Fc region). Additional examples of tags are known in the art.

The β-TCP-binding polypeptides described herein can bind to β-TCP (e.g., any of the types of β-TCP described herein) with a dissociation equilibrium constant ($K_d$) of about 1 pM to about 100 µM (or any of the subranges of this range described herein) (e.g., as measured using SPR in phosphate buffered saline).

In some embodiments, the β-TCP-binding polypeptides described herein can have a total length of about 11 amino acids to about 1400 amino acids, about 11 amino acids to about 1350 amino acids, about 11 amino acids to about 1300 amino acids, about 11 amino acids to about 1250 amino acids, about 11 amino acids to about 1200 amino acids, about 11 amino acids to about 1150 amino acids, about 11 amino acids to about 1100 amino acids, about 11 amino acid to about 1050 amino acids, about 11 amino acids to about 1000 amino acids, about 11 amino acids to about 950 amino acids, about 11 amino acids to about 900 amino acids, about 11 amino acids to about 850 amino acids, about 11 amino acids to about 800 amino acids, about 11 amino acids to about 750 amino acids, about 11 amino acids to about 700 amino acids, about 11 amino acids to about 650 amino acids, about 11 amino acids to about 600 amino acids, about 11 amino acids to about 550 amino acids, about 11 amino acids to about 500 amino acids, about 11 amino acids to about 450 amino acids, about 11 amino acids to about 400 amino acids, about 11 amino acids to about 350 amino acids, about 11 amino acids to about 300 amino acids, about 11 amino acids to about 250 amino acids, about 11 amino acids to about 200 amino acids, about 11 amino acids to about 150 amino acids, about 11 amino acids to about 100 amino acids, about 11 amino acids to about 90 amino acids, about 11 amino acids to about 80 amino acids, about 11 amino acids to about 70 amino acids, about 11 amino acids to about 60 amino acids, about 11 amino acids to about 50 amino acids, about 11 amino acids to about 45 amino acids, about 11 amino acids to about 40 amino acids, about 11 amino acids to about 35 amino acids, about 11 amino acids to about 30 amino acids, about 11 amino acids to about 25 amino acids, about 11 amino acids to about 20 amino acids, about 11 amino acids to about 18 amino acids, about 11 amino acids to about 16 amino acids, about 11 amino acids to about 14 amino acids, about 12 amino acids to about 1400 amino acids, about 12 amino acids to about 1350 amino acids, about 12 amino acids to about 1300 amino acids, about 12 amino acids to about 1250 amino acids, about 12 amino acids to about 1200 amino acids, about 12 amino acids to about 1150 amino acids, about 12 amino acids to about 1100 amino acids, about 12 amino acid to about 1050 amino acids, about 12 amino acids to about 1000 amino acids, about 12 amino acids to about 950 amino acids, about 12 amino acids to about 900 amino acids, about 12 amino acids to about 850 amino acids, about 12 amino acids to about 800 amino acids, about 12 amino acids to about 750 amino acids, about 12 amino acids to about 700 amino acids, about 12 amino acids to about 650 amino acids, about 12 amino acids to about 600 amino acids, about 12 amino acids to about 550 amino acids, about 12 amino acids to about 500 amino acids, about 12 amino acids to about 450 amino acids, about 12 amino acids to about 400 amino acids, about 12 amino acids to about 350 amino acids, about 12 amino acids to about 300 amino acids, about 12 amino acids to about 250 amino acids, about 12 amino acids to about 200 amino acids, about 12 amino acids to about 150 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 20 amino acids, about 12 amino acids to about 18 amino acids, about 12 amino acids to about 16 amino acids, about 12 amino acids to about 14 amino acids, about 14 amino acids to about 1400 amino acids, about 14 amino acids to about 1350 amino acids, about 14 amino acids to about 1300 amino acids, about 14 amino acids to about 1250 amino acids, about 14 amino acids to about 1200 amino acids, about 14 amino acids to about 1150 amino acids, about 14 amino acids to about 1100 amino acids, about 14 amino acid to about 1050 amino acids, about 14 amino acids to about 1000 amino acids, about 14 amino acids to about 950 amino acids, about 14 amino acids to about 900 amino acids, about 14 amino acids to about 850 amino acids, about 14 amino acids to about 800 amino acids, about 14 amino acids to about 750 amino acids, about 14 amino acids to about 700 amino acids, about 14 amino acids to about 650 amino acids, about 14 amino acids to about 600 amino acids, about 14 amino acids to about 550 amino acids, about 14 amino acids to about 500 amino acids, about 14 amino acids to about 450 amino acids, about 14 amino acids to about 400 amino acids, about 14 amino acids to about 350 amino acids, about 14 amino acids to about 300 amino acids, about 14 amino acids to about 250 amino acids, about 14 amino acids to about 200 amino acids, about 14 amino acids to about 150 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 20 amino acids, about 14 amino acids to about 18 amino acids, about 14 amino acids to about 16 amino acids, about 16 amino acids to about 1400 amino acids, about 16 amino acids to about 1350 amino acids, about 16 amino acids to about 1300 amino acids, about 16 amino acids to about 1250 amino acids, about 16 amino acids to about 1200 amino acids, about 16 amino acids to about 1150 amino acids, about 16 amino acids to about 1100 amino acids, about 16 amino acid to about 1050 amino acids, about 16 amino acids to about 1000 amino acids, about 16 amino acids to about 950 amino acids, about 16 amino acids to about 900 amino acids, about 16 amino acids to about 850 amino acids, about 16 amino acids to about 800 amino acids, about 16 amino acids to about 750 amino acids, about 16 amino acids to about 700 amino acids, about 16 amino acids to about 650 amino acids, about 16 amino acids to about 600 amino acids, about 16 amino acids to about 550 amino acids, about 16 amino acids to about 500 amino acids, about 16 amino acids to about 450 amino acids, about 16 amino acids to about 400 amino acids, about 16 amino acids to about 350 amino acids, about 16 amino acids to about 300 amino acids, about 16 amino acids to about 250 amino acids, about 16 amino acids to about 200 amino acids, about 16 amino acids to about 150 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 20 amino acids, about 16 amino acids to about 18 amino acids, about 18 amino acids to about 1400 amino acids, about 18 amino acids to about 1350 amino acids, about 18 amino acids to about 1300 amino acids, about 18 amino acids to about 1250 amino acids, about 18 amino acids to about 1200 amino acids, about 18 amino acids to about 1150 amino acids, about 18 amino acids to about 1100 amino acids, about 18 amino acid to about 1050 amino acids, about 18 amino acids to about 1000 amino acids, about 18 amino acids to about 950 amino acids, about 18 amino acids to about 900 amino acids, about 18 amino acids to about 850 amino acids, about 18 amino acids to about 800 amino acids, about 18 amino acids to about 750 amino acids, about 18 amino acids to about 700 amino acids, about 18 amino acids to about 650 amino acids, about 18 amino acids to about 600 amino acids, about 18 amino acids to about 550 amino acids, about 18 amino acids to about 500 amino acids, about 18 amino acids to about 450 amino acids, about 18 amino acids to about 400 amino acids, about 18 amino acids to about 350 amino acids, about 18 amino acids to about 300 amino acids, about 18 amino acids to about 250 amino acids, about 18 amino acids to about 200 amino acids, about 18 amino acids to about 150 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 20 amino acids, about 20 amino acids to about 1400 amino acids, about 20 amino acids to about 1350 amino acids, about 20 amino acids to about 1300 amino acids, about 20 amino acids to about 1250 amino acids, about 20 amino acids to about 1200 amino acids, about 20 amino acids to about 1150 amino acids, about 20 amino acids to about 1100 amino acids, about 20 amino acid to about 1050 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 250 amino acids, about 20 amino acids to about 200 amino acids, about 20 amino acids to about 150 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1400 amino acids, about 25 amino acids to about 1350 amino acids, about 25 amino acids to about 1300 amino acids, about 25 amino acids to about 1250 amino acids, about 25 amino acids to about 1200 amino acids, about 25 amino acids to about 1150 amino acids, about 25 amino acids to about 1100 amino acids, about 25 amino acid to about 1050 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 250 amino acids, about 25 amino acids to about 200 amino acids, about 25 amino acids to about 150 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1400 amino acids, about 30 amino acids to about 1350 amino acids, about 30 amino acids to about 1300 amino acids, about 30 amino acids to about 1250 amino acids, about 30 amino acids to about 1200 amino acids, about 30 amino acids to about 1150 amino acids, about 30 amino acids to about 1100 amino acids, about 30 amino acid to about 1050 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 250 amino acids, about 30 amino acids to about 200 amino acids, about 30 amino acids to about 150 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1400 amino acids, about 35 amino acids to about 1350 amino acids, about 35 amino acids to about 1300 amino acids, about 35 amino acids to about 1250 amino acids, about 35 amino acids to about 1200 amino acids, about 35 amino acids to about 1150 amino acids, about 35 amino acids to about 1100 amino acids, about 35 amino acid to about 1050 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 250 amino acids, about 35 amino acids to about 200 amino acids, about 35 amino acids to about 150 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 1400 amino acids, about 40 amino acids to about 1350 amino acids, about 40 amino acids to about 1300 amino acids, about 40 amino acids to about 1250 amino acids, about 40 amino acids to about 1200 amino acids, about 40 amino acids to about 1150 amino acids, about 40 amino acids to about 1100 amino acids, about 40 amino acid to about 1050 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 150 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 1400 amino acids, about 45 amino acids to about 1350 amino acids, about 45 amino acids to about 1300 amino acids, about 45 amino acids to about 1250 amino acids, about 45 amino acids to about 1200 amino acids, about 45 amino acids to about 1150 amino acids, about 45 amino acids to about 1100 amino acids, about 45 amino acid to about 1050 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 250 amino acids, about 45 amino acids to about 200 amino acids, about 45 amino acids to about 150 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 1400 amino acids, about 50 amino acids to about 1350 amino acids, about 50 amino acids to about 1300 amino acids, about 50 amino acids to about 1250 amino acids, about 50 amino acids to about 1200 amino acids, about 50 amino acids to about 1150 amino acids, about 50 amino acids to about 1100 amino acids, about 50 amino acid to about 1050 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 1400 amino acids, about 60 amino acids to about 1350 amino acids, about 60 amino acids to about 1300 amino acids, about 60 amino acids to about 1250 amino acids, about 60 amino acids to about 1200 amino acids, about 60 amino acids to about 1150 amino acids, about 60 amino acids to about 1100 amino acids, about 60 amino acid to about 1050 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 150 amino acids, about 60 amino acids to about 100 amino acids, about 60 amino acids to about 90 amino acids, about 60 amino acids to about 80 amino acids, about 60 amino acids to about 70 amino acids, about 70 amino acids to about 1400 amino acids, about 70 amino acids to about 1350 amino acids, about 70 amino acids to about 1300 amino acids, about 70 amino acids to about 1250 amino acids, about 70 amino acids to about 1200 amino acids, about 70 amino acids to about 1150 amino acids, about 70 amino acids to about 1100 amino acids, about 70 amino acid to about 1050 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 250 amino acids, about 70 amino acids to about 200 amino acids, about 70 amino acids to about 150 amino acids, about 70 amino acids to about 100 amino acids, about 70 amino acids to about 90 amino acids, about 70 amino acids to about 80 amino acids, about 80 amino acids to about 1400 amino acids, about 80 amino acids to about 1350 amino acids, about 80 amino acids to about 1300 amino acids, about 80 amino acids to about 1250 amino acids, about 80 amino acids to about 1200 amino acids, about 80 amino acids to about 1150 amino acids, about 80 amino acids to about 1100 amino acids, about 80 amino acid to about 1050 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 150 amino acids, about 80 amino acids to about 100 amino acids, about 80 amino acids to about 90 amino acids, about 90 amino acids to about 1400 amino acids, about 90 amino acids to about 1350 amino acids, about 90 amino acids to about 1300 amino acids, about 90 amino acids to about 1250 amino acids, about 90 amino acids to about 1200 amino acids, about 90 amino acids to about 1150 amino acids, about 90 amino acids to about 1100 amino acids, about 90 amino acid to about 1050 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 250 amino acids, about 90 amino acids to about 200 amino acids, about 90 amino acids to about 150 amino acids, about 90 amino acids to about 100 amino acids, about 100 amino acids to about 1400 amino acids, about 100 amino acids to about 1350 amino acids, about 100 amino acids to about 1300 amino acids, about 100 amino acids to about 1250 amino acids, about 100 amino acids to about 1200 amino acids, about 100 amino acids to about 1150 amino acids, about 100 amino acids to about 1100 amino acids, about 100 amino acid to about 1050 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 1400 amino acids, about 150 amino acids to about 1350 amino acids, about 150 amino acids to about 1300 amino acids, about 150 amino acids to about 1250 amino acids, about 150 amino acids to about 1200 amino acids, about 150 amino acids to about 1150 amino acids, about 150 amino acids to about 1100 amino acids, about 150 amino acid to about 1050 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 1400 amino acids, about 200 amino acids to about 1350 amino acids, about 200 amino acids to about 1300 amino acids, about 200 amino acids to about 1250 amino acids, about 200 amino acids to about 1200 amino acids, about 200 amino acids to about 1150 amino acids, about 200 amino acids to about 1100 amino acids, about 200 amino acid to about 1050 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 1400 amino acids, about 250 amino acids to about 1350 amino acids, about 250 amino acids to about 1300 amino acids, about 250 amino acids to about 1250 amino acids, about 250 amino acids to about 1200 amino acids, about 250 amino acids to about 1150 amino acids, about 250 amino acids to about 1100 amino acids, about 250 amino acid to about 1050 amino acids, about 250 amino acids to about 1000 amino acids, about 250 amino acids to about 950 amino acids, about 250 amino acids to about 900 amino acids, about 250 amino acids to about 850 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 1400 amino acids, about 300 amino acids to about 1350 amino acids, about 300 amino acids to about 1300 amino acids, about 300 amino acids to about 1250 amino acids, about 300 amino acids to about 1200 amino acids, about 300 amino acids to about 1150 amino acids, about 300 amino acids to about 1100 amino acids, about 300 amino acid to about 1050 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1400 amino acids, about 350 amino acids to about 1350 amino acids, about 350 amino acids to about 1300 amino acids, about 350 amino acids to about 1250 amino acids, about 350 amino acids to about 1200 amino acids, about 350 amino acids to about 1150 amino acids, about 350 amino acids to about 1100 amino acids, about 350 amino acid to about 1050 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1400 amino acids, about 400 amino acids to about 1350 amino acids, about 400 amino acids to about 1300 amino acids, about 400 amino acids to about 1250 amino acids, about 400 amino acids to about 1200 amino acids, about 400 amino acids to about 1150 amino acids, about 400 amino acids to about 1100 amino acids, about 400 amino acid to about 1050 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1400 amino acids, about 450 amino acids to about 1350 amino acids, about 450 amino acids to about 1300 amino acids, about 450 amino acids to about 1250 amino acids, about 450 amino acids to about 1200 amino acids, about 450 amino acids to about 1150 amino acids, about 450 amino acids to about 1100 amino acid to about 1050 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1400 amino acids, about 500 amino acids to about 1350 amino acids, about 500 amino acids to about 1300 amino acids, about 500 amino acids to about 1250 amino acids, about 500 amino acids to about 1200 amino acids, about 500 amino acids to about 1150 amino acids, about 500 amino acids to about 1100 amino acids, about 500 amino acid to about 1050 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1400 amino acids, about 550 amino acids to about 1350 amino acids, about 550 amino acids to about 1300 amino acids, about 550 amino acids to about 1250 amino acids, about 550 amino acids to about 1200 amino acids, about 550 amino acids to about 1150 amino acids, about 550 amino acids to about 1100 amino acids, about 550 amino acid to about 1050 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1400 amino acids, about 600 amino acids to about 1350 amino acids, about 600 amino acids to about 1300 amino acids, about 600 amino acids to about 1250 amino acids, about 600 amino acids to about 1200 amino acids, about 600 amino acids to about 1150 amino acids, about 600 amino acids to about 1100 amino acids, about 600 amino acid to about 1050 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1400 amino acids, about 650 amino acids to about 1350 amino acids, about 650 amino acids to about 1300 amino acids, about 650 amino acids to about 1250 amino acids, about 650 amino acids to about 1200 amino acids, about 650 amino acids to about 1150 amino acids, about 650 amino acids to about 1100 amino acids, about 650 amino acid to about 1050 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1400 amino acids, about 700 amino acids to about 1350 amino acids, about 700 amino acids to about 1300 amino acids, about 700 amino acids to about 1250 amino acids, about 700 amino acids to about 1200 amino acids, about 700 amino acids to about 1150 amino acids, about 700 amino acids to about 1100 amino acids, about 700 amino acid to about 1050 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1400 amino acids, about 750 amino acids to about 1350 amino acids, about 750 amino acids to about 1300 amino acids, about 750 amino acids to about 1250 amino acids, about 750 amino acids to about 1200 amino acids, about 750 amino acids to about 1150 amino acids, about 750 amino acids to about 1100 amino acids, about 750 amino acid to about 1050 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1400 amino acids, about 800 amino acids to about 1350 amino acids, about 800 amino acids to about 1300 amino acids, about 800 amino acids to about 1250 amino acids, about 800 amino acids to about 1200 amino acids, about 800 amino acids to about 1150 amino acids, about 800 amino acids to about 1100 amino acids, about 800 amino acid to about 1050 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1400 amino acids, about 850 amino acids to about 1350 amino acids, about 850 amino acids to about 1300 amino acids, about 850 amino acids to about 1250 amino acids, about 850 amino acids to about 1200 amino acids, about 850 amino acids to about 1150 amino acids, about 850 amino acids to about 1100 amino acids, about 850 amino acid to about 1050 amino acids, about 850 amino acids to about 1000 amino acids, about 850 amino acids to about 950 amino acids, about 850 amino acids to about 900 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acid to about 1050 amino acids, about 900 amino acids to about 1000 amino acids, about 900 amino acids to about 950 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acid to about 1050 amino acids, about 950 amino acids to about 1000 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acid to about 1050 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1400 amino acids, about 1250 amino acids to about 1350 amino acids, about 1250 amino acids to about 1300 amino acids, about 1300 amino acids to about 1400 amino acids, about 1300 amino acids to about 1350 amino acids, or about 1350 amino acids to about 1400 amino acids.

For example, the β-TCP-binding polypeptide can include the amino acid sequence of LLADTTHHRPWTVI-GESTHHRPWSIIGESSHHKPFTGLGDTTHHRPWGI-LAESTHHKPWT ATGGSGEGGTGASTGGSAGTGGS-GGTTSGEAGGSSGAG (SEQ ID NO: 44). In some instances the β-TCP-binding polypeptide includes an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 44.

For example, the β-TCP-binding polypeptide may include: LLADTTHHRPWTGLGDTTHHRPWGLLADTT-HHRPWTGLGDTTHHRPWGLLADTTHHR PWTTGG-SGEGGTGASTGGSAGTGGSGGTTSGEAGGSSGAG (SEQ ID NO: 45). In some instances the β-TCP-binding polypeptide includes an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 45.

A variety of different methods known in the art can be used to determine the $K_D$ values of any of the β-TCP-binding polypeptides described herein for binding to β-TCP (e.g., any of the types of β-TCP described herein) (e.g., an electrophoretic mobility shift assay, a filter binding assay, surface plasmon resonance, and a biomolecular binding kinetics assay, etc.)

Nucleic Acids/Vectors

Also provided herein are nucleic acids that encode any of the chimeric polypeptides or β-TCP-binding polypeptides described herein.

Also provided herein are vectors that include any of the nucleic acids provided herein. A "vector" according to the present disclosure is a polynucleotide capable of inducing the expression of a recombinant protein (e.g., any of the chimeric polypeptides or β-TCP-binding polypeptides described) in a host cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989; Miller, *Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J. Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter and/or enhancer operably linked to any of the nucleic acids described herein. Non-limiting examples of promoters include promoters from human cytomegalovirus (CMV), mouse phosphoglycerate kinase 1, polyoma adenovirus, thyroid stimulating hormone α, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQa, HLA DQP3, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the chimeric polypeptide or β-TCP-binding polypeptide. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7): 1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2). A poly(A) sequence can, e.g., be a synthetic polyadenylation site. See, e.g., Levitt el al, *Genes Dev.* 3(7): 1019-1025, 1989). In some examples, a poly(A) sequence can be the polyadenylation signal of soluble neuropilin-1: AAATAAAATACGAAATG (SEQ ID NO:111). Additional examples of poly(A) sequences are known in the art. Additional examples and aspects of vectors are also known in the art.

Methods of Making A Chimeric Polypeptide

Also provided herein are methods of making a chimeric polypeptide (e.g., any of the chimeric polypeptides described herein) or a β-TCP-binding polypeptide (e.g., any of the β-TCP-binding polypeptides described herein) that include: introducing into a cell a nucleic acid sequence encoding the chimeric polypeptide or the β-TCP-binding polypeptide to produce a recombinant cell; and culturing the recombinant cell under conditions sufficient for the expression of the chimeric polypeptide or β-TCP-binding polypeptide. In some embodiments, the introducing step includes introducing into a cell an expression vector including a nucleic acid sequence encoding the chimeric polypeptide or the β-TCP-binding polypeptide to produce a recombinant cell. In some embodiments, the expression vector includes chaperones (e.g., GroES, GroEL) and glutathione to aid with in vitro folding.

A chimeric polypeptide or β-TCP-binding polypeptide described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells.

In some embodiments, the eukaryotic cell is a yeast cell, such as *Saccharomyces cerevisiae*. In some embodiments, the eukaryotic cell is a higher eukaryote, such as mammalian, avian, plant, or insect cells. In some embodiments, the eukaryotic cell is a mammalian cell (e.g., a Chinese Hamster Ovary (CHO) cell). As used herein, the term "prokaryotic cell" refers to a cell that does not have a distinct, membrane-bound nucleus. In some embodiments, the prokaryotic cell is a bacterial cell. In some embodiments, the bacterial cell is a chemically competent *E. coli* K12 cell (e.g., Shuffle® T7; New England BioLabs) or a BL21(DE3) pLysS chemically competent *E. coli* cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the chimeric polypeptide or the β-TCP-binding polypeptide from a cell (e.g., a eukaryotic cell) using techniques well-known in the art (e.g., ammonium sulfate precipitation, polyethylene glycol precipitation, cobalt column, heparin column, ion-exchange chromatography (anion or cation), chromatography based on hydrophobic interaction, metal-affinity chromatography, ligand-affinity chromatography, and size exclusion chromatography).

In some embodiments, a hydrophobicity/hydrophilicity plot is constructed to determine variant β-TCP binding sequences that can be included in any of the chimeric polypeptides described herein.

β-TCP

Sintering of tricalcium phosphate, $Ca_3(PO_4)_2$, causes its structure to convert to β-TCP. β-TCP is an osteoconductive material that supports bone mineralization by easily dissolving at low pH and serves as a rigid substrate for cell attachment (see, e.g., Muschler et al., *J. Bone Joint Surgery* 86:1541-1558, 2004; Fleming Jr. et al., "Intraoperative Harvest and Concentration of Human Bone Marrow Osteoprogenitors for Enhancement of Spinal Fusion," in Orthopedic Tissue Engineering: Basic Science and Practice, 2004).

β-TCP as described herein can be in a variety of different forms. Examples of such forms include a granular form, a porous form, a powder, a putty (e.g., a moldable putty), a paste, a scaffold, and/or a coating on a solid surface (e.g., a coating on a medical device). In addition, the β-TCP can be used in a variety of different shapes (e.g., a cross, a ladder, a sphere, an ellipsoid, a square, a triangular pyramid, a rod, a cone, a torus, or a wedge, or any combination thereof) and sizes (e.g., largest average diameter of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, about 5 cm, about 6 cm, about 7 cm, about 8 cm, about 9 cm, or about 10 cm). In some embodiments, β-TCP can be porous (e.g., about 20% to about 80% porous, about 20% to about 75% porous, about 20% to about 70% porous, about 20% to about 65% porous, about 20% to about 60% porous, about 20% to about 55% porous, about 20% to about 50% porous, about 20% to about 45% porous, about 20% to about 40% porous, about 20% to about 35% porous, about 20% to about 30% porous, about 20% to about 25% porous, about 25% to about 80% porous, about 25% to about 75% porous, about 25% to about 70% porous, about 25% to about 65% porous, about 25% to about 60% porous, about 25% to about 55% porous, about 25% to about 50% porous, about 25% to about 45% porous, about 25% to about 40% porous, about 25% to about 35% porous, about 25% to about 30% porous, about 30% to about 80% porous, about 30% to about 75% porous, about 30% to about 70% porous, about 30% to about 65% porous, about 30% to about 60% porous, about 30% to about 55% porous, about 30% to about 50% porous, about 30% to about 45% porous, about 30% to about 40% porous, about 30% to about 35% porous, about 35% to about 80% porous, about 35% to about 75% porous, about 35% to about 70% porous, about 35% to about 65% porous, about 35% to about 60% porous, about 35% to about 55% porous, about 35% to about 50% porous, about 35% to about 45% porous, about 35% to about 40% porous, about 40% to about 80% porous, about 40% to about 75% porous, about 40% to about 70% porous, about 40% to about 65% porous, about 40% to about 60% porous, about 40% to about 55% porous, about 40% to about 50% porous, about 40% to about 45% porous, about 45% to about 80% porous, about 45% to about 75% porous, about 45% to about 70% porous, about 45% to about 65% porous, about 45% to about 60% porous, about 45% to about 55% porous, about 45% to about 50% porous, about 50% to about 80% porous, about 50% to about 75% porous, about 50% to about 70% porous, about 50% to about 65% porous, about 50% to about 60% porous, about 50% to about 55% porous, about 55% to about 80% porous, about 55% to about 75% porous, about 55% to about 70% porous, about 55% to about 65% porous, about 55% to about 60% porous, about 60% to about 80% porous, about 60% to about 75% porous, about 60% to about 70% porous, about 60% to about 65% porous, about 65% to about 80% porous, about 65% to about 75% porous, about 65% to about 70% porous, about 70% to about 80% porous, about 70% to about 75% porous, or about 75% to about 80% porous).

For example, β-TCP can have an average pore size of about 1 nm to about 50 mm, about 1 nm to about 45 mm, about 1 nm to about 40 mm, about 1 nm to about 35 mm, about 1 nm to about 30 mm, about 1 nm to about 25 mm, about 1 nm to about 20 mm, about 1 nm to about 15 mm, about 1 nm to about 10 mm, about 1 nm to about 5 mm, about 1 nm to about 1 mm, about 1 nm to about 900 Tm, about 1 nm to about 800 Tm, about 1 nm to about 700 Tm, about 1 nm to about 600 Tm, about 1 nm to about 500 Tm, about 1 nm to about 400 Tm, about 1 nm to about 300 Tm, about 1 nm to about 200 Tm, about 1 nm to about 100 Tm, about 1 nm to about 50 Tm, about 1 nm to about 10 Tm, about 1 nm to about 5 Tm, about 1 nm to about 1 Tm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, about 1 nm to about 100 nm, about 1 nm to about 50 nm, about 1 nm to about 25 nm, about 1 nm to about 10 nm, about 1 nm to about 5 nm, about 5 nm to about 50 mm, about 5 nm to about 45 mm, about 5 nm to about 40 mm, about 5 nm to about 35 mm, about 5 nm to about 30 mm, about 5 nm to about 25 mm, about 5 nm to about 20 mm, about 5 nm to about 15 mm, about 5 nm to about 10 mm, about 5 nm to about 5 mm, about 5 nm to about 1 mm, about 5 nm to about 900 Tm, about 5 nm to about 800 Tm, about 5 nm to about 700 Tm, about 5 nm to about 600 Tm, about 5 nm to about 500 Tm, about 5 nm to about 400 Tm, about 5 nm to about 300 Tm, about 5 nm to about 200 Tm, about 5 nm to about 100 Tm, about 5 nm to about 50 Tm, about 5 nm to about 10 Tm, about 5 nm to about 5 Tm, about 5 nm to about 1 Tm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, about 5 nm to about 100 nm, about 5 nm to about 50 nm, about 5 nm to about 25 nm, about 5 nm to about 10 nm, about 10 nm to about 50 mm, about 10 nm to about 45 mm, about 10 nm to about 40 mm, about 10 nm to about 35 mm, about 10 nm to about 30 mm, about 10 nm to about 25 mm, about 10 nm to about 20 mm, about 10 nm to about 15 mm, about 10 nm to about 10 mm, about 10 nm to about 5 mm, about 10 nm to about 1 mm, about 10 nm to about 900 Tm, about 10 nm to about 800 Tm, about 10 nm to about 700 Tm, about 10 nm to about 600 Tm, about 10 nm to about 500 Tm, about 10 nm to about 400 Tm, about 10 nm to about 300 Tm, about 10 nm to about 200 Tm, about 10 nm to about 100 Tm, about 10 nm to about 50 Tm, about 10 nm to about 10 Tm, about 10 nm to about 5 Tm, about 10 nm to about 1 Tm, about 10 nm to about 900 nm, about 10 nm to about 800 nm, about 10 nm to about 700 nm, about 10 nm to about 600 nm, about 10 nm to about 500 nm, about 10 nm to about 400 nm, about 10 nm to about 300 nm, about 10 nm to about 200 nm, about 10 nm to about 100 nm, about 10 nm to about 50 nm, about 10 nm to about 25 nm, about 25 nm to about 50 mm, about 25 nm to about 45 mm, about 25 nm to about 40 mm, about 25 nm to about 35 mm, about 25 nm to about 30 mm, about 25 nm to about 25 mm, about 25 nm to about 20 mm, about 25 nm to about 15 mm, about 25 nm to about 10 mm, about 25 nm to about 5 mm, about 25 nm to about 1 mm, about 25 nm to about 900 Tm, about 25 nm to about 800 Tm, about 25 nm to about 700 Tm, about 25 nm to about 600 Tm, about 25 nm to about 500 Tm, about 25 nm to about 400 Tm, about 25 nm to about 300 Tm, about 25 nm to about 200 Tm, about 25 nm to about 100 Tm, about 25 nm to about 50 Tm, about 25 nm to about 10 Tm, about 25 nm to about 5 Tm, about 25 nm to about 1 Tm, about 25 nm to about 900 nm, about 25 nm to about 800 nm, about 25 nm to about 700 nm, about 25 nm to about 600 nm, about 25 nm to about 500 nm, about 25 nm to about 400 nm, about 25 nm to about 300 nm, about 25 nm to about 200 nm, about 25 nm to about 100 nm, about 25 nm to about 50 nm, about 50 nm to about 50 mm, about 50 nm to about 45 mm, about 50 nm to about 40 mm, about 50 nm to about 35 mm, about 50 nm to about 30 mm, about 50 nm to about 25 mm, about 50 nm to about 20 mm, about 50 nm to about 15 mm, about 50 nm to about 10 mm, about 50 nm to about 5 mm, about 50 nm to about 1 mm, about 50 nm to about 900 Tm, about 50 nm to about 800 Tm, about 50 nm to about 700 Tm, about 50 nm to about 600 Tm, about 50 nm to about 500 Tm, about 50 nm to about 400 Tm, about 50 nm to about 300 Tm, about 50 nm to about 200 Tm, about 50 nm to about 100 Tm, about 50 nm to about 50 Tm, about 50 nm to about 10 Tm, about 50 nm to about 5 Tm, about 50 nm to about 1 Tm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, about 50 nm to about 100 nm, about 100 nm to about 50 mm, about 100 nm to about 45 mm, about 100 nm to about 40 mm, about 100 nm to about 35 mm, about 100 nm to about 30 mm, about 100 nm to about 25 mm, about 100 nm to about 20 mm, about 100 nm to about 15 mm, about 100 nm to about 10 mm, about 100 nm to about 5 mm, about 100 nm to about 1 mm, about 100 nm to about 900 Tm, about 100 nm to about 800 Tm, about 100 nm to about 700 Tm, about 100 nm to about 600 Tm, about 100 nm to about 500 Tm, about 100 nm to about 400 Tm, about 100 nm to about 300 Tm, about 100 nm to about 200 Tm, about 100 nm to about 100 Tm, about 100 nm to about 50 Tm, about 100 nm to about 10 Tm, about 100 nm to about 5 Tm, about 100 nm to about 1 Tm, about 100 nm to about 900 nm, about 100 nm to about 800 nm, about 100 nm to about 700 nm, about 100 nm to about 600 nm, about 100 nm to about 500 nm, about 100 nm to about 400 nm, about 100 nm to about 300 nm, about 100 nm to about 200 nm, about 200 nm to about 50 mm, about 200 nm to about 45 mm, about 200 nm to about 40 mm, about 200 nm to about 35 mm, about 200 nm to about 30 mm, about 200 nm to about 25 mm, about 200 nm to about 20 mm, about 200 nm to about 15 mm, about 200 nm to about 10 mm, about 200 nm to about 5 mm, about 200 nm to about 1 mm, about 200 nm to about 900 Tm, about 200 nm to about 800 Tm, about 200 nm to about 700 Tm, about 200 nm to about 600 Tm, about 200 nm to about 500 Tm, about 200 nm to about 400 Tm, about 200 nm to about 300 Tm, about 200 nm to about 200 Tm, about 200 nm to about 100 Tm, about 200 nm to about 50 Tm, about 200 nm to about 10 Tm, about 200 nm to about 5 Tm, about 200 nm to about 1 Tm, about 200 nm to about 900 nm, about 200 nm to about 800 nm, about 200 nm to about 700 nm, about 200 nm to about 600 nm, about 200 nm to about 500 nm, about 200 nm to about 400 nm, about 200 nm to about 300 nm, about 300 nm to about 50 mm, about 300 nm to about 45 mm, about 300 nm to about 40 mm, about 300 nm to about 35 mm, about 300 nm to about 30 mm, about 300 nm to about 25 mm, about 300 nm to about 20 mm, about 300 nm to about 15 mm, about 300 nm to about 10 mm, about 300 nm to about 5 mm, about 300 nm to about 1 mm, about 300 nm to about 900 Tm, about 300 nm to about 800 Tm, about 300 nm to about 700 Tm, about 300 nm to about 600 Tm, about 300 nm to about 500 Tm, about 300 nm to about 400 Tm, about 300 nm to about 300 Tm, about 300 nm to about 200 Tm, about 300 nm to about 100 Tm, about 300 nm to about 50 Tm, about 300 nm to about 10 Tm, about 300 nm to about 5 Tm, about 300 nm to about 1 Tm, about 300 nm to about 900 nm, about 300 nm to about 800 nm, about 300 nm to about 700 nm, about 300 nm to about 600 nm, about 300 nm to about 500 nm, about 300 nm to about 400 nm, about 400 nm to about 50 mm, about 400 nm to about 45 mm, about 400 nm to about 40 mm, about 400 nm to about 35 mm, about 400 nm to about 30 mm, about 400 nm to about 25 mm, about 400 nm to about 20 mm, about 400 nm to about 15 mm, about 400 nm to about 10 mm, about 400 nm to about 5 mm, about 400 nm to about 1 mm, about 400 nm to about 900 Tm, about 400 nm to about 800 Tm, about 400 nm to about 700 Tm, about 400 nm to about 600 Tm, about 400 nm to about 500 Tm, about 400 nm to about 400 Tm, about 400 nm to about 300 Tm, about 400 nm to about 200 Tm, about 400 nm to about 100 Tm, about 400 nm to about 50 Tm, about 400 nm to about 10 Tm, about 400 nm to about 5 Tm, about 400 nm to about 1 Tm, about 400 nm to about 900 nm, about 400 nm to about 800 nm, about 400 nm to about 700 nm, about 400 nm to about 600 nm, about 400 nm to about 500 nm, about 500 nm to about 50 mm, about 500 nm to about 45 mm, about 500 nm to about 40 mm, about 500 nm to about 35 mm, about 500 nm to about 30 mm, about 500 nm to about 25 mm, about 500 nm to about 20 mm, about 500 nm to about 15 mm, about 500 nm to about 10 mm, about 500 nm to about 5 mm, about 500 nm to about 1 mm, about 500 nm to about 900 Tm, about 500 nm to about 800 Tm, about 500 nm to about 700 Tm, about 500 nm to about 600 Tm, about 500 nm to about 500 Tm, about 500 nm to about 400 Tm, about 500 nm to about 300 Tm, about 500 nm to about 200 Tm, about 500 nm to about 100 Tm, about 500 nm to about 50 Tm, about 500 nm to about 10 Tm, about 500 nm to about 5 Tm, about 500 nm to about 1 Tm, about 500 nm to about 900 nm, about 500 nm to about 800 nm, about 500 nm to about 700 nm, about 500 nm to about 600 nm, about 600 nm to about 50 mm, about 600 nm to about 45 mm, about 600 nm to about 40 mm, about 600 nm to about 35 mm, about 600 nm to about 30 mm, about 600 nm to about 25 mm, about 600 nm to about 20 mm, about 600 nm to about 15 mm, about 600 nm to about 10 mm, about 600 nm to about 5 mm, about 600 nm to about 1 mm, about 600 nm to about 900 Tm, about 600 nm to about 800 Tm, about 600 nm to about 700 Tm, about 600 nm to about 600 Tm, about 600 nm to about 500 Tm, about 600 nm to about 400 Tm, about 600 nm to about 300 Tm, about 600 nm to about 200 Tm, about 600 nm to about 100 Tm, about 600 nm to about 50 Tm, about 600 nm to about 10 Tm, about 600 nm to about 5 Tm, about 600 nm to about 1 Tm, about 600 nm to about 900 nm, about 600 nm to about 800 nm, about 600 nm to about 700 nm, about 700 nm to about 50 mm, about 700 nm to about 45 mm, about 700 nm to about 40 mm, about 700 nm to about 35 mm, about 700 nm to about 30 mm, about 700 nm to about 25 mm, about 700 nm to about 20 mm, about 700 nm to about 15 mm, about 700 nm to about 10 mm, about 700 nm to about 5 mm, about 700 nm to about 1 mm, about 700 nm to about 900 Tm, about 700 nm to about 800 Tm, about 700 nm to about 700 Tm, about 700 nm to about 600 Tm, about 700 nm to about 500 Tm, about 700 nm to about 400 Tm, about 700 nm to about 300 Tm, about 700 nm to about 200 Tm, about 700 nm to about 100 Tm, about 700 nm to about 50 Tm, about 700 nm to about 10 Tm, about 700 nm to about 5 Tm, about 700 nm to about 1 Tm, about 700 nm to about 900 nm, about 700 nm to about 800 nm, about 800 nm to about 50 mm, about 800 nm to about 45 mm, about 800 nm to about 40 mm, about 800 nm to about 35 mm, about 800 nm to about 30 mm, about 800 nm to about 25 mm, about 800 nm to about 20 mm, about 800 nm to about 15 mm, about 800 nm to about 10 mm, about 800 nm to about 5 mm, about 800 nm to about 1 mm, about 800 nm to about 900 Tm, about 800 nm to about 800 Tm, about 800 nm to about 700 Tm, about 800 nm to about 600 Tm, about 800 nm to about 500 Tm, about 800 nm to about 400 Tm, about 800 nm to about 300 Tm, about 800 nm to about 200 Tm, about 800 nm to about 100 Tm, about 800 nm to about 50 Tm, about 800 nm to about 10 Tm, about 800 nm to about 5 Tm, about 800 nm to about 1 Tm, about 800 nm to about 900 nm, about 900 nm to about 50 mm, about 900 nm to about 45 mm, about 900 nm to about 40 mm, about 900 nm to about 35 mm, about 900 nm to about 30 mm, about 900 nm to about 25 mm, about 900 nm to about 20 mm, about 900 nm to about 15 mm, about 900 nm to about 10 mm, about 900 nm to about 5 mm, about 900 nm to about 1 mm, about 900 nm to about 900 Tm, about 900 nm to about 800 Tm, about 900 nm to about 700 Tm, about 900 nm to about 600 Tm, about 900 nm to about 500 Tm, about 900 nm to about 400 Tm, about 900 nm to about 300 Tm, about 900 nm to about 200 Tm, about 900 nm to about 100 Tm, about 900 nm to about 50 Tm, about 900 nm to about 10 Tm, about 900 nm to about 5 Tm, about 900 nm to about 1 Tm, about 1 Tm to about 50 mm, about 1 Tm to about 45 mm, about 1 Tm to about 40 mm, about 1 Tm to about 35 mm, about 1 Tm to about 30 mm, about 1 Tm to about 25 mm, about 1 Tm to about 20 mm, about 1 Tm to about 15 mm, about 1 Tm to about 10 mm, about 1 Tm to about 5 mm, about 1 Tm to about 1 mm, about 1 Tm to about 900 Tm, about 1 Tm to about 800 Tm, about 1 Tm to about 700 Tm, about 1 Tm to about 600 Tm, about 1 Tm to about 500 Tm, about 1 Tm to about 400 Tm, about 1 Tm to about 300 Tm, about 1 Tm to about 200 Tm, about 1 Tm to about 100 Tm, about 1 Tm to about 50 Tm, about 1 Tm to about 10 Tm, about 1 Tm to about 5 Tm, about 5 Tm to about 50 mm, about 5 Tm to about 45 mm, about 5 Tm to about 40 mm, about 5 Tm to about 35 mm, about 5 Tm to about 30 mm, about 5 Tm to about 25 mm, about 5 Tm to about 20 mm, about 5 Tm to about 15 mm, about 5 Tm to about 10 mm, about 5 Tm to about 5 mm, about 5 Tm to about 1 mm, about 5 Tm to about 900 Tm, about 5 Tm to about 800 Tm, about 5 Tm to about 700 Tm, about 5 Tm to about 600 Tm, about 5 Tm to about 500 Tm, about 5 Tm to about 400 Tm, about 5 Tm to about 300 Tm, about 5 Tm to about 200 Tm, about 5 Tm to about 100 Tm, about 5 Tm to about 50 Tm, about 5 Tm to about 10 Tm, about 10 Tm to about 50 mm, about 10 Tm to about 45 mm, about 10 Tm to about 40 mm, about 10 Tm to about 35 mm, about 10 Tm to about 30 mm, about 10 Tm to about 25 mm, about 10 Tm to about 20 mm, about 10 Tm to about 15 mm, about 10 Tm to about 10 mm, about 10 Tm to about 5 mm, about 10 Tm to about 1 mm, about 10 Tm to about 900 Tm, about 10 Tm to about 800 Tm, about 10 Tm to about 700 Tm, about 10 Tm to about 600 Tm, about 10 Tm to about 500 Tm, about 10 Tm to about 400 Tm, about 10 Tm to about 300 Tm, about 10 Tm to about 200 Tm, about 10 Tm to about 100 Tm, about 10 Tm to about 50 Tm, about 50 Tm to about 50 mm, about 50 Tm to about 45 mm, about 50 Tm to about 40 mm, about 50 Tm to about 35 mm, about 50 Tm to about 30 mm, about 50 Tm to about 25 mm, about 50 Tm to about 20 mm, about 50 Tm to about 15 mm, about 50 Tm to about 10 mm, about 50 Tm to about 5 mm, about 50 Tm to about 1 mm, about 50 Tm to about 900 Tm, about 50 Tm to about 800 Tm, about 50 Tm to about 700 Tm, about 50 Tm to about 600 Tm, about 50 Tm to about 500 Tm, about 50 Tm to about 400 Tm, about 50 Tm to about 300 Tm, about 50 Tm to about 200 Tm, about 50 Tm to about 100 Tm, about 100 Tm to about 50 mm, about 100 Tm to about 45 mm, about 100 Tm to about 40 mm, about 100 Tm to about 35 mm, about 100 Tm to about 30 mm, about 100 Tm to about 25 mm, about 100 Tm to about 20 mm, about 100 Tm to about 15 mm, about 100 Tm to about 10 mm, about 100 Tm to about 5 mm, about 100 Tm to about 1 mm, about 100 Tm to about 900 Tm, about 100 Tm to about 800 Tm, about 100 Tm to about 700 Tm, about 100 Tm to about 600 Tm, about 100 Tm to about 500 Tm, about 100 Tm to about 400 Tm, about 100 Tm to about 300 Tm, about 100 Tm to about 200 Tm, about 200 Tm to about 50 mm, about 200 Tm to about 45 mm, about 200 Tm to about 40 mm, about 200 Tm to about 35 mm, about 200 Tm to about 30 mm, about 200 Tm to about 25 mm, about 200 Tm to about 20 mm, about 200 Tm to about 15 mm, about 200 Tm to about 10 mm, about 200 Tm to about 5 mm, about 200 Tm to about 1 mm, about 200 Tm to about 900 Tm, about 200 Tm to about 800 Tm, about 200 Tm to about 700 Tm, about 200 Tm to about 600 Tm, about 200 Tm to about 500 Tm, about 200 Tm to about 400 Tm, about 200 Tm to about 300 Tm, about 300 Tm to about 50 mm, about 300 Tm to about 45 mm, about 300 Tm to about 40 mm, about 300 Tm to about 35 mm, about 300 Tm to about 30 mm, about 300 Tm to about 25 mm, about 300 Tm to about 20 mm, about 300 Tm to about 15 mm, about 300 Tm to about 10 mm, about 300 Tm to about 5 mm, about 300 Tm to about 1 mm, about 300 Tm to about 900 Tm, about 300 Tm to about 800 Tm, about 300 Tm to about 700 Tm, about 300 Tm to about 600 Tm, about 300 Tm to about 500 Tm, about 300 Tm to about 400 Tm, about 400 Tm to about 50 mm, about 400 Tm to about 45 mm, about 400 Tm to about 40 mm, about 400 Tm to about 35 mm, about 400 Tm to about 30 mm, about 400 Tm to about 25 mm, about 400 Tm to about 20 mm, about 400 Tm to about 15 mm, about 400 Tm to about 10 mm, about 400 Tm to about 5 mm, about 400 Tm to about 1 mm, about 400 Tm to about 900 Tm, about 400 Tm to about 800 Tm, about 400 Tm to about 700 Tm, about 400 Tm to about 600 Tm, about 400 Tm to about 500 Tm, about 500 Tm to about 50 mm, about 500 Tm to about 45 mm, about 500 Tm to about 40 mm, about 500 Tm to about 35 mm, about 500 Tm to about 30 mm, about 500 Tm to about 25 mm, about 500 Tm to about 20 mm, about 500 Tm to about 15 mm, about 500 Tm to about 10 mm, about 500 Tm to about 5 mm, about 500 Tm to about 1 mm, about 500 Tm to about 900 Tm, about 500 Tm to about 800 Tm, about 500 Tm to about 700 Tm, about 500 Tm to about 600 Tm, about 600 Tm to about 50 mm, about 600 Tm to about 45 mm, about 600 Tm to about 40 mm, about 600 Tm to about 35 mm, about 600 Tm to about 30 mm, about 600 Tm to about 25 mm, about 600 Tm to about 20 mm, about 600 Tm to about 15 mm, about 600 Tm to about 10 mm, about 600 Tm to about 5 mm, about 600 Tm to about 1 mm, about 600 Tm to about 900 Tm, about 600 Tm to about 800 Tm, about 600 Tm to about 700 Tm, about 700 Tm to about 50 mm, about 700 Tm to about 45 mm, about 700 Tm to about 40 mm, about 700 Tm to about 35 mm, about 700 Tm to about 30 mm, about 700 Tm to about 25 mm, about 700 Tm to about 20 mm, about 700 Tm to about 15 mm, about 700 Tm to about 10 mm, about 700 Tm to about 5 mm, about 700 Tm to about 1 mm, about 700 Tm to about 900 Tm, about 700 Tm to about 800 Tm, about 800 Tm to about 50 mm, about 800 Tm to about 45 mm, about 800 Tm to about 40 mm, about 800 Tm to about 35 mm, about 800 Tm to about 30 mm, about 800 Tm to about 25 mm, about 800 Tm to about 20 mm, about 800 Tm to about 15 mm, about 800 Tm to about 10 mm, about 800 Tm to about 5 mm, about 800 Tm to about 1 mm, about 800 Tm to about 900 Tm, about 900 Tm to about 50 mm, about 900 Tm to about 45 mm, about 900 Tm to about 40 mm, about 900 Tm to about 35 mm, about 900 Tm to about 30 mm, about 900 Tm to about 25 mm, about 900 Tm to about 20 mm, about 900 Tm to about 15 mm, about 900 Tm to about 10 mm, about 900 Tm to about 5 mm, about 900 Tm to about 1 mm, about 1 mm to about 50 mm, about 1 mm to about 45 mm, about 1 mm to about 40 mm, about 1 mm to about 35 mm, about 1 mm to about 30 mm, about 1 mm to about 25 mm, about 1 mm to about 20 mm, about 1 mm to about 15 mm, about 1 mm to about 10 mm, about 1 mm to about 5 mm, about 5 mm to about 50 mm, about 5 mm to about 45 mm, about 5 mm to about 40 mm, about 5 mm to about 35 mm, about 5 mm to about 30 mm, about 5 mm to about 25 mm, about 5 mm to about 20 mm, about 5 mm to about 15 mm, about 5 mm to about 10 mm, about 10 mm to about 50 mm, about 10 mm to about 45 mm, about 10 mm to about 40 mm, about 10 mm to about 35 mm, about 10 mm to about 30 mm, about 10 mm to about 25 mm, about 10 mm to about 20 mm, about 10 mm to about 15 mm, about 15 mm to about 50 mm, about 15 mm to about 45 mm, about 15 mm to about 40 mm, about 15 mm to about 35 mm, about 15 mm to about 30 mm, about 15 mm to about 25 mm, about 15 mm to about 20 mm, about 20 mm to about 50 mm, about 20 mm to about 45 mm, about 20 mm to about 40 mm, about 20 mm to about 35 mm, about 20 mm to about 30 mm, about 20 mm to about 25 mm, about 25 mm to about 50 mm, about 25 mm to about 45 mm, about 25 mm to about 40 mm, about 25 mm to about 35 mm, about 25 mm to about 30 mm, about 30 mm to about 50 mm, about 30 mm to about 45 mm, about 30 mm to about 40 mm, about 30 mm to about 35 mm, about 35 mm to about 50 mm, about 35 mm to about 45 mm, about 35 mm to about 40 mm, about 40 mm to about 50 mm, about 40 mm to about 45 mm, or about 45 mm to about 50 mm.

In some embodiments, the β-TCP is about 50% to about 70% porous, with the pores having a mean pore diameter of about 50 Tm to about 70 Tm (e.g., about 55 Tm to about 65 Tm, or about 60 Tm).

Compositions and Kits

Also provided herein are compositions (e.g., pharmaceutical compositions) that include any of the chimeric polypeptides or β-TCP-binding polypeptides described herein. In some examples, the compositions can further include β-TCP (e.g., any of the types of β-TCP described herein). In some examples, the β-TCP is formulated as a powder, a putty (e.g., a moldable putty), a paste, a scaffold (e.g., a porous scaffold), a sponge, and/or a coating on a solid surface (e.g., a coating on a medical device). In some examples, the β-TCP can be disposed on or in a scaffold, a mesh, or a sponge (e.g., a resorbable sponge).

In some instances, the compositions (e.g., pharmaceutical compositions) are disposed in a sterile vial or a pre-loaded syringe.

In some instances, the compositions (e.g., pharmaceutical compositions) are formulated for different routes of administration (e.g., intraarticular, injection into a joint, or injection proximal to a bone fissure or fracture). Single or multiple administrations of any of the pharmaceutical compositions described herein can be given to a subject depend on, for example: the dosage and frequency as required and tolerated by the subject. A dosage of the pharmaceutical composition should provide a sufficient quantity of the chimeric polypeptide to effective treat or ameliorate conditions (e.g., bone defects, bone fractures, cartilage defects, or cartilage loss), or symptoms.

Also provided herein are kits that include any of the chimeric polypeptides or any of the β-TCP-binding polypeptides described herein, or any of the compositions (e.g., pharmaceutical compositions) described herein. In some embodiments, the kits can include instructions for performing any of the methods described herein. In some instances, the kits can include at least one dose of any of the compositions (e.g., pharmaceutical compositions) described herein. In some embodiments, the kits can include a syringe for administering any of the pharmaceutical compositions described herein. The kits described herein are not so limited; other variations will be apparent to one of ordinary skill in the art.

Methods of Making a Composition

Also provided herein are methods of producing any of the compositions described herein. Any of the compositions provided herein can be produced using the methods described herein or methods known in the art. For example, to create a β-TCP scaffold, granulated β-TCP powder can be sintered, sieved, and fabricated into a desired shape (e.g., any of the shapes described herein). In some examples, the purity of the β-TCP present in any of the compositions described herein can be greater than about 75%, greater than 80%, greater than 85%, greater than 90%, greater than 95%, or greater than 99% pure. In some examples, the purity of β-TCP present in any of the compositions described herein can be greater than 1%, greater than 2%, greater than 3%, greater than 4%, greater than 5%, greater than 6%, greater than 7%, greater than 8%, greater than 9%, greater than 10%, greater than 12%, greater than 14%, greater than 15%, greater than 16%, greater than 18%, greater than 20%, greater than 22%, greater than 24%, greater than 25%, greater than 26%, greater than 28%, greater than 30%, greater than 32%, greater than 34%, greater than 35%, greater than 36%, greater 38%, greater than 40%, greater than 42%, greater than 44%, greater than 45%, greater than 46%, greater than 48%, greater than 50%, greater than 52%, greater than 54%, greater than 55%, greater than 56%, greater than 58%, greater than 60%, greater than 62%, greater than 64%, greater than 65%, greater than 66%, greater than 68%, greater than 70%, greater than 72%, greater than 74%. In some examples, the β-TCP is made using a similar method but as a composite with other agents, such as a biocompatible polymer, e.g., polylactide-co-glycolide.

As will be apparent to those of skill in the art, the composition can further include one or more pore forming agents. Examples of pore forming agents include, e.g., inorganic salts, such as sodium chloride, saccharides (e.g., sucrose or glucose), gelatin (e.g., gelatin spheres), or paraffin (e.g., paraffin spheres).

The compositions described herein can be generated by contacting any of the chimeric polypeptides or any of the β-TCP-binding polypeptides to any of the types of β-TCP described herein. In some embodiments, the β-TCP can be in the form of a granular/powder form, a porous form, a putty (e.g., a moldable putty), a paste, a scaffold, and/or a coating on a solid surface (e.g., a coating on a medical device).

Methods of Treatment

Provided herein are methods of promoting bone or cartilage formation in a subject in need thereof that include: administering to the subject a therapeutically effective amount of any of the compositions described herein. Some embodiments of these methods can further include first selecting a subject in need of bone or cartilage formation. In some embodiments, the composition is administered to the subject proximal to the desired site of bone or cartilage formation in the subject.

Also provided herein are methods of replacing and/or repairing bone or cartilage in a subject in need thereof that include: administering to the subject a therapeutically effective amount of any of the compositions described herein. Some embodiments of these methods can further include first selecting a subject in need of bone replacement, bone repair, cartilage replacement, or cartilage repair. In some embodiments, the composition is administered to the subject proximal to the desired site of bone or cartilage replacement or repair in the subject.

Also provided herein are methods of treating a bone fracture or bone loss in a subject in need thereof, the method comprising administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of repairing soft tissue in a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of localized delivery of a therapeutic to a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

In some instances, the subject has a bone fracture or a bone defect.

In some instances, the subject requires a vertebral fusion of the spine.

In some instances, the subject has a cartilage tear or cartilage defect.

In other instances, the subject has cartilage loss.

Methods of determining the efficacy of treatment of a bone fracture or bone loss in a subject are known in the art and include, e.g., imaging techniques (e.g., magnetic resonance imaging, X-ray, or computed tomography).

Methods of detecting bone or cartilage formation, or replacement or repair of bone or cartilage in a subject are also known in the art and include, e.g., imaging techniques (e.g., magnetic resonance imaging, X-ray, or computed tomography).

Suitable animal models for treatment of a bone fraction or bone loss, bone or cartilage formation, or bone or cartilage replacement or repair are known in the art. Non-limiting examples of such animal models are described in the Examples and in, e.g., Drosse et al., *Tissue Engineering Part C* 14(1):79-88, 2008; Histing et al., *Bone* 49:591-599, 2011; and Poser et al., Hindawi Publishing Corporation, BioMed Research International; Article ID 348635, 2014.

The invention is further described in the following examples, which do not limit the scope of the invention described in the claims.

EXAMPLES

Example 1. A Preclinical Study of tBMP-2 in a β-TCP Carrier in a Rat Critical Size Femoral Defect Model The aim of this study was to examine the safety and effect of modified recombinant human bone morphogenetic protein (rhBMP) known as tBMP in a beta-tricalcium phosphate (β-TCP) putty matrix in the replacement and repair of bone in a rat critical size defect model. The tBMP-2 variant exhibits very tight binding to calcium phosphate ceramics and thus allows for targeted delivery of tBMP-2 to implant sites. This was achieved by surgically creating the defect using the RatFix internal fixator system, then filling that defect with tBMP+β-TCP putty, or β-TCP putty alone as a control. The positive control was a dose-adjusted commercially available (Medtronic) preparation for human use of rhBMP with an absorbable collagen sponge (ACS). The animals were monitored clinically and had bi-weekly radiographs until their scheduled end-points at four or eight weeks post-administration of treatment. Ex vivo histology was conducted on organs and tissues, and the treated leg was subjected to pCT, histomorphometry, and/or mechanical strength testing.

This report covers animal arrival, assignment to groups, surgical creation of defect and administration of test, reference or control item. In addition, this report covers the post-operative period up to and including Week 8, and end-point in vivo and ex vivo measurements. Included are the clinical summaries, radiographs, end-point clinical pathology and organ histopathology, histomorphometry of treated legs (odd-numbered animals), and mechanical strength testing of treated legs (even-numbered animals).

On arrival at the Test Facility, all animals underwent a Veterinary health check and were weighed. Based on the weights, the animals were assigned to groups A) tBMP+β-TCP putty; B) rhBMP+ACS; or C) β-TCP putty alone. The animals then had at least five days to acclimatize to their new surroundings and diet.

On the day of surgery, the animals were anaesthetized, the defect was created and the bone supported with the internal fixator following the method supplied by the manufacturer with some refinements to the surgical procedure. The pre-prepared test, reference or control item was then inserted into the defect. The surgical site was closed and the animal went immediately for X-ray. Following completion of the baseline radiograph, post-operative pain relief was administered and the animal was returned to its cage for recovery. Post-operative analgesia and antibiotic therapy were continued for at least two days, and longer when required.

A number of the original animals were removed from the study and replaced prior to surgery as they were getting too large for the fixator system specifications. The second, replacement group also had a thorough Veterinary health check and were weighed prior to being assigned to groups. The allocation of animals to either four or eight-week end-point groups was adjusted to include animals from both weight ranges at both end-points.

A total of 61 animals were successfully administered assigned treatment and recovered from surgery. Of these, one animal was euthanized five days post-operatively due to poor recovery and inappetence. The animal was replaced. Two animals which were found to have dislodged bone plates during their 2-week post-operative radiographs were humanely killed and not replaced. Two animals did not successfully recover from surgery, one died immediately post-surgery, and the other had an unstable bone plate which could not be fixed, and so was humanely killed. Both of these animals were replaced immediately.

The animals were monitored at least once daily, and their clinical signs scored. Any animal with unusual findings, or considered to be not eating and gaining weight normally was monitored more frequently, and veterinary advice was sought. When unusual findings were noted, this resulted in possible treatment with additional antibiotic or analgesic therapy, fluid supplementation), and in four cases euthanasia (three broken bones and one with continued weight loss).

All relevant animals received bone-labelling dyes at 10 days (calcein green) and 3 days (xylenol orange) prior to their scheduled end-point date. All animals had end-point blood samples collected. There were no clinically significant differences found between any of the groups for any biochemical or haematological parameter at either end-point time. Three haematology samples were clotted and could not be analysed.

In all specimens examined, there was evidence of extensive mineralization akin to mature trabecular bone in samples from animals in the tBMP+β-TCP putty group (Group A). This mineralization appears to be lamella (mature) bone rather than the woven bone that occurs in early callus formation (presence of osteocytes). Group A animals also had osteoclasts present (suggesting active remodelling), and red blood cells and adipocytes, indicating angiogenesis and infiltration of cells to most regions of the callus. Whilst there is mineralized bone in the specimens from the rhBMP+ACS group animals, there are extensive regions of unmineralized fibrous and cartilaginous tissue within the callus region. The callus development in these samples appears to be at an earlier stage than that observed in the Group A animals. The Group C (β-TCP putty) samples show no evidence of mineralization, bone formation or bone remodeling even at eight weeks post-application of treatment.

The mechanical testing analyses showed the tBMP+β-TCP group animals (Group A) had significantly stronger bones at the four and eight week end-point times than either of the other treatment groups.

In conclusion, the bone specimens form the tBMP+β-TCP putty group clearly demonstrated vastly improved bone healing at 4 and 8 weeks post-surgery when compared to samples from animals in the rhBMP+ACS or the β-TCP putty alone treatment groups. The aim of this study was to evaluate the performance of a modified variant of recombinant human BMP-2 (rhBMP-2) called tBMP-2. The tBMP-2 variant exhibits very tight binding to calcium phosphate ceramics and thus allows for targeted delivery of tBMP-2 to implant sites. The ability to tether BMP-2 in this manner will allow for longer persistence times, lower doses, and, it is expected, superior outcomes.

Animals

The rat is a validated animal model for assessing the effect of treatments on critical-sized defects in the femur (4-6). Sixty male rats (plus spares) were required: ten animals in each group per time point. One animal was replaced after successful administration of the test item at day 5 post-surgery as he was losing weight and not eating. Animals that were euthanized or humanely killed after successful administration of the test item were necropsied and had tissue collected for histopathology. The number of animals used in this study was considered sufficient for evaluation of results.

The animals were housed in conventional conditions (targeted temperature 22±3° C., 12/12-hour light/dark cycle) in standard open top cages that satisfy the size requirements specified in the Animal Welfare Regulations (Animal Welfare Act 1985, v 15 Oct. 2015. Attorney General's Department, Gouverment of South Australia). Animals were housed individually for the entirety of the experiment. The animals had access to standard laboratory rat chow (Specialty Feeds, Glen Forest, Australia) 25-30 g/day. Immediately post-operatively, and when rats were not thriving, the food was soaked in water for easier palatability. Chlorinated tap water was provided to the animals ad libitum. Food and water were not withheld at any time.

Each animal was uniquely identified by a subcutaneously implanted microchip which was scanned using a barcode reader. For the purpose of the study, each animal was also given a number from 1-70 (to include replacement and spared required). As the initial batch of animals gained weight too quickly, some animals were replaced prior to surgery. The replacement animals were given the number of the animal they replaced and the suffix (a) was added. Numbers went up to 68a with a couple of gaps.

Animals were assigned to groups by a weight-ordered distribution. The heavier animals were used first. The animals gained weight rapidly, even on the restricted food allowance. Two weeks into the surgeries, it was deemed necessary to remove some animals from the study (n=16) as these animals were already too heavy (>425 g). These animals were replaced with animals in the 250-300 g range. The replacement animals were also assigned to treatment groups on a weight-ordered distribution. As the first surgical group had originally been assigned to the 8-week end-point group, animals were reassigned to either 4- or 8-week end-points to ensure the lighter animals were evenly distributed amongst the treatment and end-point times.

Analgesia/Antibiotic Therapy

All interventional procedures were performed under isoflurane in 02 anaesthesia. Induction and maintenance of surgical depth anesthesia was at 2-4% isoflurane (Baxter International, Sydney, Australia) in a flow of 1-2 L/minute 02. Post-operatively, after closure of the wound, a topical application of local anesthetic in the form of Marcaine (Bupivacaine, 0.5%, AstraZeneca, Frewville, SA, Australia) up to 2.5 mg/Kg was applied to the area around the wound. The animals received 0.1 mg/kg buprenorphine (Temgesic, Reckitt-Benckiser, Melrose Park, Australia) subcutaneously post-operatively after X-ray. They also received 0.1 mg/kg subcutaneously twice daily for two days post-operatively. Additionally, they were given a non-steroidal anti-inflammatory treatment in the form of Carprieve (Carprofen, 50 mg/mL, Norbrook Laboratories, Tullamarine, Australia) at a dose of 5 mg/kg subcutaneously post-operatively and once daily for at least two days post-surgery.

All animals received cephalosporin (Cefazolin, Hospira Inc, Lake Forest Ill., USA) 20 mg/kg subcutaneously intra-operatively and twice daily for two days post-operatively. Any animals that needed re-suturing of their wounds received antibiotic treatment for up to fourteen days post-repair. Antibiotic therapy was ceased if suspected to be causing diarrhea and/or weight loss.

Microchip Implantation

The microchip was inserted into the scruff of the neck (after clipping hair) using a microchip implanter. The microchip was inserted until completely covered by skin. The wounds were closed with one or two wound clips if required. The area was swabbed with betadine. This was performed under isoflurane in 02 anaesthesia at the same time as the defect surgery and test- or reference-item placement.

Critical-Size Defect Creation

The defects were created in the right femur of all rats as described for the RatFix RISystem. Briefly, all anaesthetized rats were placed on a warming pad in lateral recumbency with the right leg facing upwards. The surgical site was shaved and aseptically prepared with iodine or chlorhexidine scrub and solution. A skin incision between the greater trochanter and the knee joint was made and the superficial fascia incised. The intermuscular plane between the vastus lateralis and the biceps femoris was separated and the periosteum of the femur incised. The PEEK plate was fitter into the jug and secured with suture material. The jig-plate assembly was fixed to the craniolateral surface of the femur by pulling the sutures through under the femur, allowing the assembly to be tightened to the femur.

After predrilling the holes in the PEEL plate using the supplied drill bit, the plate was attached to the femur by six bicortical titanium screws. Standardised 6-mm defects were created (marked on the plate) using the Gigli wire saw guided by the sawing device of the jig. After defect sawing, the jig and bone piece were removed. The fresh defect was flushed with sterile saline and dried with gauze in preparation of test item or reference item, or vehicle administration into the defect size. In the event that the plate itself was damaged with the cutting wire, reducing stability, that animal would be replaced. No replacements due to plate damage were required.

Baseline Radiographs

Baseline radiographs were taken immediately after creation of the defect and administration of the test or reference item to show position of treatment articles (where visible), and placement of the plate, whilst the animal was still under anaesthesia.

Radiographic Assessments

X-rays were taken on the anaesthetized animals (isoflurane) immediately after surgery, and at 2, 4 (end-point for half of the animals), 6 and 8 weeks (end-point for the remaining animals) post-operatively. The radiographs were taken in lateromedial and craiocaudal projections for assessment of bone healing and to exclude implant loosening or failure. All in-life radiographs were taken using a Villa Visitor Mobile X-ray Unit (Villa Sistemi Medicali, Buccinasco, Italy), using a dental image capture device (Soredex, Digora Optime, Tuusula, Finland). The images were transferred to the PIRL picture archiving and communication system (PACS, Carestream Vue Motion, Rochester, USA) by the radiographer for storage and access.

Bone Labelling

At 10 days prior to their prescribed end-point, all animals received an intraperitoneal injection of calcein green (25 mg/kg in saline). At 3 days prior to their prescribed end-point all animals received an injection of xylenol orange (10 mg/mL, 25 mg/kg, intraperitoneal) to double-label the bone for histomorphometric analyses.

Blood Collection/Haematology

All blood collections were performed on anaesthetized animals at their end-point radiograph. Blood was collected via cardiac puncture.

Blood samples were evaluated for the parameters specified in Tables 1 and 2. For Table 1, samples of approximately 2 mL were collected into tubes containing $K_2EDTA$ anticoagulant for haemotological analyses. Analyses were performed on an Abbott Cell Dyn. 3700 (Abbott Laboratories, North Ryde, Australia). For Table 2, samples of approximately 5 mL were collected into tubes containing a clot activator for biochemical analysis. Analyses were performed on a Siemens Advia 1800 (Siemens Healthcare Diagnostics Inc., Flanders, N.J., USA).

TABLE 1

Haematology Parameters to be reported

| | |
|---|---|
| Haemoglobin (Hb) | White Cell Count (WCC) |
| Erythrocyte count (RBC) | Mean Corpuscular Volume (MCV) |
| Packed Cell Volume (PCV)/Haematocrit (HCT) | Mean Corpuscular Haemoglobin (MCH)* |
| Mean Corpuscular Haemoglobin Concentration (MCHC)* | Red Cell Distribution Width (RDW) |
| Platelets (Plt) | |
| White Blood Cell Differential: Neutrophils, Lymphocytes, Monocytes, Eosinophils, Basophils | |

*Calculated values

TABLE 2

Serum Chemistry Parameters to be reported

| | | |
|---|---|---|
| Electrolytes: | Anion Gap* (AG) | Albumin (Alb) |
| Sodium (Sod) | Glucose (Gluc) | Globulin* (Glob) |
| Potassium (Pot) | Urea | Protein (Tot Prot) |
| Chloride (Chl) | Creatinine (Creat) | Total bilirubin (Tot Bili) |
| Bicarbonate (Bicarb) | Cholesterol (Chol) | Lactate Dehydrogenase (LD) |
| Lipid Studies: | Urate (Uric Acid, UA) | Alkaline phosphatase (ALP) |
| Triglycerides (Trig) | Phosphate (Phos) | Total Calcium (Tot. Ca) |
| High Density Lipoproteins (HDL) | Gamma glutamyltransferase (GGT) | Alanine aminotransferase (ALT) |
| Low Density Lipoproteins (LDL) | Asparatate aminotransferase (AST) | |
| Chol/HDL* | | |

*Calculated values

Mechanical Strength Testing

This was performed on half of the animals at each time point. All tissue was placed in 0.9% NaCl-soaked gauzed in 50-mL sterile urine pots to avoid freezer burn and stored frozen at −20° C. until testing. Tissue was prepared immediately and frozen within one hour of collection to avoid autolysis. Immediately before testing, tissues were thawed, and the internal fixator device carefully cut in the middle section. Tissue was test at room temperature (approximately 23° C.). The ultimate breaking strength was measured by using a load frame (model 5542, Instron, Canton, Mass.) and a 3-point bend fixture (model 2810-400, Instron) at a crosshead speed of 10 mm/min. The load cell for this testing (Instron 2530-416) had a maximum capacity of 500 N. The data (force in kg and extension in mm) was collected and analysed with a vendor-provided commercial mathematical software package (Bluehill2, Instron).

Histological Analyses

Specimen were fixed in 10% formalin for 7 days prior to processing. Formalin-fixed bones were cut using a slow-speed saw (Buehler Ltd, IL, USA) along the sagittal plane using a diamond-tipped cutting blade before being submerged in 70% ethanol. Subsequently, bones were processed for resin embedding via several dehydration steps. Briefly, bones were submerged in 2×90% ethanol and 1×100% ethanol steps over 48 hours. Bones were then transferred into a solution containing methymethacrylate (MMA) and 10% v/v polyethylene glycol (PEG) and stored at room temperature for 10-14 days. Resin embedding then occurs by preparing a solution of MMA, 10% PEG, and 0.4% peroxydicarbonate (Perkadox) and incubation at 37° C. for 24 hours to allow the resin to harden. The exposed cut surface was placed facing down in the tube. The resin-set bones were then removed from their tubes and fixed to stubs for sectioning. For each bone, 5-μm thick sections were cut using a tungsten-carbide blade (Leica RM2255, Wetzlar, GER). Sections were placed on to gel-coated slides and dipped 2 times in a spreading solution (70% ethanol/30% 2-ethoxyethanol) heated to 70° C. To ensure adherence to the slide, sections were flattended, covered by strips of polyethylene and clamped together separated by blotting paper, before being placed into a 37° C. oven. Prior to commencing staining procedures, sections were placed in acetone for 15 minutes, unless otherwise stated. All sections were digitally scanned at 100× magnification (3D Histech scanner, TMA-MASTERO 1).

Von Koss+Haemaotoxylin and Eosin (H&E) Staining

Acetone treated sections were rinsed in demineralised water for 2 minutes. Sections were then placed in a 1% silver nitrate solution and placed in front of a UV lamp for 60 minutes. Washed slides were then treated with 2.5% sodium thiosulphate solution for 5 minutes. Washed slides were then counterstained with H&E. To stain for H&E, sections were placed in haematoxylin for 8 minutes to stain cell nuclei before being rinsed in demineralised water for 2 minutes and dipped in acid alcohol (%), typically, 4-5 minutes. After rinsing in demineralised water, sections were dipped in lithium carbonate 4-5 times and placed in eosin for 4 minutes. Once removed, excess eosin was removed with a squeeze bottle of absolute alcohol, sections were hydrated, placed in xylene and mounted in xylene-based mounting medium.

Tartrate-Resistant Acid Phosphatase (TRAP) Stain for Analysis of Osteoclasts

Acetone treated sections underwent a 60-minute incubation in Tris-HCL buffer (pH 9.4) at 37° C. for 60 minutes in an acid phosphatase (AcP) stain prepared by adding 0.0355 g of tartaric acid dissolved in 35 mL of sodium acetate (pH 5.2) to 100 μL basic fucshin in a 100 μL solution containing 0.4 mg of sodium nitrite. This solution was then added to a solution containing 0.04 g Napthol ASBI phosphate (Sigma-Aldrich, Missouri, USA) in 2 mL dimethylformamide. Subsequently, two washed were performed before the sections were counterstained in haematoxylin for 8 minutes, then rinsed in demineralised water, then dipped in acid alcohol 4 times, rinsed again, dipped in lithium carbonate 4 times and then dehydrated, placed in xylene and mounted in DPX. Quantification of osteoclast number per bone perimeter mm was performed by identifying cells (stained pink-red) on the surface of bone (stained blue-purple) and calculated by the OsteoMeasure histomorphometry system.

Double Fluorochrome Labelling of Bone Sections for Measures of Bone Formation

Acetone sections were immediately placed in xylene and mounted in DPX. Slides were viewed under a fluorescent microscope (Olympus BX53; Olympus, Tokyo, JP).

Histomorphometry

Those animals which did not have mechanical testing of femurs will undergo histological analysis of the defect and treatments. Following CT of the femurs, they were opened at the wound site, and the internal fixator device carefully removed. They were placed in 70% ethanol. Femurs were placed in PMMA, polymethyl methacrylate (10% polyethylene glycol [PEG] in methylmethacrylate) for 10-14 days, then polymerized in PMMA containing 10% Perkadox 16 (di[4-tert-butylcyclohexyl] peroxydicarbonate) at 37° C. for 24 hours. Sections were stained with H&E, and tartrate resistant acid phosphatase (TRAP) for analysis.

Humane Killing

Animals were humanely killed on day 28±2 days (n=30) or day 56±3 (n=30) immediately following their end-point radiograph and blood collection, and whilst still under anaesthesia, with an intracariac injection of a lethal dose of sodium pentobarbitone of 60 mg/mL formulation (Lethabarb®) at 200 mg/kg. Death was confirmed by lack of respiration and palpable heartbeat, loss of corneal reflex and loss of colour of mucous membranes.

Necropsy

All animals were subjected to a comprehensive necropsy. A comprehensive necropsy is defined as examination of the external surface of the body, all orifices, and the cranial, thoracic, and abdominal cavities, and their contents. If abnormalities were found in tissues or organs other than those listed below, they were also collected for histology.

Organ and Tissue Collection

Whole organs, sections of the issues listed in Table 3 below were dissected free and fixed in 10% neutral buffered formalin. This was done for twelve animals from each groups (six animals from each group at each time-point). The animals were selected such that at least one from each group was selected at each end-point (staggered as surgeries were staggered).

TABLE 3

Organ and Tissue Samples Collected From Each Animal

| | | |
|---|---|---|
| Adrenal gland | Lesions | Skin (containing implant[s]) |
| Brain | Liver | Spinal cord (cervical, thoracic, and lumbar) |
| Cecum | Lymph node (mesenteric) | Spleen |
| Duodenum | Pancreas | Sternum (+ bone marrow) |
| Eye | Pituitary Gland | Stomach |
| Heart | Rectum | Thymus |
| Ileum | Salivary gland (mandibular) | Tongue |
| Jejunum | Sciatic nerve | Epididymis |
| Kidney | Skeletal muscle (thigh) | |
| Femur with bone marrow (articular surface of the distal end) | Lung (with mainstem bronchi) | Prostate/seminal vesicles, bladder, testes |

Treated Limb Collection and Storage

Immediately following confirmation of death, the treated leg was removed and placed in either 10% neutral buffered formalin (n=5 animals/group/time point), or wrapped in saline-soaked gauze and placed at −20° C. for at least 48 hours (n=10 animals/group/time point).

μCT

All legs had CT measurements (Bruker Skyscan 1076, Brussels, Belgium) of the defect performed to quantify newly mineralized bone volume. This was done on all animals at each end-point time. The bones were either formalin-fixed (105 neutral buffered formalin) or frozen at −20° C. for 3-5 days prior to testing. The plate was adjusted to the longitudinal axis of the device. Scanning parameters and intensity were recorded and were in the vicinity of a source voltage of 70 kV with an intensity of 114 LA. The end-point CT was manually and subjectively scored as described by Chhabra et al. (2005) using the grading system described in Table 4.

TABLE 4

Radiographic Grading Scale of Fracture Callus Formation

| Grade | Amount of Callus Formation |
|---|---|
| 0 | No callus |
| 1 | Little-to-moderate callus |
| 2 | Profuse callus tissue |
| 3 | Bridging periosteal callus |
| 4 | Mature callus with interfragmentary bridging |
| 5 | Callus resorption after solid union |

Study Design

The study was performed as outlined in Table 5. There were three groups with 20 animals/group. All animals underwent surgery to create a critical-size defect (6-mm) in the mid diaphysis of the right femur (RatFix RISystem), and had inserted into the defect test item, reference item or vehicle. The animals were monitored at least once daily and were weighed at least twice weekly. They underwent radiographic evaluation immediately post-operatively, and at 2, 4, 6, and 8 weeks post-surgery. Ten animals from each group (n=30 animals) were scheduled to have end-point data (CT, mechanical testing, histomorphometry, clinical pathology) collected 4 weeks post-operatively and the remaining animals (n=30 animals) were scheduled for end-point data collection 8-weeks post operatively. Of these, six from each group (chosen such that there was a representative from each group from the majority of surgical days) at each end-point had tissues and organs collected for histology.

TABLE 5

Study design

| Group | Treatment | Nomenclature | End-Point (n) Week 4 | Week 8 |
|---|---|---|---|---|
| A | tBMP-2 + β-TCP putty | tBMP-2 + β-TCP putty | 10 | 10 |
| B | rhBMP-2 + absorbable collagen sponge (ACS) | rhBMP2 + ACS | 10 | 10 |
| C | β-TCP putty | β-TCP putty | 10 | 10 |

Group A animals received tBMP-2+β-TCP (0.615-0.620 mg tBMP-2 in β-TCP putty to fill defect); Group B animals received InFUSE™ Bone Graft of rhBMP-2+ACS (2 µg rhBMP-2 on ACS to fill defect); Group C animals received β-TCP to fill the defect. All test and control items were mixed on the day of surgery (tBMP-coated β-TCP to putty or rhBMP to ACS). Following administration of the treatment article, the wounds were closed in two muscle layers with subcutis and intracutaneous vicryl sutures. The wounds were closed exteriorly with intradermal sutures to prevent chewing by the rats. The wounds were washed with liberal amounts chlorhexidine solution. A small amount of tea tree oil was applied to the area surrounding the actual wound to prevent the animals from worrying the suture side.

Route of Administration

The anticipated route of human administration is by surgical implantation into a bone defect. Therefore, that route was used in this study. The bone defects were surgically created, the area flushed with saline, then the test or control items were placed in the defect immediately.

Preparation of Test Item (tBMP-2+β-TCP Putty)

For each rat, 195 µL of tBMP-2 (stock 3.53 mg/mL) were added to a pre-weighed aliquot of 47 mg β-TCP granules and mixed gently for 2-3 hours. All liquid was removed, and retained for analysis. The pellet was washed with 1 mL of sterile phosphate-buffered saline (PBS pH 7.4) and mixed gently to wash away any excess unbound protein. As much as possible of the liquid was removed with a pipette, and sterile pre-weighed putty was added to the protein-coated β-TCP. β-TCP and putty were mixed 1:1. The entire tBMP-2+β-TCP putty formulation was placed in the surgically-created defect. Assuming approximately 90% binding, the final dose of tBMP which was administered to the rat in the defect was 615-620 µg. Sterility was maintained at all steps. β-TCP binding to tBMP-2 was done no more than 48 hours prior to surgery. If 3-TCP was bound/washed the day before surgery, it was stored at 4° C. β-TCP and putty were not mixed more than one hour prior to implantation, as it will dehydrate with time and become less malleable.

Reference Item

Recombinant human bone morphogenetic protein+absorbable collagen sponge (InFUSE™ Bone Graft; size XX small; Medtronic Sofamor Danek, Inc) was used as per packet insert with modifications as described below. BMP-2 vial contents were reconstituted with the provided sterile water to give 1.5 mg/mL rhBMP-2. This concentration is intended for human use. To bring this concentration to the range typically used in rats, it was diluted 1 in 60 with PBS (25 jag/mL). A defect volume of approximately 75.5 mm$^3$ was assumed, therefore the ACS was trimmed to form a 6-mm×4-mm block for insertion into the defect. Diluted rhBMP solution (80 µL) were added to the ACS in a dropwise fashion at least 15 minutes prior to insertion into the defect. This resulted in 2 µg tBMP-2 in the defect. Sterility was maintained.

β-TCP Putty

β-TCP granules (46-48 mg aliquots), carboxymethyl cellulose putty (48-50 mg aliquots). Under sterile conditions, the β-TCP granules were washed with 1 mL of sterile PBS and mixed gently. As much as possible of the liquid was removed using a pipette. Pre-weighed sterile carboxymethyl cellulose (approximately 2 mg more than the β-TCP putty formulation was inserted into the defect.

Dose Formulation

The rhBMP-2+absorbable collagen sponge and the tBMP-2+β-TCP putty were prepared as described above. The final dose each rat received of the BMP-2 formulations was 2 g rhBMP-2 for the reference item and approximately 615-620 µg tBMP of the test item.

Animal Assignments and Body Weights

On arrival, the initial animals were numbered 1-63, of which 60 were assigned to the study. The animals were fed ad lib on arrival, but this was reduced to 35-30 g when it was found at their third weighing that they were gaining weight too quickly. The initial surgeries were delayed by one week, and as the animals weights continued to increase, the decision was made to remove the heaviest sixteen animals from the study and get replacement animals. The replacement animals were assigned numbers.

Figure 1B:
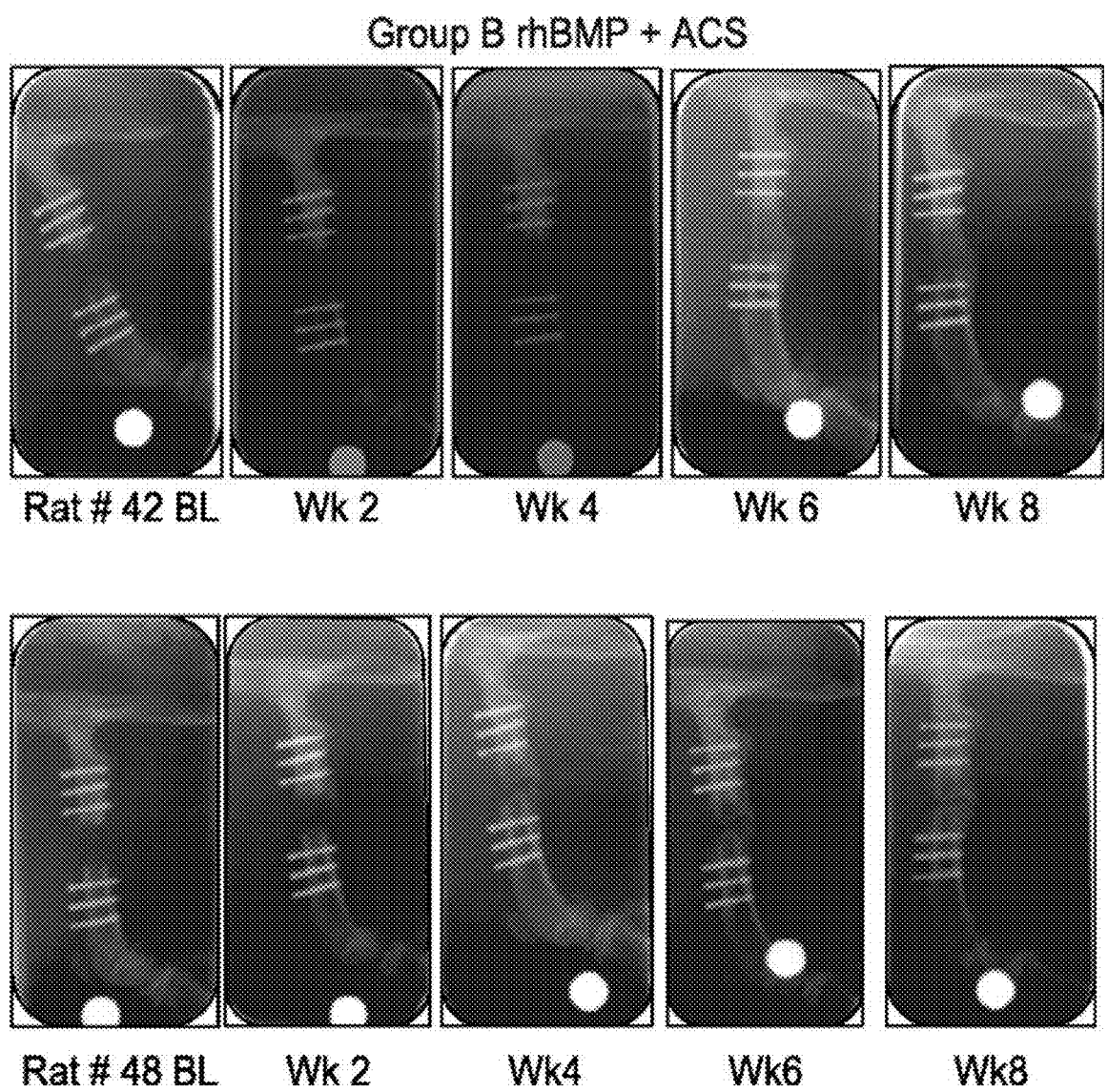
FIG. 1B are representative in vivo radiographs (lateromedial orientation) of animals from experimental Group B.
Figure 1C:
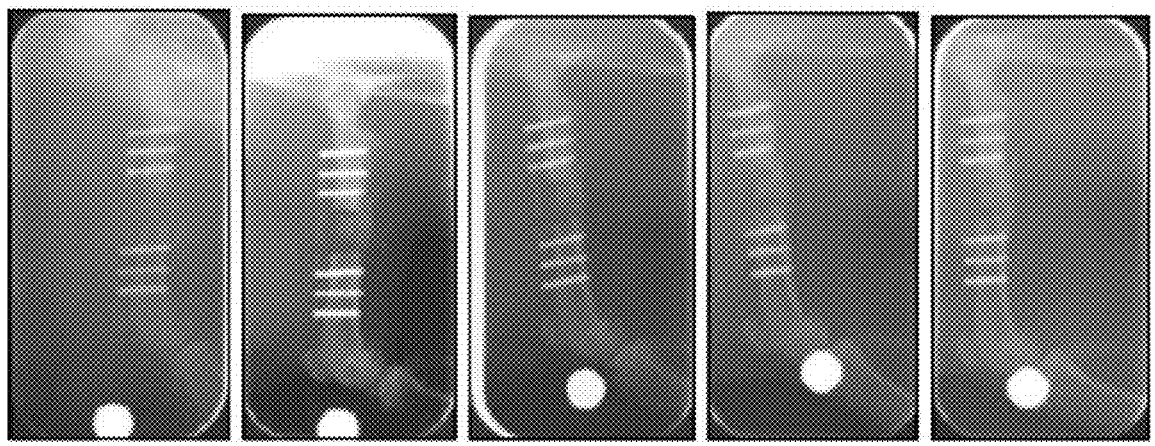
FIG. 1C are representative in vivo radiographs (lateromedial orientation) of animals from experimental Group C.
Figure 1C:
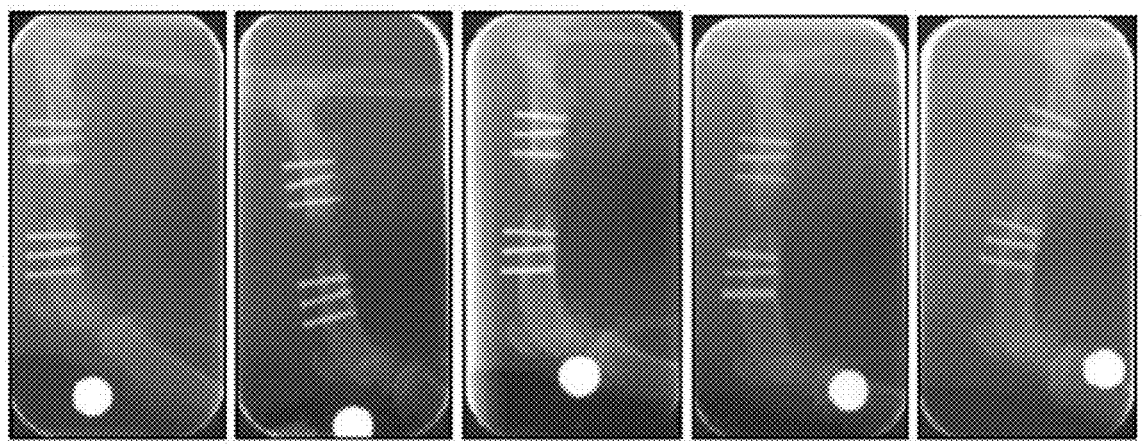

All animals were weighed on arrival and assigned to one of three groups on a weight-ordered distribution. All allocations to group and end-point times were done to ensure there were no significant differences in weight prior to the surgical intervention between any of the groups in terms of treatment to be administered, or time to end-point (either 4- or 8-weeks post-surgery). There were no significant differences in weights at assignment to study between any of the groups for either the initial group of animals or the replacement group, or at any time for the duration of the study (FIG. 1A, FIG. 1B and FIG. 1C).

Example 2. Radiographic, Mechanical, Histomorphometric and Histological Analyses of 4 and 8 Week Post-Fracture Healing in Three Experimental Rat Fracture Groups (A, B and C)

To assess the extent of mineralized bone material within the callus region of fractures in three experimental rat groups (A, B and C), radiographic scoring of callus formation, mechanical testing of the callus strength, high resolution micro computed tomography (μCT), and quantitative histological analyses of bone formation and resorption were conducted.

Radiographic Assessment

Sagittal radiographic images were generated using a Faxitron X-ray with fixed exposure settings. Radiographic scoring specifically on callus formation healing was based on Chhabra et al. (2005)*J Orthop Trauma* 19(9): 629-634, and modified from Marino et al. (1979) *Clin Orthop Relat Res* (145): 239-244 and Makley et al. (1967) *J Bone Joint Surg Am* 49(5): 903-914 (Table 4). Scoring was performed in one session on de-identified, randomised radiographs. Both the posterior and anterior aspect of the cortex at the site of fracture was scored. The average score for each specimen was recorded.

Figure 2:
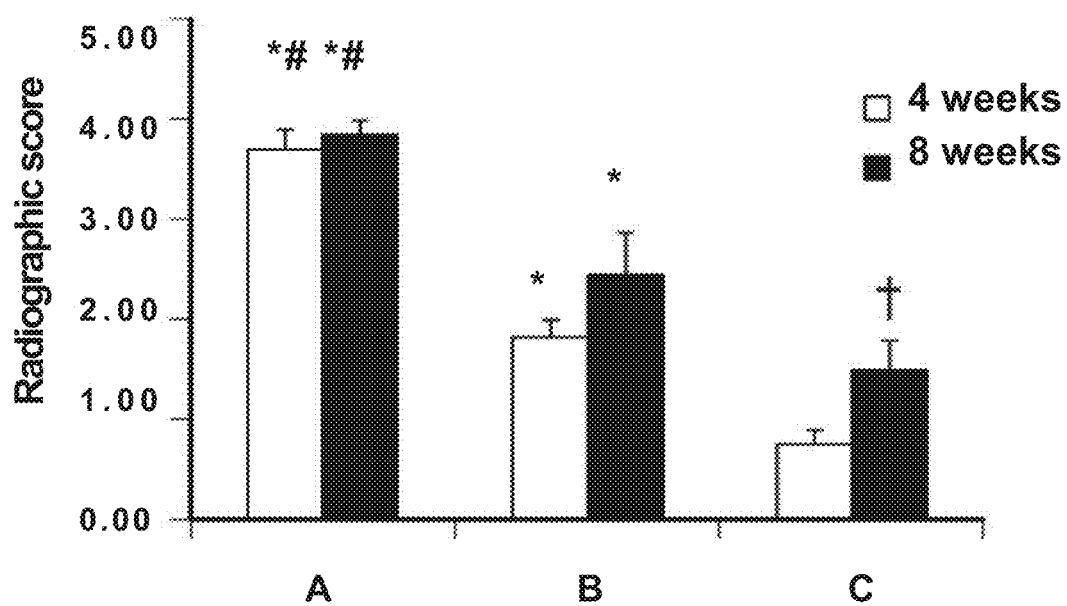
FIG. 2 is a representative graph of the mean radiographic score (+SEM, n=9-10) of animals from each Group at four weeks- and eight weeks-post-surgery. *$P<0.01$ vs Group Cl #$P<0.01$ vs Group V; † $P<0.01$ vs Group C at 4 weeks.

Baseline radiographs were taken on all animals as soon as possible after surgery whilst still under anaesthetic, at two weeks, four weeks (end-point for half of the animals), six weeks and eight weeks (end-point for remaining animals) post-surgery. They were taken in lateromedial and craniocaudal views. FIG. 2 shows representative radiographs of animals from all groups at 0, 2, 4, 6, and 8 weeks post-surgery. The defect was only visible in Group B animals that received the rhBMP+ACS. The putty (with or without protein) in animals from Groups A and C appear to be outside the confines of the defect (more obvious in mediolateral view). This was the case in all animals, even when the surgeon reported that the putty appeared to be completely contained within the defect, and touching the muscle tissue had been completely avoided on insertion of the test or control items.

Ex vivo radiographs, as with the in vivo radiographs showed that the putty and/or bone growth was not confined to the defect area in Groups A and C, as it was in Group B images (FIG. 2).

Figure 3A:
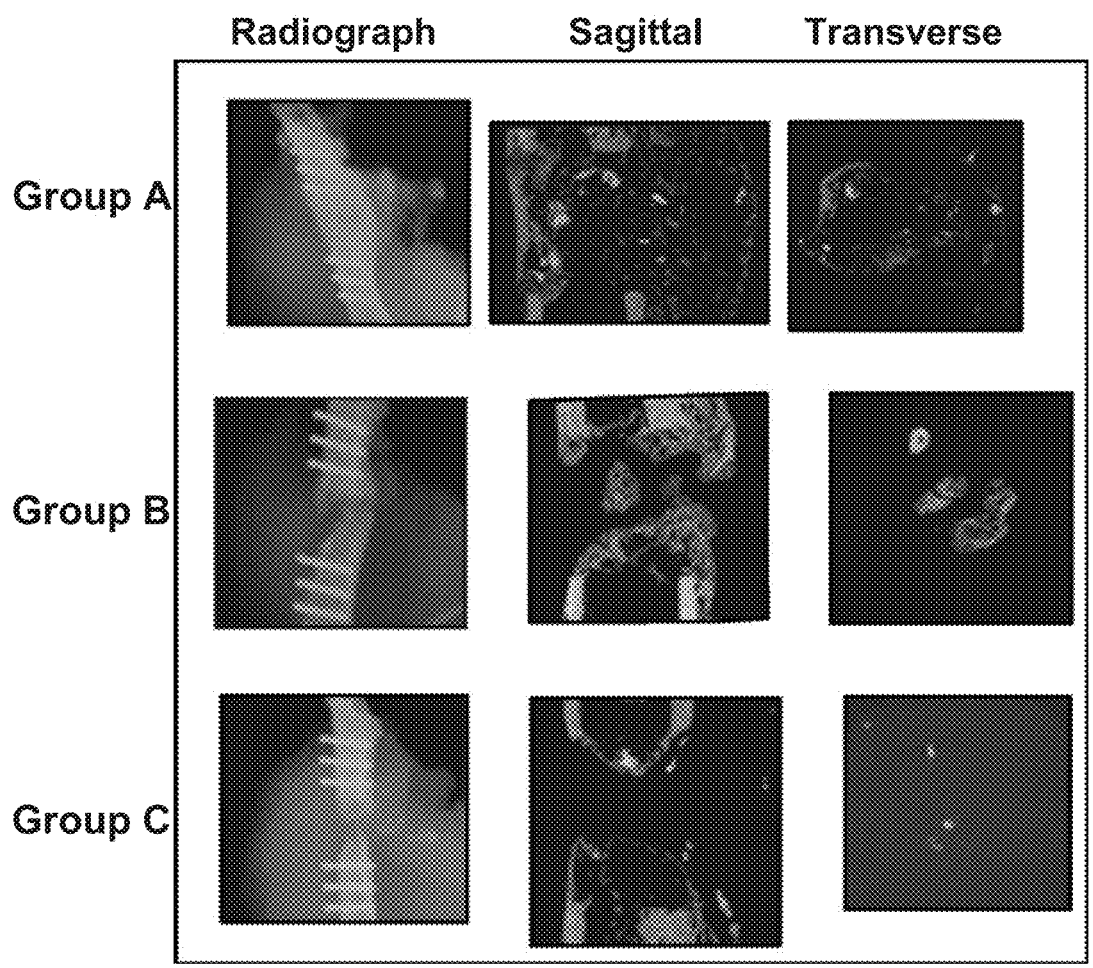
FIG. 3A are representative radiographs, sagittal, and transverse micro-CT images at 4-weeks post-operation from animals in Group A, B, or C.
Figure 3B:
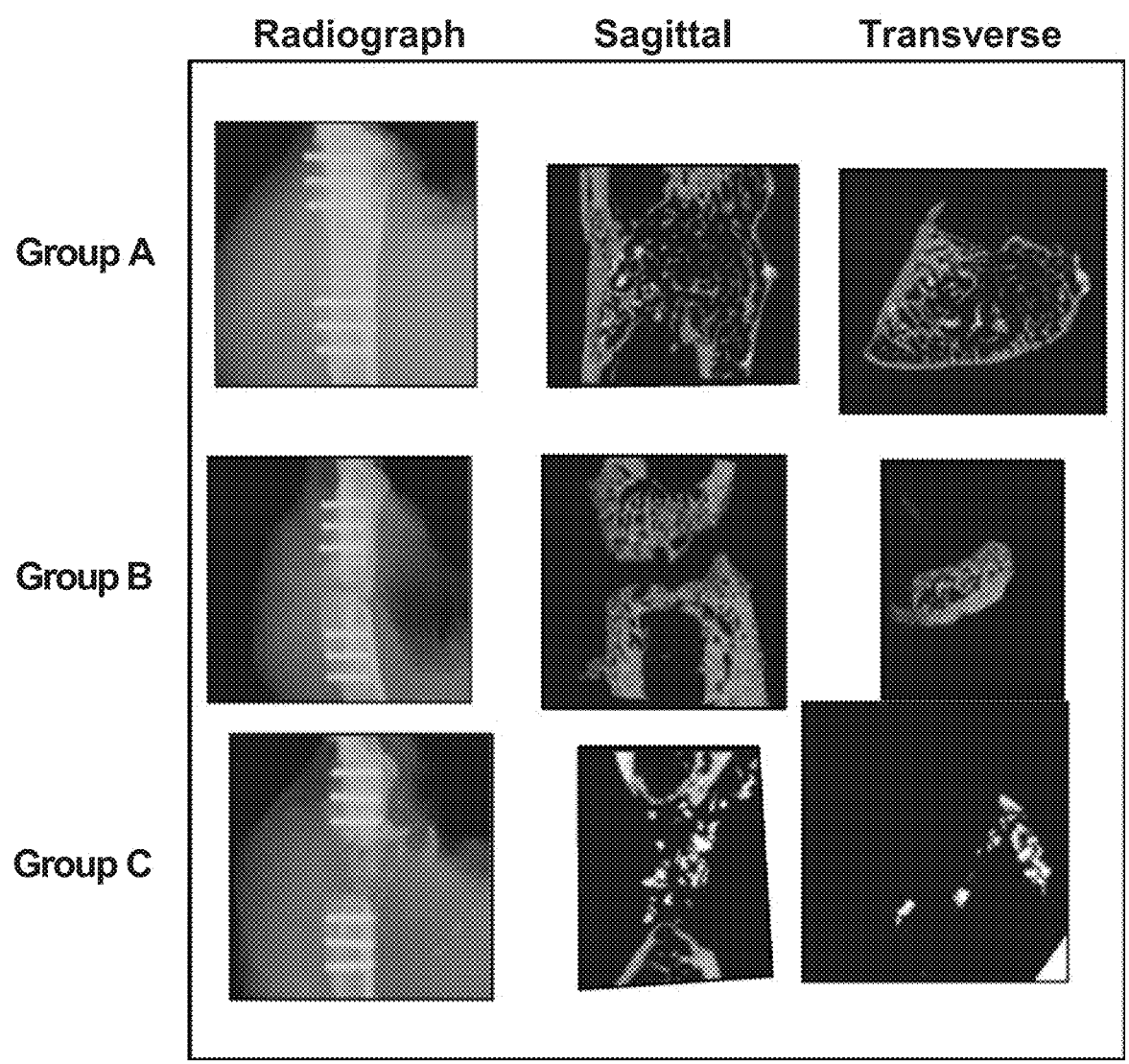
FIG. 3B are representative radiographs, sagittal, and transverse micro-CT images at 4-weeks post-operation from animals in Group A, B, or C.
Figure 4:
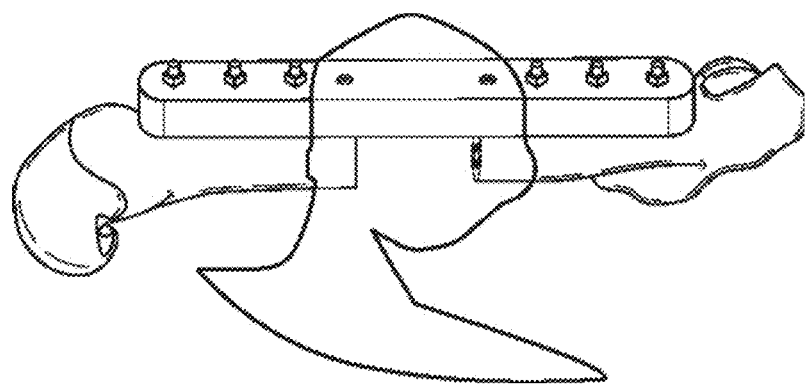
FIG. 4 is a schematic representation of the varied callus formation in animals from Group A, B, or C at 4 weeks post-surgery. The red-shaded area is an approximation of the mineralized callus volume.
Figure 4:
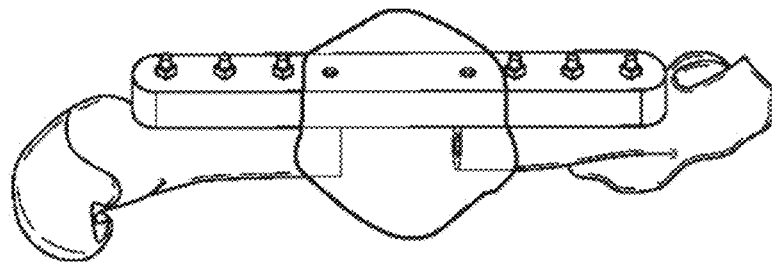
Figure 4:
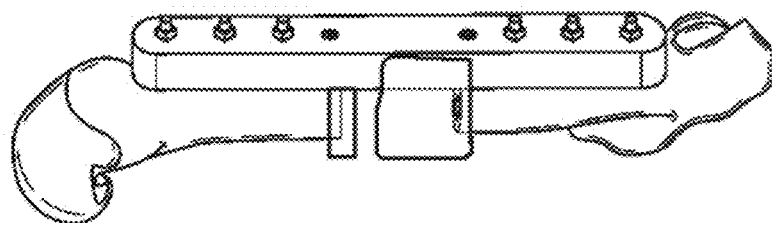
Figure 4:
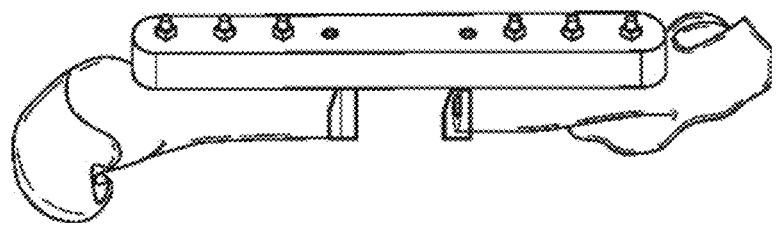

At 4-weeks post-surgery, Group A routinely demonstrated bridging of the periosteal callus and frequently demonstrated mature callus with interfragmentary bridging (FIG. 3A). This as in clear constrast to Groups B and C where only callus tissue and little or no callus scores were observed respectively. At 8-weeks post-surgery, while there appears to be no significant radiographic change in the scoring of the mature callus, Group A remained advanced in the healing stage when compared to Group B and C, both of which only marginally improved their scores in the intervening 4 weeks (FIG. 3B). It is worth noting that in Group A, frequent larger boney callus volumes were observed intact but distal to the fracture site suggesting that the treatment in this group was not contained to the fracture region. Representative images from each group at 4- and 8-weeks post-surgery are located in FIGS. 3A and 3B. A schematic of the varied callus formations is represented in FIG. 4.

Micro-Computed Tomography

To quantify the total callus and bone mineral volumes, each specimen was scanned by high resolution CT (Skyscan, Model 1174, Bruker microCT). Specimens were wrapped in PBS-soaked gauze and secured within a humidified tube prior to scanning. All scans were performed at 6.4 m voxel resolution and X-ray tube potential of 50 kV and 800 μA. Images were acquired over 180 degrees with intervals of 0.8 degrees and frames were averaged from 2 images taken at each step. For each scan, the images were then reconstructed into a z-stack of images to represent the transverse plane of the femur (N-Recon software, Bruker microCT). All reconstructions used a modified Feldkamp cone-beam algorithm with a smoothing setting of 1, a ring artefact reduction level set to 12, a beam hardening level of 20% and a post-alignment balue of no greater than +1.0. Reconstructions of the callus region excluded the adjacent screws which secured the rat-fix plate, in order to remove the interfering signal of the titanium screws from subsequent analyses. Uniform realignment of datasets were performed using Dataviewer v.1.5.1 (Bruker, BEL). Reconstructed z-stack images for each specimen were then analysed using CTan software (Bruker microCT). Analyses of bone volume in the fracture region were performed by three manually defined volumes of interest (VOI's). Prior to 3D analyses, all volumes of interest binarised using an adaptive thresholding technique using a specimen-specific hydroxyapatite standard control. 3D analyses were performed to establish total volume and bone volume fractions in each volume of interest.

During necropsy, all treated legs were removed, and placed in either 10% neutral-buffered formalin and kept at room temperature, or gauze-soaked saline and frozen at −20° C., for μCT imaging and mechanical strength testing. All legs were also X-rayed (Faxitron X-ray Imager) and the images graded as per Table 3 above. FIG. 4 shows a graphical representation of bridging of periosteal callus. Moderate callus was observed in Group B samples, whereas Group C samples showed little or no callus.

Figure 5A:
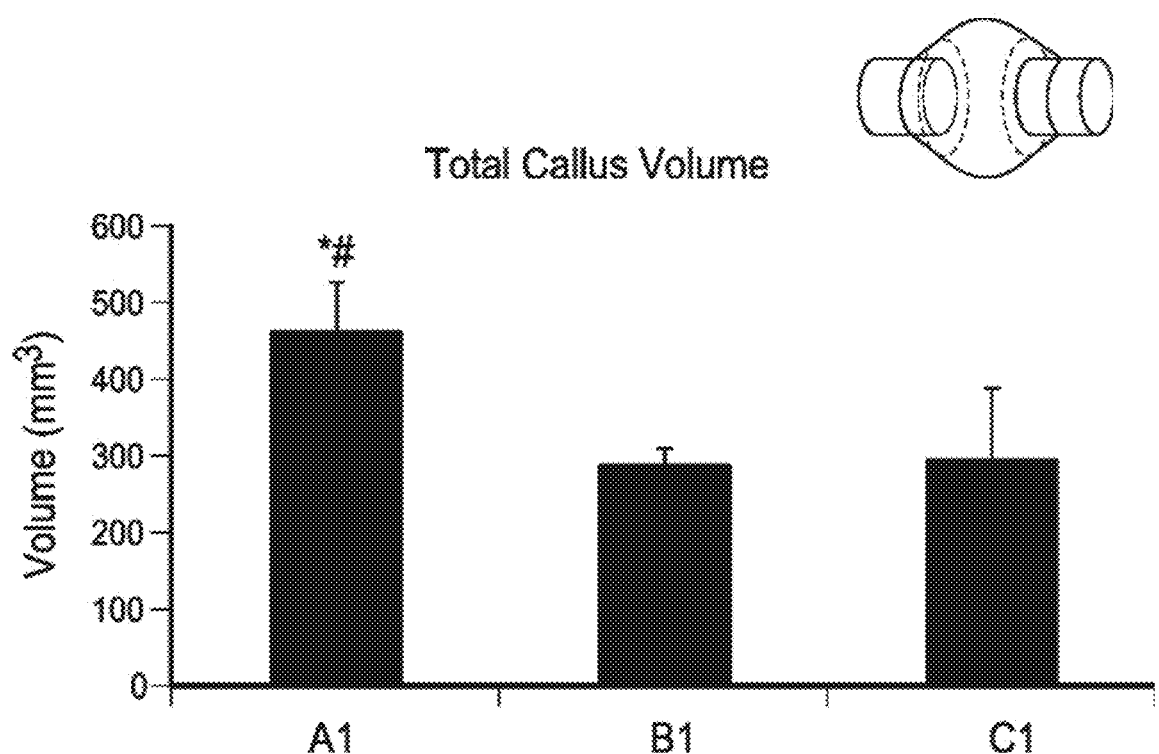
FIG. 5A is a representative graph of micro-CT analyses showing total callus volume in bone specimens obtained at 8 weeks post-surgery from animals in Group A (n=9), B (=n-7), or C (n=8). The data are represented as Mean±SEM; *$P<0.01$ vs B, #$P<0.0.1$ vs C.
Figure 5B:
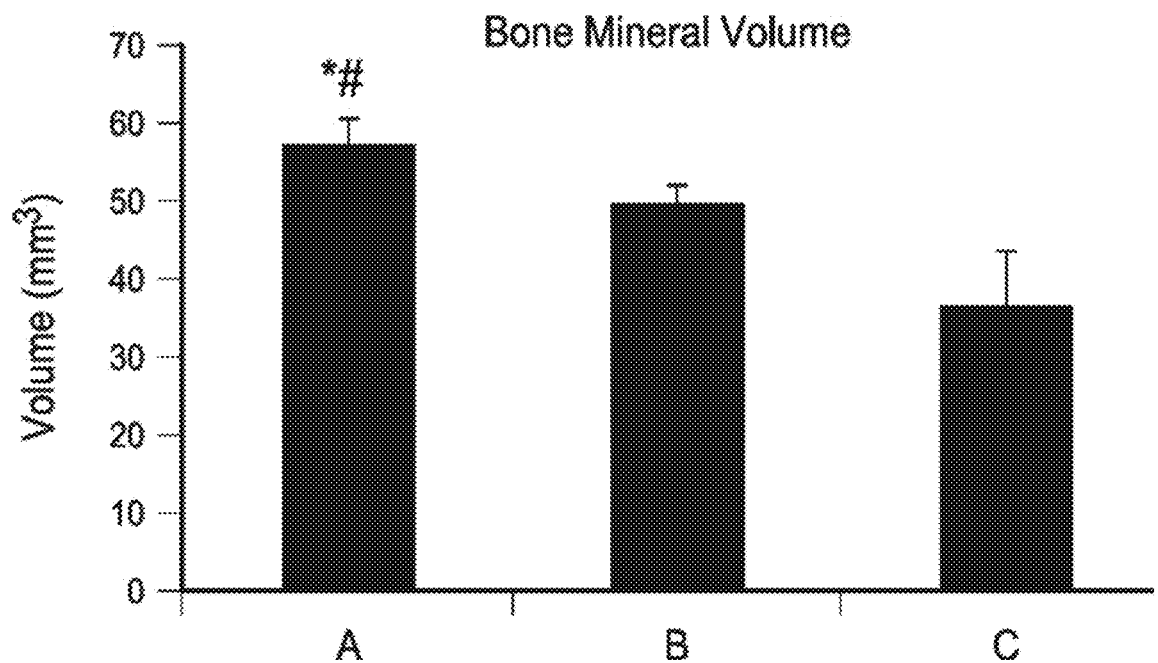
FIG. 5B is a representative graph of micro-CT analyses showing bone mineral volume in bone specimens obtained 8 weeks post-surgery from animals in Group A (n=9), B (=n-7), or C (n=8). The data are represented as Mean±SEM; *$P<0.01$ vs B, #$P<0.0.1$ vs C.
Figure 6A:
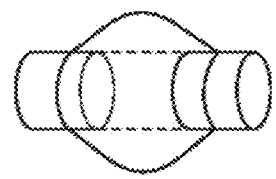
FIG. 6A is a representative graph of micro-CT analyses of the diaphyseal region volume of bone specimens obtained 4 weeks post-surgery in animals from Group A (n=10), B (n=8), or C (n=7). Bone mineral volume is expressed as the percentage of bone mineral volume to total volume. The data are represented as Mean±SEM; *$P<0.05$ vs B, #$P<0.0.5$ vs C. A1 vs B1; p=0.059.
Figure 6A:
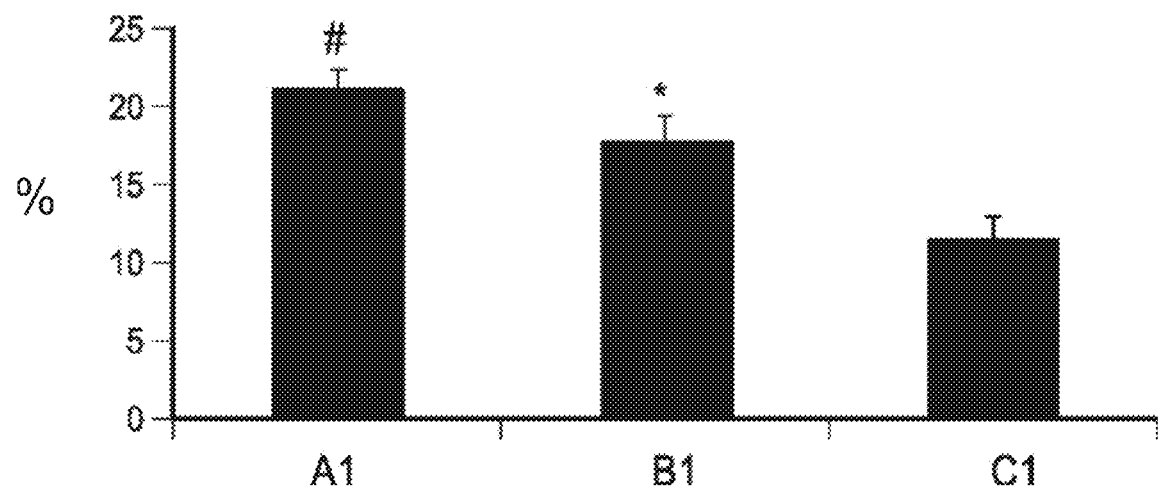
Figure 6B:
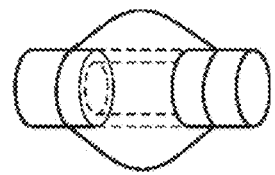
FIG. 6B is a representative graph of micro-CT analyses of the cortical bone volume of bone specimens obtained 4 weeks post-surgery in animals from Group A (n=10), B (n=8), or C (n=7). Bone mineral volume is expressed as the percentage of bone mineral volume to total volume. The data are represented as Mean±SEM; *$P<0.05$ vs B, #$P<0.0.5$ vs C.
Figure 6B:
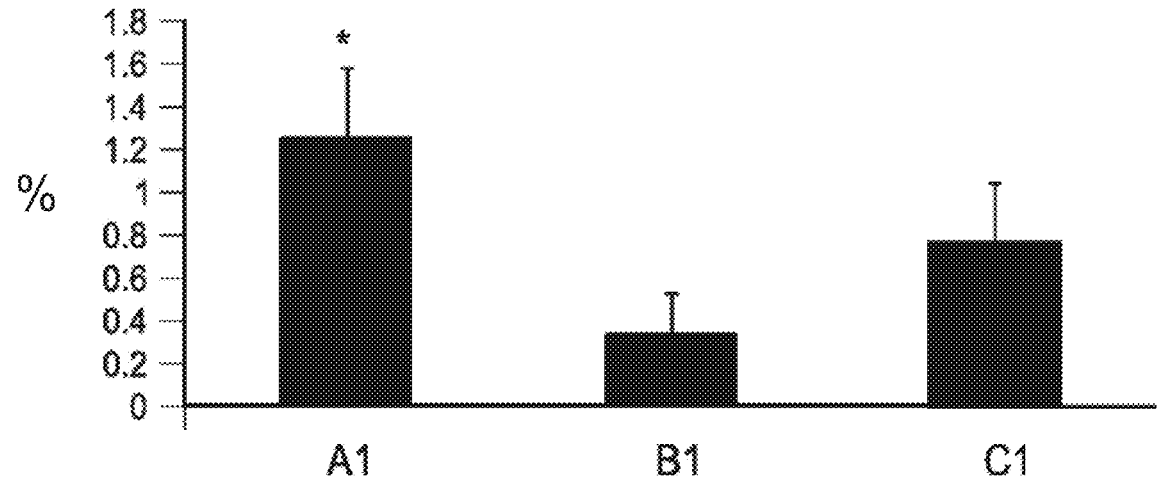

Analyses of the CT images for bone volume in the fracture region showed that the total callus volume and the bone mineral volume were significantly higher in Group A (tBMP+3-TCP putty-treated) animals than in either the β-TCP putty (Group C) or the rhBMP+ACS-treated animals ($p<0.01$ in both cases). There were no significant differences between the Group B and Group C animals for either total callus volume or bone mineral volume. These are shown in FIG. 5A and FIG. 5B. When restricting the region to the interpolated shaft region, in both Group A and Group B, the bone mineral volume as a percentage of the tissue volume (BV/TV) was approximately 2-fold greater than Group C ($P<0.05$). The BV/TV for Group A was trending to be increased by 15% when compared to Group B ($P=0.059$) (FIG. 6A). When restricting the region to the interpolated cortical bone region only, in Group A, the cortical bone mineral volume, in BV/TV terms, was 4-fold greater than levels in Group B ($P<0.05$) but not significantly greater than in Group C (FIG. 6B).

Figure 7A:
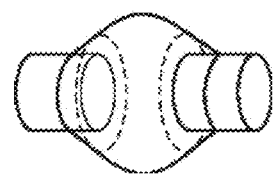
FIG. 7A is a representative graph of micro-CT analyses of total callus volume in bone specimens obtained 8 weeks post-surgery from animals in Group A (n=9), B (n=7), or C (n=8). The data are represented as Mean±SEM; *$P<0.01$ vs B, #$P<0.0.1$ vs C.
Figure 7A:
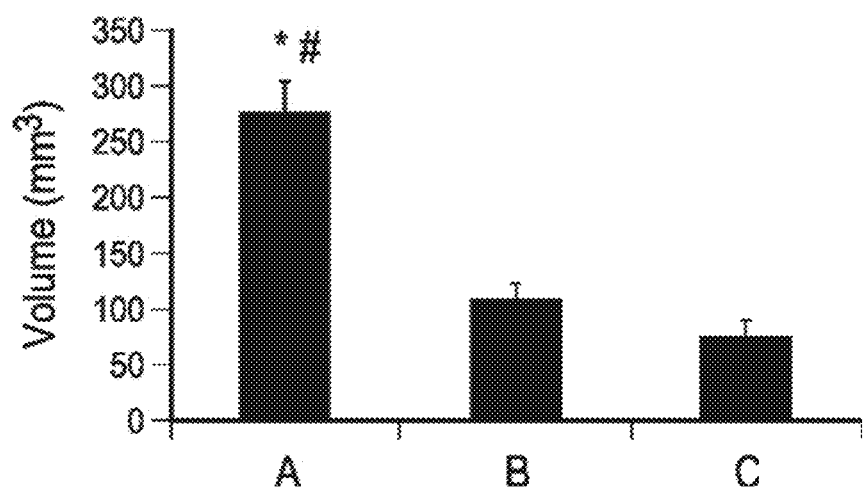
Figure 7B:
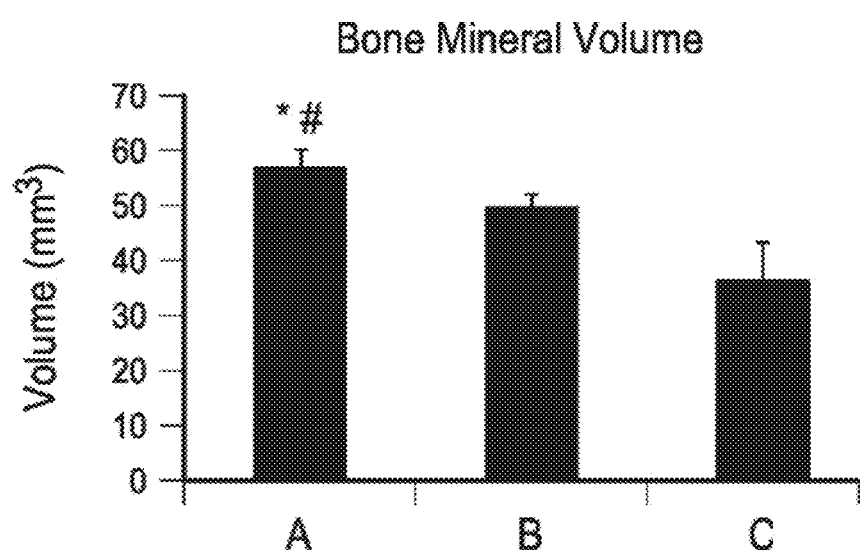
FIG. 7B is a representative graph of micro-CT analyses of bone mineral volume in bone specimens obtained 8 weeks post-surgery from animals in Group A (n=9), B (n=7), or C (n=8). The data are represented as Mean±SEM; *$P<0.01$ vs B, #$P<0.0.1$ vs C.

At 8-weeks post-surgery, TCB was markedly increased in Group A when compared to Groups B and C (FIG. 7A and FIG. 7B). However, BMV in Group A is not significantly increased when compared to Group B. These data suggested that while a larger bony callus existed in Group A, the density of bone mineral was more comparable to Group B.

Mechanical Strength Testing of Treated Femur

The mechanical strength testing of femoral callus was performed using 3 point bending method (5940 and BlueHill 3 software, v3.25, Instron, MA, USA). Each specimen was stored in PBS-soaked gauze at −80° C. until ready for testing. Prior to testing, specimens were gradually thawed to 4° C. over three days to maintain tissue integrity. On the day of testing, samples were scanned by micro-CT in a humidified chamber and kept cool prior to allowing specimens to reach room temperature for mechanical testing. For each specimen, the rat-fix plate was cut immediately prior to testing using a slow speed rotary diamond tipped saw lubricated with cooled phosphate buffered saline. The midpoint of the rat-fix plate was cut to remove the support of the plate in the fracture stabilization. This cut was done so as to cause minimal disturbance to the surrounding callus. After cutting the plate, each bone was then loaded into the 3-point jig with the rat-fix plate in contact with the low anvils with a 10 mm span such that the upper anvil was positioned directly above the cut-point on the plate. The downward motion of the upper anvil tests the resistance, and thus the strength, of the callus. As the bone deforms during testing, the plate separates at the mid-point cut, minimizing the contribution of the plate to the measure of Ultimate Load to Failure (ULF). T Compression testing was performed by gradually increasing the force applied, at a rate of 0.01 mm per second. ULF was determined by the peak force immediately prior to the failure of callus as determined by the force-displacement curve.

Figure 8:
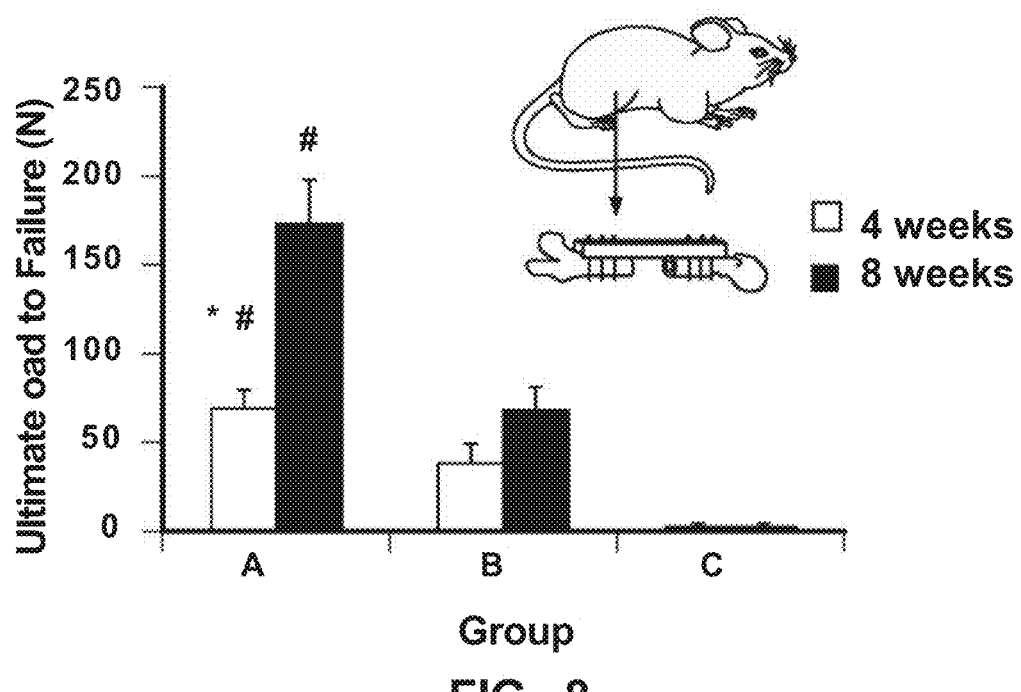
FIG. 8 is a representative graph of ultimate load to failure (ULF) at 4- and 8-weeks post-surgery for animals in Group A, B, or C. Data are represented as the mean+/−S.E.M. *$P<0.05$ vs 4-week groups; #$P<0.01$ vs 8-week groups.

The mechanical testing of femoral strength in each fracture specimen required that the contribution of the rat-fix plate be removed without disturbing the callus. Typically this would involve removing the rat-fix plate altogether. However, in numerous samples, in particular in Group A, the extent of callus enveloped the plate making removal impractical. Thus, the compromise was to cut the plate exactly at the mid-point such that it no longer contributed to femoral support. The cut was done in such a way as to only cause minimal damage to the callus. The downward motion of the upper anvil thus tests the resistance, and thus the strength, of the callus. Group A exhibited markedly increased ULF at 4 and 8 week post-surgery when compared to Groups B and C (FIG. 8). At 8 weeks post-surgery, Group A exhibited 2.5-fold increase in ULF when compared to Group B at the same time point (P<0.001). Group B demonstrated increased ULF when compared to Group C and both time points. At 8 weeks post-surgery, in Group B, a trend for increased ULF was observed when compared to 4 weeks post-surgery (P=0.059).

Histomorphometry of Treated Femur

At ten days prior to end-point, all animals were administered calcein green (25 mg/kg of 10 mg/mL), with the exception of Rat #6, 8, 9, 10, 18, 20, 23, 30 and 50, which were inadvertently administered 12.5 mg/Kg of 10 mg/mL solution. All rats received 100 mg/Kg of xylenol orange (100 mg/mL solution) at three days prior to end-point. All administrations were intraperitoneal.

Figure 9A:
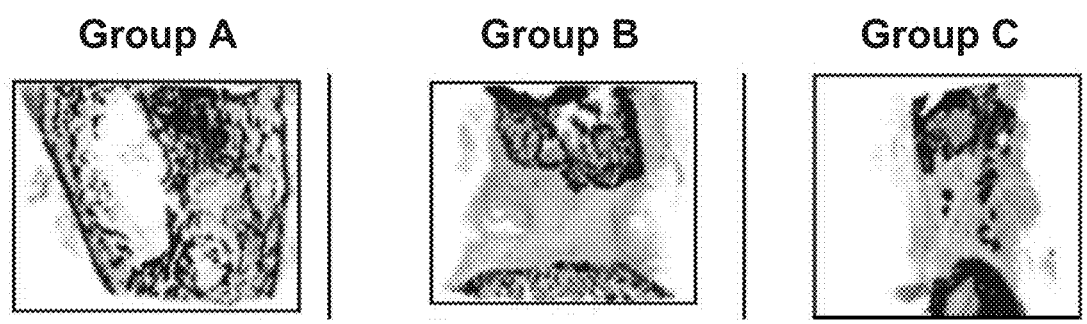
FIG. 9A are representative histological images of Von Kossa- and H&E-stained bone specimens obtained at 4 weeks post-surgery from animals in Group A, B, or C.
Figure 9B:
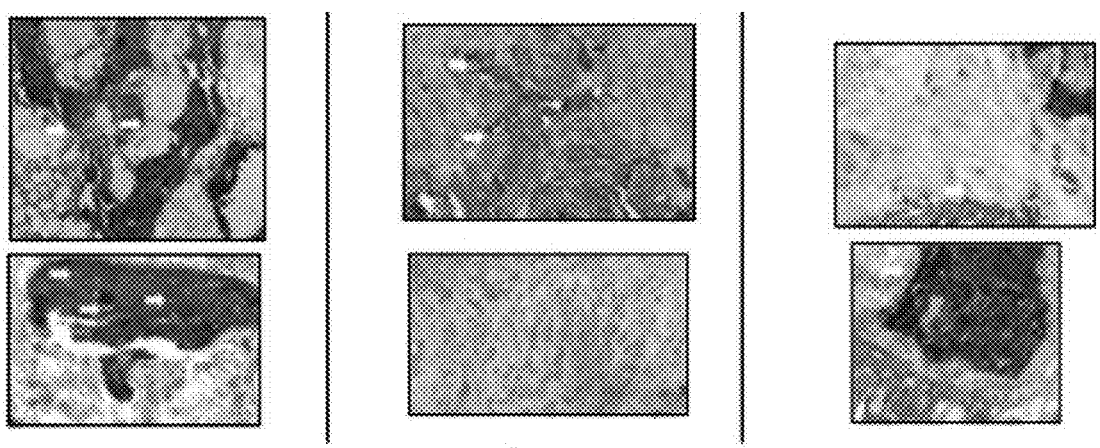
FIG. 9B are representative histological images of TRAP+ osteoclast-stained bone specimens obtained at 4 weeks post-surgery from animals in Groups A, B, or C. White arrows indicate osteoclasts, and yellow arrows indicate osteocytes.

At 4 weeks post-surgery, Group A exhibits extensive evidence of mineralization akin to mature trabecular bone (FIG. 9A). Significant remodelling of bone was observed by the presence of osteoclasts (FIG. 9B, white arrows), and the presence of osteocytes in Group A specimens (FIG. 9B, yellow arrows) which is indicative of mature mineralized bone. Osteoblastic activity was observed in the form of double-fluorochrome labelled mineral accretion. The osteoblastic bone formation was frequently observed as 'lines' colored green and red which are in association with each other (FIG. 9B, blue arrows). This represented the formation of lamella (mature) bone, rather than the ad-hoc mineralization of woven bone that occurs in early callus formation, a common observation in Group B. Furthermore, the presence of red-blood cells, and adipocytes indicated that an angiogenesis has occurred and suggested good infiltration of cells to most regions of the callus in Group A specimens.

In Group B, while bone mineral was observed, there were extensive regions of fibrous and cartilage tissue which was unmineralized within the callus region (FIG. 9A). Where new bone mineral occurs, double labels were observed indicating bone formation. However, these double labels were frequently disorganized and often occurred as single labels suggesting that woven bone formation (i.e. initial bone callus formation) was continuing to be formed at this time point (FIG. 9B). While not quantified, it appeared that osteoclasts predominantly existed in regions between the unmineralized and mineralized portions of the callus which suggested an earlier stage of callus development than what was observed for Group A animals.

In Group C, there was no evidence of mineralization, bone formation or bone remodelling. Indeed, there was no evidence of cartilage formation. A fibrous-like material with foreign mineralized spicules existed within the fracture site. There were some instances where osteoclasts as present on the surface of the foreign material, suggesting that this material could be resorbed (FIG. 9B).

Figure 10A:
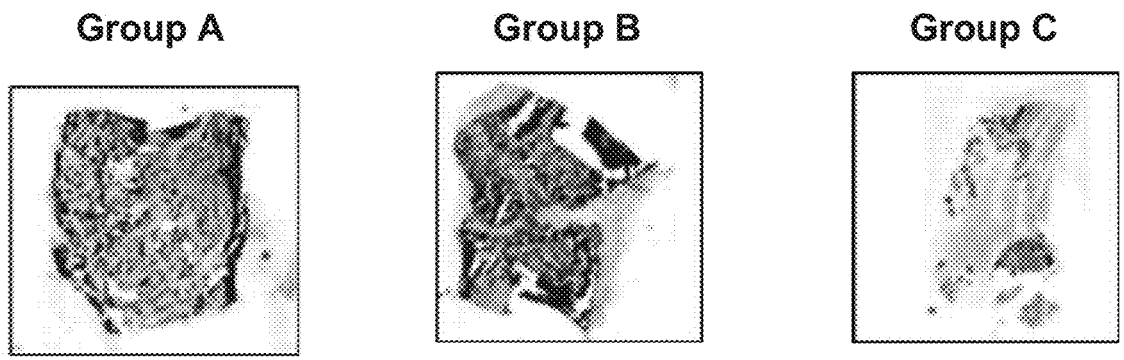
FIG. 10A are representative Von Kossa- and H&E-stained histological images of bone specimens obtained at 8 weeks post-surgery from animals in Group A, B, or C.
Figure 10B:
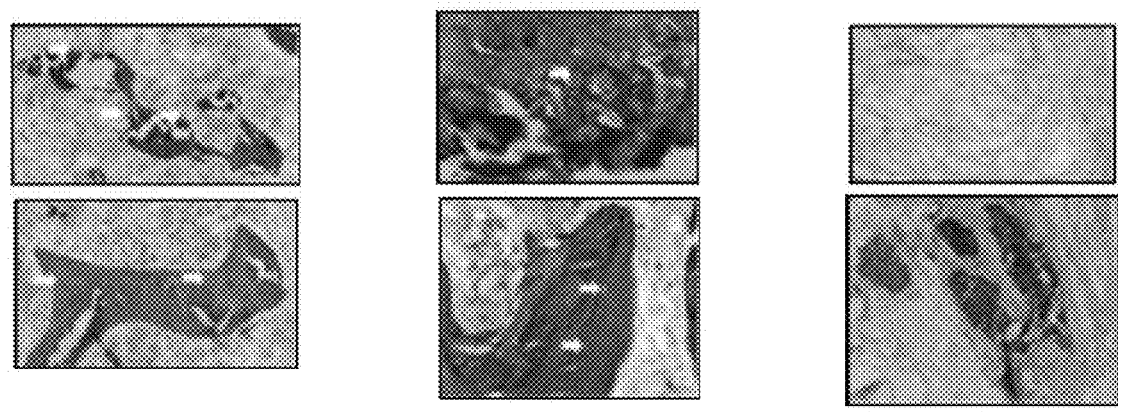
FIG. 10B are representative TRAP+ osteoclast-stained histological images of bone specimens obtained at 8 weeks post-surgery from animals in Group A, B, or C. White arrows indicate osteoclasts, and yellow arrows indicate osteocytes.

At 8 weeks post-surgery, the same pattern of activity between the groups was continued (FIG. 10A and FIG. 10B). Of note, however, in Group A, there appeared to be greater distribution of mature bone across all sections, consistent with CT analyses. Also, a degree of intra-trabecular, or intra-cortical labelling of mineral (FIG. 10B, orange arrows) suggested a further maturing of bone consistent with late-stage bone healing. Also of note, Group B specimens appeared to exhibit all stages of callus formation and remodelling. That is, there was evidence of lack of periosteal bridging at times, the presence of cartilage, woven bone, lamellae bone, and evidence of remodelling as well. In Group C, the persistent lack of healing suggested that this group contained a treatment which was most comparable to a critical-sized defect model without any scaffold of healing agents.

In summary, sixty-one animals were successfully treated with one of three test items following surgical creation of a critical size defect in the right femur. The post operative recovery was unremarkable in the majority of animals. The test items were all placed within the defects, but on X-ray, it could be seen that the compounds containing the β-TCP putty were spread out of the defect area and into the surrounding tissue. As the collagen sponge was not visible on X-ray, it was not possible to judge if the sponge had moved out of the defect area.

Most animals recovered from surgery well and in most cases were moving as per usual within 24 hours of surgery. A number of the animals were larger than the recommended weight for the plates, but the femurs were not so large that the screws of the internal fixator system were not going through the whole bone, so there should not have been loss of stability while new bone was forming at the site. Two animals had evidence of displaced bones on the two week radiographs, these animals were not heavier than others. One animal was in the rhBMP+ACS group, the other was in the β-TCP putty group. Another animal (Group C) had a broken screw and displaced bone at the six-week post-operative time point. There was no obvious reason why this had occurred.

There were no differences between any of the groups in any clinical pathology parameters or histological analyses of organs and tissues.

Radiographic and histological examination of the treated femurs showed that the Group A animals (tBMP-2+β-TCP putty) had the most evidence of formation of mature bone in the defect site compared to the other two groups. This was shown by bridging of the periosteal callus, increased mineralization, presence of osteocytes, active remodelling of the bone (as shown by the presence of osteoclasts) and evidence of angiogenesis (shown by the presence of red blood cells and adipocytes). Whilst some evidence of mineralization of callus is present in the Group B (rhBMP+ACS) samples, this appeared to be less developed than for Group A. Group C (β-TCP putty) showed no evidence of mineralization, suggesting that having a scaffold alone could not induce new bone growth within eight weeks of application into a critical-sized defect.

Group A animals also had significantly stronger bones than either Group B or Group C animals as evidenced by ultimate load to failure tests. This was evident at both four and eight weeks post-treatment.

The differences in callus formation in the process of healing are distinct between all three groups, clearly indicating that there were unambiguous differences in the treatments of fracture in each group.

In Group C, a frank lack of periosteal bridging and minimal bony callus formation at both 4 and 8 weeks was associated with a lack of cellular activity within the fracture. These observations were consistent with the near complete absence of mechanical integrity at either time point.

In Group B, the mineralized callus was more extensive than the levels in Group C both 4 and 8 weeks post-surgery. This was evident in the radiographic and histomorphometric analyses. Furthermore, while periosteal bridging was observed only in some Group B specimens at 8 week post-surgery, there was a clear and overt difference in the histological assessment at both time points with regards to bone formation and cellular activity. Unlike in Group C, the presence of bone formation, frequently in the form of woven bone and occasionally as lamellae bone, was associated with increase in mechanical strength when compared to Group C. Interestingly, neither radiographic nor mechanical strength measures were significantly improved at 8 weeks when compared to 4 weeks post-surgery. This suggested that the majority of activity in callus formation and structural integrity occurred in the first 4 weeks.

Group A exhibited the most advanced healing when compared to the other groups. At 4 weeks post-surgery radiographic evidence of periosteal bridging was a measure that no samples achieved in Group C and often was not observed in Group B, even at 8 weeks post-surgery. Interestingly, while radiographic scores at 8 weeks post-surgery were comparable to 4 week scores, the mechanical strength of the callus was more than double the levels at 4 weeks post-surgery and at least 3-fold greater than levels in Group B, suggesting that considerable bone mineralization occurred within the callus region in the second 4 week period. This observation was consistent with high levels of lamellae bone formation in Group A at 4 and 8 weeks post-surgery, which was distinct from the weaker woven bone formation that occurred in Group B, even at 8 weeks post-surgery. It is important to note that callus volume at 8 weeks of age was lower than levels at 4 weeks post-surgery, suggesting that callus volume was being remodelled into a more compact callus at the site of fracture. In Group A, this was consistent with fewer observations of extraneous mineralized callus distal to the fracture site at 8 weeks post-surgery. With regards to the histological assessment of Group A specimens, observations of osteoclastic none resorption adjacent to regions of bone undergoing bone formation is entirely typical of bone undergoing remodelling which is known to be done to provide a stronger and more efficient structure for skeletal integrity. The additional observations of the presence of osteocytes as well as other cellular structures such as vascular structures and adipocytes clearly makes the bone often indistinguishable from endogenous trabecular micro-anatomy.

In conclusion, the bone specimens form the tBMP-2+β-TCP putty group clearly demonstrated vastly improved bone healing at 4- and 8-weeks post-surgery when compared to samples from animals in the rhBMP+ACS or the β-TCP putty alone treatment groups.

Example 3. Overview of Chimeric β-TCP Polypeptides

Figure 11:
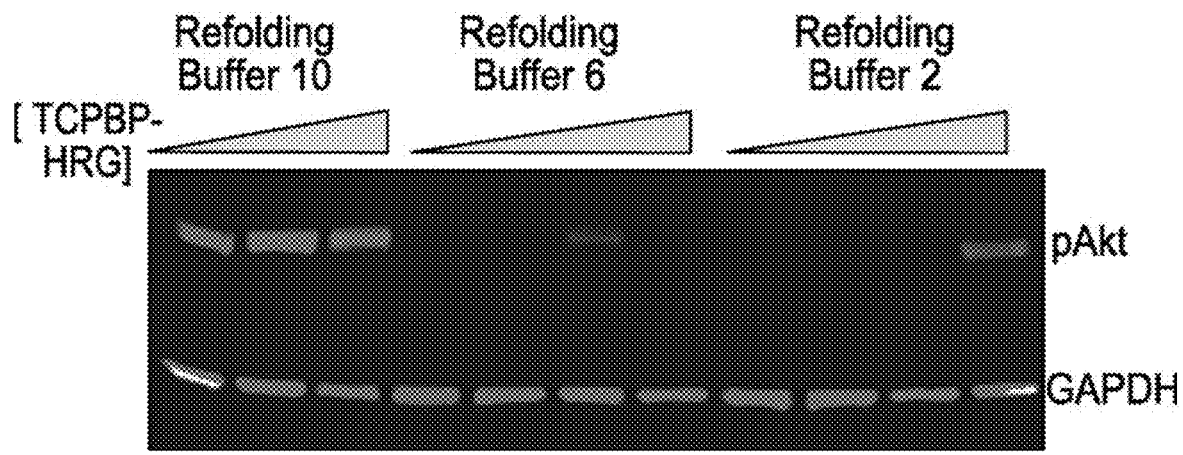
FIG. 11 is a representative immunoblot of MCF-7 cell lysate probed with an anti-P-Akt antibody, wherein the MCF-7 cells were incubated with β-TCBP-HRG.
Figure 12:
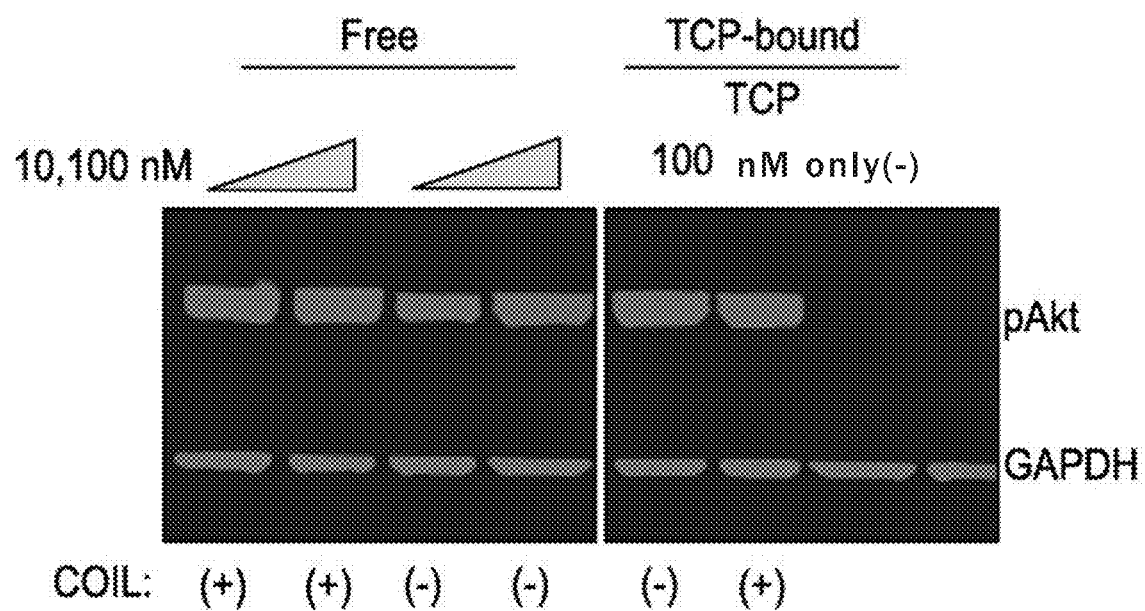
FIG. 12 is a representative immunoblot of MCF-7 lysate probed with an anti-P-Akt antibody, wherein the MCF-7 cells were incubated with β-TCBP-HRG (free) or β-TCBP-HRG (β-TCP-bound).

The present inventors found that chimeric polypeptides maintained activity of the tethered protein. The chimeric polypeptide (10×β-TCP-histidine rich glycoprotein HRG) refolded at 22° C. in buffer 10, and following incubation of the chimeric polypeptide with MCF-7 breast cancer cells, Akt activity was detected (FIG. 11). This result indicated that the chimeric polypeptide stimulated signalling activity in the target cell and was able to cause Akt phosphorylation. Next, the Akt activity was determined in 10×β-TCP-HRG bound to a β-TCP peptide (FIG. 12). The β-TCP peptide on its own was unable to cause Akt phosphorylation in MCF-7 cells, however, incubation of MCF-7 cells with β-TCP peptide bound to 10×β-TCP-HRG led to Akt phosphorylation. Interestingly, the extent of Akt phosphorylation was not affected whether the chimeric polypeptide was bound to a β-TCP peptide or not.

Example 4. Binding Affinity of tBMP2 to Various Substrate Materials

Binding assays were performed to quantify the affinity of tBMP2 protein to various substrates, including commercially available bone graft materials, ceramic powders, 3D printable scaffold materials, and a plasma-sprayed hydroxyapatite coating. First, 10 mg of each material was washed with deionized water followed by acetate buffer. Then either a 150 μg or 250 μg load of tBMP2 protein was applied to each material and allowed to bind under light agitation for 90-120 minutes. The flow through was aspirated (removing the tBMP2 which did not bind to the substrate material), and a wash was conducted with acetate buffer. A subsequent overnight elution was done by immersing the substrate material in a sodium phosphate buffer (100 mM NaPhos, 4 M Urea, 1 M NaCl, 10% 1,6 Hexanediol, pH=8) to remove the bound protein from the substrate for measurement.

The bound tBMP2 was quantified by either 1) running non-reducing SDS Page gel electrophoresis and comparing the eluted tBMP2 band to the tBMP2 load band with Image J Gel Analysis tool, or 2) conducting a Bradford assay (with a BSA standard curve) on the eluted tBMP2 and tBMP2 load. Dividing the eluted tBMP2 quantity by the original tBMP2 load quantity and multiplying by 100 gave the % of tBMP2 load that was strongly tethered to the substrate after the binding incubation step.

Table 6 summarizes the materials that were evaluated as well as the % of tBMP2 load which was effectively tethered to the substrate (% Bound).

TABLE 6

| | | | | | |
|---|---|---|---|---|---|
| | | Summary of Binding Activity | | | |
| Product | Description | Manufacturer | Load tBMP2 Applied to Material | Method of measurement | % of tBMP2 load bound to material |
| Mastergraft Strip | Biphasic TCP (85% β-Tricalcium Phosphate: 15% Hydroxyapatite)/Type I bovine collagen composite | Medtronic | 15 ug tBMP2/mg material | Bradford Assay | 69% |
| Vitoss Foam Pack | β-Tricalcium Phosphate/Type I bovine collagen composite | Stryker | 15 ug tBMP2/mg material | Bradford Assay | 82% |
| chronOS Strip | β-Tricalcium Phosphate/poly (lactide co-ε-caprolactone) composite | DePuy Synthes | 15 ug tBMP2/mg material | Image J Gel Analysis Tool | 75% |
| Vitoss Micromorsels | β-Tricalcium Phosphate granules (1 mm-2 mm) | Stryker | 15 ug tBMP2/mg material | Image J Gel Analysis Tool | 74% |
| LifeInk 500 | Calcium Phosphate Cement 3D printable ink | Advanced Biomatrix | 15 ug tBMP2/mg material | Image J Gel Analysis Tool | 87% |
| Hyperelastic Bone | Hydroxapatite/Poly (lactic-co-glycolic acid) 3D printable ink | Dimension Inx | 15 ug tBMP2/mg material | Image J Gel Analysis Tool | 58% |
| Bioactive Glass | Combeite 45S5 Bioactive Glass powder | Stryker | 25 ug tBMP2/mg material | Image J Gel Analysis Tool | 49% |
| Silicon Nitride Powder | $Si_3N_4$ powder, 99% purity | Chemsavers | 25 ug tBMP2/mg material | Image J Gel Analysis Tool | 54% |
| β-TCP Powder | β-Tricalcium Phosphate powder, 3-5 μm particle size | CaP Biomaterials | 25 ug tBMP2/mg material | Image J Gel Analysis Tool | 79% |
| β-TCP Spray Dried Powder | β-Tricalcium Phosphate spray dried powder, <38 μm particle size | CaP Biomaterials | 25 ug tBMP2/mg material | Image J Gel Analysis Tool | 78% |
| Hydroxyapatite Powder | Hydroxyapatite powder, 3-5 μm particle size | CaP Biomaterials | 25 ug tBMP2/mg material | Image J Gel Analysis Tool | 57% |
| HA-coated Bone Screw | Hydroxyapatite plasma spray-coated stainless steel bone screw (6 mm dia × 5 mm long piece cut from screw) | Citieffe | 25 ug tBMP2/mg material | Bradford Assay | 44% |
| β-TCP Granules | β-Tricalcium Phosphate granules, 250-1000 μm particle size | CaP Biomaterials | 15 ug tBMP2/mg material | Bradford Assay | 70% |
| Hydroxyapatite Granules | Hydroxyapatite granules, 250-1000 μm particle size | CaP Biomaterials | 15 ug tBMP2/mg material | Bradford Assay | 52% |
| ReBOSSIS | Cotton-like bone void filler. Main ingredients are β-Tricalcium Phosphate, bioabsorbable polymer, and SiV (silicon-containing calcium carbonate) | Orthorebirth | 15 ug tBMP2/mg material | Bradford Assay | 83% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising: (a) a sequence at least 80% identical to SEQ ID NO: 2 (VIGESTHHRPWS), (b) a sequence at least 80% identical to SEQ ID NO: 4 (ILAESTHHKPWT), (c) a sequence at least 80% identical to SEQ ID NO: 6 (IIGESSHHKPFT), (d) a sequence at least 80% identical to SEQ ID NO: 7 (GLGDTTHHRPWG), or (e) a combination comprising two or more sequences of (a)-(d).

2. The polypeptide of claim 1, comprising a sequence at least 90% identical to SEQ ID NO: 2.

3. The polypeptide of claim 2, comprising SEQ ID NO: 2.

4. The polypeptide of claim 1, comprising a combination of the sequence at least 80% identical to SEQ ID NO: 2, and the sequence at least 80% identical to SEQ ID NO: 4.

5. The polypeptide of claim 1, comprising a combination of the sequence at least 80% identical to SEQ ID NO: 2, and the sequence at least 80% identical to SEQ ID NO: 6.

6. The polypeptide of claim 1, comprising a combination of the sequence at least 80% identical to SEQ ID NO: 2, and the sequence at least 80% identical to SEQ ID NO: 7.

7. The polypeptide of claim 1, comprising a combination of the sequence at least 80% identical to SEQ ID NO: 2, and a sequence at least 80% identical to SEQ ID NO: 1 (LLADTTHHRPWT).

8. The polypeptide of claim 1, comprising a sequence at least 90% identical to SEQ ID NO: 4.

9. The polypeptide of claim 8, comprising SEQ ID NO: 4.

10. The polypeptide of claim 1, comprising a combination of the sequence at least 80% identical to SEQ ID NO: 4, and the sequence at least 80% identical to SEQ ID NO: 6.

11. The polypeptide of claim 1, comprising a combination of the sequence at least 80% identical to SEQ ID NO: 4, and the sequence at least 80% identical to SEQ ID NO: 7.

12. The polypeptide of claim 1, comprising a combination of the sequence at least 80% identical to SEQ ID NO: 4, and a sequence at least 80% identical to SEQ ID NO: 1 (LLADTTHHRPWT).

13. The polypeptide of claim 1, comprising a sequence at least 90% identical to SEQ ID NO: 6.

14. The polypeptide of claim 13, comprising SEQ ID NO: 6.

15. The polypeptide of claim 1, comprising a combination of the sequence at least 80% identical to SEQ ID NO: 6, and the sequence at least 80% identical to SEQ ID NO: 7.

16. The polypeptide of claim 1, comprising a combination of the sequence at least 80% identical to SEQ ID NO: 6, and a sequence at least 80% identical to SEQ ID NO: 1 (LLADTTHHRPWT).

17. The polypeptide of claim 1, comprising a sequence at least 90% identical to SEQ ID NO: 7.

18. The polypeptide of claim 17, comprising SEQ ID NO: 7.

19. The polypeptide of claim 1, comprising a combination of the sequence at least 80% identical to SEQ ID NO: 7, and a sequence at least 80% identical to SEQ ID NO: 1 (LLADTTHHRPWT).

20. The polypeptide of claim 1, further comprising a sequence at least 80% identical to SEQ ID NO: 1 (LLADTTHHRPWT).

* * * * *